(12) United States Patent
Kashihara et al.

(10) Patent No.: US 10,100,327 B2
(45) Date of Patent: Oct. 16, 2018

(54) NUCLEIC ACID IMPARTING HIGH-YIELDING PROPERTY TO PLANT, METHOD FOR PRODUCING TRANSGENIC PLANT WITH INCREASED YIELD, AND METHOD FOR INCREASING PLANT YIELD

(71) Applicant: JAPAN TOBACCO INC., Tokyo (JP)

(72) Inventors: Masakazu Kashihara, Shizuoka (JP); Toshiyuki Komori, Shizuoka (JP); Toshihiko Komari, Shizuoka (JP); Masahiko Maekawa, Okayama (JP)

(73) Assignee: JAPAN TOBACCO INC., Tokyo (JP)

( * ) Notice: Subject to any disclaimer, the term of this patent is extended or adjusted under 35 U.S.C. 154(b) by 261 days.

(21) Appl. No.: 14/434,149

(22) PCT Filed: Oct. 18, 2013

(86) PCT No.: PCT/JP2013/078889
§ 371 (c)(1),
(2) Date: Jun. 19, 2015

(87) PCT Pub. No.: WO2014/069339
PCT Pub. Date: May 8, 2014

(65) Prior Publication Data
US 2016/0032309 A1    Feb. 4, 2016

(30) Foreign Application Priority Data
Oct. 31, 2012   (JP) ................................ 2012-241287

(51) Int. Cl.
*C12N 15/82* (2006.01)
*C12Q 1/6895* (2018.01)
*C07K 14/415* (2006.01)

(52) U.S. Cl.
CPC ........ *C12N 15/8261* (2013.01); *C07K 14/415* (2013.01); *C12N 15/8237* (2013.01); *C12Q 1/6895* (2013.01); *C12Q 2600/13* (2013.01); *Y02A 40/146* (2018.01)

(58) Field of Classification Search
None
See application file for complete search history.

(56) References Cited

U.S. PATENT DOCUMENTS

| 2007/0020621 A1* | 1/2007 | Boukharov .......... C07K 14/415 435/6.12 |
| 2007/0130633 A1* | 6/2007 | Urban ...................... A01H 5/00 800/278 |
| 2011/0145949 A1 | 6/2011 | Hatzfeld et al. |
| 2012/0278948 A1 | 11/2012 | Sakakibara et al. |

FOREIGN PATENT DOCUMENTS

| CN | 102186877 A | 9/2011 |
| WO | WO 2010/020555 A1 | 2/2010 |
| WO | WO 2011/049243 A1 | 4/2011 |

OTHER PUBLICATIONS

Benfey et al (1989, EMBO J, 8(8):2195-2202).*
Benfey et al (1990, Science 250:959-966).*
Matsushika et al (2007, Bioscience, Biotechnology and Biochemistry 71(2): 535-544).*
McConnell et al, Nature 411 (6838):709-713, 2001.*
Bowie et al, Science 247:1306-1310, 1990.*
Database GenBank: AB189039.1, Accession AB189039, Version AB189039.1 , Murakami et al., Definition: *Oryza sativa* Japonica Group OSPRR37 mRNA for pseudo-response regulator 37, complete cds, Feb. 15, 2008, pp. 1-2.
Database GenBank: AP005199.3, Accession AP005199, Version AP005199.3, Sasaki et al., Definition: *Oryza sativa* Japonica Group genomic DNA, chromosome 7, PAC clone: P0627E10, Feb. 16, 2008, 42 pgs.
Ashikari et al., "Cytokinin Oxidase Regulates Rice Grain Production," Science, vol. 309, Jul. 29, 2005 (Published online Jun. 23, 2005), pp. 741-745.
Ditta et al., "Broad host range DNA cloning system for Gram-negative bacteria: Construction of a gene bank of Rhizobium meliloti," Proceedings of the National Academy of Sciences USA, Genetics, vol. 77, No. 12, Dec. 1980, pp. 7347-7351.
Harushima et al., "A High-Density Rice Genetic Linkage Map with 2275 Markers Using a Single $F_2$ Population," Genetics, vol. 148, Jan. 1998, pp. 479-494.
Hiel et al., "Efficient transformation of rice (*Oryza sativa* L.) mediated by Agrobacterium and sequence analysis of the boundaries of the T-DNA," The Plant Journal, vol. 6, No. 2, Aug. 1994, pp. 271-282.
International Search Report (Form PCT/ISA/210) for International Application No. PCT/JP2013/078889, dated Jan. 7, 2014, with an English translation.
Ishida et al., "Agrobacterium-mediated transformation of maize," Nature Protocols, vol. 2, No. 7, 2007 (Published online Jun. 21, 2007), pp. 1614-1621.
Komari et al., "Vectors carrying two separate T-DNAs for co-transformation of higher plants mediated by Agrobacterium tumefaciens and segregation of transformants free from selection markers," The Plant Journal, vol. 10, No. 1, 1996, pp. 165-174.
Maekawa et al., "Isolation and functional analysis of a responsible gene relating to vegetative vigor in a wild-type rice . . . ," Norin Suisansho . . . , Genetic and molecular dissection of quantitative traits in rice, vol. 473, Feb. 2009, pp. 40-43 (132 pages total), with a partial English translation.

(Continued)

Primary Examiner — Stuart F Baum
(74) Attorney, Agent, or Firm — Birch, Stewart, Kolasch & Birch, LLP

(57) ABSTRACT

An object of the present invention is to provide nucleic acids capable of imparting high-yielding ability to plants. Another object of the present invention is to use such nucleic acids to produce transgenic plants at increased yield, as well as to provide methods for increasing the yield of plants. By introducing into a plant a construct in which a promoter of a pseudo-response regulator gene in *O. longistaminata* and/or a structural gene of a pseudo-response regulator in a plant are operably linked, a transgenic plant is obtained that has acquired high-yielding ability.

3 Claims, 14 Drawing Sheets
(10 of 14 Drawing Sheet(s) Filed in Color)
Specification includes a Sequence Listing.

(56) References Cited

OTHER PUBLICATIONS

Matsushika et al., "Circadian Waves of Expression of the APRR1/TOC1 Family of Pseudo-Response Regulators in *Arabidopsis thaliana*: Insight into the Plant Circadian Clock," Plant Cell Physiology, vol. 41, No. 9, 2000, pp. 1002-1012.
Miura et al, "OsSPL14 promotes panicle branching and higher grain productivity in rice," Nature Genetics, Letters, Published online May 23, 2010, 21 pages.
Murakami et al., "Characterization of the Rice Circadian Clock-Associated Pseudo-Response Regulators in *Arabidopsis thaliana*," Bioscience, Biotechnology, and Biochemistry, vol. 71, No. 4, 2007 (Online Publication Apr. 7, 2007), pp. 1107-1110.
Murakami et al., "Circadian-Associated Rice Pseudo Response Regulators (OsPRRs): Insight into the Control of Flowering Time," Bioscience, Biotechnology, and Biochemistry, vol. 69, No. 2, 2005, pp. 410-414.
Murakami et al., "The Evolutionarily Conserved OsPRR Quintet: Rice Pseudo-Response Regulators Implicated in Circadian Rhythm," Plant Cell Physiology, vol. 44, No. 11, 2003, pp. 1229-1236.
Ogiso et al., "The Role of Casein Kinase II in Flowering Time Regulation Has Diversified during Evolution," Plant Physiology, vol. 152, Feb. 2010, pp. 808-820 (27 pages total).

\* cited by examiner

Fig. 7

| identity / similarity | Nipponbare | longi | Sorghum | Arabidopsis |
|---|---|---|---|---|
| Nipponbare |  | 98.2 | 62.0 | 37.1 |
| longi | 99.5 |  | 62.6 | 36.8 |
| Sorghum | 89.1 | 88.0 |  | 38.8 |
| Arabidopsis | 75.7 | 76.1 | 78.6 |  |

SEQUENCE LISTING

<160> NUMBER OF SEQ ID NOS: 21

<210> SEQ ID NO 1
<211> LENGTH: 82355
<212> TYPE: DNA
<213> ORGANISM: Oryza longistaminata

<400> SEQUENCE: 1

```
gcggccgcgc cctcccctcc gccggatccg gccggagagg aggtggtgga cctttgggaa    60
cggccgccgg cggtggccgc ggcgctgtcc cctccgctcg atccgaccgg aggggagatg   120
gcggacctca gggacagcaa cggcagccac cgcacactcc cctccgtcag atccggttgg   180
aggggaggcg gcgggcggtg gcgcctgagg aattttttgg gatgattttg tagattcttt   240
taagatgttt ttttatttgt ggatgatttt cttgttgaat atgttttgat ctgtgattgg   300
tggatgatct gtgatgtggg gatttgggga tttcaaaaaa ctagatgtag ggcatggcgc   360
agtgacggcg attgtgagtt ccggctcgat tcgagccggc tcttttttt tttttgctc    420 gtataaacct ataggtgccg gttctatttt tggtataggt gccggctgct tgtattggtg   480
ttgatcaata ggtgccggta ggaaaaccgg cacatataag ccggttggga accgacacct   540
atgatggttt tttatatact aatgatgggg gagtcgaacc caagtatcag gggaatattc   600
tcttttagag tcaacccgtc ccatctagcc ccacaattat acatctataa aagcggattc   660
gacctaacct gacccagcaa atctctgcaa ccaaacacat actaaattac atgcagacca   720
taacatcgtg cgcctacgat aatacaacat actggtatgg taccaccagg taccaaatta   780
aatacaacca ttcatttaac ataggcatga taggtaatga agtaaagcag aggtgcgcga   840
cctcaatgtt tcacgcgaga cgctgaaata tctcctctcc gtcacgcatg cgacatcaca   900
taattgaagt gtaattgtat tgtaactacg atgtaactta tataaaactt gtattcaact   960
atgatttggt tggttagcat agggatctta cgtgtgacat gcgtgaaaat ttctttctag  1020
caattttttt agagataatc caagaaatgc tattgacaag cgttcaaatc caagaaatac  1080
catcgacaag tgtgagttcc aagaaattcc atcgtacaaa cgattttgtc ctaaaaatgc  1140
catcgccgtc cattttgcgc tgttaaatac actattcatc ctatagaact taacggcgcg  1200
gaatggatgg aaccctaaca gcgatggcat ttttgggaca aagtcgtttg tacgatggca  1260
tttcttggaa ctcacactta tcaatggcat ttctaagatt tggacgcttg tcaatggaat  1320
ttcttggaga ttatctcttt tttttacgtt aatgcacaaa tctcaaaagt tttgggggca  1380 aaaaaaaaa aacttgcgga agttttctag caattccgtt ccttgagccg gtaccatctc  1440
tcagattaga tggcgttgtc tggtacctac attattgaac cattgaatct agcacaatca  1500
acggtcatga tttggtacct gcctccgctg ttgatttatt tatacatcgt gtgtgtccat  1560
gctacaagag aaaaccagca gaaatgacat gtgttggaca agatttaacc tatgtctatg  1620
atgcacgggt tgatcaactt acagagcgag tgactaaaaa tttcaccctc cacacaggtt  1680
gtggtatatc actgatttat tttgctagtg aatatattgt cactcttact taaaaagaga  1740
ccgagaatcg caaagactca acgtaagtaa ggtgcaaaca tgcatgtagt attgcagagt  1800
acttccttgc agcttaatta accgtgaaca cacaccacgt atacgtgtat atatatttat  1860
atgcaggtag gagtaggagt gtgggttttg gagattatat tgacgatcga tgattaagga  1920
agaagaatga aattaagcta ggtagagcct acagcgtagt ttggatgcgc cagagcatga  1980
tttgggagca atcggagtcc ggcatccccc tcgtcgtcga ctggttgtat tcctccaccg  2040
ccacccgctg cacgaacttc actgattcct gcatatgtat atatatagta catattatta  2100
atctcaatta ctagctttgt acgtactcct acttcgtact ccctccgtcc caaaaaaaaa  2160
caaaccatgg gtttctgtgt ccaactttaa ctgtccgtct tatatgaaac tttttataa   2220 ttcgtatttt cattattgtt agatgataaa acatgtttaa tatttatgc gtgacttgtc   2280 tttttaattt ttttcatatt ttttttaaat aagacggacg gtcaaacgtt gggcgcggaa  2340
actaggattg tctattttt tagacggagg gagtaattgt caatagttat tgtgtactta  2400
```

```
tgtaatgatg aatctgcaga ttgggatcca aactgtacag taaatatagt acatgtacta    2460
cacgctgaaa ggcttctagc tagtgaggct ggctaactat ctccaataat atatggaaat    2520
gattgatgaa attaggtaaa caaacaaaca aacaaacaaa ccaaaaagca agcagacaga    2580
cccggagctt gtgcgtgtgt agtgtcgtgt gcgtacgtga attgtgcatt atattcttcc    2640
gacttttaat ctcttttcag ttagctagct actacttata tatagctggg accagccgca    2700
ggacatgaca agaaagtact cccttcgtat tataaggtat gacatcgttc accttttaac    2760
caacatttaa tcattcgttt tataaaaaaa ttatataact attattgttt tttttattat    2820
gacttaagat atcatcaaat gttttataag catgacataa atacttctat atttgcacaa    2880
aaattttaaa taagacaaat tatcaaaatt tagttaaaaa gtcaacgaca tcatatatta    2940
aaatatagag gaagtaataa gtaaaaaatt gagaatcata atataatact tcctccttcc    3000
ctaaatgctt acgccattga cttttttaaa tatgtttgac cgttcatatt attcaaaata    3060
tttaagtaat tattaattct ttttctatca tttgatttat ttattgttaa atatattttt    3120
atgtatacgt atagttttac atatttcgta aaaaatttta aataaaacga atggtcaaac    3180
atgtttaaaa aagtcaacga cattaaatat ttatggaagg agggaatata ttagtactaa    3240
atcaaaactc cggtccggct gaaggtgggt ggggtggacg acgtcgttga tcgagtgaga    3300
gggagcgatg atgggtgggc agtggccagt ggctgacctg cgaggcgtcg gggtcggaga    3360
gggggaagcg gtcccacctg tgcgggtccc acagcatcca gctgctgaag gcgaagccgc    3420
ccacttccat taacatctcc ggaggcggcc ggtcagctgc cgctcgccgc tcgccgccgg    3480
ccgccgccat gtccatgtcc atgtcgaacc agccgcgggt gatcaccgac ggcgacgacg    3540
aggaggatgt gttgatgcag agtgggcctt gcaccatcac ctttcgctcg tacgccgaca    3600
ctgtcgccac gggccacgca ccaaatgtcc tgcatttaca tatgccagcc ccatcaaatc    3660
attcattctt gccgacacat cctgtactat actgcactgt acggccatat acaataatta    3720
acgcgctact gctacgacat ccctctcatt ttaaattcag ctatcatttt tcaagctcaa    3780
ctttaaatta gtagtaagta ctaagtactc cctccgtttc aaaaaaaaaa aaaaaaggca    3840
aaccatgagt tttcgtgtcc aactttgact gtccgtctta tatgaaattt ttttataatt    3900
tgtattttca ttgttgttgg atgataaaac atgattaata ttttatgcgt gacttgtctt    3960 tttaatttt ttcataattt tttcaaataa gacggatggg caaacgttgg acacggaaac    4020
cagggtttgt cttttttttt ttgggacgga gggagtacat gataaattat agagtactct    4080
ccccgtctta aaaagatact gcctccgtcc catattattt atcgctttga gttttttattt    4140 gtaatgtttg atcattcgtc ttattaaaaa aatttagaat tattgtttat tttatttgtg    4200
atttgcttta ttatcaaaag tattttaagt atgacttatc ctttttatat ttgcacaaaa    4260
ttttcaaata aaacgaatgg tcaaacgtta taggaaaaa gtcaaagcga taagtaatat    4320
gggacggagg tagtaccttt tgagaatgaa tttatccagg tttatctcta attttattat    4380
tttagggatg gagggtgcac tatagagtaa aatggggaga aatttcaatg agtgattgga    4440
gagaaaaatg tgaataggat gacacacata taattttgaa tcctaaggag tagctattgt    4500
agtagtaggg agggcccttc catccaccga caccctagct tcgtagtact ccctacgctc    4560
aaaaataagc gtagttatga gtttttttt ttcaattttg atcatctatt ttatttggtt    4620
tttttatgat tagtattttt tgttgttatt aaattataaa gcatgaatag tatttatgtg    4680
tgacttatat tttttagtt tttaaaaaag aataaataaa atggacgatt aaagttagac    4740
```

```
atgaaaattt atggctatgc ttattttggg atggagggag tacctgctaa cgtataaaaa    4800
ctagcactcc gggagcctcc atgttatgtg tacactgttt gtctctagct agctagctca    4860
ctgctactcc ctctgtccca aaaaaaagac aaaccctgat ttccgtgtcc aatatttgac    4920
cttccgtctt atttgaaaaa attatgaaaa aaattaaaaa gataagtcac gcataaagta    4980
ttcatcatgt tttatcatct aacaacaata aaaatactaa ttataaaaat atttcatatc    5040
aaacgttggc acgcaaaccc gcggtttgtc ttttttttag acggagggag tactgaagta    5100
ctacagtata tataacggaa tgtagttgag tgttggctaa aatatcttta tctctactat    5160
agccgtgttt agttggtgtg ctaaaatttt tttaactgta tggacacaca tttaaaatat    5220
taaatgtaga ctaataacaa aacaaattat agattccgca tataaatcgc gagacgaatt    5280
tattaagcct aattaatccg tcattagcaa atatttacta tagcatcatg ttgtcaaatc    5340
atggcgtaat taggctcaaa agatttgtct cgcaatttac atgtaaactg tgtaattggt    5400
ttttttcgtc cacatttaat gctccatgca tgtgtacaaa tatttgatgt gacggaattt    5460
ttagaagttt gaagagaact aaaacacaacc tacattataa aaattgaaga tattttttatc    5520 ggtactttgg cacgtcattc gtgtagagtc gattttcaat ttcgttcgtt tttgaaaata    5580
catatctggt ttttaagttc gttctctttt ggtaatacag agagaatcgt ataaaaatat    5640
ctttaaaaaa ctcgcatact aagttgtgat gatcggactc atcggacttc taactgtagc    5700
tcatgatttt ctaaaaatat atagatccaa gtgaattcac atagtgaatt tcatcgtaac    5760
taaatcatca cctgcagcaa tgcacgagta tcttttctaa gtctgtagtg tacgcatata    5820
cgtacggagt aggtatgtaa tgtgatgatg tacctgatgt ccctgaggtg gtggaggagg    5880
cggaggtcgt agatgtcggc gaggcccccg aagagcacga cgccggcgat gcggtggtcc    5940
tcgatgtggc gcagagccac gttcctctgc tgctctctcc tcttcgatat ctgcatgcta    6000
aaatcatcat ctccttgttt catgaggagg tggcggtgca ccaccccgt gcgccgcagc    6060 agccgcgccg tgggcggcgc cgcgtgcttc tccgcggggg cctcctccac caccagccag    6120
agaagcggcg gcgacaccag ccgcagcgcg tgcgccgtgc gcgtcagccc ggcggcccgc    6180
cgctcggggt cgtcggactg ctcggtggtg gtgaccacta ccaccagctg cggctgctgc    6240
ggcctattgc tactgctact gcgactgaag atgacattgc tggcacggag cgtgcggagg    6300
aagacggcgg cgccggcggc agcgggccag tcggagggggg cgacgaggcc ggcaaggagg    6360
ccgaggagga agcagaggga cgaatgcagc atcgccctcc gcagcaccac cgggctacga    6420
gggctcctac tacgactatt ccccgtcttc ttcttgcagc cacctgccga cgccatgctg    6480
cccgcctgcc ctgcccggat cgatctgatc tgatctgctg ctctcctatc ctacctcaga    6540
tcaactcctc tctgctacta gctgcgatct gctagctagt acagttgtag tagtgagctg    6600
cagctagcac gcaccatcct ccatcctaca attaagtagc tgtggaagca gcagtgagaa    6660
tgagagtgag ggtgcgggtt ttcctttaaa caaattaaca aaaaaagac caaacaacat    6720 caacagcaat gaagggaaga gggtggtgag tagtactact gttagtagga gtagctatta    6780
atcgttcgat tccttttgct ttgtcgtgct tgatcgaacc cccattggat ggaagcctcg    6840
tttccaaata taaataatc gatcgattat aggtcttgtg gtggagtggg ctgggctacc    6900
acaggccgcg ggacttgtgt tcgaattggg ccccgcagca gctgccacca atcaaaatgt    6960
taacccatac gtatgtcgta ccgtgtcgtg cttataaagg gagtttgtgt caacaaatca    7020
attgttagta atgcacctgc ataacaaaaa aaaaataact cttaaaattg tttgcatttt    7080
gtatttcttt gtaaggctaa aacataatta atttaaagat agtactttac acatatgtgt    7140
```

```
tgtaacattg gaagtacgag tacatttttt taacaaaaaa attgagatat tttgcaccga    7200
aagcttatgt aggcagaata tgttttctag atataacggt gaggtataca aactttgtt     7260 gagagctaca tatgttttga ttaaagtaac atttaataga aatgcctctg aaaggcaaac    7320
acaggactaa aaagaagaaa aacttaagag cagatgtaaa ggtgaatata taatccaaat    7380
cagttttggt taatatttt atggagaagt atgatttcaa ggccctgctt agttaccaaa     7440
caaaaacttt tccccccgtc acatcgaatg tttggacaca tcacacatgc atggagtatt    7500
aaatataaaa aaaaaaacta attacacaga ttgtgtcgaa attgcgagac gaatcttttg    7560
agcctaattg ctccatgatt tgacaatgtg gtgctacaat aaacatttgc taatgacgga    7620
ttaattaggc ttaataaatt cgtcttgcag tttacaagtg aaatatgtat tttgttttgt    7680
tagtctacgt ttaatacttc aaatatgttt tcgttatccg atgtgacatg tcaaaacttt    7740
tcgtctcgcg aattaaacaa ggcctaaggg gggcttgttt agttggcaaa aaattttgca    7800
tctgcatgtc acatcggata tacgacaca catttgaagt attaaacata gtgtaataac     7860
aaaataaatt acaaattccg ccaggaaatt gcgagacgaa tttattaagc ctaattaatc    7920
tgtcattagc aaatgtttac tgtagcacca tattgtcaaa tcatggcgca attaacctaa    7980
ttaatcctag cgaactgtat aattggtttg ttttttttct acatttaatt ctccatgcat    8040
gtgtccaaac attagatgtg acaacgcgaa aaattgtgtt tgagaactaa gcaggcccta    8100
agttggtgtt tgaatctcct gaagatgaag attaagtgtt tcatgttaga tttaattggg    8160
taattgatct atttaaatca aataaattcc aagggtcatt atgctaggaa ttcatgtgta    8220
ttcattctct tatgggatat caatgggatg aagagttttg agaattaatc catttattag    8280
ggaattggta acttatatca attactccta attgatggat ggttgatggt tgtgtagtgg    8340
aggatggttc atggctggtt gatgacaatt agttgctcta tttctcttcc tattccattg    8400
gtaacctaat tcaattactc ctaattgatg gttggttgat ggttgtgtag tggaggatgg    8460
ttgatggcta attgatgaga attagttact ctattcctct ttctattcca tgactcctac    8520
tcttcatctt ccattcctcc tataaaatga gaatggattt gatctcccta aggagaagtg    8580
agacacactt tcatctattt ccaaggttgt tgttgctatg gtaattccat ccaacgagtg    8640
tgtgcacacg cgttgggaga gtaggcctcc gaaaccatgc gctgctgcga cgtttgcacg    8700
gacaggcggg cgatcaggtt tttggggagc gcaaggcgtg actactcact gttcgtcaac    8760
atctacttcg tcttcaccaa catgtcgaac actggagaca acggcaacac cagagacaag    8820
gagaaggagg ttcccgtcaa caccaacgga ggcaatactg cctcaaactc cagcggagga    8880
ccattcttgg ggtataaccct tcttagatta ttttaattag aagttttacg gttaatgttc    8940
atcgcaatgt caacattaca ttattatgtg attgttgatg cttattctac gttaagcatg    9000
ctcatgttga ttacattcac tactatcact ggatcaaatc ccactgtaaa tatcatgttt    9060
attatcttgt tattttggat taaaatatac cgaattatga ccaaattttc aacctttcac    9120
gcaaatgagg tgataataac gtgtgattaa ttgagtttta attattataa acttaaaaaa    9180
tagattaatc tgtatttta aaataacttt tatataaaat tttttacac aaaacacacc      9240 gtttagtagt ttcgaaaaac gggccatgaa aatccaaaag tttatccatt ggattcgaac    9300
gggagtattg gaagattgga agagaggttg ttttttagtag atgagatgag attgatgttt    9360
acccctgatt taactttgcc gtgctacagt agtagtaaat aataacagta gcagtgaggc    9420
acagcatcac tgacaaaccc tcatcctcct cctcagtact ccaccagtag agagtagtca    9480
```

```
ctcacaggag agaggagagg agaggagagg aggctactag agaagagaag aggagggtgg      9540
attggatcat ccattccatt cctccgccca aagcctctca agtctcaagc ccaaaccaaa      9600
gaatccagtc cgctccgatc gatcgatcga tcgatcccca cttttcccat ccaaaccccta    9660 gcttgcgccc accatgtcca ccccccttcga cctcaactcc gccgctgacc cccaaaccct    9720
agcgccgccc aagcgtggcc gcggccgccc caggaagaat ccccccaccgc caccgccacc    9780 gccaccggct acgatccga atcctcatcc tccatcagga gcaggagcag gagcaggagc      9840
aggtgcatgc cccttcgccc ccggcgacct ggtctgggc aagaagctct cccacccggc      9900
ctggcccgga gaggtcatct ccgctcccc caccggcgcc cagctcctcg tctccttctt      9960
cggcgacaag gccctcgcct ggtgcgacgc cgcccagctc aggcctacg agccctactt     10020 ccccgtcgcc gagctctacg atggcgaggc cgacgacttc gacgccgccc tcgatgcctc    10080
cctcctcgag ttcgagcgcc gcgtcgagct tgccctcacc gctcccggcc gcatcgcccg    10140
ccccttcctc ccccgcgatt tcatcgccct gctgcacgat ttggccgccc accgcatggg    10200
cttctccaac cgtgtccacg ccgccgtcgc taaggcgcat ctcagagcct cgacaagtt    10260 caggggccta cccgacccctc ccgagtacac cctccacctc ggcctaccca atgtctctgc    10320
cgccaccgcc actgccgcca ctcccaacaa ctgcaaccccc tacccccat ccaggaggag     10380 ggggaggaag aggaaggagg tggaggagga aatcctcgat gactctgatg aggattggga    10440
cccacgcaag aagggtgcca ctgactccga ttccgaagtc gatttccacc gcaagagggt    10500
ctccaagggc ggcaggggca gcggtgcacc acgcgggagg ccacgcggga ggcctaggaa    10560
aaacaatgct gggaggcctg cacacctcaa ggacgacgac gaggtgatcc aagaaacagt    10620
ggagtatcaa tatccaccag ccgctgacat gtttctacag cttacatccg ttgctgccga    10680
tccattcaac ttcaagggct atgactctgt gcctgtcatt cttagcttct tctcaaaata    10740
caaggactca gaagtgccgg ccacatacga cgacaaggag ctgctgcaga cattgggtgg    10800
caagaaaggt ggaaaaaaata cggaagaag cttgtacccg gctgcaaaag aaggtgactt    10860
agaggtggcg gatggccata ggggtcggag gaagtcagca gggagtatct actcagcaag    10920
aaaggcagaa gactcatatt ggtgtgatat tataatcagt gattttgatg atggagacac    10980
atcaagtgac tatgagggcc gcaaaatgaa gcggttgtct cagaacagga gttttaataa    11040
gaagatgaag caggaggttg cacctcaaga tgaggcctct gctgattcac ctgctgtgaa    11100
acaggcagat ggaccggcag ctctgatctt acatttagt aatgcagaag ccatcccttc     11160
tgtggatgac atcaatagta tattccgtat gcacgggcca atcatggagg gtgcgactga    11220
aatcaacaag aaatcaaaga tcgcaagagt agtgttttct aagagtgctg atgctgaaca    11280
ggcatatagc agttcgggaa agtataatgc atttggtcca gcccttctca ggtatgatct    11340 caaataccctg ccaatggctc ctcaagttcc ttagatggtg caggctaaac tggatatgtc    11400
gccatttgga ggtaaataga accctgatca tttatcccaa ccatgttcat tgttcatttg    11460
cacatgctaa catattttgc cttgcatcaa ctttgcatgt tctaaattca gggaaatgcg    11520
taatgaagac tggagctaag ggatcataag atgttcgcgt tactgactta gagctaggaa    11580
tgcccactgg ccaggccgga cgacttgttc gctggtcgag tgagcaattt tttaggtttt    11640
atctggttaa atgcattccg aggactggtt ggttgtgtac ttgagttcag aggtagttta    11700
tattattaaa ttatttagat ggtagatgat ctcggcgcga tccctctctt tgttatctta    11760
gcgatttatc cttttttgta ttgcctagaa atcattgcac agctgtggat ctttatgcta    11820
tgttgttctc tgagctaata tttccgtcgt tagatcctgt ctcacattat cctagcttgc    11880
```

```
aggatgcagt atcaacattt gttttcagta gttataattt cagcagtcag caatttatca   11940
tgcaatgctg aaagctagct gcggagtctc tcatgaccat taaattaaag ctatgcttgt   12000
gtaagtgaga agttctcaaa ccatgttttc tccttcagct gtttagccag tgtcagcaag   12060
gctatttgaa cagctgtatc agcgtcatcc agcttcaaag gtgaatgcgt tgtgatgttg   12120
atacgctatt gtttccaatt ttatctcttc tggttaacct tgttcgctta ctgtatatct   12180
gagcatgaaa acatctgtgt tcattgcagc aagttgttct agtttgatcc gacttcaaaa   12240
ggacctgttg cattggattg gtaggtgtgt tcgggttatc tggacatgtg aatttaacgt   12300
tgaagatggt aagagcacca ggaaccagga taagaacaga gaacagtgat gggagttcct   12360
ccaagttttc aatgatttga tcaataccta ccgaaacgcc ttatatatgt tgccatgctg   12420
atatgcctat tccaccaatg gacatgatca acctttgcga ttactaacgt catacgtaac   12480
atctgcaagc ctgaaagttc taactgcctt agctatttgg cattgaaact attgatagca   12540
tcattaagat ggtcataagt ttctggctct tgttcaaagc cactgctaat gcctaatgct   12600
catgctctag aatatttttt ttttaaaaaa aaatgacaac gagataacac aacataagcg   12660
atgatgtggt actcgtaaaa aatctgtgaa tcaacagaca aatctcagta taaaaaagga   12720
aatgccgaac tgtaatgaca accaaccaat tctttggcct tagctttgat atctcatcac   12780
tgttcttttg ggtaagtggg atattgcata aaggcccctt tcaaaaggaa atcgtgacta   12840
acacaacaat gagaacttaa aaacaagaac aaaacatcgt gcacctttgt gccattctct   12900
ctatcaatat gccatatcgt taccctccaa gttagtacca cttctgctat cggtgcttcc   12960
aagttggcga tagaaccaat cgtaagctca ttcatgataa cgctggtccc tggatggcaa   13020
aacaacttaa gcattagaat ggtagcatca ttggtttgca aaataaaata aaaaaatgca   13080
tattaacatt atttgaatag gatttgcaga gtgcaatact caagctgcca cttagtttgt   13140
gttggaccgt gtgtgcatat ttttcatta gttcttcgat gaaattgggt ttattacaca   13200
aaattaacag aaagatcaat aaattacaag caacattctt cttcagattc cactctaaat   13260
tattctaggg aggcattcct ctatcctagg tagcatgact cattacttag caaatgttag   13320
cttcatggga acgatgaacg cggcatgcca ccaaaggctg tgtaatgttg ggtcaccgta   13380
attcttatgc agcttgcatg agaagtctca cacttgaata aaatgaccag agtgacattc   13440
agaaagttca ttcaagaaga gaaggaataa ttttgaatag aaataaactg tagatttagg   13500
tcacaaaatg tttctcgtta tgaactaaaa agaaaaagga aggattctct tctggagcca   13560
aacattgatt gtgaaagcat ttatttactc acaagtatat tcaaaacagg tacttgacaa   13620
ttcatgcttc actgacatcg gtaggatagc tcccaagaac tcttagaaag gttgcgaact   13680
cctgcccatg aaaagaaaga atagagaatt gagtcactgc aatcttagtt acttctagac   13740
catgagaaca tacctttaag tttgccagag cattttgagc atttggatca gccattgacg   13800
cctcaagatc tacatagaag aggtagtcga aatgcctgct ccacatgata atttaaggga   13860
ggaataggtg ggagcgagga tcttatcaca gtgagtatta ttaaagggaa gttaaacagg   13920
aaaaaaacat tacttcagtg gtgcagaaca attatcatca gctatacgta gaggcttttt   13980
cttgtgtgga cggcttttcca tctgcatacc atgcaaaaaa aaggagagga aaaaatgatg   14040
aactattaaa gcaatcatga taaagagtga gaaatagaac tgttaaagca tggtagcaga   14100
gtgttcacct tggtgaggtt aattttttctc agtgcaaaca ctgccagcgc cttaaatagt   14160
tgcccaggcc cttcttccaa agaaaagact atgctagtct ggatatcata tgatacaaga   14220
```

```
ccagattttc tttaattcac aaagaaaggg tgaacaataa acttgaatat tctctgcata    14280
cggtaccttg aatggcttat cagtacgagg aataatgggt tcccgagcca gcatcataaa    14340
gcgtgttaca ttatcggtgt catcctacac aatgagttga gtcgctgttg aaagaatagg    14400
aagagcaggt gacttcttcc aaattaggta tggcattgtt ctacctgaat attttctgca    14460
agaatatcca gtccataaag ttgagctgcc aatgaactag caactgctcc agtgtcctgg    14520
agcttttgtt ctgtaataag ctagggaaca acattatttg attagtgacc acagacttaa    14580
catgatggtt ccctcgctgt tctaaactac taaattatgt tatccaaata gattgaattg    14640
acttatcgtg attatagtcc atcgtgatta tagtccaatg taccaggtaa atataaacac    14700
catcctacct ttgctgcacc tgctgtatcg tcaacagctt ctctatgctc gatgcctaac    14760
tttgtcagtg tttgttcaca ctgtgcaaga gcctacaaaa ttaattaaga agaaagaaaa    14820
tgaccctaaa ggttcattct gacaagcaaa taacaaaggg tcgagaatag attagtattg    14880 ttggggtaa acttacttga ggatggctca tggcacttct caaattttgg atcttcacac     14940
cacgatttgc taacaagcaa tggcgaactg caaggcgcac ctcaccaaca atgtgcagcc    15000
tatggcgaag tagaaggtca tagtttcgat ggatgctacc acccaaggaa ttctcaagtg    15060
gcaggaccgc gcggtcagct acccaatttt cgacagcctg aaagaagcgt ggatcgtatt    15120
gaaactttga tggatgaaat ttggttgact ttccaaatga ggataggaaa tggaaattgc    15180
taatgcttgt catgtaagct ggaatcccca gccttaagct tgtattcaga catcttatgc    15240
tttttcagta aagctgggcg tcagcctctt gatctaaaat aggaaatgga aatttgtgcc    15300
tttatctgtt tcttcaatag cttagggact ctataaaaaa agatggtgca ttgtggacaa    15360
atattgcaca taatgatata ttgtaaaggt tgcattggca tgagacatgt acattaccta    15420
tatacatatt gcaaaacaag cagaagtaag attatgggat gatgatatga tagcagcaaa    15480
cctgaaaggc ggtctcgaag tattcgcagg gcacggtgtg gcaactcggg tacgccttct    15540
tggcggcggc ctcactgtag gcacccgggc atccctgaaa ttgcaggagg aggaagagga    15600
agagggatta ttttagttga ttggattgaa ggagggaggg ggaggggag ggggaggcaa     15660 gagggcaacc tggtatgcga ccttcaaacc gtctccgctg gcctccatca gatccgcgct    15720
ggtgagcggc cctggtcgtg acctcacctt ggtgagaatg accaaaaagt aaggaaaaga    15780
ggcagaggca gaggcaggcg gctccttact cggcagtact acatgtgaga tggggtcgcg    15840
ggtggaggcg tcccccggcg gtgaagcgga ggcagcgatg gggcggcggc tgcgcatgcg    15900
catgacgacg gcgtggggcg gagggcagcg ggtgttgatg gcggggtcga agacgcgcgc    15960
ggccgcgggg atccgaagcg aaggggaaac catgctcaag ctcaatgcta gacgccgccg    16020
cctcctcgtc tttctttctc tctctgggct agcaacagcg ttgcgttccc atctgctcac    16080
attcaactcg tttgaaatgt gcaattctaa tagggacatc gatggatggt tggtaggttg    16140
gttccacatg actgtttaaa gtggcaaaaa gttaaaatgc accagttttc acatataagc    16200 cattttatc tttacattgc ctcattttt cacatcatat ccaaacacta gcattaagga      16260
ttatgcaatt ggttacaaca attcctttct aaaataatat attacaataa caaaataata    16320
aatacaaatt acgtataaag gttatttaca cataggatat gtcgtatgtc ctcctgtttg    16380
cgcgtgacat actataacca aactcattta ttagtcacaa tagagttggt tcgcgtcaca    16440
catatcatac aacataataa gtattttgca agttttgtat tataaattgt atccatctaa    16500
taagtttgtg tatcaccaac gtaaattttg tcacattgtg actgaatctt gattcttttt    16560
aatagctttt gaggctcagt tcaattgttg tgaattttg ttagtaagaa gtctataaga     16620
```

```
accactcttg aaaaatacca tacatggcac acatttgttt aggccacatg acaccatgaa    16680
tagttgcatt tgatcgtttt aatcgacctg tatatattaa tatgtttatt tatatcgaca    16740
ctacaaaaaa tatatgcttt aaagtgtcac caacagttcc cttaaacaaa tcccaattat    16800
acgatttaag ctaaagaaaa aatagatgct ctgacagtac tatttgtttc ggtctccaca    16860
agtcgtgcaa ccagccaatc actcgcaatc caacgatcgt gcagagcgga gggcggatga    16920 agcagggta ggggagctac aaaaggttcc caactcaccc ctctcttttt tcgtgcgcat     16980
ggcgatcgat ggccgcacaa acgaaacgga aactctaatg ggcgatcgat cgccggggcc    17040
atggggtagc gatcgccccc ctcccccctc cctccctcca cgtttccttt tttacaccgc    17100
attactttcc tattttagta aatttatgca cctaaagttt atagacccaa agtttataaa    17160
tcaaaagttt atatatccta ttcaaattta aatttgaatt caaatatttt ttttatatat    17220
agtatttcta tacatctaaa atttatacac ctaaagttta tagacccaaa gtttataaat    17280
caaaagttta tacccgat tcaaatttga atttaaaata tatccgattc aaatttgaat     17340
ttgaattcaa atatttttta tatatagtat ttagatacat ctaaagttta tacacctaaa    17400
gtttataaga cccaaagttt acatgcccga ttcaaatttg aatttgaatt caaatatttt    17460
ctatatatag tatttctata catctaaagt ttatacacct aaagtttata agtcaaaagt    17520
ttacataccc gattcaaata tgattttgaa ttcaaatatt agtttataga cccaaagttt    17580
ataagtcaaa agtttacata ccccttttcaa ttctgaattt aaatttaaat atttatggtg    17640
taggaagaga aaaaggagag gagggagcga cggaggtagg ggaggggggg cggatctaat    17700
cgcttgggcg tcgatcgctt tagcgccccc ccccccccccc caaaaaaaaa aacgaaagct    17760 gaagaagg caaacaacaa cagttggttc atccatcaag gggaattcaa tccatagtta      17820
tcttgacagc aaatagcttg gtaactttga aactccacag tacaatacgg cggtctagag    17880
gtccagacaa agagcatcaa agcaagaatg aagagaagga caattggaat cacataaaac    17940
gatggcccaa agcacactaa tttttattac aaccgccacg acagtcttga tcgtaccgac    18000
tctaaggcgc aaaatacaaa tcggcattaa tcttttgcgg atatcccgct ctctaaaggc    18060
ttcttattcc tcagcaaatc tgaaacccac aaacacaaca ataattagtg aaactctggc    18120
acaaagcact ccaataacgc atcacagaca agcacaccag ttgcatccct taccccagtt    18180
cagagagctt gaggtgggcc tcggcgtaat ccgcaaagaa ggcgtcctca tcctacatat    18240
caggcaacaa tcatctactt tttaagagac caacaatgat ccatttctct tatttctttt    18300
attaaaaaaa aaaacaactc tttagaaaga agacgagaga aaataatgca aggatcaagg    18360
ggtgtaccgc agcatatttc tccactagtg gacggaaggc tgggtcagcc atgagggctt    18420
tgtcacttgg cagctgaaga aggccttcct tctcgccact cacaagctcg ctgttgagag    18480
gagattttgg tttcattct ttagcataca aggaaacagg ctgtggctgg ctgtttatca     18540
acagacagga tgcatcttta aaaagaatca gagatcacgc acgtgaagta agagttgtca    18600
aagatcaaag ggttggacgt ccaggctccc tcaaagccag atctctcctt gtggcatctt    18660
ccctacagaa gatgaagtga agctgcatga ataacccttc cggttacaag atatgagaaa    18720
cacattaggg caattgcaca agtgtaccaa ccagggtgtg accaccagaa agagcaacta    18780
tgtccttgtc actcaaaccc atctgcgcag aaaagacctg ccttaggtgg tcagaacctg    18840
gaccaacagc cagaagacca tgacatatta gttatctcgc atccacaaat tggcacactg    18900
ttaattaaag aacacacagg taacatgtat gctccatata agaagaaga ataaacagga     18960
```

```
acacaaaaca aactttagta atgtggtttg cataaacagg gttggaaaat tttagtctta    19020
tgtaggttac acaacttact taagcatgaa agaattctgg taatggactt gcaatatgaa    19080
ctattccatc agtagcacat acaaatgctg gtcatagatc tagaaaattt aatcaccaac    19140
acattgggaa atgcattgtc acactcatac agaggatttt tgcataaatc ttaccttgtg    19200
tggcatcagg aagacggcct tcaggaggag gctcaggctt gtcctagaaa caaacaaaca    19260
cattacatca tcaacattca caagcaacag tggagaattc agggaaagga aacagcggcg    19320
tacaagatga cgaaagaaaa gaattgactt aagaaaaata ccatttgcat ctaccagaag    19380
aagaaagaag aaggggagag cgagagggag agggtttagg gatgggaaat gtgattctga    19440
cctgcctgcc cggatggaag gggacctcag gtccgccggt gacctcgacg gccacaacgc    19500
cagcaagctg ccaatagaga gggagagact ccaattaaga ggttgatgag ttgagaggaa    19560
ggaagggagg aagtgaggga agtgaacctt acctggtaga agtcggcgta ggagaggatg    19620
ggaagttggt ccttgatggg gtcgagaagc ctgacggcga tgtcgaggcc ggcgttggcg    19680
gcgtgggact gctcgccggg gttcttcatg gtgccgaagg gccgccggt cctcgacgac     19740
acatcgaagg tgccagcaga gtgccacctg cagccagcca gccactgcaa ttcaacatct    19800
actcctccta ggctcctact cctactccta ctctttaatc agtagaagaa gaagaagaag    19860
aagaaagtta cgcgaggcgg agcatgagtg gggcgcagtt cttctcggcg atgaggccgc    19920
ggagcttgcg cttcgccttg cccacggccg ccaggtacte atcgctcacc gtcgggtacg    19980
acttgctgcc catgcttcgt cgtcgtcttc ttcttcttct tcccgatccg aatcaatcaa    20040
tccccaactc agctcacctc accaaggagg tagtaatata aaggcgaggc gcgagggtgc    20100
gtaccaccca cgaccagaag aagtttctag tagcggagcc cccgccgtcg gatctcacat    20160
cctgcgcccc gcactccagt ggcgttgccg taatttcgga acctcccgtg tgaacgcgcc    20220
agattccacc cgggacctgc ccacgtggcc acctcccatt ggtggttcca ccgatatgga    20280
cccttggatc cgagtttttc tcttgtccaa gcactcactt ttccaatgca atatattccg    20340
tcttcttctt cgtctcccac ttttttaggc ccttgcgtcg tcttgtctta ctttaccatc    20400
ctctttcata acaacgcta gtatttttt ttatactgtg gccgtgttta gatttaattt      20460
ttttcttcga atttccaatt tttcccatca cattgaatgt ttaaacatat gtatgtagca    20520
ttaaacgtgg gccaaaagaa aaccaattgc atagtttgca tgtaaatcgt gtgacaaatc    20580
ttttgagcct aattacacat gatttaacaa tgtgatacta cagtaaacat ttgctaataa    20640
cagattaatt atgtttaata gatttgtctc gcagttaca ggtagaatat gcaatttgtt     20700
ttgttattag tctatgttta atactttaaa tgtgcgtccg tttactttaa aaaaaattga    20760
cacaccaact aaacacagcc tgtatattac tccctccatc tactttttgat agtcatattt   20820
catcttgaca cacagaccaa ggataagtag ttctacttat cattcattta agcatgctac    20880
tagtcattca tcgtaaacaa acgattcatt aatatttaca tttctcaaag cccatgtagc    20940
caatcatgtg tagaagaatg gcgagtcatg cattaaattc gagaaaatca ttaagatgat    21000
aggttgttgg attgaaatat gcctatcaaa aataaaattt tcagatttga aaatatgact    21060
atcaaaagta gatgaaaagt agattgaggg agtattatta ctccactact cgacgacgac    21120
tagtactgca ctcctttttt tcattacaga atcatataat catcatcatg taatcagata    21180
agccaacgga tatggtatta cacttgcacg gtacctgcca ctgccagcaa ggcacttcct    21240
acatcaccat aatgcaggtc catccgcgtt tcacgatttg cgctgtcaca gctcttgaag    21300
tcacgttagg cccggatagt tctccaaaag ttttttctaa aaacatcacg tcgaatcttt    21360
```

```
agacacatat atgaatcatt aaatatagat taaaagaaaa actaaagtta gggaggaaat    21420
cgcgagacga atcttttaag cctaattagt ccctaattag ctataagtgc tacagtaacc    21480
tacatgtgct aatgacggat taattaggct caacagattc gtctcgcggt ttctaggcga    21540
gttatgaaat tagttttttc attcgtgtcc aaaaacccct tctgacatcc catcaaacat    21600
ccgatgcgac atctacacat tttcatttta cgaagtaaac atgcccttaa tctacttaaa    21660
aagaagaggc acttccatga ctcatatgcc ccggtttgaa actgtttttt attcagtaaa    21720
ttattattaa aaaattactt gataaatcaa atataattta tagaaaagtt tcttttaaga    21780
atacatattt ttagagtcgt ggagaaaaca atatattgta ctaataatcc aatgaagtag    21840
ccagaaagaa cgtgtggctt cctttcgtct aaaccccgt aaaggtgcaa acaactatca    21900
tggctgtgct tagatccaaa gtttggatcc aaacttcagt tcttttccat cacatcaacc    21960
tgtcatacac acacaacttt tcaatcgcat tatctctaat ttcaaccaaa attcaaactt    22020
tgcgctgaac taaacatagc ccatgtcgac tcttcctcat tgtctattcc ctctggatcc    22080
gtttggttgg gtaaagtttt aggagggatt gggtttagag agataagact attacttatt    22140
ctgtttggtt gggatttatt gggagacatg aaatttcagt gggatggaaa tggaaaattt    22200
tctaacacat ggataagggg tggtaattgg aagagaaatc cttctttatt ttgcctaaac    22260
taaactccct atcattttct accacctcta ccaaacaaga gattgaaact taaaaaaata    22320
attaaattct catgttaatc tcaccgtcaa ttctctcgtc caatcgtctt ccctcaagtt    22380
accaaataaa ccgtctatcc cataaaaaaa taaacctaac atttgacttc gatttacttt    22440
ttttacgaac caaagagagt attttaccaa aaaaaagtca atcttattg ttgtcaaggc    22500 ttttctttt catttttttt ttgaaagtcc tgccagcccc aatctttttcc tttctctttc    22560 tcgccagctc ccacaatcct tttgcgcgtt tgcgcaaaac gattgcacgt caatatatta    22620
gaagaaaaag aatttttgtt actaaacaca atcaaccaga tcaacttatg ccaagggaag    22680 ggagaaaag caaagccaaa aactgaagcc cagctcaatc agccagaacg acttatgaca    22740
agggaagaga gaaaaagcaa agccaaaaac tgaagcccca gctcccacag tcccacccaa    22800
acaaccttgg tgtcttagta caaaattatc cgttatttaa tatagcttgt agaaaatcaa    22860
taaaatatga agtgtacgct aaattttcta ctaaagccaa ttgaaaacat ttggatcgat    22920
tttcaatttt ggtaaacacg catgggcacc tagcagttgc tatagtagtc ggttcaacgt    22980
cctaaaacca gaccccttc ttaatcaacc gcaaaagctg acattgccga agataggagt    23040
atcgtccagc accacggcta ccaatctttt ttttaccctc tctactagta agcggtgggt    23100
tctcagattc tacaacgtcc tggcaccata aattacccta aattaaagcg ctaaaccaag    23160
ccattgcgtt atggacaatg caatgtgatg aaccatttta cgcatataca aggctcttac    23220
ttgatccatt gaaaaatcca caagacagaa cgtgtcattc gtggttcgtg ccacagtggt    23280
tctgacgagg tttcagcccc agcaaggatt cccacaatag tcagctacat ttgctcctga    23340
acaatgttgt aaacagatat caggatctcc acactaatca aaattatgat aagccattcc    23400
agaaaatcag acttcctgtt ctgaaggatc tcttgaagaa aacgaatgtt gtgctgcagg    23460
gtaaaagtac ggggaataac ataaggacac aatgcaaata tttacaatgc aagtaaataa    23520
tcaagtgaat tataagacgt tctacattac atgagcctta cctcaacaaa tttcaactta    23580
aaatcaaggt tccaaatct ttgggttaac tcatattcat ctcgaaggta ttcccaaatc    23640
tgagcatagt ttgcgttctt ccaagcaatg tctgacctgg aattgacaaa gctctacagt    23700
```

```
aagtatgtga gaacagataa agctttctaa atagtggcag caaagataaa gttaaaatgc    23760
agaactccaa aagattgatc caatgcatgt gagacagtgc tgggataaaa agtaataaga    23820
ctgaactaac aacctcagtg aagcaataca gctcacacac cgactaccaa acaacagacc    23880
taattccagt ggacaacaaa tactgtgttc cgcatgattc tggcatcccg ctttaggagc    23940
tttgcattcc aaaataatag tattctaaac cagtttgcat ggatataaat aaaaatgtct    24000
gagcattgca tgaaataaat agtactctag tctagcagga taaggcaaat gcattcacaa    24060
aatatgtgta tttctaagta atatgcaaca gagccgaaca gcatgcaaaa aaaatgctct    24120
taacatgggg aatgaaagaa ggaggtttat aaaatacata gttctcagta tggtgttcta    24180 ctcaccttc aaaaagccca agcttgagaa taacatccgc caggttagag ttagcctttc    24240
ctaccaactg gaaaagcttt ttcctttcca tagtgaaggt accagtcttt tccattccac    24300
gatttatatc cgtgaactca gctaccattc catctacctg acaatgaaga taactaaata    24360
gatatttcca agtttcaacg tttcataacc atacatgtga aatgaacttg tacatacttg    24420
ccggatataa tagtcaaggg caatactctg accaaggaca cttccaattg tacgaatccc    24480
atcgatactt aggtccctga gtatgatgaa gtcaagtcca ccctgcatcc atgtctccaa    24540
ggtaggcttc tcaacgacag cataatctga agttgaaggt ttcaaaattt tatgtcccaa    24600
aaagttccaa cgaaacataa tactacaata gtagtcacac ttataagatg cagaaaacag    24660
tggacatgca tatatgtacg taatagcttt attatgggac tattggatgt ccagctggtt    24720
ctgtccagcc tagctaggct gaagtggcat acatggggta tatgtgcggc aagattgtta    24780
gtttggttcc ttggctcctt agttggaaaa tcaaaatgta tttcagcagt gaatagctcc    24840
ttatccagat atttagtcat ttttagctca ttcaaattga ccacatgcta ccttgtaata    24900
agcaagccaa tgaagtcaag ccaggatgtg aataagaaag caaatattgt aagttacaac    24960
tatgtataca ttgcaaatat tgtaagtcaa gccaacactg ctctaaagtt gtaacttgca    25020
actatgcaag tttgtttgcc agctgttgat caatggaaac agttaaattt gaagtgtagc    25080
ctactatgga gcagtgttgc agaagacgga tgtcggacag agagggtacc gccaaacgtt    25140
taatcgttat gtggataatt aatcggaatc tgatggaaat ttaacgtttt ataaatatga    25200
gtacatagtt gataatagtt tgccattctt tgagatgtaa atgcatattg aacatattct    25260
tactatgttt aaatagaacc accatgaagt ggcattaatt caacatatat taagttcat    25320 aatgcatagt tgtgcatcaa acagtgagct gtgggtgggt agttgtcgtg ggctggggcg    25380
tgtgatcatg cccgattata cagacgatta gtcaaaaaat gacggattaa tcagtaatga    25440
tggtgattac atgttcagga acgactaatg aagaccgttt cgcggacggg agctcgctga    25500
ctccatttta acagttgtat caacagtttt ccacaacact gctatggagg cttctttcag    25560
catggatatg ctctactcaa catcatatca ccatctcaca tggactagga aaacagcaaa    25620
tatccagtgt tccagtacta acttctgatt aatcctcaac acaagattga catgataagg    25680
aaagaccaca gtggccacat aggacaaata ttgaagtact ctaccaattc aggaaaaaat    25740
gaggatatct tgagaagaac aagggcttac catcttttct catctctgga agtaagcctg    25800
acgcatgctt ctcaacaatt ttcaggtatc catctgcttc atgatcagat acattaaaca    25860
gcacaatgga cccatattgg aacaccacca tatagtggca atgactttca tctatgatgc    25920
cagccttaaa accctgaaga aaacacgcag gcgagaagca ttagagcaat catacccgca    25980
tcgttactac aagcaagcaa gtactttctc tagcatggtt taataaaaca gaaaagaag    26040 cagtcaactc attaggcaaa agaaaaacca agttgcaagg acacttgaac ataaattccg    26100
```

```
gccgcattca gcctaaaaaa tccataaaag caaaaggaac gcttgtgaag ctatgttgta   26160
taccactaaa gcatgagtat gttatcaggc agagcagagt ggagagtgtc tccattgaac   26220
taaccacaac ctaataactg aacattgcat taactgaaaa tatgtcatta caactgaaca   26280
ttgcattaac aggacaattt tctgaattat agcaaattcc agggatagca ttccaccaag   26340
ttgagcaccg gacatggaat tgtgcgaaaa gaaagagtag atggtgcgat tggctaacct   26400
ctgggtctcc cttgacatcg tagtacctga ggacgacgta gttggtagca cgcgaagtgg   26460
ggggtatgac attgaaggaa ttctgggact ggaggctctt gaggttgatg ctgcagcaga   26520
gagagagaga gagagagaga gagaatcagg gaatggaatc acatggatgg aggcgaagaa   26580
gaggagagga gaggagagga gagaagcaac aagtaacctg gtgcagggga agtaggcctt   26640
gactggaacg aggcgacttt ggtcctcctg cgtggcctcg agaatgtgct cgtggtagta   26700
ggcgtcgtcg tcggaggcga gctcgtcggg cggcaagggc gcgggcgggg cgggggggca   26760
ttcgcctgtc ccgctcccgg gggccggacc cggagagacg gaggcgaagg aggtgcggag   26820
gaggaggagg aggagcgggg ggcggcggcg ggggggccgg aacaccgagg gcgaagggga   26880
ccgccctagg gtttggaggg ttctacaagg ggcgtgctgg aggaggagga ggggcctcag   26940
taggctcttc tggaaggttc gaatcctaca cagctccatc atctctcaca aatcacacat   27000
tacactgtat tttttttgga gaagaagaag aagaagatat gatatgagta tgacggcggc   27060
ggcggccccc ctcccttcct gttcctgtgc gctttgtggt ggtggatgcc aatgcaatga   27120
gaagaacgga aatcgggatc gggatttcct aaattggagc tcacgctgat ctcatccaac   27180
tcggcccatg acccacttgt aactgatggg ccgcgaccaa ctgcttgcta cagtactact   27240
attatcttct cctaccacgc acaaggggaa gggggcttct agttaggaac gtactagtac   27300
tattctttac attgtatttc tcttaaggat attgggtttt tgggaaaaac acgataagct   27360
gtcaggcaaa tcgagggtta gttcaaaatt ttatacatga gcaaggaggt ttttgcaaaa   27420
ttaccagatc tcacgtggca tgcatgcaag gtgaaaccag gcaccagcgg tggaaggagc   27480
aggctcgcga gattaaccgt gagattaccg gcaaattgtg ttttcccgat cgcacacgcg   27540
ctcacgagga gccgtaatcg caagacgaca atgtgcaaat taaacaagga gaccaaaaaa   27600
ttaaaaaaaa ggagaaaaag ggtacggtta ggctggttat tgattgatga tatgtcacac   27660 gcacccctt cctattacaa cgttgtgaaa actcttttaa tgtttttagc ttccattact   27720
gcccacgcaa ttgtaacaaa gtggctcatg ctttagcagc ctatagatat aatagttccc   27780
agacgactca gttcagctgg gatggttttc ctccagatgt ggaggagctg gttgccggcg   27840
atttagccga atcagtggta taatggaatt taatgttcct ctaaaaaaaa cctgcttgct   27900
ccaaggatga ggtggatcag actccacttc caaactactc taatccactt attaaaaatt   27960
tccaacttgt gtttcaaaat tttatctcta atagaaaaaa aatgtccgtg cgttgcaacg   28020
ggtgaaaact atttttaattt ttattatttt tatacgaaat tcactatgag aatttgcttg   28080
gatatatatt tttttgaaaa aatcatgagc tgcaattagg agtccgatca tctcaagtta   28140
gcatgcgagt ttttttaaaa gagatttctt atgactcctg tattttataa aagcgaacga   28200
acttaaaacc tgactcaaat acggatatgt atctccaaat gcgaacgaac ttaaaaaccg   28260
actcatacac ggatgacgta ccaaagtacc ggcaaaaaca tcttcaactt ttataatagt   28320
agagatacta gaaaaaatat ccgtgcgttg caacgagtga agcctatctt aatctgtggg   28380
aattcacttg atattgtttt tacaagttag catgctgttt ttttataata gattacttat   28440
```

```
acaactccctt ctatgtgcca gggttacgga taaggcatac cttctatcct acgacttacg    28500
gaatatacag ataaggtgta ccttcatgta cacggatcgt ttccttgtac accatttgga    28560
atccgttcca aattatggaa aatatctcta cgagttaagc gatttccaaa gtcctactcg    28620
gaagggatag aatttcggtt acaccgtacc atatccaata tccttaggtc tttcttgggg    28680
gtcaagatga ttcacggtat aaaagggacc cccgaggagg ggtgaaaggg catccaattt    28740
aatcgccaac acacccacta tagtttacaa agccagagta cgcggagcca aatcgctggg    28800
agatctcgtc gaaaccctcg accacgatct cgtcggtatc atctatttcg actactctct    28860
ttgtaatatg ttcttgtcat tataaatccc atataaactg gactagggct attagtatta    28920
cctaataagg ggtctgaacc agtataatcc ttgtcttttg tttgcttgat gtcgtactac    28980
gtagaccctc gtaccaatgt accccaatac tctattcatc cggtccgcga gtatcactcg    29040
tcgacactat gtttccaaaa gagaatggaa ttaaaagctg actcaaatac gaatatgtaa    29100
ttccaaaagt caataaaaac ttaaagaacg actcaaatat ggatgatgta ccaatttacc    29160
ggtaaaaaca tctttaattt ttataatagt agagatctct aattttttgta atctgtgtgg    29220 tattcccata cataatacat ataaactaga gtatggttat tactcatcta gaggacccga    29280
gccagtataa atacatgtcc tttgtctgct tgatccgatc tcgcatatac actggttcca    29340
acgatctcca tactctacaa atactacttg cggtgagaca acaaaccttg ttgttatagc    29400
taaatatttc atgaaccgca ttaagttcaa acgattggt cttgccttag actgcaagtt     29460
gttcaaatgc tcatggataa cgaaattatt tgagtaaatt tcaagaaact actactattt    29520
tgtcaaaact atcagttatg acatttcagg taactggaac agtggtatac aattgtatcg    29580
aaaagcttct actttatgtg tctgacaagt tttggcccat gtgtcataca tatatatggg    29640
gaaatgctgc attttttaaa taagcagtt ctctattatt cccattttt ttgaaatatt      29700 caactaaagt tatagcaaag tgatagtttt gaccaaataa ttgcaatttt atgaaatgta    29760
ctcacattgt tttgttggat gattttttt attatgttta caaatctcgt ctctcttcta    29820
tctatatatg tggttactta accacaattc gtgggaatag aactcatttc ctccaagata    29880
gtagataagg atgtagtttt gtgctcaagc atgctaggaa aaagctaatg tcatgacaac    29940
gagttcccac ttggagtgtt gcctagcctt tcatgagatt ccatttattt tatgcctact    30000
tatgttattc ctattgatga cttcatggtt tactattggt tttgtgtatt agggaccaat    30060
taaatatata ctaatttttt aatctgggag aggggggcatt attaatattg atcgtatcat    30120
ataccaaaac taacacttat gtctaatgtt ttggtaagcg ccatcattgg acattcttct    30180
tggtgtaata cttaagataa ttttcaatga attgctccct catgttaagg atatttgacg    30240 ttggggggtat tggttttagt actcatagta tatttaactg tagggagtat tggttttgtt    30300
ttatatattt ttagggtgtt cctctgaaat catacattag tgggataagg aacaccattt    30360
tttgaaaacg tactaaaaag tggatttcac tggcctatat gattttttgga atttcctctt    30420 cttgttctat caactagtgg ctcatggtta cttgtacgta gcccacttaa tatagttcaa    30480
actcgtactc atgttttgac tagcttgagc tcatcatgtt accaagttca tgctctatgt    30540
ttatttgaat gttttaggt ctcggggaat aaattggtta aaacacaatg tttaggtgtt     30600
tgtatttcta actaaaacat attgtaaact taaatatcaa gttgtggtgt ttcaaatgaa    30660 tgtggaatc tcccatgaat gtcaccttag ttgtgctcag gtttacatat gtatgttaat     30720
gtcacttcca gaaattctta ggcactatat attaggctac aacaaatgaa acttctctta    30780
aaaagtgaga taccaaatga attcctatag cttcattttt taaaagaggg ggctcaattt    30840
```

```
tatttaaaga aacaacaaaa tataaacact tacataaccg catgtttgtt catcaatgac   30900
caacatgaat gagcataaag agtagaggca acagaaaaca ctagtgcgcc accaagatat   30960
ttgaccaaga gaagagttag caacatataa aatgtttatc taaagaggag ttaccaaatc   31020
aacatccatt tcaccagaat tatctaagaa acacattcca ttaagcttcc ttgtcattgg   31080
tgcccaaccc atagactttc taaacacgtc ctcaatcact tgttagagtt tttttttttt   31140
gcacaatctg gcatctcata gcgttttcct tcaaattgga ttaatgttta tgttgtacat   31200
caacaagttg gatccaataa acggcatact taggaagttt tccacatcac ccaataaata   31260
tatgaagtaa tcacaacatt atcatttctc attttttttgg aatatgttct agcaatgaat   31320
tcaaaccaaa aggtatattg ccaatctgaa atcacaccta acaaatggat aaaagcttac   31380
cttcacccac ttaccctagt tcccctttttt ttctttggca atttctcata gtgaattagt   31440
caaaaagcag cacccaaatg atataatcac ttctatgaaa ttttattttc aaataagaca   31500
aatgtgcaaa taagcacaaa attgttttca tgttcaaaga acttttcttt atcatcttcc   31560
attataaaga cgatgtcatc aacatactgt agaattgaga ccctagcatt cagcaaaatg   31620 tgacacccctt cctttgatca aaccttttca attgttggt taataagcaa agtcaatgca   31680
acatcccccg ctatgttaaa agggagtgga gcaatatata ttcttgcctt aaaaccttat   31740
aagacacatg cttataagtt cattaagcat agttgcaaca caacctcccc ttactacctt   31800
aaaaatcgaa ccacaccatt tatctatctc caaaacattt ttggccataa atttgttata   31860
caaaagaacc atctcgcatt ttgtcacata ctttctcaaa gtttaccttta aaaggcaccc   31920 atacattttt ttcccatatg aacttcttga attatttcat gtaaacttaa tatcccttttc   31980 cattatgaac caatatttca agaatgcaac ttgactattg aactcaacct tttggatcac   32040
tctaaccaac ctacttatca cccctttggt gagaattta taactcatca cgtcgagtac   32100
acaaaaaggc ctaaatttct atatggtcaa agtatcaagt gttgtaggta tcaaggttat   32160
acatagttta atctctctat atctaaaacc gcattgtaaa aaccctaaaa aactttcaga   32220
agatcctatg tgatcacttc ctagaagaat tggtaaaata tttgtaggaa gctattagga   32280
ccatgggcgg ccttattctt tctcttctaa ataaaacatg tggtttaatt tcttccaatg   32340
aaaaaggtcc attcagagat ttcggattca gttcatccat ttatatattc ctaatatatt   32400
agtgtcactg tggggccaaa caatttttta tataaagaa gatgtcacat gttccatcaa   32460
ttccttctca tcttctgtca tcttgaagaa gtcactttta ttatatccaa agtgattgca   32520
cggtttagaa taacgtcact aagtctgtat ttaataactg tagctcccgg agttaccatg   32580
ctcctcttca tctggtattt tgtccataat tgtggccttt aacaagcctt agtttgtacc   32640
cctttctata tctcttataa ataaaagagg aagatctcct gctcctttttt ttttatataa   32700 aaaggaatat atatatttta caataggcca accaaatgaa gttctttcga accatgtgtt   32760
tcaactttca acaatggaat tgaaaccaaa gctccaagag ttcctgagat tttctgaaaa   32820
aaaacaggtg ttatattgag caaatgaaaa gagagaagtt tcagatggct tagtgagcaa   32880
cgaagtccaa aatcacaagg ttagcacatg atgtcggtta ccatttaatt tgcttctcta   32940
taaattgtgc tgtccaaact aaaatcgttt ttgtgttctg gttagttgtg aatttctttt   33000
gaggtgataa ataggaagaa atgtgtacga cgttctcttg tgttaagcaa actcagcaga   33060
gcttcagtgt gtactagtag tagtatagta tagcaaaaga agtgacgaat taattgtctt   33120
tagaataaaa tgttcttgct acattgcaca agtgaattat ttaacggtga cagcacgtgt   33180
```

```
tgacataaaa taaaactgaa gagagaaata attaaaatac gtactcgatc cacttttata   33240
agaaaagaga aaacgttgtc ctcaagacct gtgtgtgcca tgtgaagcaa ggcgagaaaa   33300
ggcatgaaga gaatcagggg tggtgaagaa ggatgggaga atatggagca agccagccag   33360
gtgaagctga agctgcaagg gccaagggct aggctacgag gaaggatgga agatgagaag   33420
aagaagaaaa aaaaaagagg cactactgta catgtggggg taggaaatca aaaggattca   33480
gctcaagcca cacaagagga aagcaaaaaa ggaagatgca aagcagtgca catatataaa   33540
aagcactgct cctcagccac accaagcaaa ggatatgaga aagctaacct agatgatgcc   33600
cgcagaatct gatggcacgc tctctgcctc ttccatcgct cactccaagc ttctttctac   33660
tcgatcgatc ttgctacata gactgcttcc accaagtggc attcaactgg ccaggagtac   33720
tcactacagt tcatttgttc cttaattaga tactacagta actcttaaat acgtacacta   33780
ttaattacta taatactgta tataggagta cttaattatc cttcttaatt aactttgttc   33840
attttgataa acaaaaaaga ggaagtatat attttagctt cctctctaaa ttataaacac   33900
acgtacggcg gtactttaat taatttgtgc gttgttgtta gcttgtcgat cgtcagtgct   33960
tctggccaag agtgttccaa attaaccgac cgatcaacaa atgatggata aagatagcag   34020
atatcatcat cattcatgta tgagtatgac cggtccattc agttcatagg agataagcta   34080
gcattcttac ttgcgctggg ccgggcgcgt cagcagctga ctgctttagt tggctagctc   34140
ttgtgcgtct tgcaatggat ttgctttact actggactac tagaggagag gatgaacttc   34200
gagtgtgctg tgctgtgctg tgctgtggtg atagatagca tacatgcata tgcagcatat   34260
ggacatatgg tgggggtact ccgaatatat ttctggattg tggttggttc ttttgctact   34320
gcttgccttt tctgactcgc tctctctctc tctatatgga gtatatagct ttttttttcct   34380 actagtatga gagagagaag ccattattat ttttcccgga agaacaagag gaaacgaata   34440
aaaaggaaat ctacatcaat aaagctaatt cacagttcct tgtgctatac aaacgtatag   34500
tagattattg attagcaaca gatcctcact ggattatatc gtgaaaatta gaaatatgta   34560
ctgctggtgg ttctgtgttt cctctgtttg agctgacaat acgtctgcta tactacacgg   34620
gtttagtttc ttataatctc tgaatagtag tatgtcaact gtagttttg ttttcctttc   34680 tagagattat tttcctgttt acgacacata aataaagtta ataatttgcg ggggcgataa   34740
taattgaatt aattaaataa ataaatagaa taattatgct tggagtgttt tgaggagaaa   34800
tgatactagg gatttggaga agagaatgag attctttgtt ttggacgggt ggcccagcat   34860
tgacgggaga tgggccggat aggcccagaa gaggagccca aagaaagaag gaggtggaca   34920
cgtgggagat ctgcgcggat ctcggggagc gcgcggcttt tgatttcgtg ggatctcagg   34980
ggcgggccca ccagcggcgc tccccacctc catttgttcc acgtcaccgc cctccccaat   35040
atctagtagc agtagcagcg gagggagcgg cacacgatac gcgccgcgcg gatcccctcc   35100
cttccctcct cttcttcctc cgccgccgcc gccgattact cgcttccgcc tccgcctcaa   35160
ccccggccgt ccccaaccaa ccaaccaacc aaccgcaggt aacttcccct ctggatcttc   35220
cacagtcagt attcctcgat tcatttcatt ttcatccggg ttcatcagtc caatccaagc   35280
gaatactaag ctcacttgaa ttcggttggt gcctcgtcgt cattctgcca ctgcttgaga   35340
gttccttcat acacacacca ctcgcagtct cagcagcagc agcagcgcag gtaatttcac   35400
tttacagttt cttctactac tatcatagtc ctcgtcctag tactatacta ctataatact   35460
atgtgtctga tgcaactctc tctagtctgt agcaaagctg ctgttatctt ccttagtccg   35520
cggccagtgt ccactgatcc accgctcgcc ttgcaaattt gcatacgccc actacgtacg   35580
```

```
taagctggat catatccttc tcattttttt tttctctatc tctattcttt ctcatttgtg   35640
agattgattt gcacaactgc acaagcacag atgcggatgc agcccagcta gctaataagc   35700
taggttagct gctgctgttg gtcttggagg caaactagtg taatatgtgc cgcaccgcct   35760
gcctttcttc atgaaccaaa cccctgccac cactcaaccc ggccaacctc ttcgagtcag   35820
gctgatgatg ggaaccgctc atcacaacca aaccgccggc tctgccctcg gagtcggagt   35880
cggagatgcc aacgacgccg tgcctgggc tgggggtggg ggctacagcg acccggatgg   35940
cggaccaacc tccggtgtgc agccgccacc gcaggtctgc tgggagcgct tcatccagaa   36000
gaagactatc aaagtcttgc tagttgagag cgatgactcc accaggcagg tggtcagtgc   36060
cctgcttcgt cactgcatgt atgaaggtct gtctcttctt tcctccttct accttctcac   36120
ttctgtctat ttatttatat gtttgccttt ttcacaacat attttcctat tattacttac   36180
tgtctgactc tcaaactgtt aattttcctg ctcctcatct ctgtttaatc acacgtaccg   36240
cctctgcttt acaatttgct atagtgattt tatccggaaa ctatcttctt aaggattgta   36300
ccaaacacaa tttttcacca caaattagac gattgtcagg ttcagaacaa gattttgaac   36360
acctacatca caaggacgat aagcaagcaa caagatcatt tggtacataa atctgttgaa   36420
tactttgttt tgaaacataa agtatgctgt tccaaagtct tgtttgagag actgacttga   36480
accctgcaaa atccatgcac acttcgtcat gctagccgct aaagccaaat ttaaactagg   36540
cctgattagg tcaactggaa actctttctg attttttttt tttttttgaa aaaggggtg   36600 cagattgtgg tactgataat catctcaagg tcctcctttt tttttctac tgaaatcatg   36660 tcaaggtcct tgaacggaca cgttaccaaa tcaatttgtt gaagaaggga gagataactt   36720
tttaatccaa gattaatctc cacgttgtat gagaggccac cttgaattga tggtttctaa   36780
tgattttggg ttttcttttt tatttcaata cttgtatgaa tttctagtgc caatattttg   36840
gaccaatgct cttgtattcc ttatctttaa tttggatgca acttttccat tggatacatc   36900
aaacatgaat gaagtcatag ggatagtttg ttgttgttgt gttgtgttgg atacctcctt   36960
ttggcaccca gttcaccttc ttcttgtaag ccaatgggta ccactagaa tctccagcca   37020 tctgtggaca gcactatata ttgcaggctt gtttctttcg aagtattttt acgccttccc   37080
tgtcttcgta tcatattgat gtatgatttt ggactggaaa atgatttgat tctatttcga   37140
tcgctagcct actgttaggt ttgtcctatt ctgctgcttt ggtgtggttg cttcagctca   37200 tgaaggggt tgctgcggat gggcacatca aaaccatttt ttttcattcc attggtagca   37260
tcacttctgg ggagcgacca tcaaatgcta cgtagataac cataccttgt ccttctccct   37320
tggctgttgg ccatgggaga attgttttca ttgcctaagc cagagggtcc ttttcatcgc   37380
atgttggaaa gtccagctat gcagtagccc gaaactcctc ttctgccacc caacattgcc   37440
tccctacagg tgacatgtgc caaatggcga cggcagcaag actagaccac ccagcttggc   37500
gataggaatt ggaggttgtc ggcctcttct tgtatgtggg gtggcagatt tactgccacc   37560
accattagag tctgtttaaa agagtatata tacttggaca gcaaaaagca catgctagat   37620
tacatgaaag taggaaaagt ctaggtagct caatgaaggt tttgttataa catggtcaag   37680
taagggtgta gggcctgatt acagggcact cccaatttga ttgatgagta cttctacagt   37740
gctctctgaa tactacaagt attgttacca atagaagcga tagaaggcag tgatttatga   37800
gttctactac cactagaaaa aaatttctg ctaccagtag ttgaggtggt agcataaata   37860
gatatggccc attggatgag aaaagatgac aggactagat tgatttact accagtaaaa   37920
```

```
accaccgaat aaagtttcta actattcttt cctcacacta ttgagaagaa ggcacttcca    37980
ttaaaaagga aaacactttc gatatcaagg catcaatttg tttttcatta aaaaggaagc    38040
tgaatgaggg gataaaaacc ttcctttggg ctttgcatgc gaatagtcta ataaatactc    38100
cctctgtttt cttttatttg acacctttga ctccacacac aaaactaggc aatcattgta    38160
ctttctagag atgactattt tactcttaga gaaatttagt gttgttggta gggtatgctc    38220
acacaagaac tttctagatt agtgtggatg aatacatagt tgtttcttat atgggcaaaa    38280
tgggaaagta aagattgagt ttcgtgccgt gccaattatt tgcaaacaac tttggtccaa    38340
gttgtctaat taaaagagaa ctgagggagt aaagaattct agctcagcct aggaaagtag    38400
agccaacaac ataagtcaat gagtccatgt tgcttttgag ccaactaatt gagcaacaag    38460
tttggcatct actacaaaag agagaataac catgtgagaa gggtatatca tttagtagga    38520
agggtatatc ctcaaatgat tgtcttggct tggcttcggt ttagctggca catttattag    38580
gaggaagggt ttcttggagc ttttcttcat tgcttgctgg cacatttgga aacagcgtaa    38640
tgaaaagatt tttcagcata ttgatccttc tttgatgcct ggtggtctgc ctttcagaca    38700
tgagattctc ctatataact ataggatgaa tggcccctac gacaaatagt tgttgattgg    38760
ttactacttt tgtagttctt tggttttttgt ttttgccttt tatgtacata ttcctataaa    38820
acttttttgt tctctgacct ggggtagttc ttcccctaaa aaaaacactc aattcaccgg    38880
tctgacctgt ggaccattta tctcctttgc acgttcaac tggggcagtt taatgtccaa    38940
tttagcttaa actaggccag tccgcccagt ccaatccagc tcaaatgcat gttcggtctt    39000
tgagtgcaac cgtggcgacc ttttgttctg tttttttagg tcgacttgtt gacccggttc    39060
agttttttta cactatgacg cctggagata caactgctgg ttcaaaatgg gttgagcaac    39120
tgtcgagttg gcctgagcaa aggaacggcc cacacaactc tgcccatgtt tctggaaaga    39180
gaatcttcgc tccgattctt ctctcttcta ggctagtttg agcaattccc aggtcagctc    39240
ataacaatgt gatatcagag ctcgtcaatc ctagagaagt cgtgattccg aacacgtatg    39300
cagcaacagg tcgaggatat ggattttagg aaagtattcc aaacacataa gtgtgggcct    39360
ttccttgctc ggcccaaccc atcggttgct tgacccattt catcagttga cccaagaatt    39420
gtatttctag gtgtatgtgg gtccgctata tttgagagtg aaatctagat tttggaggca    39480
ccgaggcagg gtgtgatatc aagattgtaa tcctactcat gagtaataca atgaacatat    39540
cttgattgtt ttaaaaaaac cgacaaggct gtgatgttct tttcacaaaa agaaagaaag    39600
aaaagaagac gccaatgttg tgctggtctt ttggcctgta atggctcttt atggacgaga    39660
acattgttat taagctattg ttgctggtga cttgtctaga acacattaca catacactct    39720
cctcggaaat ttcattatcc acaagtgtta gcacctccaa cctaatccca tcctgaagga    39780
cctagaactt gattttatcc attatctaaa aagaaaggac ctagaacttg ccttcccaca    39840
gaaaggaatt acgagggtct tgtcatgttg ctagccgatg ataatatctg ccaaatattc    39900
ttgaagtgca ggaagttacc cttgtaagca tcgaagaaac aggatcctaa gtgcctcgca    39960
agcttgtgca caacatgacc caatggttgg aatagtggca acaccggac taaaatttag    40020 tatagactag tccactggtt tgacatatgc ttgttctcag tctgactata ttggggagta    40080
aaggtttttt tttttcattt ttcaacatta gaaactttaa attgttggtc tagtactcat    40140
acttggctgt gttcgcatat gtgggttggg aactcattcc ctccgcacgg aaaacggagt    40200
ggtccattag cacgtgatta attaagtatt agctattttt tttcaaaaat ggattaattt    40260 gatttttta agcaactttc gtatagaaac ttttacaaa aaacacaccg tttagcagtt    40320
```

```
tgaaaagcgt gcgtgtggaa aatgagggag aagggttggg aaaagggat gccgaacaca    40380 gccttaagtt tgttggtcgc actgtaccca agcatgtgga gctttgattt ccttcagtct    40440
gtacaatttt gggtgagata tgcacaacag cacaagataa atatagcgtg ttctaatatt    40500
ttaactcatc cgctaattta cccagttgcc aatattttc atgattgacc tagcctgtac    40560
aaattcgatc cttattttt ctaatttgtt atggactagc tagggtaagg gtttgaatac    40620
aaggtgctcc gtgggaacca ttaatggcat cagatggacc ttttatact ggagtttgaa    40680 tgtttgggga atagacaaga gacttatgca tcatttatt gagaaggaaa gggtctggta    40740
taaatccaaa aaatgaaaaa caaacaaca aagaaactag aaatgtcaaa tgtggtgggt    40800
ggtggtgaat aatgctgctt gctagcggga gatgcctgcc cattggctat ctctcgcaaa    40860
atgatagtgt gaccaagaaa agataaagca ctctatgcct tgagctgtgg gatcatcact    40920
ccagtccagc agcacttgat ccttttttc tcattgcagg cattatattc aatttgctaa    40980
cgactttaac tgggatcact gatttatggt ccccattctt tgactaaaac ggcccggtga    41040
aaaaaattct ttgactaaaa ctcatttctg cattgtgcac ttgcttgctg tttcaagtat    41100
tattcatatt tcttgtggat cttccattcg attatactct tgtttattcg gcttcttttgt    41160 taaggacagg gagccaagca cactagagta atattctgaa tgcagactgg cttttgtgac    41220
ctttgtcggc cccggttttg ggtgcttctt cttagttgca atacctcggg gaagttcttt    41280 cccccttgggg ccaaggtttt tttttaatgc acaagatatt ttatctttgt tggtctttga    41340
ctgagtgtta ttaattatt tctgtgaagt catccctgct gaaaatggcc agcaagcatg    41400
gacatatcta gaagatatgc aaaacagcat tgatcttgtt ttgacagagg ttgttatgcc    41460
tggtgtatct ggaatttctc tattgagtag gatcatgaac cacaatattt gcaagaatat    41520
tccagtgatt agtaagtagc tttcctcaac tctacagtac aattcttgta caaaatgttg    41580
cccttgtcat ttatttactt tctatgcttt tagctgctac actgatgtgg tttgtgtgca    41640
gtgatgtctt caaatgatgc tatgggtaca gttttaagt gtttgtcaaa gggcgctgtt    41700
gacttcttag tcaagcccat acgtaagaat gaacttaaga acctatgcca gcatgtgtgg    41760
agacggtgcc acagcgtaag ttgttgttgg tccagtttat cttatatatt agatgttcag    41820
gcaaatccat caagtactga ctgctgcttc acccttttat ggttacaata tgtgatgact    41880
ctaaactaaa gttgttattt tcaaattcag tccagtggca gtggaagtga aagtggcatt    41940
cagacacaaa agtgtgccaa atcaaaaagt ggggatgaat ccgataataa cagtggcagc    42000
aatgacgatg acgacgacga tggtgtaagc atgggactta atgcaagaga tggcagtgat    42060
aacggcagtg gcactcaagt atgaaacttg atctttttat tccaacatag ctttactact    42120
acctgttaac aaagctgtaa ttagaatgag aagaaaaaac tgaagttaaa aactgaataa    42180
acctgtcagt aacaatgatt tctgaaggca taaatgacat ttttttgcat agctgataaa    42240 tttatttag aatagtggga aataggaaga gttcaccatg tcactgtaaa gttttgaat    42300 taaccaaacc agtaaaatac catggatcat ctgcatataa caatcttaat attgtacaaa    42360
cacaacagat gaaacacata ctgaagaaaa tatagttatc gcctctcgta tagtttacat    42420
gtgtgttcat gtggcactat cgtttgtctt aactaatacc aaggtgccaa ataaccagc    42480 ggttggttca ttgcattttg gagcacatat agtatttata aatctcgata gcatgtgtgt    42540
agaatgttcc accagaagtt gatagcactg tgctttttgc atgttcaagg aatcaaatgg    42600
attgtacaat acatgcaacc aaactttgat gtagggaatt tctttgtttt ggcttggatg    42660
```

```
tccaacttat agtttctcac cagttggatt aacttctttt ccttgttctc ccattgtaaa    42720
tgtgaattga acaatccttg ccttttaaga taaatgtggg gtctatgctt tatgctgccc    42780
tttaaatttt tgaaatgcta ataagtagtt tgcatgcatc gtgcttctct aaatgtcatc    42840
aagttgacta atatacagtt cactatcaat cagctaatac cacttaattt tatgtgtttc    42900
ctattataaa ttgaacattt tgtttcctta ccaactagaa atcatactac agatacatat    42960
tgtatagtta ttttcggttt attcatgaat ttgtgttaga attagactat aaagacattg    43020
ctggttaaaa ggtactcatc ccctaacact gtgggaagag tacagaacta ctagtgtgtt    43080
aacaccattg gcctcttgac attcaaaact gctacccaat gaacacattc cccatcaatg    43140
gtccaataat cccgaagtct aaagtcctta atcaactcgt gcataattat tcacttggta    43200
aggaaatagg aaaaggatgg atgcacacaa atgttttgtc cattttttgct aagcctccag    43260 tatttttact tctgtgtttt gagcttcata atggcttcca tgtctttttct tcaattaacg    43320 cttttgtcct gtattttgat ttctatttgc accatttaat gaatcttcca aatttgggtt    43380
tttcctcttg atgattttta acttcacatc tcaattgatc tttaaaatat gcctaattat    43440
ttaatactac ctccgtccca aaatatagca acctaagact ggataggaca tatcctagtc    43500
caatgaatct ggacaaccct tgtccagatt tcttggacta ggatatgtcc catccaatcc    43560
taaattgcta tattttggga tggagggagt atcatctaat taattacctg caaatctgca    43620
atgctctgct taaacatatt gtatattttc tatactaatt tactatactt attatcaaaa    43680
tgaaacgtat attaaaaatt aaatatctgc tgcaatatgt gccctcaaaa ctagtataaa    43740
catattgtat attttctttt caaagttacc tttaatttgg cgacatgttt ggattgataa    43800
aatcaagtct aagcttgcaa atttggttct cctgatgctg tatgtttgat tccactaaat    43860
agattctctt caatgaccta ggcaagctgt cgtagtttat cccaaatgtg ttgaaaaggt    43920
tgttctgggt atcaccgtac agatagattg atcctgaaat tcgtatgcag agtaaacaaa    43980
atagtcttat caacatagat aatgctaaac atcatatcat cagctcatta gtgcaggact    44040
gccttgacat ataatggttg cctgaaatgg caatgaaata aaaaatcttt tatttaaaaa    44100
gcaagattca attgtgaatt agcaatagtt ggagaaattt agagttacag gatatggcac    44160
acgaggtgta cttgagaact gtcggtttgt agctagagat ggctacgaat gccgccgggg    44220
ggtacctagc ttatcggcgg tggatgaaaa ctagtgtaaa cttgaaatta gtccacgttt    44280
attatgaaac gttgactaca gaccctaccg agataaactg tatcttatgt gttgctgtca    44340
agttctcttt tattacagtg ttatggagtg gggtaaaatt ttttttcctgt cagttagtta    44400 tgaatcacat aagattttgc cactgaaatg ttcagtgaca tggccgatat gtcaatgtaa    44460
gaaacaactt agaataaatt ccacattaca atattcagaa ataattactg tagatcggat    44520
cactttgtga agtgcattct catcattttt ttaaggcgca gagctcatgg acaaagcgcg    44580
ctgttgagat tgacagtcca caggctatgt ctccagatca attagctgat ccacctgata    44640
gcacttgtgc acaagtgatc caccccgaagt cagagatatg cagcaataga tggttaccat    44700
gtacaagcaa caaaaattcc aagaaacaaa aagaaactaa tggtattgta tgctcaactg    44760
attcattgtg caacttgata aaacaaaagc tccatagcac tgtatattaa taaatttcaa    44820
catgtttttt tttcagatga cttcaagggg aaggacttgg aaataggttc tcctagaaat    44880
ttaaacacag cttatcaatc ctctccgaat gagagatcca tcaaaccaac agatagacgg    44940
aatgaatatc cactgcaaaa caattcaaag gaggcagcga tggaaaatct ggaggagtca    45000
agtgttcgag ctgctgactt aattggttcg atggccaaaa acatggatgc acaacaggca    45060
```

```
gcaagagccg caaatgcccc taattgctcc tccaaagtgc cagaagggaa agataagaac    45120
cgtgataata ttatgccatc acttgaatta agtttgaaaa ggtcaagatc gactgggat    45180 ggtgcaaatg caatccaaga ggaacaacgg aatgttttga gacgatccga tctctcggca    45240
tttacgaggt gcaaaacata atatcagtgt cgctagtgag ttaggaaacc attgttaagt    45300
tgcatactaa ctgttacttt tgttgcaagg taccatacac ctgtggcttc caatcaaggt    45360
gggacaggat tcgtgggaag ctgttcgccg catgataata gctcagaggc tatgaaaacg    45420
gattctactt acaacatgaa gtcaaactca gatgctgcac caataaaaca aggttctaat    45480
ggtagtagca ataacaatga catgggttcc actacaaaga acgttgtgac aaagcctagt    45540
acaaataagg agagagtaat gtcaccctca gctgttaagg ctaatggaca cacatcagca    45600
tttcatcctg cacagcactg gacgtctcca gctaatacaa caggaaaaga aaagactgat    45660
gaagtggcta acaatgcagc aaagagggct cagcctggtg aagtacagag caacctcgta    45720
caacaccctc gcccaatact tcattatgtt catttcgatg tgtcacgtga aatggtgga    45780 tccggggccc ctcaatgtgg ttcatccaat gtatttgatc ctcctgtcga aggtcatgct    45840
gccaactatg gtgtcaatgg aagcaactca ggcagtaaca atggaagcaa tgggcagaat    45900
gggagtacga ctgctgtaaa tgctgaacgg ccaaatatgg agatcgctaa tggcaccatc    45960
aacaaaagtg gacctggagg tggcaatgga agtggaagcg gcagtggcaa tgacatgtat    46020
ctgaaacgct tcactcaaca agagcataga gtggctgcag tgatcaagtt tagacagaaa    46080
aggaaagagc gcaacttcgg aaaaaaggta gcctgttttc aattgcatgt tttctgttcc    46140
tttggtttta gcattcctgt ttaactcgtc taaattagct aaagaacatg ttactggaag    46200
tagttgtcaa aagcatatta ctggaagttt ctcccaaacg actagctaaa tgggatcggg    46260
catgaacata atttgtttat atactagtat tatctgattt ctaaaaggaa tctcacaaga    46320
taatcttcca aaaagttgca cgttttggt cccatagccg tgttgctgaa atttcttgcc    46380
aatgacattt cttggatttt tctcataatt taatggtagc tacttagagc ggcaattcaa    46440
ttttactctt gaaacactgt cctttacttt tcggcgcggg tgagtacaat ttggatagga    46500
ggctctttat atatatat atatatat atgatgtgct tgattaagct ttggatagga    46560
ccggtttctt tctgatggct gtctgccatt tcaggtgcg gtaccagagc agaaagaggc    46620
tggccgagca gcggccaagg gtccgcggac agttcgtgcg gcaagctgtg caagaccaac    46680
aacagcaggg tggtgggcgc gaagcagcag cggacagatg acctacctac ctacctacgc    46740
aatggctttg gactccaaac agctaattaa cagttagtag acaacagata atgattcttc    46800
ttccttggcc gatcgatcaa caacatccca tgcatccggc atcccaccac cattgattcc    46860
atcatattta gagtctggaa taaataagga actcctatcc tatttatccc ctatctatat    46920
atgaagatat gataatggtg atctgcgtta ctactagtag aagaatatgg tgtggctgac    46980
tccacttcag gtggacctat aatactactc cagtagtatg tgcctgtgga gtcaagctcg    47040
aacgtactac tccatattta agcatgtcat gtactgctac tatgagacga gagtgctctg    47100
ccctgtaggg acagcactat tgtcaatgtc atgtgtttgt tggatcactg gtcttcttag    47160
atttgcgtcc gtgtctggca gcagcactcc attgtagttg gctcacgcat gttgttgaaa    47220
tgagccacat gccttgcctt gagatagaac ttgctgtcac tgtttctcct taatcgaaat    47280
atactggagt ggagtatttt attatctatg atctgtaatc aggtgatcga caaggctcgt    47340
caaatttcta tgcctttggt aggagagtat caaactttt ttttatgact cgcacgagac    47400
```

```
ggtaaaaaga aatacaaaag gttgtaacca agaaaaaaaa ggaaaaatta caccactatc   47460
cacacaccga cagcgccaac acataggtcc ggaaaaaggc tagcaccgga ccggctgttg   47520
ctaagcgtga tcgaccaccg ctgagccaac aacggaacat agatgagatc gccgaaaaaa   47580
cacccttaca accaacacaa ggcccaactc tacccatgtc ttttagattt agggatagaa   47640
ggtgagagag atgaaacacc cctcccccta ggcccttcga cgtggtcaac ttgtaaaaac   47700
taggatacca tcataagagg atgagaattt agagcgtgct tgcaccaatt gtacatgtgt   47760
tttcagcaag aggatgctta ggtgacatct ccaaggagag aagcgataga aaaccgccgc   47820
cgccgtccgt caaggtctca aaagagcaa  agactgggct ttcgcccttc aaccatcctt   47880
gaggggtgag acggcacgac aacggcctca ggaggggaa  tgacactcga gcgccatcgt   47940
tgtcggtccg gccaaggcta ggctgggttt tcacccacca ctcaccacct gcgagtccat   48000
ggctgacgca ctgatgctcc accactgccc aatctctact gacatgtggg accaatgcac   48060
cggcgcctcc cgccggccag cctttgtgca cagtagaccg tgccacatct accggcagct   48120
cctccgtaca ccgtggtcgc gtcctccacc gccagccgcg tatcacgtat tgaatgtatc   48180
ttatctagta ctactagatt atactagtgt tatgggacgg agggagagta tcctgtttac   48240
ggtaggtttt gtccggctgc aaagaaaacg gaaagctcct ttattacgac cgagatggcc   48300
attctctaga acaatcgtgg accgaccttg ctttctccgc tggatgacac ccgtgcttct   48360
ttcctcaact gtccgcgtga tcgcctttct tttcttttc  gtgtctcggt tcgatctggt   48420
gctgaatttc tttgtggatt ttacgctaga aaagagaagt aagcttggac agctcctaga   48480 atctttttt  tttattttct actgatttta tagctgtaga ttcttaaagt ctgaggagaa   48540
tgtaaaatgt ttgaggaatt tggaggctgt accaaacatg ctatagtatt tgtgaaagaa   48600
aaacgtcact cattatctcc attttaaaag ctcctcaaac agtcactcgt cttatttacc   48660
gacagcaaag tggtaatggt actggtatcc tcgaggcctt gtatattgct tttgcattaa   48720
aggatcctct caatctaaat acagtctttt tttttctgaa atttactacg tcatccaaca   48780
agaaaagtaa agaaaaaaca cattacatgt aaattggagc atactgtatt gttttttcata  48840 ggaaagggct agaaagatgg atgaatttgg taaactttca gtgaaaaact aagctctcta   48900
tctttgtaat ttgaagttgt ggtagaatat ctatctttgt aatttaaagt tgtggtagaa   48960
aggtactagg atggaggaac tagcggctga atgtatgttc tggaagcgaa aggaagggga   49020
gagattttga gtagctcaaa aatatggagt attttcttca ccttcttccc cacgcggaag   49080
cggaagctga agcgcacaca attacaatta cagggcgact actctctcct ctctgctccc   49140
tgctccctgg agagctctct ctagagagag agagagagag aagccatcag ccatggcgtg   49200
ctgcttcgcc tgcctgggcg ctggcggcg  gaagatgatg atgaagaaga tgtcgccgcc   49260
tcagatccca ccggcctcag gtgatccgta cctgccccct cggtcgcttc tttctttctt   49320
tctttctttc tttctcgcag agagcgtatt gccttacctg gttaggttgg gtggtgatta   49380
gctagacttc cgagaaattc aaaaaaaata aaaataaaaa ccactcaact gtagaacggg   49440
aagtcgtcaa ttgttccttc ctgttgaaaa gattttaatc tgcttccaac caatagagaa   49500
atttcgtatg aatgaacata taattaagca gcagggtttg ggttttttctg acacaaggcg   49560 aggtttgttt gtttctccag aaagagataa cccaccaaac ctgacctcat cgacagtgat   49620
gaagcaggat caggattcgt ttcaattagc tgctaacgag gacatccttg tgagcaatgg   49680
atcatccgag aaccgccgca ttgcagctcg gaccttcacc tttagggagc tcgctgcggc   49740
cacaagcaac ttcagggccg attgcctgct cggtgagggc ggttttggaa gagtgtacaa   49800
```

```
aggctatttg gagactgtcg accaggctag taacttatac tccgcttctt gctaccatac   49860
tgcaaatttc tgtttaatca aactagaatc tctgcaactg actgtatgag atgaaatgaa   49920
atgctccata tactaaatta tttccttcat cttccatgga gcagttccat ccattattaa   49980
catgaattaa tgcactttat aaccatcata ggttgtcgca ataaagcagc tcgatcgcaa   50040
cggactgcaa ggcaacaggg agtttcttgt tgaagttctt atgctcagca tgctgcacca   50100
cccaaatctt gttaacctta ttggatattg cccgatggt gatcagaggc ttttagttta   50160
tgagtatatg ccattaggtt ctttggaaga ccatcttcac ggtatgccac cgaaaaacct   50220
taattggatc actgcttgct ttgctactgg atgattcatg atgtgtgtgc tcacaactag   50280
attttgtttt acccagatcc tccaccaggc aagtcacggc ttgattggaa tacaaggatg   50340
aagatagctg ctggtgcagc gaagggtttg gaatatttgc atgacaaagc caatcctcca   50400
gtcatatacc gagatttgaa gtgttcaaat atcttgcttg gggagggata tcacccaaaa   50460
ttgtctgact ttggattggc aaagctcggc ccaattggcg ataaaaccca tgtttccact   50520
agagtgatgg gtacatatgg atactgtgct cctgagtatg ctatgactgg ccagctgact   50580
ctcaagtcag atgtttatag ttttggtgtt gttctgttgg agatcattac aggacgaaga   50640
gctatcgaca acacccgagc agcagggag caaaatcttg ttgcatgggt aaggcggcaa   50700
gcttcttctt tatagcggca actggcaagc ttctcttcta aatagtgttg ctaaaaaacc   50760
taaatgaaat atgccagtat caatctgaat aggttctagt atggttgatt ggttgtttat   50820
ccaaaggagt aatctgtttc catccattca tatttggtgg tgtacaattt caggcccggc   50880
ccttgttcaa ggacaggagg aagttccccc agatggcaga tccagcgctt catggtcagt   50940
atccatcgag aggattgtac caggccttgg ctgttgctgc gatgtgtgtc caagagcaac   51000
cgaccatgag acccctgatc ggggatgttg ttacagctct cgcttacctt gcctcccaga   51060
cttatgatcc agaggcacat ggcgtccatc acacgtcacg tttgatgtca cccggcacac   51120
aaggtgtatg agggatgcag acttaggctg aggaggtgct gtagaacaga aagcaggaat   51180
taaggcttca gaaagcctag aatatttttt gctagatatc gtacctgagg agaagatgtt   51240
gctgacagtc catggagatg accagcccag agattttgtt catagcaaga gaaagagaga   51300
atcatagaga gaaatgagat ggttcctggt ttctgcaaca tggaatggtg atagattgat   51360
ttgttttctc atgataggga tggctgctgt tgttgtacat gtgaatttct ttctcgagtc   51420
tgtatttaca tcagtgtagg agtagcctgt agcgtagtac atttgggttc aaggaatttt   51480
tgtcatctct ttgttccctg tgggtgtgag tttcggttgc gtgctggagg ttgtcagct   51540 gcagtttcag ttgcctggtg atgttattgc gtatgcctca gacagtatgc catcacttac   51600
tattgatgcg gtttcttatc atgcaccacc atccttctgat atatgctaat gtctctgcat   51660
ctagggccct tcatctgaaa acagactagg ggcatgaatg cattctaatt tccataatca   51720
ccacatcatc ttgcataaac attcgacagg cccaagacac cactagtaat taatatacag   51780
ggcctctttt tgagtagtca atgtaatgaa caaattaatg aaatagctag gttgcataca   51840
gatcgctaaa atgacaagcg tgatgcgtgc atcagatggc cggagctagc tctccatgga   51900
actccctcaa aattaaaact catgttctac tctcagaaac cataatttta acactagaga   51960
ctacccttgt gtacaatata tcaaatgcca ataagttttg cctccaaaat aatagcaaat   52020
ctatggtaac aagcatgtgt tcccatctaa taagctgggt gacaccacga gattcgaccg   52080
cctggggtcc agctccaagc gaacccaagt atatgaatgg ttactagtta catgtattct   52140
```

```
acagcgtctg ccaactgcaa gcaaagacag acaagttagc tactgaaatg agcccaggat    52200
atatattaac acaagtgctc acagccaaaa aagaagaaaa aaaagaagta tgcgcacctc    52260
acagatcgct gaactgtttc tgcaacgtag gatttatgca ggcaaatatt gatttcttct    52320
tcggctttgt gccgaatagg aagttccgca atggcactct tgttctagtc gggaagtgtt    52380
tgaattggct gtggtagctg gtgctgctgc tttcttcctc caccaaagat gacctcctgc    52440
atgaaagatc aaagctctca cgcagcttct gcaagccgtc attgaccttg ccttcaagtt    52500
ctctcatgcg cttcagtgct gactgtaact ccctctcgat cttaccacta gactgttgca    52560
tgttcagtac ctccccttga aacttggctg cttcgtatgg tgtaaaccta ccaccaccag    52620
tctctgcact agcacgcaag gcttcagcta tctcctcctg caatctgcaa agagacatgg    52680
ttttgagctg caggtcttga tcaagaagtg cattctgttc aaaccataca tccagttcag    52740
ttcttagctc tctcaacttc ttttcagcag gatcagactc ggctgcagca tcaggttctc    52800
ctgtcttctt aacttcaaaa tcccccattc ccttttgtag ctcctgatat tgctgtcaa    52860 agtcctgcat gcggtggcaa gccatgctaa accttaccaa gaactgcaag ttttcctcaa    52920
ccagagcatc aatctcagat ctgaacttca cttcgaaagg tgaagtattc ttccgtacac    52980
cagtgtggct tacatcgatt ccctccagca cagaaatttc tgtgtccaaa ggatgatttg    53040
atctgttaaa acccatttta ctatgtgtgg atgatatatc ttctgaagga tccaggagat    53100
ctcttaggga ctggatctca acatatttca tggaatttgc attcctcaac tcccttatta    53160
ctgtctttgt ctcttcgaga tgttgctcat ttttcttttc caattcagca agccttctct    53220
ttgtttcttt atagttccgg agaattaaag tgtagtcgtc tagcaataat gcttctctac    53280
cttcaatgcc atcaaggaga aactcctgcc agctaggtgc atctctttct gcaaccaaac    53340
tagaattgac gtgcaagctc atgcttccag gcttgctcaa ggtacttgct tgtcttgtat    53400
gttctctgcc atccgaactt ctcgtctcta gctcaccatg aggaatgcaa ctagcaatat    53460
tgtttgattt tgttgttact ttgggtactt gctgatacac tcttgacgaa tgtgcatcca    53520
caagttcact agtctttcaaa tcctgtatgc tgttcatatg ctctaatgaa gtgcggccac    53580 cttttctcaga tgagtcaact ttgctgcctc cgttcaaact tttcatagtt tctggggcaa    53640
tcagctgacc atcttgtttt ggccattctt caacagatat tgcttcttca gtatgacata    53700
attccagtct catatctgca tcactgaaac aactattaga aactttgggt aatgagattt    53760
cttcagtggt gcttccatca ctcaaactat gttggtttgt agaaccaacc aaattaacat    53820
atccaggtgt ttttagtgat ttgtcatctc tgagttcttc ctggatcaag ctgttcccag    53880
acatagaatt ttcatcgcca ccaatcctta agccttgtat tctcttgctg cctccgaatg    53940
aattcacagt aacaaccact gatgacccct tctcatcaga gtcactttta ttggttaaag    54000
tatctaaaca ttctgagtgt gggaggtgag tctgacttat taccgttggt ggatgttcac    54060
ctttcaaact ttcccccttga gtagagttgt caataacatc atttcctatg tctctatatt    54120
tcttcgtatt acctgatggg ctgcaatcta ttttgccttc acatgcgttg ttaaaaccat    54180
tttctttgcc tggaataaca attcgatcaa tgttattgct agcttgtatt gaccttttat    54240
ccgtcaagtc ttcttggatt aagcgatttt cactttgaaa gttttcctcg ttgccattct    54300
tacagtcatc aatgccatca gtaccatcta gtgaatcatg accctcaact cctgaagcat    54360 cttctttct acacctgtct ctgcccaaat tatcatctgt agttgcttcc tctgtacccc    54420
tgaattcttc ttctggcagt gaggtgctga tatcatctga tgttatttcc ccatcatttt    54480
caactgcagc tgataaaacta gtcatgtcct ctggatcaat agatccaaag gcctttgaga    54540
```

```
tattagtgat gcaactaaca acttcagaaa agactgtgct aacaagaact tcttcctcaa   54600
taacagatct ttcaagagcc ttgactctgt tcaactcatc ttctgctaac ttgagctgtt   54660
cacttaagtc acttggatca tctcgaagtg ctatctcatc ttgtagatca tccaacctat   54720
ctttgaggct atcattatct tccttcagct gcttgatttg agcggactgc tttgggaatt   54780
tgagctccaa gttcatgacc ttatcaacaa gctcatcaac tctctctgcc atctcctcca   54840
caacagattc agagttgagc tcaaaaaacc tttcgatttt ttcatatata ggctgcaggt   54900
ccagtatttc ctgagtatta ggataaactc tattttcac tgcgatgttt gttgtgccaa   54960
cttctccctt agacgggtca atgatgtagt tcatagcata cagttttgt cggagatgat   55020 ttacttttg ggactcccct gctgcaaccc tgactaactc ttcaaatatt ttcacaagat   55080
tagctactgt gccctgacaa gatctaagag ctgtaatggt catcagggca cgggcttcat   55140
catcctcgat ggacgcatgt gcatcaaact cattttggat gtggcatacc tggtcctgca   55200
tatctgcaat ctgcttctcg atctcccgat acttggtaat cccagtctcg taagagctct   55260
taacgaattc tttctcggtt tgcaggacaa gtatagcctt ttgaagtgtg tcgatctctt   55320
gttgcgcatt ctgtttggtg aagtgaggag cacaggggcg cgcatgtcct tttgggttca   55380
aaacctcctg tacagtagta gtggattcct gtattctgat gggtgtgaat tcaacatcgt   55440
cttgttcatg taacaaggag acgtcgtgtt gtgggcatgc agtagcaatg gtgtggttgg   55500
ccttatgcag ctccttggat aagtggtcgt agcgttcaac gagagctctg taggccctgt   55560
aaacctcttc cacatggtta atcacctctg gcctcctgcg gtagtacatc tcggctctct   55620
tgccgaacgt atcggcttcc tctcccagga gcttgagcat gatcttgact ctggtttcca   55680
tctctgcgtg cgccaaaata atagtactct catctcatct catctagtgt agtgactaca   55740
aagggggatt acatttacat cccatcccta acaagtagta gtaagactaa gaagaaaggg   55800
ggatcgaagc ggaaacaaac cttggagatt ggcgtcgagc catttggact gcgtggtgcg   55860
gatgtggctc gcccaccacc acgagtaggc attgcttgcc gcccgctgca gcatccgccg   55920
caaccacagc gcgacgccga cgaggatcga tctatggctg cctgctactg ctacacggat   55980
agatagatag atagatcgag atcgccttcg atttctttga cccaacttgc tttctttaca   56040
actactacta tactactagt acggtggagt agtatataat cggagttctt cttggcataa   56100
tcaaagctga aatcgaacac atctcatctc tcaagaaaag aaaggaaaag gaagggagga   56160
tcatctcaaa agagagggga aagaaacgaa gaaagaagga aaaggaaaaa agtggtaacg   56220
caaagagagg ggagacgcaa cgcgcacgtc ggtcccaatg ccaaagccca gtcaattaat   56280
tagtcaatcg catcagtccg cagcccacgt caacgcggcg cggccttccc atctccacgg   56340 cccttcgac gttgacgttg tctgtctggt cggttccgtt tgaggacctg acggcgacga   56400
gacgcgttca tcggttcctc cacggtatgg ccatgggcca gcagcccagc gctaaacagg   56460
aatttatcct ctttgtttgt tctccctccg tttcacaacg aatattttc acattcatat   56520 taatgttaat aaatttatat attatgaatg acttacattg tgaaacggag gaagtaggac   56580
ttatcttttt tacttatatg ctggtactta tcgatgaatt ttcaactttta aatttgtaac   56640 tcattttgag attttttaa tcaaaattta ttttcaacc tttgctttta gatggttaag   56700
aacacgtata taaaatttt attcataaat catttctcgt ttgtaaatat gccgtttcac   56760
tatcccacga ataagcgaaa cgatgggaat accatctctc caaccgagtt tagcctccat   56820
tgaaaatata ttctctcgaa ataaaattta gaggtgaaac cgggtttagc ctgtgttctt   56880
```

```
tagtctactt ttccaattc acattcctca tttttacacg cacacttccc caactactca    56940
acggtgtgtt tttttaaaaa aaatctatag aaaagttgtt tttaaaaaaa tcatattatt    57000
tcattttcca agttttatag caaatactta actaaaaaat gcgctaaact gtcacttcgt    57060
tttgtgtgca acgagggaag tgctcccaac tataactgga gaacacagac tgctccacaa    57120
ctctgctcca gatcctgatt tagtggttag agcactatca aacaaaccct aaatgaggag    57180
gcaataccat attccaaccg atgattttaa ccatgccaat cctatgggtg caaacgagtg    57240
ttacttggtg gtactgcatc tcctaggtat ttgatggtgg gagaaaattg acattgtgcc    57300
attttttata tgggatttca ctaaaatggt aatttgaaat atggtctcgt tgaaatgaca    57360
ctatcaaagg agaccaactt gatatgccat tttctctatt ttcaataatt tctttctttg    57420
ttggcagttt ggcacatgca cactggcctt tatgcccatg gcatattcct ttacaagcct    57480
gagaaagcgg atagatcctc tcctctctcc atgaactcaa tctcgtcgcc accgcgcgtc    57540
acccagcaca tgcaccacct tctcccaccg tcgccgcaag cgcaaccaca tatcgatcta    57600
ggaaccgatt agcgagcctt agggccttat tgacgcagat gtcgccgccc atgccgcatc    57660
aggtaccccg ttgcagccca tcgcctcggc cactggcgac ggcacattca ctccatgctt    57720
gtaccacgtg caccatcgat atcgatggac gacgccgaga ggcgggacat gaagaagatc    57780
cttcgacatg gctgagctca tcgacacggg gtgaacggtt agctgatgtc ggccgtggca    57840
aaatcgagat cggtgacgtt ggatgaccaa gctgccttgg ggcaccctga gaggagcgc    57900
cagcgctggt ggcaccccat cccccgttgt tacagccagc cgtacaacga cataatgagc    57960
ttggcccctt cccgggcgat ggctaattgg gaggagcgtg aggtcttgtc tcggtcggcg    58020
gctgtggccc gccacgacca ccactaccga ccacacgggt tttttggtca ggtcaacatg    58080
gaaaaaggag ggtaaaaaca ttaagaaaca cacctcaaat gaaagaaaat ggtaatatgg    58140
cgtgatgata tgtttgagcg tggcatttta acgaaaccat attttggagt gacatttcag    58200
cggaaccccg ttcttaagat ggtatagtgt caattttctc agcacgaggg taaatttgta    58260
ctttggcatg tacatgctgg aatcgattca agcgagaatc acattcgtgg cggccccatg    58320
gtgtgacttt cgacgtgctt tggtggcgga ggcatcccca cagtcctgga gcaacacttt    58380
gaccggttgc cacaaaaatt tcagaaaggg aacatctaaa aagctattgc atacttggct    58440
ggcgttgatg ttgttggagt gctgagttaa atatggaaga aattcatgta aaatatatg    58500
aaagaatttt agtcgattgc tagtgtcatg acccagaagt gttatactac tatcttatac    58560
cccttcgtta gtacaataaa tttgaataga gatatattca aatttaaaat attagaatgt    58620
gtcacatcca gtattagatt ggtctcttgc ggacggggaa ggagtagaac actgaacaca    58680
cacgatttct gttgcggtct ccacgagcgt gaaataggag aaggaaaaaa aaagagaaaa    58740
ggacaatgaa aatggacgac cgcgacctgg actccgccgc gctctgggcc gccgtcgact    58800
cggcggccgc cgcccaagcc tcccgccgcg accacgaccg tacgcacctc cgcaatctgg    58860
aggacgacga gcatcgagat cgaggaggcg aggtggtgca gcccgcccgt cccttcaagg    58920
tccctcgact cctgactacg ccgcccccgc cctctcctcg gcctctgcaa ctgcagatgg    58980
ccccccggcc ccattcctcg cccaacctca ccctcacgcc cgacgccacc aggctcgtcg    59040
tcgtcgacac cccacctccc acacctaccg cctgcttcgc cgcccacgac ctcttccccg    59100
ccatctccgt cgccaacttc agaaagtacc aggaggcagc cctctcggta tgtacgtacg    59160
gccctaatcc tcctccaacc tctaaattat tactattaat taattcgtga cactggagta    59220
ctcccattta gtactagtac tgctactttta ctaaccagct ctctgtaaat tatgctacta    59280
```

```
ctcctactac ttactgaata ctgaattgtt actgatgctg ctatttcaga ttctagataa    59340
aagcgactac acctccatca gtgggaatcc atacatcaag aaatcaggtc ctttgattga    59400
ctcatactcc taattgttgt tgtgatctgt gatgatctac tcactcaagc atccttttcc    59460
atatcccttt tcaggctgga ggaaaatatc atgcttcttc aatatctcat ttgaaatcaa    59520
ggaccgctcc attgagttcg atgaaaaccg caatgtcaac cgtgccgagt ttctcgttcg    59580
agcatcgatg cagttagtat gctttgtctt tcttacagaa ttatcactat aactcatctt    59640
gtttaaatta aacgtacccc ctcgcttact ttacttgtat catcaactgt tgttgttaac    59700
tctttctttc ttttgtgttt aaagaggtgg caggttttcg gatggttggg gttcatgtga    59760
tcggcgtgag aaaaaattta acaaaccaaa ccatgatgtt cccagcacag ctgaaaccag    59820
agctaagaac aaagcctgtc aggtaaggag aattgtcact atgttttcac tttgtctcag    59880
ttaggtagta ttattattac ataccagaaa ttcatgccag catgcatatg ctcttttagt    59940
aattttagat ttgaaccgtt ctagtcgctt gcttccaggg gcggagccag gattttgagg    60000
caccagggtc acattagcta gcctaagcta ctgtcatatt tgatagggct ctaattctaa    60060
gatcaatttt ttaagctaca tagttttaga tccaaaagtt tttggaacta aattaatggt    60120
gaatcgaggt aatttcggtg ggatatcaat attttagact aaacataaag tgttaaatca    60180
ctttaattag ttatttagac tataaactct aaaggtggca ataatttatg agctaaaacc    60240
atcaaaattg gctaactacg cctaattatt ttggcaaaaa aagttcttaa agttgtttat    60300
taacttaaaa aggactaatt tgtagtacca ctttagtaga attactagct agcctaattg    60360
catgtataaa cacactacat tgctaaaaat agctaatttg taagtgctca aacatgctaa    60420
tgggtgagca gttctcacac tagtctgtaa ctattatgta ttgctagtag tgtttactct    60480
gtgagctgct gcagttcatc gggctggggt caacaagcat cggctaatgc ggccactgct    60540
cgcaatatac aaaggaacat actggttggt cagatattgt cggtgtcatc tgaccctagt    60600
gatacaacat agctccgccc ctgcttgcta caatgttcaa taaaacaaac agaacggtca    60660
gcaaacaatt tttagtttcc aattgggtcg tattgtagat caaggaggca gaagcaaaaa    60720
aaaactgcta gaggggggcca gactgctaag acgagtggga agtgaaatat atatatggtg    60780
ctcaacatgg atggagtttc agatcgagga ggctgcaatg atgagaatat taggatcgca    60840
tagtgctgat accttggggt aggttgctgt agatggtatt ttgtcaagtt gtgttcacta    60900
gctcctgttc tgttttttta gctgtttgat gttgcctgta agggtagaat tcctagaaaa    60960
gttaactgtt ttttgctgg ttaccctctc ctaaccagga tggatacctg gagaaggatg    61020
aatttgctgg aagtcatgca catttggtag tttctcattt ctatcaacgg gaattttttt    61080 tttgggggt gggtcccgca gaagttacag tctgcaaggc ccacccacaa aagagaatct    61140
ttgagggaaa gaatggcatt gtactgagtt atcttatttg atgaagaaac gatgcatgca    61200
tttagagatg tgtagcttag aactaaagtg tgtgttactg gatatatatg gtgggtaagc    61260 atgttttga ctgggtcatg acaggcgtgt gcttgtgtgg tgcttttacg tactacattc    61320
ttttatgcat cattagggta ctggctttta cagtttagct agacgtagat gtgaaatatc    61380
atgagttcac gacaagtctg tactcaggac aatccttaca taagctagtg tggaccattg    61440
ctatagttta taggagtatt tttatttcac tatagatcaa tcaatatgtt gggagtaacc    61500
gtttgttgct gtaaacatgc atattccgca ggaccttgtt ggtatcggaa atagccatac    61560
attgaagaac agccttggct gataatctgc taaactgagg accggcgaaa cagtgagtga    61620
```

```
acaaaaagcg tcgggaagct tctgcttctc ccgatggaca tatcacacaa cgtatttct    61680 caaaatcttt ttgattacaa tccttggatg gatgctgttg aggctagctt gttataacta    61740
gttaactcga caatcattgg gtggtgttca ggtaacttga tgttgccctt agaaatacga    61800
cgcagggcag aagagctagg ttgcgtactt gcgtcattgc gccaggtgaa agcgaacgac    61860
tcgtgaagtg gtatggcagg attagtatgt acttattttt aagtaaattg catatcggga    61920
tactcttttg taccatattg ttacaaattg gactaggggt aaacaaagtt tttcactttg    61980
gacggaccac ttatctttat cagtcgcttc ctctctttat tatcacagat tcacagtcct    62040
ttgccttcat aaacacctct attcgacaat gtatgcaact taaaattcta ctaggctact    62100
tactatgcaa tggatgtgtt catagtggtt ttcccatcca aatacctgtt ggccattcga    62160
ttgaagtgac gctttacatt tgatttaatt accttgacca ctcagtatat gattagtaac    62220
ctagctttgg tttacatcaa cttaagtggg atagttgaag cgtcacctgg agttttgagt    62280
tgttcaactt tagatgaggg acctaaagtg aactttctcc ccaaagaaat caatgagaaa    62340
acgcggcgtc gtgtatgggt cgggcccatg aaaaaaggcc aacagaaagc tttcagtcga    62400
gagtcgccgc cacgatgaca cacacgccac gcgccccgaa acctagacat ggtggagatg    62460
gaccgaggcg aggcgacgat gaggatgcgg ctttgaagtt gaactaggcg gcggtgggcc    62520
caccgcttcc attcttctcg cctttttctt ccaccgttgc gagttctctc tgcctgcgct    62580
gcggctgcac ccttccccaa gtcggatttc cattgcattc tcgattccat tccttccccc    62640 tcccctccc cctctttctt cgacttggac ttggccttcc ttcttcctcc tcctcaacct    62700
cgacctcgat ctaggtctac gctccgccct ccgcccgccg ccgccgccgc cgccaggtat    62760
gtattcttct ctcctcctgg ggcctgggct aggaggctag ggggctaggg ggctagggag    62820
acgatgcgac gagatttgca atactgatga atgctgtttc gattcgattc gattccaggg    62880
agggagccgg agccggagcc gatcgatggc gtggctccgc gccgcctcgg gcctcgcccg    62940
ccacgccctc cgccgccgcg tgcccgccgc ttccgtttc ttccactcgg cgcggccggc    63000
ctggaggtcc tccgcccgg tgccccgcgc cgtcccgctg tccaggctta ccgacagctt    63060
cctcgacggc accagcagcg tctacctcga ggagctccag cgcgcatggg aggccgaccc    63120
ctcctccgtc gacgaatcct gggacaactt cttccgcaac ttcctcggcc aggccgcgcc    63180
ctcctccgcc ggcctctccg gccagaccat ccaggagagc atgcagctcc tcctcctcgt    63240
ccgtgcctac caggttaacg gccacatgaa ggccaagctc gacccgctcc gactcgacga    63300
ccgcgccgtc ccggacgacc tcgaccttc cctctacggc ttcaccgaag ctgacctcga    63360
ccgcgagttc ttcctcggcg tttggaggat ggccggtttc ctctccgaca accgcccgt    63420 cctcacccctc cgcgagatcc tcagcaagct cgagcaggcc tactgcggcc ccatcggcta    63480
cgagtacatg cacatccctg acagggacaa gtgcaactgg ctaagggaca agatcgagac    63540
cgccaagctc aaggagtaca acaaggaccg ccgcctcgtc atgctggaca ggctcatctg    63600
gagcacccag tttgagaact tcctcgccac caagtgggcc actgccaagc gctttggcct    63660
cgagggcggc gagaccctca tccctggcat gaaagagatg tttgacaggg ctgccgacct    63720
tggcgtcgag aacattgtaa tcggcatgcc acacaggggga aggcttaatg tgcttggcaa    63780
tgttgtccgc aagcccttgt cgcagatttt cagtgagttc accggtggga ctaggcccgt    63840
cgaaggcgag gatggcctct acactggaac cggtgatgtc aagtaccatc tgggcacctc    63900
ctatgacagg ccaactcgag gtggaaagag gatccaccta tcgttggttg cgaatcccag    63960
tcacctcgag gctgtcgatc ctgttgtcat aggcaagacg cgggcaaagc aattttactc    64020
```

```
caatgatctt gacaggacaa agaacatggg cattctcatc catggagatg gcagctttgc   64080
tgggcagggt gttgtctatg agacacttca tctgagtgcc cttccaaact atacaactgg   64140
aggaaccatc cacatcgttg tcaataacca agttgccttc acaacagatc caagagccgg   64200
cagatcttcg cagtattgta cggatgttgc caaagccttg aacgctccta tattccatgt   64260
aaacggtgat gatctggagg cagttgtacg agtttgtgag cttgcagctg agtggcgcca   64320
gactttccat tctgatgtgg tagtcgatct gatctgttac cgacgatttg gacataatga   64380
aatcgatgag ccctccttca cacagccaaa gatgtatcag gtgatcctca ttctactgat   64440
ttcaattatt tgtttatgga tagctgatcg ttttctcata taggttgcac tcgcccattg   64500
ctttatacct ttgttacttc cttgcatttg atgttcagtt gctgtcaata tgattgctac   64560
ttgtgctgtt ttactattct ttttccttt cctttccttt ccttttggag tgttcctgat   64620
gaaacttttt ctgtggcagg ttattaagaa ccatcctagt tcattaaagc tttatgaaca   64680
gaaactgcta ggaacaggcg aagtctcaaa agaagacgtt cagaagatcc acgagaaagt   64740
caacagaatc ctgaatgaag agtttgcaaa aagcaaagat tatgttccca ataagaggga   64800 ctggcttcg gcttactgga ctggcttcaa gtctcctgag cagatttcac gcgtccgcaa   64860
cactgggtaa ccgcatcctt tatactgatc atctctttgt aatttattcc ttcaccaaat   64920
accatccatc atcatcgaga gtgctttccc tgcagggtta atccagggg gctgaaacgt   64980 gttggacagg caattactac tttacctgaa gacttcaagc cccacagggc agtgaagaag   65040 attttttgagc agcgtgcagc aatgatcgag agcggtgaag gaattgattg ggccgttgct   65100
gaagcccttg cctttgcaac actcattgtg gaaggcaacc atgttaggct gagtggacag   65160
gacgtggaaa gaggaacttt tagccaccgt catgcagttc tgcatgacca ggaaaacggg   65220
aggaaacatt gcccacttga ccatgttgtg atgaatcaaa acgaggagct gtttaccgtt   65280
agcaacaggt aattacactt tttggttctt tcgtatgtac tttttttgt ctagatgtta   65340 aatttggata aaacatcatc tgccttttc ctattcttta attaagcctc tagaacctta   65400
tcgtaaatga aacaaatat tgtctgatat tatgtgttat tgcagttcac tttcagaatt   65460
tgctgttctt ggttttgaaa tggggtactc catggagaac cctaattcac tagtgctctg   65520
ggaagctcag tttggtgact tttccaatgg tgcacaagtg atgtttgacc agttttgag   65580 tagtggagag gcaaaatggc tgcgtcaaac tggccttgtt gttctactgc ctcatggtta   65640
tgatggccaa ggcccagagc attccagtgc ccgtttggag cgctttcttc aggtaattct   65700
ttgcagcaaa ctttcttcct ctctgtcaga tgcatctagt ttagcccaag cccattcaat   65760
cacaagaagt ctctttgttg attcaaactg ctacataaaa tgcgatgcac ttctaaaatg   65820
ccaattcttt atgtttggcg aatcaatgac catgtctggt attcatattt ccaaggcata   65880
aattgttata tactccctcc gtttcataat gtaagacttt ctagcattgc tcatattcat   65940
atagatgtta attaatctag acacacatat atgtttagat tcattaacat ctatatgaat   66000
gtggacaatg ctagaaagac ttacattatg aaacggagga agtacttgag atagtgtagc   66060
catagtgatg atcaagctct cttgcatttt cataatttct ggttgaatgg tacgctcaat   66120
tcttgtatat acactgctca catgagattc taaattctgt ccagatgagt gatgataatc   66180
cttttgtcat acctgagatg gaaccaacac tccgcaagca gatccaggag tgtaattggc   66240
aagttgtgaa cgtgacaacg cctgcaaact atttccatgt gctgcgtcgt caggtctgtc   66300
tatcttcagt atgcattcca gatgctagca tgcaaattgc ttttattaat tttcgtctgt   66360
```

-continued

```
tgttttgagg gcattagata catagggagt tccggaagcc cctgattgta atggccccca    66420
agaacctact tcggcacaag gattgcaagt caaatctctc tgagtttgat gatgttgaag    66480
gccatccagg tttcgataag caaggaacac gcttcaagcg gttgataaag gaccggaatg    66540
accacaagca agtcgaggag ggtatcaaac gccttgtatt gtgttctggg aaggtacata    66600
agactttgaa atttgatcat attaccagtt caatacaaat atgtgctgtt attaaattgc    66660
cattttgcag gtgtactatg agcttgatga agaacggaag aagactgaac gcagtgatgt    66720
tgcaatttgc agagttgaac aactttgtcc attcccatat gatcttatcc agagagagct    66780
aaaaagatat ccaagtatga atgcttttcc ccatgtattt aatccattac ttgtgtgaat    66840
gcatgcatca tggtttgcca tttccaccag cagttcctgg aattttggt cctcccggaa     66900 actgatgttg gtaacctaac atttcaaata ttttcatgcg gtgatattgc tttctttatg    66960
gtatgctttg gtatttctgc accaatattt ttgttttccg ctccatgtgc tgcacatatc    67020
tgaggactga gtacacagct tcttgtttag aaaatattca cttgtcctcc acatgtctga    67080
ggacagagtt tgttgcttct tgataagaaa acctaggcag tcttggcact aatagttggt    67140
gatgcacaga tcgcgcacaa gtatcactgg gtggtctttg ttccttactg atatggtggc    67200
tagtctccac cagtgcactt ttacgtgaag gcatcccaag ttgttacaat gtactccatc    67260
cgttttatat tataagtcat ttaactttt tttctagtca aacactgtta agtttggcca     67320
agtttataga aaaattaac aatatctaaa atatgagatt agtttcatta aatctaacat     67380
ggagtattgt ttgacaatat gtttgttttg tgttgaaaat actactatat ttttatataa    67440
atttgatcaa atttgaagaa gtttgactag aaaaaaagtc aaatgactta taatatgaaa    67500
tggagggagt agtatgcatt gttatgccct accacatttt agttgctgaa ctgttctgat    67560
tatcataatt gcaccatctt aatttgtaga tgcggagatt gtctggtgcc aagaggaacc    67620
catgaatatg ggcgcatata gttacatctc ccctcgcctg tacgcctcta tgaagactct    67680
tgggcgtggt tcattcgatg acatcaagta tgtgggcagg gcgccttcag ctgcgacagc    67740
tactggcttc ctgtcggttc atgcgcagga gcagacagag ctggtaaaga aagcactgca    67800
ggcagagcct atcaagttcc cctgatatga tgcatctgtg gtttccactt ggtgcttata    67860
cttgtgcaag acaagtgtgt gcgagctcag ctcgtccagc ctttgcacac ataccatacc    67920
atcttaaaag ttttgctatg tatttacaag ctactgtttc tctagcttgt ttgaggcgat    67980
ccgatttgaa tgtcgtgaat aatgcactat ttgagccttc ttaccgttga ggaggaacct    68040
gtttcgacgt gagcaacaaa ttttgcaata tagtagaagc tttagcttcc ttttcttttt    68100
tctcttgata tgcaatatga tgtagcacat ctgcacattg ttgtttgatc tccttgccac    68160
acttgaacaa aaagatagga gtaactcgtt taagaagaaa acaccatagg aagatgaggg    68220
caatcatcta ttcatcttaa caaaatcatg atgtgtaccg tattggtgaa ggtgtacagc    68280
gttgttctcg tgtcaatcgt cgcatccaag taactgtggg cggcggactg aggtgtcgat    68340
gcacaacagt ttggaggacg aaacagttgt gcttagattt ttaatcaaag aaaagctcgg    68400
ctgttccttt agcaatgagt ggttcagact tgggttaatg caaaggactc atctgtaaga    68460
gcatctacga gaggtgtcca aaattagacc ccaaaaattc tatattagga gcatgcaaaa    68520
ggataagagc caatgcagag atccgagtcc gtcggagctg caagcctgca actacaacat    68580
gatgaggaaa cgaacaaacg gggcagttaa atcactcata acttatgatc tgagtctcat    68640
gtgtttaaca atttaccgct cataatctat gatgtgagcc tcgtgtgttt atgatgtggg    68700
ttagtgataa attgttcaat atcatgtcta aaaaggaaac ccgttaaaag agagttgaaa    68760
```

```
ttttatcgct ggtttaaatt attattgtaa tactgctata aaaaattaga aaaaatactc    68820
atcaaacaat atacttgtaa aattaagaaa accaacgaca aaaagttgca aaagtatcgg    68880
tagttaaata tatctaagtt gggattcctt tggaggcttt ctcgctttcg acccagctgc    68940
ggcctgcggg aggcgtcccc atctagacta atataaaaag cacgagttgt gttaattgca    69000
attaacatag cagttgcaat tagcgcttaa ccctccaatt agcgcttctc gtaccaaacc    69060
gtcgctcgaa aaaataaga aatcgaaaaa accoctcgcc agaccgccca cgcctcctcc    69120
gcctccgcct tctccgcctt tgtgtgggac ccacctgtca tccggcccaa acaaaccgca    69180
caccatcggc tgaccacgtc gcaccccct gatcgcgctc cccattcgc ccgcaacccc    69240 ttcccgtgtc gacggttcct tcaccgccgt cggccgccgc tcgcggaatc ccggtcgccg    69300
ctcccttgtc tgcccgctct cccgctcccc cttaccacca cttcccccgc cgccaccgcc    69360
tccatccaac tgccgcacgt cgccgccgtc gctgcctcct cctcgcacgc gccggccgga    69420
gctgcgcgcc ctaccccgtc gcctcctcgc gcgcgcccac cagacaaccg ggcgccgccg    69480
tctaccctcg tgcatgatct gtcgtcgccg ccgccgcgcg cccgcccgcc ggagccgcgg    69540
cccgcatcgc cgctgcggcc tcccgccgga gctgctcgcc tcgtgcgatc ccgccgccgc    69600
cactccgctc gcgcgcggct gcgctcccgc cgctgccgcc tcccgctgga gccgctcgcc    69660
tcgtgtgagc ccgccgccgc cgctccgctc gtgcgcggct gcgctcccgt cgccgccgcc    69720
tcccgccgga gccgctcgcc tcgtgcgagc ctgccgccgc ccctccgctc gcgcgcggct    69780
gcgctctcgc cgccgcagcc tcccgctgga gccgccctgc ttcctgcctc gccggtctcc    69840
tccgtgccgc acccaatctc cgtccccgcc tgccgctgcc tcctcctcct cctcctcaca    69900
cgcccacgct actccacggt gctccctgct tctctgctcg cgccgctttc aggtccgtcc    69960
gccctcgccg cctcgcgccc tcgccaattt gttccacccg tccccgatgg gtgcaggtcc    70020
gtcgcctggt gcactttgtc atcggagttt atttccatca tccctgttgc agtttatctc    70080
aatcttcaac tccttcatgt gcagatccgg cttcctcgac atcatccttg aaagcgacct    70140
cgtgcaggtt tgccgaatgc actcccggcg tcctctacct cctgtgccat tatgtgcaat    70200
ttttgtgctg cactttgtgc tgaattgtgt gctcgtattt aaaagcactt tgtatgtatg    70260
atgcatattt cctatgctac taaatataaa ttttaattgg tgttactatt atctgactag    70320
atgccaatac gtatcgatta catcaaatac tgagtttgca tcaaacattg gtgtgattac    70380
ataaaagata atgctagacc aacgtcaagt tgttaaatga caacctaaag tttgctagct    70440
acgtactggt attggacatg cagctgaatg aaactgcagg cacgcaacat caagatcgga    70500
atgagcactc taacagaaag tgaaaccact gaaaattagc cttttctttt ctggtccttc    70560
ctacatggta ttggtctgct tggagggact caaagccatt ttacatgcta tgattgtctt    70620
catgattttc atgtgttacc gagaattgac gccgcaaaag tctatacatg gctgtgtcat    70680
ctggaaatga aatgaaagat attcttagca ggactactac ttttatctct tattttactc    70740
agagttctat attggcatct ttttcacgct gatgtttggt tttatttggc agcagtgctt    70800
caagggagtt tatttgattc tgatgacaag accaggatcc tagctagcaa tttagccaga    70860
tcaaatttaa gatctttcct ttctgagtta atattgcaag cagagatgct actttacaaa    70920
gttcagcacg aacttgttaa ttttcactgc tgcaggttct atatggtgct tcacttaatt    70980
tttttggcat gactttcaat tctgatatgg gtattggtaa agcttgccat gactctgaat    71040
tcagatgcac ttactgtaca aatatggacc tgctctccag ttgaccactg cttatatttt    71100
```

```
gcatctttat gcatttactg gacaaatttg gatatttgtt cagtttgttt atgtgcagct   71160
ctaacggaag ctaagagggc aaagggaaag gcttaatagt tatcaattca gttccatttt   71220
ctgaatggtt ttccgttttt cacatggatt atgctctgct ctgtttcgtt tatgaaagga   71280
gcatatctca ttttacacta atctctttta cttggtgtat gcatatattt attctagcct   71340
gctagatata ttgctagcgt tcagaaagta tccacggaat gctattattc atctaaatat   71400
aattgtttat atgttttag gtgctactgg tttatctcat gaaatggtct gaataacact   71460
tgatgtgtaa aaacatcaga gcgtgttata tattatcagt tgttcatttc accaaagtgt   71520
ttttttggat tgcccgcaaa aagagttatt ttttttattt cacatttcta ctatataaag   71580
tttctctttt cttttctgtg ccttctaggc aaacatcgat tcgctgaaag cttcagcaaa   71640
gtagcacttg aagaataagt gatcgccatc ttcgtcttga tgcaagcaga ttttgtattt   71700
tgctgtttgc acagtgttct tcgtgggcaa atttgtcttt gttggtagtc gattttgaa   71760 gagaaagcca ggcaaaagtt attgcaccca gagggggggt tgaattcttc tatacaaatt   71820
cccagattgg aaaaggcgca gaagtagagg tattgatctg atcatatagg gcctttgatg   71880
tgagagcttg agttcaacca gcagccggac tgtactgttg tctatcttct ttgtcatcga   71940
ggtgcactac attggtgaca tcaggtcatg gtaggtgaga aacaagtttt gacgcgcgac   72000
actacgttgg tcataagaaa taaaacgcaa tatgagagga tcatgcaacg gcctgctttt   72060
ccagtttgta ggaactgtga tggttttagg atttcttgtt cttttgtgaa gtttaggggt   72120
tgaggagaca acaaagaaga ggtagagtaa tttgagattt ggatttcatt taacaatttt   72180
ttttcctttc acctcattta actttatttc tttgcagtgg tgagatgaat ctatgtgtac   72240
tagagatgcc tactgtgttg atatcttgag acaatgcagg tacatccaaa tactcacttc   72300
attaattcaa tatatgtaaa ttactggctt attgaatttc agtttgattg ctatgcattt   72360
atatcctata gaaatccatt tctttatatt gtattttaag gaacaataca ttttttatag   72420
atattatttt agaatcaaaa caacaaaata caaaatcaga ttgtaccttc caagagcaaa   72480
atgcactaaa attacagttc tttgagcttt gcaaatcgta attgtagcca acaacagtaa   72540
aaagtgcatt tctaatcttt gatatagagt tcagtaaaat aatactattt atgataatat   72600
gagctaatag catttccaag acacagtcaa atatttctaa ctcagatact tcatatattt   72660
agggcctgtt cactttgatg aaaaaaaaaa accttaccaa attttggtaa agttgccaca   72720
aaaaggctac atttagtttg ctaccaaatt ttagtaacta tataagaaat cctgttaaaa   72780
ttttggtaag tttgccaaaa ttttggcaac tataccaaaa tttggcaatg ccaaaatttg   72840
gtaaggtttt tttttggcat caaagtgaac aggcccttag tccttagtga atagcaaaac   72900
ttaaatagaa aggatagaga aagtagaact tgcgttttg ggtgttggaa ataaaacgtc   72960
agttaagtta tgacgaatgg atatacttta gcagaggtag catgcaatga tgtcagatca   73020
atgaaatgga tggaactttg gacctttggt atttcagctc gttgaaaggg aaaccatggt   73080
aagtgagctt cattcaatct tcgatgattt gaatggtggc tcttccagta tcgtgctgtg   73140
ggtgttgttt ttctaaagtt gttttcacca cagggttact actgattttt cgataaatgt   73200 tttttagat acattaaggt tattgctgtt catgactgta tattacaatt gtcactgttg   73260
ttgctctcca agctgtctgt ataatgtata atcttacaca tgccaagtgg tatgtgaatt   73320
gactaaagga acaatttacc agtatgtgtt tgatattgtg taaaatacaa ttttgagttg   73380
aaataattaa tgttggttgc atctcaacca ttttatgta aattgccgcc tgtgcgatta   73440
gggtcgatca ggcgatttga agacattgta atctggtcga tattttttt tcatacaaac   73500
```

```
aaaataattt aataaagtgt tggcacacaa tttggttgtt ttgcagcatg ttcgtgaacc   73560
ttgtaactct ttattaccaa aaaagtgaga tgtacggttc tcttcgaggt acatgcacat   73620
attttatttc ttctacttaa atatacaaaa tacataatac taaatgtgtc gtattatata   73680
catgtgcatc gagatgttca agacgaccta ctaaacgata tcaggatcca tgattacctc   73740
aagaatgccc tcaatgtagg acggccaaat cagagatgaa cgatactatc tcatctcaga   73800
tccatgaata cctcaagaat gccctcagat gtaggacggt caaattagag ctaaacgacg   73860
ctacctcatt tcatgaaagc gaccggtctg gaagtggata tggaatctat cataagaaat   73920
aatttacatt ttttccattc cgttgctatg taataaaata acaaattagg tttatttcat   73980
gaatgaccat tgcaataatt atattttac cggtgcctat gatgattctt taatactgta    74040
tcagtatatg atcagcaaaa atatatatta tgaaaacgtg tattgcacgt gcacgttcac   74100
tagttgccgt aaaaaagaaa gaagagaaaa gaaaagggta ggagaaagaa accgccgccg   74160
ccgccgccat gactcccgcc gatgccttcc tcatcctcga cttcctcgcc ggcaaccgcc   74220 tcatcccca ctccgtcttc accaccctcc tcgcctccct cccatccgtc tcgccccaca    74280
cctctcctcg cctccgcgca ggcctcgctc tccgcgctct cgactccgcc ctctcggtct   74340
cggagtcgtc ggagatggac gcccccaccc tcctgcgcaa ggcgcgggct gtcctcgccg   74400
acccagacct tgccccccttc tttccgcagc acctcgctgc acccgcctct gccgacgacg   74460
ccccggccgc cgccgtggct cacctcaacc gccttctcga cgttgagtgg gcgagcctcc   74520
ctccttcctc gctcgagatc gcggccgaac ggatcgttgg ctctcaagcc ctccattcgt   74580
gggcaaatgc cgaccacgcc caacgttcaa agcttcgtct actcggtggg catcccttt    74640 cctaatcttc gagttcaatc ccctcttcat catcgctgac tgctcttcct gttatgtaat   74700
ttgggtgtta cttagctcaa attccaggtc ttgaaattac tgctatttca taaattttgg   74760
catatgcctc tgtgcagctg aaaaatactc cacttctttg tatcagtttt actcacccttt  74820 agccgtttct gcagtaggag agtccacagc gcttgagatt ttagacacgc ttcaacggcc   74880
ggatgcatcc acaaatcatc caggaacgct gcctcaagtt gataatgcac cggaaacaaa   74940
cggtgcttct cattgtgctc aacaaaacga tggggccaag agcggtcttg ttaaacaaaa   75000
tgctgaagcc gatcgtcctc aacaagatag tactcgacat caacaagact cggtgcaagg   75060
agcatccaat tcccaactta aagaaagttc agtaacaatg gaatctatta gaggcacggg   75120
tcctgatatc acaggcttta tggaagaagc tacacctcgt gttgctggac agtttgcccc   75180
tgacaacatc aagaaccatc aagtcacagg ttctaagcgc agtttaatgg agaagaatcc   75240
gactgccagc acttatgagg ttatctcgtt atgcttttgt tgtactggtg atgggaaaga   75300
aacaatattg ccaaggttgt gcatattaga tgtagtcatt ctatctcgta gcccatcaac   75360
atgcttagcc agctctttag tttgttatga ccatggctag tgtagaacct ccttgtttga   75420
aatattttgc ttaatacaga atggatgagt tgctctgatg tatcacttgc aggttgttag   75480
ttaatctagt caccttttgat actttgttac gcttctattt ctgtgccctt cgcgaggagt   75540
ggagatggac cccatgtctt gttgactcga ttttttttc ttgtgaagtg cagttgactg    75600
gtttacctac gatctactca taacatatac taattcatgt gcggttatct gttattatat   75660 tatataggg gagcatttgt gtaatattag agcaagttta atagtatagc caactactag    75720
ctccaatttg tttatagcca atctaatagc tcatttatac aataattaca tactacacta   75780
ttaatatttg gtcccacctg tcatacacac actgcgtctt ggagtccgtg ctacagctgg   75840
```

```
ctacaaatct gtagcccgct gcccttctct cttctcattt atcttcttaa aatatgttta    75900
cagctggctt atagtctgct attgtacctg ctcttatgat ggtatctcat cgtattttg     75960 aagtgcagtg ggatggcagc gattccgaag ggaaaaggcc tgcagcaaag cgtcggttac    76020 ccattttga aaggacagca aaaccttctc ctacagctgc ataagacg agaaaaaagt       76080 ggagcgagaa acaagaaaaa accttgctgg aaggggtgga gaagtatgtt tttttcatt    76140 caagcgtgca ttcttggttt ggatttgctg tttaactttc aattttttt tggggaaatc    76200 tatccaattt ccgacacagt cggatgtgct ttgagacgtg tgcaggtgtg atggggtaaa    76260
aaactttggg ttgatcgcac gcaacccact gagctaccca cctttgtga cttacacatc     76320 acttgcaccc tggttatatt gtaattacat gctaattaca tacatttgac agattttttt    76380 gggggtctg tcgaatgtgg aagttccttc ttggtttggt tgctctatga tggtattgat    76440
ccattgagta tgatgagttt tcattgtgaa cataggtatg aaaaggcaa ctggaaagat     76500 atcaaaatgg catccctga tgtatttgaa gatagatcga cagtacgtac tttgatttgc     76560
ttatactatt ttgcttgttt ttagtaaact cgaaggttaa tttggtccct gtgcaggtag    76620
atttgaagga taaattcaga aatttggaaa ggcacctgtg cgcttgaggc gtgcctactt    76680
taggaggaat tgttatggta atatatagcg acttgaagtt agctatgcca aagcagacgc    76740
attctgtagt cctggatgga tgatggtagc tatgtttata gtgccttttt tggttgtgat    76800
tttgtgaagt gtagccagct agtttttattt ggtcggctat ccttgttttg ttttgtacag   76860
gatagaggag cgatatcggt gggaacttcc tgctctgaac gcttatttc tatcttctat     76920 cttcatggct atccttgttt tgttttgtac aggatagagg agcgatgtcg gtgggaactt   76980
cctgctctga acgcttattt tctatcttct atcttaatgt gtctgtattg ttgtttgtcc    77040
ttgctacaat ttccagtggt gctgccagct gtgaatgagc cagttttagt tttcagatat    77100
cttttagcac ttgtctcttg ctttcataat tactagctgg gtgcccatgc gttgcaattg    77160
gaaataatta gagcaacttt aaatcttaat gggtgggatg ataaaaaatg aaccccgtt    77220 gcaaacataa acatcattgt taacacagac aatagctata ttccatttct atggttttca    77280
catattagta acatgaacgg tggaaaaaca taatataaaa gaaatagaat ggcacacaat   77340
tattacggag tgatcaacat gtcaaagttt aaaagtctat tgagggcata tatatcacca   77400
aaataaaaat atacaatcgt gaattttgat attacagaag cacaatgcat tgcatgtagc    77460
atccgaaatc agttaaaaat caggtatctt caccaaattc taaaatcata ttcaaattta    77520
ccaaataact ttgccccaga tgcacaaaag gattaaaaaa atcaagattg tcaacaatgc    77580
actggttgta attagacaac tcttaatcag ccacctcatc tttgctgaac atacaactct    77640
gatagagtct ccatttctct atctggttgt ctggtcctcc atgcaccaag aaagaagtat    77700
attgtttcga aagataaatg gacacattcg cttcttttgc tttctttaaa ccttttgtt     77760 aggttttaaa gcaatcaaag agatatatag agaaatggag gactcctact ggattacctc    77820
cacttgctgg agggctgatc ttatgaaaca gaaagcaact tcagttaaaa gacacagaag    77880
tatagcttaa ggaaaaaggt ccaatgagca tgtcagccaa atatcattat atatctcaga   77940
acttaactgc aagtgtgcaa aatagcaaaa tggatactcg aatatttta ttaaacacgt     78000 ggatgcaatt taaattataa tcaaatatgg taaattttgg agagttaaaa attataccat    78060
acgaacatct gtgttttgat atgataaaat agttttgatg tttctagaac acatatactg    78120
tttttgagtc tataaacaac tggattatct taacctcaaa atgtattcca gatttttatta   78180 aaaatggact gtatcatagc aaattcaaat gactgaaata agtcagtaca caaatcagat    78240
```

| | |
|---|---|
| tttagtatca ttcctgaggg atatagagaa ggaaaattca gaaccaaatt ttcagataag | 78300 |
| tgatgcactg cctaagtgcc tatgtactttt tttatcactc tgacaaggcc acacaaaagt | 78360 |
| tcaaccctaa ttgcactcat gagaaaagac cagggtaacc aaatctagaa ccactaacaa | 78420 |
| acaatatcct tatttgttaa aagataaaaa agtaaattat actcacaata aaagttcagt | 78480 |
| tcttcggtaa tttatctcca agattcagtc tcactgcatt tcacaatgtt gttaaggctt | 78540 |
| aatttcttta gaccctgagg tcaagtataa ttaatttttt agatcatacc aatttacaaa | 78600 |
| aaatgtctgc aaagcaccca tggatcaaaa tatcagtatt atttagatct tgtagtgata | 78660 |
| tgccagaata atatatttgt aaaataggcc aacattgatt atatttgagt gcaatgaaat | 78720 |
| attcaatgta ctacggtcat attatatata gcacatcgaa gcatcatagc cctcctttgt | 78780 |
| taattttggt aattaatgac aagcgctaat tgtggactaa ctattctatt gagcgatata | 78840 |
| tttgagttag gaccacatga tgtacatgcc atggatgatc accgtggatt aaaattaatg | 78900 |
| gcacaaagca atggaacaaa gatggtaaat ctagcatttt attttaattt gatcgaagtg | 78960 |
| ttaggtgatc aaattttgct aggtttattt ctagctttgt cgcactatca agagaggtaa | 79020 |
| tgacctaggt aaagagttga tcaaaatgcc acattaggtc atttgcattg tcacttggtt | 79080 |
| cgagttcatt tcatacatca ttttctgctt gaggacggtc tgaccgaggg cttcatgccg | 79140 |
| gtctaactgg catttcttgg ctggtctgac cgggcggttg gtgagccggg atgtgtgcct | 79200 |
| tggcttgacg atctagagcc gctagagctg acgccggtct gactgggctg ccggcggttt | 79260 |
| gactggagcc gatggcggtc tgactggcta gctgctgccc gtgcattaag tgcacagtaa | 79320 |
| cggctggtgg gcgatttgac tggcaggcaa ttgaggttgg cgatttcgac cccaacgact | 79380 |
| agttttggtg ggtatactcc cccaccagca ggaaggggac cctcttggca cttgcttcac | 79440 |
| ttgcatacac ccccttgcatc cactctcaca ccacttgagc ttttcttcgt ccattgttgg | 79500 |
| tgtcaggagg gttgattgag ccaagacaag tgcattgctt cagtgttaag agttagtgtg | 79560 |
| gcacttgatc atctcctagc cgagtggtta cttgttactc ttttatgttg acgcctccta | 79620 |
| aacggcttgg aggagttgcc cggttgtgat ctcttcgaga agattgtgga gaaggcctag | 79680 |
| tgttggttgt aagtggtttg gagttcacca ccttcaaagt gaacgaagaa ctaccctact | 79740 |
| gatcgaggct tgggtagtcc acccggctcc caccttgccc acctctagac gaaggggact | 79800 |
| cggtggcttt atggattgag cggtgaagtt gggctcgcct caacagggat taggaaacta | 79860 |
| gcgagttttc gaaccttggg tgaaaaattc cttgtctctt gtctctttta cttttgtgca | 79920 |
| atttactttc atagagacat acttaagccc tttcaccc taggcttgca aaacataatc | 79980 |
| tagatgctta gttgtatctc tcgcctacct taccaactta ggttagtttt gattaagtgc | 80040 |
| tactacctct gtcccagatt aattgtaatt ctaggttgtt tagcatatat taaggtttga | 80100 |
| gaaaaaaga ctaatacccct tattaaatgg tttataggta agagtggagg gtagttgatg | 80160 |
| gtaaaatacg aagaaatttg aataagaagt gattgatgag atcattagta ctctattgtc | 80220 |
| acaattattt tgggacaaat tcaaatccta gaaatacaat tattatggta caaaggtagt | 80280 |
| atttatttt aatatcgcct aatcatcccc ctctagtcga catctcaatc ctaggtatca | 80340 |
| gagtttggtc tctcttgatt tgactttacc acctagagag aagatgttga ataaggtgaa | 80400 |
| ctatataggg aaggctccta tgttcaatgg cacaaattat tcccttggaa aattaagatg | 80460 |
| tctactcacc ttaaggctat gagctttcat atagggtttg atagagttag caatcttaag | 80520 |
| gccgcttatg agatttggaa caatttgagt gaaattcatg agggcacaaa tgagtacaag | 80580 |

```
gacaccaagc ttcactttct caagatacga tatgagattt ttggcatatt gcccaaaatt    80640
atagaagata cgcattaatt tatttccaaa aggtatactc atgaagcttg gccgaaggca    80700
aactgtaggt cgaatggaaa aatcatgaat gttttgtcct gaggttaata cttgggaact    80760
tcatgtccaa tgtaacaaca ttccatatct aacactcgtg agattttgga tggaagaaaa    80820
atattcagcc atttcccccc aaggtcaatg ctcattattt tttttccaaa ggctgactca    80880
tgaaatcata atgaagggaa aaatcatgat gtcaacgatt gcaaggccaa cactcatgaa    80940
agattgaccg ggagaagtat tcatgcgttt tcctcaaaag gtaatactca tgaatttcgt    81000
ccgaagacta attataggcc aatgaaaatt ttagtggcaa ccttagtatt agtgaattta    81060
ttgctcaact atcccaaggc taacactcac aaaactctag aaagagaaa aatgtccatt    81120 cattcttttc taaagatta atactcatga attttgattg aaggttatag ctatcgaaat    81180
tatatgctca gggcgataaa atttcgtgcc caacgatccc aaggctgatg agatttttta   81240
tgggagaaaa atatttgtgt ttttactcct aatgtaatca taagctgaag gggaaaaaca    81300
agaaatttgt tttcgaaagg ttaatattta tgattttcat gcctaacaat cccaaggcta    81360
gcactcatga aagattgatc ggggaaacgt attcgtgcat ttcccaccaa aaggttaaca    81420
ctcatgaatt ttggtcaaac cctatatctc acgaaattat aggccaaagg ggaaaattcc    81480
tcaatttttt tcctaagttt agtatttctg aatttcatgc ccaaggatcc caattctaac    81540
actcatgata ttttgggtgg gagaaaagta tttgcgcgtt ttcccgacga agttaatac    81600 tcataaattt atgacgaagg ctataactca tgaaattata ggtcgacagg aaaaatcatg    81660 aatttttttag tcccaaagtt agtattagta aattaatgca caacgatccc aaggctaaca    81720
ctcatgaaac tctacgaagg aatcgagcta acattgccta ccggtcatgg aatcgagcta    81780
ggattttttt gacggctgca gaatcacggg cctcaccctg gagagactgg atttcgagag    81840
gtggaccccc agagattttt ctagaaatga cttaccatag ccacgaagc agcggttgtt    81900 tcggcgaaac gttgaatatc tgagggtcca caacaggttc tcaaggaggt ggttagtgta    81960
ggaatggcac ataggatgtt agggtggata gcttagacga tgtcggtgtc aagcgcgttg    82020
actaaccgcg ccgttaaggt aggctggcgg gcgccacagc gtggaatgct gatggagaat    82080
tatgggcgat attaaaacct tgataacatt gcctaccggt catggaatcg agctaggttt    82140 ttttttgacgg ctgcagaatc atgggcctca ccctggagag actagatttc gagaggtgga    82200
tccccagaga ttttttctaga aatgacttac cataggccac gaagcagcgg ttgtttcggc    82260
gaatggtcga agatctgagg gtccacaact ggtttccaac gaggtggtta gtataggaat    82320
ggcacatagg acgttagggt ggatagatta gacga                               82355

<210> SEQ ID NO 2
<211> LENGTH: 2223
<212> TYPE: DNA
<213> ORGANISM: Oryza longistaminata

<400> SEQUENCE: 2
atgatgggaa ccgctcatca caaccaaacc gccggctctg ccctcggagt cggagtcgga      60
gatgccaacg acgccgtgcc tggggctggg ggtggggggct acagcgaccc ggatggcgga    120
ccaacctccg gtgtgcagcc gccaccgcag gtctgctggg agcgcttcat ccagaagaag    180
actatcaaag tcttgctagt tgagagcgat gactccacca ggcaggtggt cagtgccctg    240
cttcgtcact gcatgtatga agtcatccct gctgaaaatg ccagcaagc atggacatat    300 ctagaagata tgcaaaacag cattgatctt gttttgacag aggttgttat gcctggtgta    360
```

```
tctggaatttc tctattgag taggatcatg aaccacaata tttgcaagaa tattccagtg    420
attatgatgt cttcaaatga tgctatgggt acagttttta agtgtttgtc aaagggcgct    480
gttgacttct tagtcaagcc catacgtaag aatgaactta agaacctatg cagcatgtg    540 tggagacggt gccacagctc cagtggcagt ggaagtgaaa gtggcattca gacacaaaag    600
tgtgccaaat caaaaagtgg ggatgaatcc gataataaca gtggcagcaa tgacgatgac    660
gacgacgatg tgtaagcat gggacttaat gcaagagtg gcagtgataa cggcagtggc    720
actcaaagct catggacaaa gcgcgctgtt gagattgaca gtccacaggc tatgtctcca    780
gatcaattag ctgatccacc tgatagcact tgtgcacaag tgatccaccc gaagtcagag    840
atatgcagca atagatggtt accatgtaca agcaacaaaa attccaagaa acaaaaagaa    900
actaatgatg acttcaaggg gaaggacttg gaaataggtt ctcctagaaa tttaaacaca    960
gcttatcaat cctctccgaa tgagagatcc atcaaaccaa cagatagacg gaatgaatat   1020
ccactgcaaa acaattcaaa ggaggcagcg atggaaaatc tggaggagtc aagtgttcga   1080
gctgctgact taattggttc gatggccaaa acatggatg cacaacaggc agcaagagcc   1140
gcaaatgccc ctaattgctc ctccaaagtg ccagaaggga agataagaa ccgtgataat   1200 attatgccat cacttgaatt aagtttgaaa aggtcaagat cgactgggga tggtgcaaat   1260
gcaatccaag aggaacaacg gaatgttttg agacgatccg atctctcggc atttacgagg   1320
taccatacac ctgtggcttc caatcaaggt gggacaggat tcgtgggaag ctgttcgccg   1380
catgataata gctcagaggc tatgaaaacg gattctactt acaacatgaa gtcaaactca   1440
gatgctgcac caataaaaca aggttctaat ggtagtagca ataacaatga catgggttcc   1500
actacaaaga acgttgtgac aaagcctagt acaaataagg agagagtaat gtcaccctca   1560
gctgttaagg ctaatggaca cacatcagca tttcatcctg cacagcactg gacgtctcca   1620
gctaatacaa caggaaaaga aaagactgat gaagtggcta acaatgcagc aaagagggct   1680
cagcctggtg aagtacagag caacctcgta caacaccctc gcccaatact tcattatgtt   1740
catttcgatg tgtcacgtga aatggtggta tccggggccc ctcaatgtgg ttcatccaat   1800
gtatttgatc ctcctgtcga aggtcatgct gccaactatg tgtcaatgg aagcaactca   1860 ggcagtaaca atggaagcaa tgggcagaat gggagtacga ctgctgtaaa tgctgaacgg   1920
ccaaatatgg agatcgctaa tggcaccatc aacaaaagtg gacctggagg tgcaatgga   1980 agtggaagcg gcagtggcaa tgacatgtat ctgaaacgct tcactcaaca agagcataga   2040
gtggctgcag tgatcaagtt tagacagaaa aggaaagagc gcaacttcgg aaaaaaggtg   2100
cggtaccaga gcagaaagag gctggccgag cagcggccaa gggtccgcgg acagttcgtg   2160
cggcaagctg tgcaagacca acaacagcag ggtggtgggc gcgaagcagc agcggacaga   2220
tga                                                                 2223
```

<210> SEQ ID NO 3
<211> LENGTH: 740
<212> TYPE: PRT
<213> ORGANISM: Oryza longistaminata

<400> SEQUENCE: 3

Met Met Gly Thr Ala His His Asn Gln Thr Ala Gly Ser Ala Leu Gly
1               5                   10                  15

Val Gly Val Gly Asp Ala Asn Asp Ala Val Pro Gly Ala Gly Gly Gly
            20                  25                  30

-continued

Gly Tyr Ser Asp Pro Asp Gly Pro Thr Ser Gly Val Gln Pro Pro
         35                  40                  45

Pro Gln Val Cys Trp Glu Arg Phe Ile Gln Lys Thr Ile Lys Val
 50                  55                  60

Leu Leu Val Glu Ser Asp Asp Ser Thr Arg Gln Val Val Ser Ala Leu
 65                  70                  75                  80

Leu Arg His Cys Met Tyr Glu Val Ile Pro Ala Glu Asn Gly Gln Gln
                     85                  90                  95

Ala Trp Thr Tyr Leu Glu Asp Met Gln Asn Ser Ile Asp Leu Val Leu
                 100                 105                 110

Thr Glu Val Val Met Pro Gly Val Ser Gly Ile Ser Leu Leu Ser Arg
             115                 120                 125

Ile Met Asn His Asn Ile Cys Lys Asn Ile Pro Val Ile Met Met Ser
130                 135                 140

Ser Asn Asp Ala Met Gly Thr Val Phe Lys Cys Leu Ser Lys Gly Ala
145                 150                 155                 160

Val Asp Phe Leu Val Lys Pro Ile Arg Lys Asn Glu Leu Lys Asn Leu
                 165                 170                 175

Trp Gln His Val Trp Arg Arg Cys His Ser Ser Gly Ser Gly Ser
                 180                 185                 190

Glu Ser Gly Ile Gln Thr Gln Lys Cys Ala Lys Ser Lys Ser Gly Asp
            195                 200                 205

Glu Ser Asp Asn Asn Ser Gly Ser Asn Asp Asp Asp Asp Asp Gly
            210                 215                 220

Val Ser Met Gly Leu Asn Ala Arg Asp Gly Ser Asp Asn Gly Ser Gly
225                 230                 235                 240

Thr Gln Ser Ser Trp Thr Lys Arg Ala Val Glu Ile Asp Ser Pro Gln
                245                 250                 255

Ala Met Ser Pro Asp Gln Leu Ala Asp Pro Pro Asp Ser Thr Cys Ala
                260                 265                 270

Gln Val Ile His Pro Lys Ser Glu Ile Cys Ser Asn Arg Trp Leu Pro
            275                 280                 285

Cys Thr Ser Asn Lys Asn Ser Lys Lys Gln Lys Glu Thr Asn Asp Asp
290                 295                 300

Phe Lys Gly Lys Asp Leu Glu Ile Gly Ser Pro Arg Asn Leu Asn Thr
305                 310                 315                 320

Ala Tyr Gln Ser Ser Pro Asn Glu Arg Ser Ile Lys Pro Thr Asp Arg
                325                 330                 335

Arg Asn Glu Tyr Pro Leu Gln Asn Asn Ser Lys Glu Ala Ala Met Glu
                340                 345                 350

Asn Leu Glu Glu Ser Ser Val Arg Ala Ala Asp Leu Ile Gly Ser Met
                355                 360                 365

Ala Lys Asn Met Asp Ala Gln Gln Ala Ala Arg Ala Ala Asn Ala Pro
            370                 375                 380

Asn Cys Ser Ser Lys Val Pro Glu Gly Lys Asp Lys Asn Arg Asp Asn
385                 390                 395                 400

Ile Met Pro Ser Leu Glu Leu Ser Leu Lys Arg Ser Arg Ser Thr Gly
                405                 410                 415

Asp Gly Ala Asn Ala Ile Gln Glu Gln Arg Asn Val Leu Arg Arg
                420                 425                 430

Ser Asp Leu Ser Ala Phe Thr Arg Tyr His Thr Pro Val Ala Ser Asn
            435                 440                 445

Gln Gly Gly Thr Gly Phe Val Gly Ser Cys Ser Pro His Asp Asn Ser

```
        450             455             460
Ser Glu Ala Met Lys Thr Asp Ser Thr Tyr Asn Met Lys Ser Asn Ser
465                     470                     475                 480

Asp Ala Ala Pro Ile Lys Gln Gly Ser Asn Gly Ser Ser Asn Asn Asn
                485                     490                     495

Asp Met Gly Ser Thr Thr Lys Asn Val Val Lys Pro Ser Thr Asn
            500                     505                     510

Lys Glu Arg Val Met Ser Pro Ser Ala Val Lys Ala Asn Gly His Thr
            515                     520                     525

Ser Ala Phe His Pro Ala Gln His Trp Thr Ser Pro Ala Asn Thr Thr
530                     535                     540

Gly Lys Glu Lys Thr Asp Glu Val Ala Asn Asn Ala Ala Lys Arg Ala
545                     550                     555                 560

Gln Pro Gly Glu Val Gln Ser Asn Leu Val Gln His Pro Arg Pro Ile
                565                     570                     575

Leu His Tyr Val His Phe Asp Val Ser Arg Glu Asn Gly Gly Ser Gly
            580                     585                     590

Ala Pro Gln Cys Gly Ser Ser Asn Val Phe Asp Pro Val Glu Gly
            595                     600                     605

His Ala Ala Asn Tyr Gly Val Asn Gly Ser Asn Ser Gly Ser Asn Asn
610                     615                     620

Gly Ser Asn Gly Gln Asn Gly Ser Thr Thr Ala Val Asn Ala Glu Arg
625                     630                     635                 640

Pro Asn Met Glu Ile Ala Asn Gly Thr Ile Asn Lys Ser Gly Pro Gly
                645                     650                     655

Gly Gly Asn Gly Ser Gly Ser Gly Ser Gly Asn Asp Met Tyr Leu Lys
            660                     665                     670

Arg Phe Thr Gln Gln Glu His Arg Val Ala Ala Val Ile Lys Phe Arg
            675                     680                     685

Gln Lys Arg Lys Glu Arg Asn Phe Gly Lys Lys Val Arg Tyr Gln Ser
690                     695                     700

Arg Lys Arg Leu Ala Glu Gln Arg Pro Arg Val Arg Gly Gln Phe Val
705                     710                     715                 720

Arg Gln Ala Val Gln Asp Gln Gln Gln Gly Gly Arg Glu Ala
                725                     730                     735

Ala Ala Asp Arg
            740

<210> SEQ ID NO 4
<211> LENGTH: 2229
<212> TYPE: DNA
<213> ORGANISM: Oryza sativa (cv. Nipponbare)

<400> SEQUENCE: 4
atgatgggaa ccgctcatca caaccaaacc gccggctctg ccctcggagt cggagtcgga      60
gatgccaacg acgccgtgcc tggggctggg ggtggggggct acagcgaccc ggatggcgga     120
ccaatctccg gtgtgcagcg gccaccgcag gtctgctggg agcgcttcat ccagaagaag     180
actatcaaag tcttgctagt tgatagcgat gactccacca ggcaggtggt cagtgccctg     240
cttcgtcact gcatgtatga agtcatccct gctgaaaatg ccagcaagc atggacatat      300 ctagaagata tgcaaaacag cattgatctt gttttgacag aggttgttat gcctggtgta     360
tctggaattt ctctattgag taggatcatg aaccacaata tttgcaagaa tattccagtg     420
attatgatgt cttcaaatga tgctatgggt acagttttta agtgtttgtc aaagggcgct     480
```

```
gttgacttct tagtcaagcc catacgtaag aatgaactta agaacctatg gcagcatgtg    540
tggagacggt gccacagctc cagtggcagt ggaagtgaaa gtggcattca gacacaaaag    600
tgtgccaaat caaaaagtgg ggatgaatcc aataataaca atggcagcaa tgacgatgat    660
gacgacgatg gtgtaatcat gggacttaat gcaagagatg gcagtgataa cggcagtggc    720
actcaagcgc agagctcatg gacaaagcgc gctgttgaga ttgacagtcc acaggctatg    780
tctccagatc aattagctga tccacctgat agcacttgtg cacaagtgat ccacctgaag    840
tcagatatat gcagcaatag atggttacca tgtacaagca acaaaaattc caagaaacaa    900
aaagaaacta atgatgactt caaggggaag gacttggaaa taggttctcc tagaaattta    960
aacacagctt atcaatcctc tccgaatgag agatccatca accaacagat agacggaat    1020
gaatatccac tgcaaaacaa ttcaaaggag gcagcgatgg aaaatctgga ggagtcaagt   1080
gttcgagctg ctgacttaat tggttcgatg gccaaaaaca tggatgcaca acaggcagca   1140
agagccgcaa atgcccctaa ttgctcctcc aaagtgccag aagggaaaga taagaaccgt   1200
gataatatta tgccatcact tgaattaagt ttgaaaaggt caagatcgac tggggatggt   1260
gcaaacgcaa tccaagagga acaacggaat gttttgagac gatcagatct ctcggcattt   1320
acgaggtacc atacacctgt ggcttccaat caaggtggga caggattcat gggaagctgt   1380
tcgctgcatg ataatagctc agaggctatg aaaacggatt ctgcttacaa catgaagtca   1440
aactcagatg ctgcaccaat aaaacaaggt tctaatggta gtagcaataa caatgacatg   1500
ggttccacta caaagaacgt tgtgacaaag cctagtacaa ataaggagag agtaatgtca   1560
ccctcagctg ttaaggctaa tggacacaca tcagcatttc atcctgcaca gcactggacg   1620
tctccagcta atacaacagg aaaagaaaag actgatgaag tggctaacaa tgcagcaaag   1680
agggctcagc ctggtgaagt acagagcaac ctcgtacaac accctcgccc aatacttcat   1740
tatgttcatt tcgatgtgtc acgtgagaat ggtggatccg gggcccctca atgtggttca   1800
tccaatgtat ttgatcctcc tgtcgaaggt catgctgcca actatggtgt caatggaagc   1860
aactcaggca gtaacaatgg aagcaatggg cagaatggga gtacgactgc tgtaaatgct   1920
gaacggccaa atatggagat cgctaatggc accatcaaca aaagtggacc tggaggtggc   1980
aatggaagtg gaagcggcag tgcaatgac atgtatctga aacgcttcac tcaacgagag   2040
catagagtgg ctgcagtgat caagtttaga cagaaaagga aagagcgcaa cttcggaaaa   2100
aaggtgcggt accagagcag aaagaggctg gccgagcagc ggccaagggt ccgcggacag   2160
ttcgtgcggc aagctgtgca agaccaacaa cagcagggtg gtgggcgcga agcggcagcg   2220
gacagatga                                                          2229
```

<210> SEQ ID NO 5
<211> LENGTH: 742
<212> TYPE: PRT
<213> ORGANISM: Oryza sativa (cv.Nipponbare)

<400> SEQUENCE: 5

```
Met Met Gly Thr Ala His His Asn Gln Thr Ala Gly Ser Ala Leu Gly
1               5                   10                  15

Val Gly Val Gly Asp Ala Asn Asp Ala Val Pro Gly Ala Gly Gly Gly
            20                  25                  30

Gly Tyr Ser Asp Pro Asp Gly Gly Pro Ile Ser Gly Val Gln Arg Pro
        35                  40                  45

Pro Gln Val Cys Trp Glu Arg Phe Ile Gln Lys Lys Thr Ile Lys Val
```

-continued

```
                   50                  55                  60
Leu Leu Val Asp Ser Asp Ser Thr Arg Gln Val Ser Ala Leu
 65                  70                  75                  80
Leu Arg His Cys Met Tyr Glu Val Ile Pro Ala Glu Asn Gly Gln Gln
                     85                  90                  95
Ala Trp Thr Tyr Leu Glu Asp Met Gln Asn Ser Ile Asp Leu Val Leu
                    100                 105                 110
Thr Glu Val Val Met Pro Gly Val Ser Gly Ile Ser Leu Leu Ser Arg
                    115                 120                 125
Ile Met Asn His Asn Ile Cys Lys Asn Ile Pro Val Ile Met Met Ser
                130                 135                 140
Ser Asn Asp Ala Met Gly Thr Val Phe Lys Cys Leu Ser Lys Gly Ala
145                 150                 155                 160
Val Asp Phe Leu Val Lys Pro Ile Arg Lys Asn Glu Leu Lys Asn Leu
                    165                 170                 175
Trp Gln His Val Trp Arg Arg Cys His Ser Ser Ser Gly Ser Gly Ser
                    180                 185                 190
Glu Ser Gly Ile Gln Thr Gln Lys Cys Ala Lys Ser Lys Ser Gly Asp
                195                 200                 205
Glu Ser Asn Asn Asn Gly Ser Asn Asp Asp Asp Asp Asp Gly
210                 215                 220
Val Ile Met Gly Leu Asn Ala Arg Asp Gly Ser Asp Asn Gly Ser Gly
225                 230                 235                 240
Thr Gln Ala Gln Ser Ser Trp Thr Lys Arg Ala Val Glu Ile Asp Ser
                    245                 250                 255
Pro Gln Ala Met Ser Pro Asp Gln Leu Ala Asp Pro Pro Asp Ser Thr
                    260                 265                 270
Cys Ala Gln Val Ile His Leu Lys Ser Asp Ile Cys Ser Asn Arg Trp
                    275                 280                 285
Leu Pro Cys Thr Ser Asn Lys Asn Ser Lys Lys Gln Lys Glu Thr Asn
                290                 295                 300
Asp Asp Phe Lys Gly Lys Asp Leu Glu Ile Gly Ser Pro Arg Asn Leu
305                 310                 315                 320
Asn Thr Ala Tyr Gln Ser Ser Pro Asn Glu Arg Ser Ile Lys Pro Thr
                    325                 330                 335
Asp Arg Arg Asn Glu Tyr Pro Leu Gln Asn Asn Ser Lys Glu Ala Ala
                340                 345                 350
Met Glu Asn Leu Glu Glu Ser Ser Val Arg Ala Ala Asp Leu Ile Gly
                355                 360                 365
Ser Met Ala Lys Asn Met Asp Ala Gln Gln Ala Ala Arg Ala Ala Asn
370                 375                 380
Ala Pro Asn Cys Ser Ser Lys Val Pro Glu Gly Lys Asp Lys Asn Arg
385                 390                 395                 400
Asp Asn Ile Met Pro Ser Leu Glu Leu Ser Leu Lys Arg Ser Arg Ser
                    405                 410                 415
Thr Gly Asp Gly Ala Asn Ala Ile Gln Glu Glu Gln Arg Asn Val Leu
                    420                 425                 430
Arg Arg Ser Asp Leu Ser Ala Phe Thr Arg Tyr His Thr Pro Val Ala
                435                 440                 445
Ser Asn Gln Gly Gly Thr Gly Phe Met Gly Ser Cys Ser Leu His Asp
                450                 455                 460
Asn Ser Ser Glu Ala Met Lys Thr Asp Ser Ala Tyr Asn Met Lys Ser
465                 470                 475                 480
```

```
Asn Ser Asp Ala Ala Pro Ile Lys Gln Gly Ser Asn Gly Ser Ser Asn
            485                 490                 495
Asn Asn Asp Met Gly Ser Thr Thr Lys Asn Val Val Thr Lys Pro Ser
        500                 505                 510
Thr Asn Lys Glu Arg Val Met Ser Pro Ser Ala Val Lys Ala Asn Gly
    515                 520                 525
His Thr Ser Ala Phe His Pro Ala Gln His Trp Thr Ser Pro Ala Asn
530                 535                 540
Thr Thr Gly Lys Glu Lys Thr Asp Glu Val Ala Asn Asn Ala Ala Lys
545                 550                 555                 560
Arg Ala Gln Pro Gly Glu Val Gln Ser Asn Leu Val Gln His Pro Arg
                565                 570                 575
Pro Ile Leu His Tyr Val His Phe Asp Val Ser Arg Glu Asn Gly Gly
            580                 585                 590
Ser Gly Ala Pro Gln Cys Gly Ser Ser Asn Val Phe Asp Pro Pro Val
        595                 600                 605
Glu Gly His Ala Ala Asn Tyr Gly Val Asn Gly Ser Asn Ser Gly Ser
    610                 615                 620
Asn Asn Gly Ser Asn Gly Gln Asn Gly Ser Thr Thr Ala Val Asn Ala
625                 630                 635                 640
Glu Arg Pro Asn Met Glu Ile Ala Asn Gly Thr Ile Asn Lys Ser Gly
                645                 650                 655
Pro Gly Gly Gly Asn Gly Ser Gly Ser Gly Ser Gly Asn Asp Met Tyr
            660                 665                 670
Leu Lys Arg Phe Thr Gln Arg Glu His Arg Val Ala Ala Val Ile Lys
        675                 680                 685
Phe Arg Gln Lys Arg Lys Glu Arg Asn Phe Gly Lys Lys Val Arg Tyr
    690                 695                 700
Gln Ser Arg Lys Arg Leu Ala Glu Gln Arg Pro Arg Val Arg Gly Gln
705                 710                 715                 720
Phe Val Arg Gln Ala Val Gln Asp Gln Gln Gln Gly Gly Gly Arg
                725                 730                 735
Glu Ala Ala Ala Asp Arg
            740

<210> SEQ ID NO 6
<211> LENGTH: 23
<212> TYPE: DNA
<213> ORGANISM: Artificial Sequence
<220> FEATURE:
<223> OTHER INFORMATION: Primer longi-PRR 2F

<400> SEQUENCE: 6
accaaaccgc cggctctgcc ctc                                          23

<210> SEQ ID NO 7
<211> LENGTH: 23
<212> TYPE: DNA
<213> ORGANISM: Artificial Sequence
<220> FEATURE:
<223> OTHER INFORMATION: Primer longi-PRR 2R

<400> SEQUENCE: 7
ggtaggtagg taggtcatct gtc                                          23

<210> SEQ ID NO 8
<211> LENGTH: 34
```

```
<212> TYPE: DNA
<213> ORGANISM: Artificial Sequence
<220> FEATURE:
<223> OTHER INFORMATION: Primer longi-PRR 1F

<400> SEQUENCE: 8
cgcttcgaag atatcatcat cattcatgta tgag                             34

<210> SEQ ID NO 9
<211> LENGTH: 24
<212> TYPE: DNA
<213> ORGANISM: Artificial Sequence
<220> FEATURE:
<223> OTHER INFORMATION: Primer longi-PRR 1R

<400> SEQUENCE: 9
agccggcggt ttggttgtga tgag                                        24

<210> SEQ ID NO 10
<211> LENGTH: 24
<212> TYPE: DNA
<213> ORGANISM: Artificial Sequence
<220> FEATURE:
<223> OTHER INFORMATION: Primer longi-PRR 3F

<400> SEQUENCE: 10
acctacctac ctacctacgc aatg                                        24

<210> SEQ ID NO 11
<211> LENGTH: 31
<212> TYPE: DNA
<213> ORGANISM: Artificial Sequence
<220> FEATURE:
<223> OTHER INFORMATION: Primer longi-PRR 3R

<400> SEQUENCE: 11
gctagaattc gagctctcca gggagcaggg a                                31

<210> SEQ ID NO 12
<211> LENGTH: 24
<212> TYPE: DNA
<213> ORGANISM: Artificial Sequence
<220> FEATURE:
<223> OTHER INFORMATION: Primer for PCR of PRR gene

<400> SEQUENCE: 12
cgaggtacca tacacctgtg gctt                                        24

<210> SEQ ID NO 13
<211> LENGTH: 24
<212> TYPE: DNA
<213> ORGANISM: Artificial Sequence
<220> FEATURE:
<223> OTHER INFORMATION: Primer for PCR of PRR gene

<400> SEQUENCE: 13
gcatctgagt ttgacttcat gttg                                        24

<210> SEQ ID NO 14
<211> LENGTH: 2184
<212> TYPE: DNA
<213> ORGANISM: Arabidopsis thaliana

<400> SEQUENCE: 14
atgaatgcta atgaggaggg ggagggttca cgttacccaa tcactgatcg aaagaccgga    60
```

| | | | |
|---|---|---|---|
| gagacgaaat | tcgatagggt tgagagtcgg acagagaagc atagtgaaga agagaaaact | 120 |
| aatggaatta | ctatggatgt gagaaatggg agttcaggtg gactgcaaat tccattgtcg | 180 |
| caacaaacag | cggcaactgt ctgttgggaa aggtttcttc atgtgagaac cattagagtt | 240 |
| ctgcttgtcg | aaaatgacga ctgcactcgt tatatcgtta ctgcacttct tcgcaattgt | 300 |
| agctatgaag | ttgttgaggc gtcaaatggg atacaagctt ggaaggtgtt agaagatcta | 360 |
| aacaatcata | ttgatattgt gctaacagag gtgatcatgc cttacttatc tggtatcggt | 420 |
| ctcttgtgca | agattttgaa ccacaaatct cgtcggaaca tccctgtcat catgatgtca | 480 |
| tctcatgact | caatggggct ggtctttaag tgcttatcga aaggagctgt tgactttctt | 540 |
| gttaagccaa | taagaaaaaa tgagcttaag atcctttggc agcatgtttg agaagatgc | 600 |
| caaagttcta | gtggtagtgg aagtgagagc ggaacgcatc aaactcaaaa gtctgtgaaa | 660 |
| tcgaaaagta | ttaaaaaatc tgatcaagat tcaggaagca gtgatgagaa tgaaaatggg | 720 |
| agcattggcc | tgaatgctag tgatggaagt agtgatggga gtggcgctca gagctcttgg | 780 |
| acgaaaaaag | ctgtggatgt tgatgacagt ccacgagcgg tatctctatg ggaccgagtt | 840 |
| gatagcactt | gcgcccaagt ggtacattct aaccctgagt ttccaagtaa tcagttggtt | 900 |
| gcaccacctg | ctgagaagga gactcaagaa catgatgata aatttgaaga tgtcacaatg | 960 |
| ggtagagact | tggagattag cattcgtaga aactgtgatc tggccctgga gccaaaagat | 1020 |
| gaaccccctat | ctaaaactac tggcattatg agacaggata attcgtttga aaagagctct | 1080 |
| agtaaatgga | aaatgaaagt tggaaaagga ccattggacc tcagtagcga aagtccttca | 1140 |
| agtaaacaaa | tgcatgaaga tggaggctcg agtttcaaag ctatgtctag ccaccttcaa | 1200 |
| gataacagag | aacctgaggc gcctaacact cacttgaaaa ctttagatac aaatgaagct | 1260 |
| tctgttaaaa | tttctgaaga gctaatgcac gtggaacata gttcaaagag gcatagagga | 1320 |
| actaaagatg | atgggacact agttagggat gatcggaatg tgctgaggcg ttcagagggc | 1380 |
| tcagcttttct | caaggtataa tccagcctca aatgccaata agattctgg tgggaactta | 1440 |
| ggaagcactt | cgcttcagga taataatagt caggatctta taaaaaagac tgaagcagca | 1500 |
| tatgattgtc | actcgaacat gaatgagagt ctcccccata atcatcgctc acatgtcggt | 1560 |
| agcaataact | ttgatatgag ttccacgact gagaacaacg ctttcacaaa accaggagct | 1620 |
| ccaaaagtaa | gctcagcagg atcttcatca gtgaagcatt catcgtttca gcctttaccc | 1680 |
| tgtgatcatc | ataataatca tgcctcctat aaccttgtcc atgtcgctga gaggaagaag | 1740 |
| ctaccgccac | aatgtggatc ctcaaatgtg tacaacgaaa cgattgaagg taacaacaac | 1800 |
| acagtgaatt | acagtgtgaa tggaagtgta tcaggtagtg gtcatggaag taatgggcca | 1860 |
| tatgaagca | gtaacggtat gaatgctgga ggaatgaata tgggaagtga taatggtgct | 1920 |
| ggcaaaaatg | gaaatggcga tggtagtgga agcggaagtg gaagtggtag cggaaacttg | 1980 |
| gcggatgaaa | ataagatctc tcaaagggaa gctgctttga caaagttccg tcagaagaga | 2040 |
| aaagagaggt | gcttccgaaa gaaggtacga taccaaagcc ggaaaaaact agcagaacaa | 2100 |
| cgccctcgag | tgcgaggcca atttgtgcgt aaaacagccg ctgcaactga tgataacgac | 2160 |
| ataaaaaaca | ttgaggatag ctaa | 2184 |

<210> SEQ ID NO 15
<211> LENGTH: 727
<212> TYPE: PRT
<213> ORGANISM: Arabidopsis thaliana
<400> SEQUENCE: 15

-continued

```
Met Asn Ala Asn Glu Glu Gly Glu Gly Ser Arg Tyr Pro Ile Thr Asp
  1               5                  10                  15

Arg Lys Thr Gly Glu Thr Lys Phe Asp Arg Val Glu Ser Arg Thr Glu
                 20                  25                  30

Lys His Ser Glu Glu Glu Lys Thr Asn Gly Ile Thr Met Asp Val Arg
                 35                  40                  45

Asn Gly Ser Ser Gly Gly Leu Gln Ile Pro Leu Ser Gln Gln Thr Ala
 50                  55                      60

Ala Thr Val Cys Trp Glu Arg Phe Leu His Val Arg Thr Ile Arg Val
 65              70                  75                  80

Leu Leu Val Glu Asn Asp Cys Thr Arg Tyr Ile Val Thr Ala Leu
                 85                  90                  95

Leu Arg Asn Cys Ser Tyr Glu Val Val Glu Ala Ser Asn Gly Ile Gln
                100                 105                 110

Ala Trp Lys Val Leu Glu Asp Leu Asn Asn His Ile Asp Ile Val Leu
            115                 120                 125

Thr Glu Val Ile Met Pro Tyr Leu Ser Gly Ile Gly Leu Leu Cys Lys
130                 135                 140

Ile Leu Asn His Lys Ser Arg Arg Asn Ile Pro Val Ile Met Met Ser
145                 150                 155                 160

Ser His Asp Ser Met Gly Leu Val Phe Lys Cys Leu Ser Lys Gly Ala
                165                 170                 175

Val Asp Phe Leu Val Lys Pro Ile Arg Lys Asn Glu Leu Lys Ile Leu
            180                 185                 190

Trp Gln His Val Trp Arg Arg Cys Gln Ser Ser Gly Ser Gly Ser
            195                 200                 205

Glu Ser Gly Thr His Gln Thr Gln Lys Ser Val Lys Ser Lys Ser Ile
210                 215                 220

Lys Lys Ser Asp Gln Asp Ser Gly Ser Ser Asp Glu Asn Glu Asn Gly
225                 230                 235                 240

Ser Ile Gly Leu Asn Ala Ser Asp Gly Ser Ser Asp Gly Ser Gly Ala
                245                 250                 255

Gln Ser Ser Trp Thr Lys Lys Ala Val Asp Val Asp Ser Pro Arg
            260                 265                 270

Ala Val Ser Leu Trp Asp Arg Val Asp Ser Thr Cys Ala Gln Val Val
            275                 280                 285

His Ser Asn Pro Glu Phe Pro Ser Asn Gln Leu Val Ala Pro Pro Ala
290                 295                 300

Glu Lys Glu Thr Gln Glu His Asp Asp Lys Phe Glu Asp Val Thr Met
305                 310                 315                 320

Gly Arg Asp Leu Glu Ile Ser Ile Arg Arg Asn Cys Asp Leu Ala Leu
                325                 330                 335

Glu Pro Lys Asp Glu Pro Leu Ser Lys Thr Thr Gly Ile Met Arg Gln
            340                 345                 350

Asp Asn Ser Phe Glu Lys Ser Ser Lys Trp Lys Met Lys Val Gly
            355                 360                 365

Lys Gly Pro Leu Asp Leu Ser Ser Glu Ser Pro Ser Ser Lys Gln Met
370                 375                 380

His Glu Asp Gly Gly Ser Ser Phe Lys Ala Met Ser Ser His Leu Gln
385                 390                 395                 400

Asp Asn Arg Glu Pro Glu Ala Pro Asn Thr His Leu Lys Thr Leu Asp
                405                 410                 415
```

```
Thr Asn Glu Ala Ser Val Lys Ile Ser Glu Leu Met His Val Glu
            420                 425                 430

His Ser Ser Lys Arg His Arg Gly Thr Lys Asp Asp Gly Thr Leu Val
        435                 440                 445

Arg Asp Asp Arg Asn Val Leu Arg Arg Ser Glu Gly Ser Ala Phe Ser
450                 455                 460

Arg Tyr Asn Pro Ala Ser Asn Ala Asn Lys Ile Ser Gly Gly Asn Leu
465                 470                 475                 480

Gly Ser Thr Ser Leu Gln Asp Asn Asn Ser Gln Asp Leu Ile Lys Lys
                485                 490                 495

Thr Glu Ala Ala Tyr Asp Cys His Ser Asn Met Asn Glu Ser Leu Pro
            500                 505                 510

His Asn His Arg Ser His Val Gly Ser Asn Asn Phe Asp Met Ser Ser
        515                 520                 525

Thr Thr Glu Asn Asn Ala Phe Thr Lys Pro Gly Ala Pro Lys Val Ser
530                 535                 540

Ser Ala Gly Ser Ser Val Lys His Ser Ser Phe Gln Pro Leu Pro
545                 550                 555                 560

Cys Asp His His Asn Asn His Ala Ser Tyr Asn Leu Val His Val Ala
                565                 570                 575

Glu Arg Lys Lys Leu Pro Pro Gln Cys Gly Ser Ser Asn Val Tyr Asn
            580                 585                 590

Glu Thr Ile Glu Gly Asn Asn Asn Thr Val Asn Tyr Ser Val Asn Gly
        595                 600                 605

Ser Val Ser Gly Ser Gly His Gly Ser Asn Gly Pro Tyr Gly Ser Ser
610                 615                 620

Asn Gly Met Asn Ala Gly Gly Met Asn Met Gly Ser Asp Asn Gly Ala
625                 630                 635                 640

Gly Lys Asn Gly Asn Gly Asp Gly Ser Gly Ser Gly Ser Gly
                645                 650                 655

Ser Gly Asn Leu Ala Asp Glu Asn Lys Ile Ser Gln Arg Glu Ala Ala
                660                 665                 670

Leu Thr Lys Phe Arg Gln Lys Arg Lys Glu Arg Cys Phe Arg Lys Lys
            675                 680                 685

Val Arg Tyr Gln Ser Arg Lys Lys Leu Ala Glu Gln Arg Pro Arg Val
        690                 695                 700

Arg Gly Gln Phe Val Arg Lys Thr Ala Ala Ala Thr Asp Asp Asn Asp
705                 710                 715                 720

Ile Lys Asn Ile Glu Asp Ser
                725

<210> SEQ ID NO 16
<211> LENGTH: 2298
<212> TYPE: DNA
<213> ORGANISM: Sorghum

<400> SEQUENCE: 16
atgggtagcg cttgccaagc tggcatggac gggccttccc gcaaggatgt gttgggata      60 gggaatgtcg ccttagagaa tggccaccat gaggttggag ctgatgcaga tgaatggagg    120
gaaaaggaag aggacttggc caatgggcac agtgcgccac cgggcatgca gcaggtggat    180
gagcaggagc aacaaggaca aagcattcac tgggagaggt tcctacctgt gaagacactg    240
agagtcatgc tggtggagaa tgatgactct actcgtcagg tggtcagtgc cctgctcctg    300
aagtgctgct atgaagttat ccctgctgaa atggttcac atgcatggcg atatcttgaa    360
```

```
gatctgcaga acaacattga ccttgtattg actgaggttt tcatgccttg tctatctggc      420
atcggtctgc ttagcaaaat cacaagtcac aaaatttgca aggacattcc tgtgattatg      480
atgtcttcaa atgactctat gagtatggtg tttaagtgtt tgtcgaaggg agcagttgac      540
ttcttggtaa agccactacg taagaatgag cttaagaacc tttggcagca cgtttggagg      600
cgatgccaca gttccagtgg cagtggaagt gaaagcggca tccagacaca gaagtgtgcc      660
aaaccaaata ctggtgatga gtatgagaac gacagtgaca gcaatcatga tgatgaagaa      720
aatgatgaag acgacgacga tgacttcagt gtcggactca atgctaggga tggaagtgat      780
aatggcagtg gtactcaaag ctcatggaca aaacgtgctg tggagattga cagtccagaa      840
cctatgtctc ctgatcaact agcagatcca cctgatagta catgtgcaca agtaattcac      900
cccaaatcag agatatgcag taacaagtgg ctaccgacag caaacaaaag gaatggcaag      960
aaacataagg agaataaaga tgaatctatg ggaagatact tagaaatagg tgctcctagg     1020
aactcaagtg cagaatatca atcatctctc aatgacgtat ctgttaatcc aacagaaaaa     1080
cgtcatgaga ctcacatgcc caatgcaaa tccaaaaaga aatgatggc agaagatgat      1140 tgtacagaca tacctagtga aataaatact gaaactgctg atttgattag ctcaatagcc     1200
agaaacacag aaggccaaca agcagtacga gctgttgatg cacctgatgg cccttccaag     1260
atgcccgatg aaatgataa gaatcatgat tctcatatcg tggtgacacc ccatgagttg      1320
ggtttgaaga gattgagaac agatggagct gcagatgaaa tccatgatga gcgaaatatt     1380
ctcaaaagat cagatcagtc agccttcacc aggtaccata catctgtggc ttccaatcaa     1440
ggtggagcaa gatgtgggga agctcttca ccacaagata acagttctga ggctgtgaaa      1500
acagactcta catgcaagat gaagtcaaat tcagatgctg ctccaataaa gcagggctcc     1560
aatggcagta gcaacaacga tgtgggctcc agtacaaaga atgttattgc aaagccttca     1620
gctaacaggg agagagtaac gtcaccatca gccatcaaat ctacccagca tgcctcagca     1680
tttcatacta tacagaatca aacatcacct gctaatctgg ttggtaaaga caaagctgat     1740
gaaggaattt ccaatgcagt gaaaatgagc cacccaacag aggttccaca agctgcgtc     1800 cagcatcatc accacgtgca ttattacctc catgttatga cacagaaaca gtcatcaatc     1860
gaccgtggat catcagatgt tcagtgtggt tcgtcaaatg tgtttgatcc tcctgttgaa     1920
ggacatgctg caaactatag tgtgaatggg ggtgtctcag ttggtcataa tgggtgcaat     1980
ggccagaatg gaacgagcac tgtccccaat attgcaagac caaacataga gagtgttaat     2040
ggtaccgtga gccaaaatat cgctggaggt ggcattgtaa gtgggagtgg gagtggcaat     2100
gatgtgtatc agaatcgatt cccccaacga gaagctgcat tgaacaaatt cagactgaag     2160
cggaaagatc ggaactttgg taaaaaggtt cgctaccaaa gcaggaagag gcttgctgag     2220
cagcggcctc gggtccgtgg acagtttgtg cgacaatctg ggcaagaaga tcaagcagca     2280
caaggttcag aaagatga                                                   2298
```

<210> SEQ ID NO 17
<211> LENGTH: 765
<212> TYPE: PRT
<213> ORGANISM: Sorghum

<400> SEQUENCE: 17

Met Gly Ser Ala Cys Gln Ala Gly Met Asp Gly Pro Ser Arg Lys Asp
1               5                   10                  15

Val Leu Gly Ile Gly Asn Val Ala Leu Glu Asn Gly His His Glu Val

```
                20                  25                  30
Gly Ala Asp Ala Asp Glu Trp Arg Glu Lys Glu Glu Asp Leu Ala Asn
             35                  40                  45
Gly His Ser Ala Pro Pro Gly Met Gln Gln Val Asp Glu Gln Glu Gln
         50                  55                  60
Gln Gly Gln Ser Ile His Trp Glu Arg Phe Leu Pro Val Lys Thr Leu
 65                  70                  75                  80
Arg Val Met Leu Val Glu Asn Asp Asp Ser Thr Arg Gln Val Val Ser
                 85                  90                  95
Ala Leu Leu Arg Lys Cys Cys Tyr Glu Val Ile Pro Ala Glu Asn Gly
            100                 105                 110
Ser His Ala Trp Arg Tyr Leu Glu Asp Leu Gln Asn Asn Ile Asp Leu
        115                 120                 125
Val Leu Thr Glu Val Phe Met Pro Cys Leu Ser Gly Ile Gly Leu Leu
    130                 135                 140
Ser Lys Ile Thr Ser His Lys Ile Cys Lys Asp Ile Pro Val Ile Met
145                 150                 155                 160
Met Ser Ser Asn Asp Ser Met Ser Met Val Phe Lys Cys Leu Ser Lys
                165                 170                 175
Gly Ala Val Asp Phe Leu Val Lys Pro Leu Arg Lys Asn Glu Leu Lys
            180                 185                 190
Asn Leu Trp Gln His Val Trp Arg Arg Cys His Ser Ser Ser Gly Ser
        195                 200                 205
Gly Ser Glu Ser Gly Ile Gln Thr Gln Lys Cys Ala Lys Pro Asn Thr
    210                 215                 220
Gly Asp Glu Tyr Glu Asn Asp Ser Asp Ser Asn His Asp Asp Glu Glu
225                 230                 235                 240
Asn Asp Glu Asp Asp Asp Asp Phe Ser Val Gly Leu Asn Ala Arg
                245                 250                 255
Asp Gly Ser Asp Asn Gly Ser Gly Thr Gln Ser Ser Trp Thr Lys Arg
            260                 265                 270
Ala Val Glu Ile Asp Ser Pro Glu Pro Met Ser Pro Asp Gln Leu Ala
        275                 280                 285
Asp Pro Pro Asp Ser Thr Cys Ala Gln Val Ile His Pro Lys Ser Glu
    290                 295                 300
Ile Cys Ser Asn Lys Trp Leu Pro Thr Ala Asn Lys Arg Asn Gly Lys
305                 310                 315                 320
Lys His Lys Glu Asn Lys Asp Glu Ser Met Gly Arg Tyr Leu Glu Ile
                325                 330                 335
Gly Ala Pro Arg Asn Ser Ser Ala Glu Tyr Gln Ser Ser Leu Asn Asp
            340                 345                 350
Val Ser Val Asn Pro Thr Glu Lys Arg His Glu Thr His Met Pro Gln
        355                 360                 365
Cys Lys Ser Lys Lys Lys Met Met Ala Glu Asp Asp Cys Thr Asp Ile
    370                 375                 380
Pro Ser Glu Ile Asn Thr Glu Thr Ala Asp Leu Ile Ser Ser Ile Ala
385                 390                 395                 400
Arg Asn Thr Glu Gly Gln Gln Ala Val Arg Ala Val Asp Ala Pro Asp
                405                 410                 415
Gly Pro Ser Lys Met Pro Asp Gly Asn Asp Lys Asn His Asp Ser His
            420                 425                 430
Ile Val Val Thr Pro His Glu Leu Gly Leu Lys Arg Leu Arg Thr Asp
        435                 440                 445
```

Gly Ala Ala Asp Glu Ile His Asp Glu Arg Asn Ile Leu Lys Arg Ser
            450                 455                 460

Asp Gln Ser Ala Phe Thr Arg Tyr His Thr Ser Val Ala Ser Asn Gln
465                 470                 475                 480

Gly Gly Ala Arg Cys Gly Glu Ser Ser Pro Gln Asp Asn Ser Ser
            485                 490                 495

Glu Ala Val Lys Thr Asp Ser Thr Cys Lys Met Lys Ser Asn Ser Asp
            500                 505                 510

Ala Ala Pro Ile Lys Gln Gly Ser Asn Gly Ser Ser Asn Asn Asp Val
            515                 520                 525

Gly Ser Ser Thr Lys Asn Val Ile Ala Lys Pro Ser Ala Asn Arg Glu
            530                 535                 540

Arg Val Thr Ser Pro Ser Ala Ile Lys Ser Thr Gln His Ala Ser Ala
545                 550                 555                 560

Phe His Thr Ile Gln Asn Gln Thr Ser Pro Ala Asn Leu Val Gly Lys
            565                 570                 575

Asp Lys Ala Asp Glu Gly Ile Ser Asn Ala Val Lys Met Ser His Pro
            580                 585                 590

Thr Glu Val Pro Gln Ser Cys Val Gln His His His Val His Tyr
            595                 600                 605

Tyr Leu His Val Met Thr Gln Lys Gln Ser Ser Ile Asp Arg Gly Ser
            610                 615                 620

Ser Asp Val Gln Cys Gly Ser Ser Asn Val Phe Asp Pro Pro Val Glu
625                 630                 635                 640

Gly His Ala Ala Asn Tyr Ser Val Asn Gly Gly Val Ser Val Gly His
            645                 650                 655

Asn Gly Cys Asn Gly Gln Asn Gly Thr Ser Thr Val Pro Asn Ile Ala
            660                 665                 670

Arg Pro Asn Ile Glu Ser Val Asn Gly Thr Val Ser Gln Asn Ile Ala
            675                 680                 685

Gly Gly Gly Ile Val Ser Gly Ser Gly Ser Gly Asn Asp Val Tyr Gln
            690                 695                 700

Asn Arg Phe Pro Gln Arg Glu Ala Ala Leu Asn Lys Phe Arg Leu Lys
705                 710                 715                 720

Arg Lys Asp Arg Asn Phe Gly Lys Lys Val Arg Tyr Gln Ser Arg Lys
            725                 730                 735

Arg Leu Ala Glu Gln Arg Pro Arg Val Arg Gly Gln Phe Val Arg Gln
            740                 745                 750

Ser Gly Gln Glu Asp Gln Ala Ala Gln Gly Ser Glu Arg
            755                 760                 765

<210> SEQ ID NO 18
<211> LENGTH: 13780
<212> TYPE: DNA
<213> ORGANISM: Artificial Sequence
<220> FEATURE:
<223> OTHER INFORMATION: Synthetic construct

<400> SEQUENCE: 18
gggggccgga cccggagaga cggaggcgaa ggaggtgcgg aggaggagga ggaggagcgg     60
ggggcggcgg cggggggggcc ggaacaccga gggcgaaggg gaccgcccta gggtttggag    120
ggttctacaa ggggcgtgct ggaggaggag gaggggcctc agtaggctct tctggaaggt    180
tcgaatccta cacagctcca tcatctctca caaatcacac attacactgt attttttttg    240

```
gagaagaaga agaagaagat atgatatgag tatgacggcg gcggcggccc ccctcccttc    300
ctgttcctgt gcgctttgtg gtggtggatg ccaatgcaat gagaagaacg gaaatcggga    360
tcgggatttc ctaaattgga gctcacgctg atctcatcca actcggccca tgacccactt    420
gtaactgatg ggccgcgacc aactgcttgc tacagtacta ctattatctt ctcctaccac    480
gcacaagggg aaggggggctt ctagttagga acgtactagt actattcttt acattgtatt    540
tctcttaagg atattgggtt tttgggaaaa acacgataag ctgtcaggca atcgagggt    600
tagttcaaaa ttttatacat gagcaaggag gttttgcaa aattaccaga tctcacgtgg      660
catgcatgca aggtgaaacc aggcaccagc ggtggaagga gcaggctcgc gagattaacc    720
gtgagattac cggcaaattg tgttttcccg atcgcacacg cgctcacgag gagccgtaat    780
cgcaagacga caatgtgcaa attaaacaag gagaccaaaa aattaaaaaa aaggagaaaa    840
agggtacggt taggctggtt attgattgat gatatgtcac acgcaccct ttcctattac      900
aacgttgtga aaactctttt aatgttttta gcttccatta ctgcccacgc aattgtaaca    960
aagtggctca tgctttagca gcctatagat ataatagttc ccagacgact cagttcagct   1020
gggatggttt tcctccagat gtggaggagc tggttgccgg cgatttagcc gaatcagtgg   1080
tataatggaa tttaatgttc ctctaaaaaa aacctgcttg ctccaaggat gaggtggatc   1140
agactccact tccaaactac tctaatccac ttattaaaaa tttccaactt gtgtttcaaa   1200
attttatctc taatagaaaa aaaatgtccg tgcgttgcaa cgggtgaaaa ctattttaat   1260
ttttattatt tttatacgaa attcactatg agaatttgct tggatatata tttttttgaa   1320
aaaatcatga gctgcaatta ggagtccgat catctcaagt tagcatgcga gttttttaa    1380
aagagatttc ttatgactcc tgtatttat aaaagcgaac gaacttaaaa cctgactcaa     1440
atacggatat gtatctccaa atgcgaacga acttaaaaac cgactcatac acggatgacg   1500
taccaaagta ccggcaaaaa catcttcaac ttttataata gtagagatac tagaaaaaat   1560
atccgtgcgt tgcaacgagt gaagcctatc ttaatctgtg ggaattcact tgatattgtt   1620
tttacaagtt agcatgctgt ttttttataa tagattactt atacaactcc ttctatgtgc   1680
cagggttacg gataaggcat accttctatc ctacgactta cggaatatac agataaggtg   1740
taccttcatg tacacggatc gtttccttgt acaccatttg gaatccgttc caaattatgg   1800
aaaatatctc tacgagttaa gcgatttcca aagtcctact cggaagggat agaatttcgg   1860
ttacaccgta ccatatccaa tatccttagg tctttcttgg gggtcaagat gattcacggt   1920
ataaagggaa cccccgagga ggggtgaaag ggcatccaat ttaatcgcca acacacccac   1980
tatagtttac aaagccagag tacgcggagc caaatcgctg ggagatctcg tcgaaaccct   2040
cgaccacgat ctcgtcggta tcatctattt cgactactct cttgtaata tgttcttgtc     2100
attataaatc ccatataaac tggactaggg ctattagtat tacctaataa ggggtctgaa   2160
ccagtataat ccttgtcttt tgtttgcttg atgtcgtact acgtagaccc tcgtaccaat   2220
gtaccccaat actctattca tccggtccgc gagtatcact cgtcgacact atgtttccaa   2280
aagagaatgg aattaaaagc tgactcaaat acgaatatgt aattccaaaa gtcaataaaa   2340
acttaaagaa cgactcaaat atggatgatg taccaattta ccggtaaaaa catctttaat   2400
ttttataata gtagagatct ctaattttg taatctgtgt ggtattccca tacataatac     2460
atataaacta gagtatggtt attactcatc tagaggaccc gagccagtat aaatacatgt   2520
cctttgtctg cttgatccga tctcgcatat acactggttc caacgatctc catactctac   2580
aaatactact tgcggtgaga caacaaacct tgttgttata gctaaatatt tcatgaaccg   2640
```

```
cattaagttc aaacggattg gtcttgcctt agactgcaag ttgttcaaat gctcatggat    2700
aacgaaatta tttgagtaaa tttcaaagaa ctactactat tttgtcaaaa ctatcagtta    2760
tgacatttca ggtaactgga acagtggtat acaattgtat cgaaaagctt ctactttatg    2820
tgtctgacaa gttttggccc atgtgtcata catatatatg gggaaatgct gcattttta     2880 aataaagcag ttctctatta ttcccatttt ttttgaaata ttcaactaaa gttatagcaa    2940
agtgatagtt ttgaccaaat aattgcaatt ttatgaaatg tactcacatt gttttgttgg    3000
atgatttttt ttattatgtt tacaaatctc gtctctcttc tatctatata tgtggttact    3060
taaccacaat tcgtgggaat agaactcatt tcctccaaga tagtagataa ggatgtagtt    3120
ttgtgctcaa gcatgctagg aaaaagctaa tgtcatgaca acgagttccc acttggagtg    3180
ttgcctagcc tttcatgaga ttccatttat tttatgccta cttatgttat tcctattgat    3240
gacttcatgg tttactattg gttttgtgta ttagggacca attaaatata tactaatttt    3300
ttaatctggg agagggggca ttattaatat tgatcgtatc ataccaaa actaacactt      3360 atgtctaatg ttttggtaag cgccatcatt ggacattctt cttggtgtaa tacttaagat    3420
aattttcaat gaattgctcc ctcatgttaa ggatatttga cgttggggt attggtttta    3480 gtactcatag tatatttaac tgtagggagt attggttttg ttttatatat ttttagggtg    3540
ttcctctgaa atcatacatt agtgggataa ggaacaccat tttttgaaaa cgtactaaaa    3600
agtggatttc actggcctat atgatttttg gaatttcctc ttcttgttct atcaactagt    3660
ggctcatggt tacttgtacg tagcccactt aatatagttc aaactcgtac tcatgttttg    3720
actagcttga gctcatcatg ttaccaagtt catgctctat gtttatttga atgttttag     3780 gtctcgggga ataaattggt taaaacacaa tgtttaggtg tttgtatttc taactaaaac    3840
atattgtaaa cttaaatatc aagttgtggt gtttcaaatg aattgtggaa tctcccatga    3900
atgtcacctt agttgtgctc aggtttacat atgtatgtta atgtcacttc cagaaattct    3960
taggcactat atattaggct acaacaaatg aaacttctct taaaaagtga gataccaaat    4020
gaattcctat agcttcatttt tttaaaagag ggggctcaat tttatttaaa gaaacaacaa   4080
aatataaaca cttacataac cgcatgtttg ttcatcaatg accaacatga atgagcataa    4140
agagtagagg caacagaaaa cactagtgcg ccaccaagat atttgaccaa gagaagagtt    4200
agcaacatat aaaatgttta tctaaagagg agttaccaaa tcaacatcca tttcaccaga    4260
attatctaag aaacacattc cattaagctt ccttgtcatt ggtgcccaac ccatagactt    4320
tctaaacacg tcctcaatca cttgttagag tttttttttt ttgcacaatc tggcatctca    4380
tagcgttttc cttcaaattg gattaatgtt tatgttgtac atcaacaagt tggatccaat    4440
aaacggcata cttaggaagt tttccacatc acccaataaa tatatgaagt aatcacaaca    4500
ttatcatttc tcattttttt ggaatatgtt ctagcaatga attcaaacca aaaggtatat    4560
tgccaatctg aaatcacacc taacaaatgg ataaaagctt accttcaccc acttacccta    4620
gttccccttt ttttctttgg caatttctca tagtgaatta gtcaaaaagc agcacccaaa    4680
tgatataatc acttctatga aattttattt tcaaataaga caaatgtgca aataagcaca    4740
aaattgtttt catgttcaaa gaacttttct ttatcatctt ccattataaa gacgatgtca    4800
tcaacatact gtagaattga gaccctagca ttcagcaaaa tgtgacaccc ttcctttgat    4860
caaacctttt caattgtttg gttaataagc aaagtcaatg caacatcccc cgctatgtta    4920
aaagggagtg gagcaatata tattcttgcc ttaaaacctt ataagacaca tgcttataag    4980
```

-continued

```
ttcattaagc atagttgcaa cacaacctcc ccttactacc ttaaaaatcg aaccacacca    5040
tttatctatc tccaaaacat ttttggccat aaatttgtta tacaaaagaa ccatctcgca    5100
ttttgtcaca tactttctca agtttacct taaaaggcac ccatacattt ttttcccata    5160
tgaacttctt gaattatttc atgtaaactt aatatccctt tccattatga accaatattt    5220
caagaatgca acttgactat tgaactcaac cttttggatc actctaacca acctacttat    5280 caccccttg gtgagaattt tataactcat cacgtcgagt acacaaaaag gcctaaattt    5340
ctatatggtc aaagtatcaa gtgttgtagg tatcaaggtt atacatagtt taatctctct    5400
atatctaaaa ccgcattgta aaaccctaa aaaactttca gaagatccta tgtgatcact    5460
tcctagaaga attggtaaaa tatttgtagg aagctattag gaccatgggc ggccttattc    5520
tttctcttct aaataaaaca tgtggtttaa tttcttccaa tgaaaaaggt ccattcagag    5580
atttcggatt cagttcatcc atttatatat tcctaatata ttagtgtcac tgtggggcca    5640 aacaatttt tatataaaag aagatgtcac atgttccatc aattccttct catcttctgt    5700
catcttgaag aagtcacttt tattatatcc aaagtgattg cacggtttag aataacgtca    5760
ctaagtctgt atttaataac tgtagctccc ggagttacca tgctcctctt catctggtat    5820
tttgtccata attgtggcct ttaacaagcc ttagtttgta cccctttcta tatctcttat    5880
aaataaaaga ggaagatctc ctgctccttt ttttttatat aaaaaggaat atatatattt    5940
tacaataggc caaccaaatg aagttctttc gaaccatgtg tttcaacttt caacaatgga    6000
attgaaacca aagctccaag agttcctgag attttctgaa aaaaacagg tgttatattg    6060 agcaaatgaa aagagagaag tttcagatgg cttagtgagc aacgaagtcc aaaatcacaa    6120
ggttagcaca tgatgtcggt taccatttaa tttgcttctc tataaattgt gctgtccaaa    6180
ctaaaatcgt ttttgtgttc tggttagttg tgaatttctt ttgaggtgat aaataggaag    6240
aaatgtgtac gacgttctct tgtgttaagc aaactcagca gagcttcagt gtgtactagt    6300
agtagtatag tatagcaaaa gaagtgacga attaattgtc tttagaataa aatgttcttg    6360
ctacattgca caagtgaatt atttaacggt gacagcacgt gttgacataa aataaaactg    6420
aagagagaaa taattaaaat acgtactcga tccacttta taagaaaaga gaaacgttg    6480 tcctcaagac ctgtgtgtgc catgtgaagc aaggcgagaa aaggcatgaa gagaatcagg    6540
ggtggtgaag aaggatggga gaatatggag caagccagcc aggtgaagct gaagctgcaa    6600
gggccaaggg ctaggctacg aggaaggatg gaagatgaga agaagaagaa aaaaaaaaga    6660
ggcactactg tacatgtggg ggtaggaaat caaaaggatt cagctcaagc cacacaagag    6720
gaaagcaaaa aaggaagatg caaagcagtg cacatatata aaaagcactg ctcctcagcc    6780
acaccaagca aaggatatga gaaagctaac ctagatgatg cccgcagaat ctgatggcac    6840
gctctctgcc tcttccatcg ctcactccaa gcttctttct actcgatcga tcttgctaca    6900
tagactgctt ccaccaagtg gcattcaact ggccaggagt actcactaca gttcatttgt    6960
tccttaatta gatactacag taactcttaa atacgtacac tattaattac tataatactg    7020
tatataggag tacttaatta tccttcttaa ttaactttgt tcattttgat aaacaaaaaa    7080
gaggaagtat atattttagc ttcctctcta aattataaac acacgtacgg cggtacttta    7140
attaatttgt gcgttgttgt tagcttgtcg atcgtcagtg cttctggcca agagtgttcc    7200
aaattaaccg accgatcaac aaatgatgga taaagatagc agatatcatc atcattcatg    7260
tatgagtatg accggtccat tcagttcata ggagataagc tagcattctt acttgcgctg    7320
ggccgggcgc gtcagcagct gactgcttta gttggctagc tcttgtgcgt cttgcaatgg    7380
```

```
atttgcttta ctactggact actagaggag aggatgaact tcgagtgtgc tgtgctgtgc    7440
tgtgctgtgg tgatagatag catacatgca tatgcagcat atggacatat ggtgggggta    7500
ctccgaatat atttctggat tgtggttggt tcttttgcta ctgcttgcct tttctgactc    7560
gctctctctc tctctatatg gagtatatag ctttttttc ctactagtat gagagagaga     7620
agccattatt attttccccg gaagaacaag aggaaacgaa taaaaggaa atctacatca      7680 ataaagctaa ttcacagttc cttgtgctat acaaacgtat agtagattat tgattagcaa    7740
cagatcctca ctggattata tcgtgaaaat tagaaatatg tactgctggt ggttctgtgt    7800
ttcctctgtt tgagctgaca atacgtctgc tatactacac gggtttagtt tcttataatc    7860
tctgaatagt agtatgtcaa ctgtagtttt tgttttcctt tctagagatt attttcctgt    7920
ttacgacaca taaataaagt taataatttg cgggggcgat aataattgaa ttaattaaat    7980
aaataaatag aataattatg cttggagtgt tttgaggaga aatgatacta gggatttgga    8040
gaagagaatg agattctttg ttttggacgg gtggcccagc attacgggga gatgggccgg    8100
ataggcccag aagaggagcc caaagaaaga aggaggtgga cacgtgggag atctgcgcgg    8160
atctcgggga gcgcgcggct tttgatttcg tgggatctca ggggcgggcc caccagcggc    8220
gctccccacc tccatttgtt ccacgtcacc gccctcccca atatctagta gcagtagcag    8280
cggagggagc ggcacacgat acgcgccgcg cggatcccct ccttccctc ctcttcttcc     8340 tccgccgccg ccgccgatta ctcgcttccg cctccgcctc aaccccggcc gtccccaacc    8400
aaccaaccaa ccaaccgcag gtaacttccc ctctggatct tccacagtca gtattcctcg    8460
attcatttca ttttcatccg ggttcatcag tccaatccaa gcgaatacta agctcacttg    8520
aattcggttg gtgcctcgtc gtcattctgc cactgcttga gagttccttc atacacacac    8580
cactcgcagt ctcagcagca gcagcagcgc aggtaatttc actttacagt tcttctact     8640 actatcatag tcctcgtcct agtactatac tactataata ctatgtgtct gatgcaactc    8700
tctctagtct gtagcaaagc tgctgttatc ttccttagtc cgcggccagt gtccactgat    8760
ccaccgctcg ccttgcaaat ttgcatacgc ccactacgta cgtaagctgg atcatatcct    8820
tctcattttt tttttctcta tctctattct ttctcatttg tgagattgat ttgcacaact    8880
gcacaagcac agatgcggat gcagcccagc tagctaataa gctaggttag ctgctgctgt    8940
tggtcttgga ggcaaactag tgtaatatgt gccgcaccgc ctgcctttct tcatgaacca    9000 aaccccctgcc accactcaac ccggccaacc tcttcgagtc aggctgatgg gtagcgcttg   9060
ccaagctggc atggacgggc cttcccgcaa ggatgtgttg gggataggga atgtcgcctt    9120
agagaatggc caccatgagg ttggagctga tgcagatgaa tggagggaaa aggaagagga    9180
cttggccaat gggcacagtg cgccaccggg catgcagcag gtggatgagc aggagcaaca    9240
aggacaaagc attcactggg agaggttcct acctgtgaag acactgagag tcatgctggt    9300
ggagaatgat gactctactc gtcaggtggt cagtgccctg ctccgtaagt gctgctatga    9360
agttatccct gctgaaaatg gttcacatgc atggcgatat cttgaagatc tgcagaacaa    9420
cattgacctt gtattgactg aggttttcat gccttgtcta tctggcatcg gtctgcttag    9480
caaaatcaca agtcacaaaa tttgcaagga cattcctgtg attatgatgt cttcaaatga    9540
ctctatgagt atggtgttta agtgtttgtc gaagggagca gttgacttct tggtaaagcc    9600
actacgtaag aatgagctta agaaccttg gcagcacgtt tggaggcgat gccacagttc      9660
cagtggcagt ggaagtgaaa gcggcatcca gacacagaag tgtgccaaac caaatactgg    9720
```

```
tgatgagtat gagaacgaca gtgacagcaa tcatgatgat gaagaaaatg atgaagacga    9780
cgacgatgac ttcagtgtcg gactcaatgc tagggatgga agtgataatg gcagtggtac    9840
tcaaagctca tggacaaaac gtgctgtgga gattgacagt ccagaaccta tgtctcctga    9900
tcaactagca gatccacctg atagtacatg tgcacaagta attcacccca aatcagagat    9960
atgcagtaac aagtggctac cgacagcaaa caaaaggaat ggcaagaaac ataaggagaa   10020
taaagatgaa tctatgggaa gatacttaga aataggtgct cctaggaact caagtgcaga   10080
atatcaatca tctctcaatg acgtatctgt taatccaaca gaaaaacgtc atgagactca   10140
catgccccaa tgcaaatcca aaagaaaat gatggcagaa gatgattgta cagacatacc    10200
tagtgaaata aatactgaaa ctgctgattt gattagctca atagccagaa acacagaagg   10260
ccaacaagca gtacgagctg ttgatgcacc tgatggccct tccaagatgc ccgatggaaa   10320
tgataagaat catgattctc atatcgtggt gacaccccat gagttgggtt tgaagagatt   10380
gagaacagat ggagctgcag atgaaatcca tgatgagcga aatattctca aaagatcaga   10440
tcagtcagcc ttcaccaggt accatacatc tgtggcttcc aatcaaggtg gagcaagatg   10500
tggggaaagc tcttcaccac aagataacag ttctgaggct gtgaaaacag actctacatg   10560
caagatgaag tcaaattcag atgctgctcc aataaagcag ggctccaatg gcagtagcaa   10620
caacgatgtg ggctccagta caaagaatgt tattgcaaag ccttcagcta acagggagag   10680
agtaacgtca ccatcagcca tcaaatctac ccagcatgcc tcagcatttc atactataca   10740
gaatcaaaca tcacctgcta atctggttgg taaagacaaa gctgatgaag aatttccaa    10800 tgcagtgaaa atgagccacc caacagaggt tccacaaagc tgcgtccagc atcatcacca   10860
cgtgcattat tacctccatg ttatgacaca gaaacagtca tcaatcgacc gtggatcatc   10920
agatgttcag tgtggttcgt caatgtgtt tgatcctcct gttgaaggac atgctgcaaa    10980
ctatagtgtg aatgggggtg tctcagttgg tcataatggg tgcaatggcc agaatggaac   11040
gagcactgtc cccaatattg caagaccaaa catagagagt gttaatggta ccgtgagcca   11100
aaatatcgct ggaggtggca ttgtaagtgg gagtgggagt ggcaatgatg tgtatcagaa   11160
tcgattcccc caacgagaag ctgcattgaa caaattcaga ctgaagcgga agatcgaa    11220 ctttggtaaa aaggttcgct accaaagcag gaagaggctt gctgagcagc ggcctcgggt   11280
ccgtggacag tttgtgcgac aatctgggca agaagatcaa gcagcacaag gttcagaaag   11340
atgacctacc tacctaccta cgcaatggct ttggactcca aacagctaat taacagttag   11400
tagacaacag ataatgattc ttcttccttg gccgatcgat caacaacatc ccatgcatcc   11460
ggcatcccac caccattgat tccatcatat ttagagtctg gaataaataa ggaactccta   11520
tcctatttat cccctatcta tatatgaaga tatgataatg gtgatctgcg ttactactag   11580
tagaagaata tggtgtggct gactccactt caggtggacc tataatacta ctccagtagt   11640
atgtgcctgt ggagtcaagc tcgaacgtac tactccatat ttaagcatgt catgtactgc   11700
tactatgaga cgagagtgct ctgccctgta gggacagcac tattgtcaat gtcatgtgtt   11760
tgttggatca ctggtcttct tagatttgcg tccgtgtctg gcagcagcac tccattgtag   11820
ttggctcacg catgttgttg aaatgagcca catgccttgc cttgagatag aacttgctgt   11880
cactgtttct ccttaatcga aatatactgg agtggagtat tttattatct atgatctgta   11940
atcaggtgat cgacaaggct cgtcaaattt ctatgccttt ggtaggagag tatcaaactt   12000 ttttttttatg actcgcacga gacggtaaaa agaaatacaa aaggttgtaa ccaagaaaaa   12060
aaaggaaaaa ttacaccact atccacacac cgacagcgcc aacacatagg tccggaaaaa   12120
```

```
ggctagcacc ggaccggctg ttgctaagcg tgatcgacca ccgctgagcc aacaacggaa    12180
catagatgag atcgccgaaa aaacaccctt acaaccaaca caaggcccaa ctctacccat    12240
gtcttttaga tttagggata gaaggtgaga gagatgaaac acccctcccc ctaggccctt    12300
cgacgtggtc aacttgtaaa aactaggata ccatcataag aggatgagaa tttagagcgt    12360
gcttgcacca attgtacatg tgttttcagc aagaggatgc ttaggtgaca tctccaagga    12420
gagaagcgat agaaaaccgc cgccgccgtc cgtcaaggtc tcaaaaagag caaagactgg    12480
gctttcgccc ttcaaccatc cttgaggggt gagacggcac gacaacggcc tcaggagggg    12540
gaatgacact cgagcgccat cgttgtcggt ccggccaagg ctaggctggg ttttcaccca    12600
ccactcacca cctgcgagtc catggctgac gcactgatgc tccaccactg cccaatctct    12660
actgacatgt gggaccaatg caccggcgcc tcccgccggc cagcctttgt gcacagtaga    12720
ccgtgccaca tctaccggca gctcctccgt acaccgtggt cgcgtcctcc accgccagcc    12780
gcgtatcacg tattgaatgt atcttatcta gtactactag attatactag tgttatggga    12840
cggagggaga gtatcctgtt tacggtaggt tttgtccggc tgcaaagaaa acggaaagct    12900
cctttattac gaccgagatg gccattctct agaacaatcg tggaccgacc ttactttctc    12960
cgctggatga cacccgtgct tctttcctca actgtccgcg tgatcgcctt tcttttcttt    13020
ttcgtgtctc ggttcgatct ggtgctgaat ttctttgtgg attttacgct agaaaagaga    13080
agtaagcttg gacagctcct agaatctttt ttttttattt tctactgatt ttatagctgt    13140
agattcttaa agtctgagga gaatgtaaaa tgtttgagga atttggaggc tgtaccaaac    13200
atgctatagt atttgtgaaa gaaaaacgtc actcattatc tccattttaa aagctcctca    13260
aacagtcact cgtcttattt accgacagca aagtggtaat ggtactggta tcctcgaggc    13320
cttgtatatt gcttttgcat taaggatcc tctcaatcta aatacagtct ttttttttct    13380
gaaatttact acgtcatcca acaagaaaag taaagaaaaa acacattaca tgtaaattgg    13440
agcatactgt attgtttttc ataggaaagg gctagaaaga tggatgaatt tggtaaactt    13500
tcagtgaaaa actaagctct ctatctttgt aatttgaagt tgtggtagaa tatctatctt    13560
tgtaatttaa agttgtggta gaaggtact aggatggagg aactagcggc tgaatgtatg    13620
ttctggaagc gaaaggaagg ggagagattt tgagtagctc aaaaatatgg agtattttct    13680
tcaccttctt ccccacgcgg aagcggaagc tgaagcgcac acaattacaa ttacagggcg    13740
actactctct cctctctgct ccctgctccc tggagagctc                          13780
```

<210> SEQ ID NO 19
<211> LENGTH: 9049
<212> TYPE: DNA
<213> ORGANISM: Sorghum

<400> SEQUENCE: 19

```
gaagggtggt gactactgat tagtatgtca aatgatttga taattagatt tgtgttgtgt      60
tagagcaatt ctacctatca atgttccagg gaaggtttca tggtgaattg tacatgcccc     120
tgaaacaatt ttgattgctt aaactctaga gtgcttgtgt tttcttatac gctggagtgt     180
cgtgggatat aaatttgcac tgtcgtttca gattagagaa aactctgaca gtaaaaggga     240
aagtccactt acgcaatgac agaactcaag cattcaggta agttgtaaca atagaatcag     300
agttggaaat tcttctggat agctaaagcg actctcttat tcactgtgca cgatttcttt     360
attgtatgaa cattcacttg ctttgaaatc acatccacat aatcatccat ttggtgtgtg     420
```

```
ctaatttcct tcactggtat tgattgttgt ccttttttttt ttgaagctta ttgttgtcct    480
aatttgagga atgtatctag tctaatggag gacactagtc atgtggttga tgacaatggt    540
ttgagttgca ctctgcaagt taggtgagtt tgcagtgaat tttcttggat taggtcccgt    600
gaacgaagcc ttaatcccag tcctgtatgc atgactctga caaccaagtg caccctttgt    660
gacaaacagg tactaaagtt ttttttttgtt tgtttgtttt gcattagagt ggcagtttct    720
aaagtttagg catcagaaat taagaatgca gtttgcagga ttttttcttta acatggtact    780 ggttatgaac atggaatttc tagcagaggc ggagggtggg agccgccctc ccccaaagga    840
aagggattat cgcattttttg gctctgcttc tggtatcatg aagcattatt tgatgcacag    900
attcttgtag ttgtagcctt gtaggtcctg gtcttctggt tgtgttatgt atttacatcc    960 acaataccttt ctattcagtt ttcttttgta gccatcaatc atgactagtt tgatttggca   1020
atgaaaatat gtggagctgt cagtttgttg caacatatat ggtgccatcc aggtaaatat   1080
atgttttgtt tttttagaaa cacaatactg gcagaggctc acacatacac acaattcacc   1140
acacgcccgc acagattcat gcctatgaat acctatatgt ttgttctatg tgcaatgcag   1200
cagtcactca gttagcaaat gaattatgct cctgctattt ctggagcttt ccttggtgaa   1260
gcaaaatggt gaaaccatag ttttttccata atgtgttctt gtagtagtct tcagtgttca   1320
ttatcttccc attaatcagt aatgtagcat tctaagcttg tcactgaatc gttgttattt   1380
tgactggagg cgattttcac agctgaaaga tgcaaccgct cgatatacca tatacataaa   1440
gtttgaactt agcacatcat tacaacagac tttcagtgaa cttggtgtac atgtctatac   1500
atatccaaaa tttatctgag caccatgtgc atcaattctt gctgtttagt gttattaata   1560
tgctgtgttt atcagatctg aaaatgaaca agatctgata cctttgttgg atgataatgt   1620
gaacataatt atgctctagc ggttgtaaaa ttaggtatct tttgaaccta attgagtaat   1680
tgtacaatta ggtatcatgg ggtgattgtt ttgcttggct aatttcaggc gcatttatgt   1740
tatcctaaag cgtcagaatc aggcacgcgt ccttgtggca actgacaagc gacccagcct   1800
tgtcattgcc ctcgagcttg acgcttgagg attttcaatc gttgccggac gtcgatctgc   1860
aatctttctt tacatgagct ggcaaatggc aattgctatt tgcacctcca taggagtgtc   1920
actagtcact accaaaatgg tggagttctc ctagtgtttt taattagtaa taaaacacta   1980
ccactagtca aaacactagg gaatcttcac tacgaggcat ttacttagaa aatttatact   2040
aaattttgaa tgctaaaaca ttaggagaat ctcatatcac taggagaact tgaaaatcta   2100
gttgtgtgtt ttggtgtttt tgggtttaaa tatctgactg aggccttgtt tacttcaccc   2160
caaaatctaa aaagttttca agattctccg tcacatcaaa tcttgtggca catgcatgaa   2220
acattaaata tagacgaaaa caaaaactaa ttgcacagtt tgtctgttaa ccgcaagacg   2280
aatcttttga tcctagttag ttcatgatta gacaatatttt gtcaaaataa aaacgaaagt   2340
gctacagtcg cgaaattcga aatttttttcg gaactaaaca aggcctgaat caatcgatta   2400
tagcgattgt ggatatgaaa ctaaaatttt aaatggcact acatatgcgg tggtatccgt   2460
aaaggtggat cccatgtttc agcaggataa aaagcaacaa attcgagaga ataatcgttg   2520
tggctgggtt gggactgaaa gccatcgttc tctggacagc aaattgttga acgcttttttc   2580 tgtatctaac acaatgtaac ttgccttaat acacttcgta cacttgccat catgcgaatc   2640
accactgcca tcattgtttt gtgatctatt tatattgagt acatgtttga ggcactactt   2700
tgtttaactt gataaggtaa tcaacataaa gtaaagtgct aggctgctag ccatacatct   2760
ctaaatatga tccatacata tggtggagca tggcatctat gagattggtg tcatcttttca   2820
```

```
catgtttcta cgtactcata gtccgccaga tcctcttggt tgatctacaa gtttagtata    2880
gtgcgaaact ataatctaaa taaattatca aaagcaataa aaataatagg aattgaaata    2940
aataagtccc acataactct aaatatgtca tcaataaatg gataaatttt tttagagaaa    3000
atgttgatac taggttcatg tagtatttct gatttaaaat aaattagtta tgtatatttt    3060
agaaattaaa ccatattctt aatattcttt taaaaaaata gaaatcaccct ttgaaactag    3120 ctaaatgacc aattttttt tatctagaac aatgagaggg cgcattgaaa aaccaaattg    3180
acatgcaagt tgatgatgaa ggttgaaaaa atatatatgt tttcttttc tctttcatga    3240 aaactagcac tgctgcacgc ctccaacagc aagggtatgt tttgatgatg agtcggtctt    3300
ctgttttaga gacgtgtgat atgaggtatt cggcttttca aattccctga gacattgcgt    3360
tgctggacga atttagtatt ttgtattcgt accaatccga agggtgcgcg ctgtcgggtc    3420
agacgagcaa cgtttaggca cgctctcgcc tgatccggag cggcccgtca ccgtctcgcg    3480
atgccaaatc ataaggagcc gtcacactgg caccatgaca aaatcaaaat ctagaccagc    3540
tagaggccat ctcccgggcg gagccgaaca caaaggccgg ccttgtttat tcacctgaaa    3600
aatcaaaaaa aattcaagat tccgtcacat cgaattttgc aggatatatg aagcattaaa    3660
tataaacgaa aacaaaaact aattagacag tttgtctgta aaacgtgaaa caaattttt    3720 gatcctagtt agtctatgat tggacaatat ttatcacaaa caaacaaatg ctacagtagc    3780
aaaatctaaa aaaacacatc taaacaagac cttaggcctt gtttagttcg caaaaatttt    3840
caagattccc cgtcacatcg aatctttggt tgcatgcatg gagcattaaa tatagacaaa    3900
aataaaaact aactgcacaa attacctata atttgtgaga tgaatcgttt gagtctagtt    3960
actccgtgat tggataatat ttgtcaaata aaaacgaaat gctgcgaact aaacaaggcc    4020
ttagtatccc catcaggaca acgccgcacg gcgcgacggc gacgcatccg cccgccgcgt    4080
gggcaacgag tgcacgagga aacctggtcc tcaggatgaa cccgcagcca cgtgaaggtg    4140
aatcgagcca ggtgcgcgcc cggttacgcg agcaacggaa aggctcggcc cgcggccaca    4200
cagccaaagc agatacgggc gggatgcaaa gccaggcgcg accccgggga aaagcacggc    4260
gtctcggcca caccgtgctg gggattgggg aataaggaa aggcgggcga tgctgctgcc    4320
ccgctccccc cctgaactct agtagaatcg atctgatggc ggccacccct cacgtcgtac    4380
gaccgacacg accgcctctg cgcgcaccgc gaaggtgctc ggcgcccggc gcaagttttc    4440
ttgcaaagat tttacagaga gaaatgcatg cttgcagaga gagagagaaa aaaaaaagag    4500
cttaacctat tcgcaagctc gatcatctct gtgagctcgg caacaacaat ctttgcaaac    4560
gacccacaga agcttgccga gctcaaacgc acgcgcgccc acggatgatc gaacgacggc    4620
agggcgaata ggataagctc tgtggatcga gatgcact ggtccgcttc cggtccggat    4680
cgacgtggtt gctcctgtcc tgacatggac tcgttagtta gctcttggtg ctggttcact    4740
gtctcggaac tttgcacgac gggctgagac tgaaaggtag tcgtgccttg gtgggggtca    4800
gtgctcccag aatatatatc ttcgcctgca ttggctcttt acatgatgct gtatctagcg    4860
gcccttgagt ctttgactgc gttttatttg tgacgtgccc ctagaatata tatctccacc    4920
tccattggct ctttacatga tcgtatgtaa tgcattctat ggaatactac ttttcgactt    4980
ggactagtat ttcataaata caaaaaatgt gtaagaaacg gtttaattta tgcagacatc    5040
agtcgtttag gtactaaaaa ccataactct aggttataca aggcgcttca ggtaaaactt    5100
actaactgtt aaaaacaaaa tgtcgcttat tcgtgtgttt gagagtgttg ctagtcattt    5160
```

```
tggaagagct ataattcatg acggtttctc cttttttccac ttaggctttg tttagatgcg   5220
aaaagaattt ggatttcgct actgtagcac ttttcgtttg tttgtggcaa atattatcta   5280
atcatagact aactaggatc aaaagtttcg tctcgcaatt tacaagtaaa ctgtgcaatt   5340
agttttttatt tttgtctata tttaatgctt catgcatgtg ctgaaagatt cgatgtgaca   5400
tgaaatcttg aaaacttttt ggttttttggg tgaactaaac aaggccttag aaatagctca   5460
aaaacaacaa ctcctactag accatttgat aggacttctt cataggagct agatacagct   5520
aaaagaagct atcaaacggc ttttataatt gttttttcttc aacaaatgag ctttagttat   5580
gtcagtttct gtctcctctg cggtcattgt gtatctaaaa gaaaagcatg gcggtacctt   5640
ttgtgattgt tccttatcta caagtcgtcc attcttagag gtagggaact ctagtacgaa   5700
gaaaaaagag cctttgtttg gcgagaatgc gaggacacaa gaatctagat acgcggttgg   5760
caaaaaggat atgccacatt gcaattgtac tattttagca tccaaaggtg agggatacga   5820
tcgtacatgg attagtttag gctctattcg cacccccgttt ggctaatgtt tagtccagct   5880
ttagcacttg aaatgaatgg actaaagatt agcctctggg ttatttggat acatgactaa   5940
agggtgaaat gagaggagaa agaaagcaaa gtcacctgtt agcactttta tcccttattt   6000
tcagtccttc tgtttgaacc tccaaggtta aaaggtggtt aaaaggagag agctattctt   6060
taaccttcaa tggaccttag ccaataggcg tatatttggt gttgtttgct tggtcccatg   6120
ccttgatcgt gcttttcaac ttgcttgcta atagtacatc gtttgccgtt ccaacagaaa   6180
ttctcaccta gtttagttac tgcctttctt ttttgaagaa aaaagagcc ttagttgcga   6240
gatgttcttc ttcgtgtaac aaccaattaa gaacctattt gcttgagatt attttatcga   6300
atttatcagt catttaatag cgtttttctc tcataataaa tcagttactt ccggccatga   6360
tttttcggat aagcgaacat gctagccgaa ctcttccatc tccactctca gtgattatga   6420
aacgtgtttc cagtgcgaaa taaatagtaa tcataacctt ttatagacga actaaaaaaa   6480
cataaattca gctcagactc ggagccagcg ctgcagaatg ttctcttttt tgttaggtgg   6540
tctggacacg actgcaaagc atctgtgaga ctgatcgctt ggaatgggaa acaacttgc    6600
gatgtggctg gtgcgacaaa ggaaatccct ggttaattaa ttaactgaac acacagtgac   6660
tgccgtgggt gattggtttc aatacttaat ttatttcctt cgagaccgac caaagaatgc   6720
agtacaagcc tccatgctct agaaagttct gggctgattc cgtgctggtc gccgatgact   6780
caccgccgtc gccatcctca gcttaatcaa acgagaaaat taaccaggaa acgacaggag   6840
ctcgattact aatgacagcc gtcctcctaa tgacaaccgc taacatgtac gagtgggtca   6900
cacgagctca caactaacat gacacacaag tacagcactg ccaaatttgt gtgaactgct   6960
tttgtccaaa aataaaagtt gcataacctt tctcgctctc tcttttaaaa cttgcctaac   7020
cttttcaagtt tcaagtgttc aattaaaggc cgtttcctgt ccaatttgga ttggatagag   7080
gcgagccatg gatccaacaa tgctaatata acttcattcc atgcctcgat agaagaaatt   7140
atatagaagg tcaaaaatat aatggagaac atcttattct tataaatatt aatgaagcaa   7200
agtatatgtt cttttttttca aaaggtttag gcttggttta gttcacaaaa attttcaaga   7260
tttcccgtca catcgaatct ttgatcgcat atatggagca ttaaatataa atataaataa   7320
aaactaattg tacagtttaa ctgtaatttg tgagatgaat cttttgagca tagttactcc   7380
atgattggac aatgttttgtc aaataaaaac aaaagtgcta cagtagccaa aacccaaaaa   7440
ttttgcgaac taaacaaggc ctatccgatt ttttttttgaa ttttgacact gtagcacttt   7500
cgttttttatt tgacaaacat tgtccaatca tagattaact aagcttaaaa gattcatctc   7560
```

```
gtgatttaca gataaactgc gcaattagtt tttgtttcta tctatattat ttaatgctcc    7620
gtgcatgtgc cgcaagattc aatgtgacag agaatcttga aaagttttta gttttgggg    7680 tgaactaaac caggccttac tcagtggtga gatatatagt caaagtcaaa tcataactgg    7740
aaagcatttg atttgatgac ctcccatccc ggaaacaaaa gccaacgcta gccagcgaaa    7800
cgggagtgcc ctgcttccca aatcgcactc caggtcccgc ttaaacgccg ttaatgcccc    7860
gccgtgacga tctttccatc caagccgcgg gccaagcact cccccggccc cacaccacct    7920
ccacaagccc accccaaccc accgacgtgc gggtcccatc gacttccagg accccaccag    7980
ccagtgacga atccacgacg gacccgcgcg tgccgctcga agtggccccc gggcgatcta    8040
cggattcggt ggagcgcagg gagcgcgcgg ctttagatct cgtcggatct cggctggggc    8100
gcgggccccg cccccacgcc ctgcccacct ccacttgctc cacgtcacgg cgagcgcctc    8160
ccctcctccc ccccgttatc tatcgcctcc tccgcagcct cctcgccatc gcaattcgca    8220
ccagtcacca gcgcatcgcc tctcccgccc atttggcccg gaaccctcg cgacctcatc    8280 tcctcctcgt catcccacgc gtaggtgcgc accgcgccct gctgcggc taccgggaga    8340 tagctcgtaa attcaactct tctcatatat atatatattt ttttttctaa attgatttag    8400 ctggttttt ttggggttgt ttctgcggta gagttcgtca gggtcgcctc cagtggatct    8460
cgagaagtcc gatttcccag gcgctgctgt taccttgggt ggaggcaagt tggaactgcg    8520
ctgtttgctt cacagacttt tccttctgaa gttttgctct gatgaggttt atcttttgt    8580 tctatgttta gctcggaccg cggattagtg ggattttgaa gggagacggt gtttactgac    8640
ttcctttcac tactcatacc aaatcctttg tttcgtactg cctcaaatct ctattgtcag    8700
ttttgtgtag gggaatttcg tatataatta tccttattat atgagatgtt taatgtttca    8760
caggagtcgg aagcaactga ttttgggcgt cgcggcttaa gaataatttc ttccagcccg    8820
gatacatgta atcctctctg gctgtgacca atactgcaaa atggagtgct tattctgagc    8880
atctgttatg ctcatgacag attggtgttt gattccccct gcagattcgt acttggattc    8940
agcgtatgca ttttttatgc tgacatagga tgtgctccac catctgtgaa ctccctctag    9000
ttgcacaaac caaccactgc agtgctctct ctctcttcga atcaggcta             9049

<210> SEQ ID NO 20
<211> LENGTH: 200
<212> TYPE: DNA
<213> ORGANISM: Oryza sativa (cv. Nipponbare)

<400> SEQUENCE: 20
gatcagatct ctcggcattt acgaggtacc atacacctgt ggcttccaat caaggtggga      60
caggattcat gggaagctgt tcgctgcatg ataatagctc agaggctatg aaaacggatt     120
ctgcttacaa catgaagtca aactcagatg ctgcaccaat aaaacaaggt tctaatggta     180
gtagcaataa caatgacatg                                                200

<210> SEQ ID NO 21
<211> LENGTH: 200
<212> TYPE: DNA
<213> ORGANISM: Oryza longistaminata

<400> SEQUENCE: 21
gatccgatct ctcggcattt acgaggtacc atacacctgt ggcttccaat caaggtggga      60
caggattcgt gggaagctgt tcgccgcatg ataatagctc agaggctatg aaaacggatt     120
```

-continued

```
ctacttacaa catgaagtca aactcagatg ctgcaccaat aaaacaaggt tctaatggta    180
gtagcaataa caatgacatg                                                200
```

NUCLEIC ACID IMPARTING HIGH-YIELDING PROPERTY TO PLANT, METHOD FOR PRODUCING TRANSGENIC PLANT WITH INCREASED YIELD, AND METHOD FOR INCREASING PLANT YIELD

REFERENCE TO SEQUENCE LISTING SUBMITTED VIA EFS-WEB

This application includes an electronically submitted sequence listing in .txt format. The .txt file contains a sequence listing entitled "2015-10-09_0230-0333PUS1_ST25.txt" created on Oct. 9, 2015 and is 177,677 bytes in size. The sequence listing contained in this .txt file is part of the specification and is hereby incorporated by reference herein in its entirety.

TECHNICAL FIELD

The present invention relates to nucleic acids that impart high-yielding ability to plants, in particular, nucleic acids that comprise a promoter of a pseudo-response regulator and/or a coding region of the pseudo-response regulator derived from the wild rice species *Oryza longistaminata*. The present invention further relates to methods for producing transgenic plants with increased yield using the said nucleic acids, and methods for increasing the yield of plants.

BACKGROUND ART

1. Studies on Genes that Increase the Quantitative Traits of Plants

For raising new varieties that are agriculturally useful, various breeding methods have been practiced, two examples of which are crossbreeding that involves crossing two plants and selecting the progeny and mutation breeding that induces mutation in plants. In recent years, genetically modified plants are also raised by introducing useful genes and causing their functions to be expressed. Effective for this purpose of raising new varieties is a method of accumulating genes that impart superior properties but under the circumstances where further improvements in crop productivity are desired, the availability of genes that can be used is far from being satisfactory and it is especially desirable to identify genes that govern high-yielding and other quantitative traits.

With the recent progress of techniques in molecular biology, it has become possible to perform gene analyses of quantitative traits using DNA markers. Active studies are also being made to clone agriculturally useful genes by techniques in molecular biology using genetic maps. In organisms whose genetic maps have been constructed, attempts are being made to perform techniques such as a linkage analysis for a trait that shows a particular phenotype and an associated marker and the subsequent chromosomal walking to thereby identify the physical position of the gene that governs the trait and then isolate the gene (this technique is called "map-based cloning"). However, the region including the gene that governs a particular quantitative trait can usually be specified only roughly and what can be identified is simply a DNA fragment which theoretically includes a lot of genes. It is by no means easy to identify the gene of interest on a fragment small enough to be cloned or one that is small enough to be transferred into a plant by transformation. The procedure of preparing a detailed genetic map, specifying the gene of interest based on the map information, and cloning the desired gene involves a prolonged time and much labor. Actually, there are cases in which genes capable of increasing quantitative traits were cloned by map-based cloning (Non-Patent Document 1: Ashikari et al. 2005; Non-Patent Document 2: Miura et al. 2010) but their number is quite limited.

*Oryza longistaminata* (*O. longistaminata*), a wild rice species native of Africa, is known to have the same A genome as the cultivated species *Oryza sativa* (*O. sativa L*) but show a larger biomass than the latter. The present inventors raised BC7F6 line No. 645 with increased growth in the process of introducing the long anther of *O. longistaminata* into the rice cultivar Shiokari. They then successfully applied map-based cloning to narrow down the increased growth imparting region to within approximately 180 kb in the farthest end portion of chromosome 7. Subsequently, the inventors determined the nucleotide sequence of approximately 82 kb of that region and investigated transformants created on the basis of the thus determined sequence but they were unable to obtain transformants showing increased growth (Non-Patent Document 3).

2. Clock-Associated Genes in Plants

As regards clock-associated genes in plants, three genes have been discovered in a study using *Arabidopsis* and they are CIRCADIAN CLOCK ASSOCIATED 1 (CCA1), LATE ELONGATED HYPOCOTYL (LHY), and TIMING OF CAB EXPRESSION 1 (TOC1). It has been found that a mechanism underlying the circadian clock of plants is a feedback loop for the expression of these genes, among which the TOC1 gene is known as one of pseudo-response regulators (PRRs). On the following pages, pseudo-response regulators are designated by the acronym PRR. Currently known PRR genes that have been identified in *Arabidopsis* are five, i.e., PRR3, PRR5, PRR7, and PRR9 in addition to TOC1 (PRR1). It was also found that PRR9, PRR7, PRR5, PRR3 and PRR1 (TOC1) are responsible for the circadian phenomenon as the result of their expression levels being elevated and attenuated in the order written (Non-Patent Document 4: Matsushika et al. 2000).

Following that discovery, five orthologs corresponding to the PRR genes of the dicotyledonous *Arabidopsis* were identified in the monocotyledonous rice and shown to display a circadian rhythm as does *Arabidopsis*. Further, these orthologs of rice, i.e., OsPRR1, OsPRR37, OsPRR59, OsPRR73, and OsPRR95, were mapped on chromosomes 1, 7, 11, 3 and 9, respectively, on the genome of rice (Non-Patent Document 5: Murakami et al. 2003). It was also reported that introduction of a construct that controls the expression of rice OsPRR37 cDNA by a promoter of the *Arabidopsis* PRR7 gene into a mutant of the *Arabidopsis* PRR7 gene led to a functional supplementation (Non-Patent Document 6: Murakami et al. 2007).

A comparison of an expression profile showed that the OsPRR gene of the *Japonica* rice variety Nipponbare was quite similar to that of the Indica rice Kasalath, indicating that the gene is well conserved in both *Japonica* and Indica varieties (Non-Patent Document 7: Murakami M et al. 2005).

Concerning PPR genes, it has been reported that by linking constitutive promoters to the said genes, the yield of plants increased. Two specific known cases are as follows: when a construct in which a promoter capable of constitutive expression in rice (GOS2 promoter) was linked to the tomato-derived structural gene PRR2 was introduced into rice, its yield increased (Patent Document 1); and when a construct in which a constitutive promoter (RICE ACTIN promoter) was linked to the *Arabidopsis*-derived PRR5 gene was introduced into rice, the number of rice culms increased and so did the plant height (Patent Document 2). To date, however, no case has been reported where researchers focused on PRR promoters.

CITATION LIST

Patent Documents

Patent Document 1: US Patent Application Publication 2011/0145949
Patent Document 2: WO2011/049243

Non-Patent Documents

Non-Patent Document 1: Ashikari M., Sakakibara H., Lin S., Yamamoto T., Takashi T., Nishimura A., Angeles E R., Qian Q., Kitano H., and Matsuoka M. (2005) Cytokinin oxidase regulates rice grain production Science 309:741-745
Non-Patent Document 2: Miura K., Ikeda M., Matsubara A., Song X. J., Ito M., Asano K., Matsuoka M., Kitano H. and Ashikari M. (2010) OsSPL14 promotes panicle branching and higher grain productivity in rice Nature Genetics 42: 545-549
Non-Patent Document 3: Maekawa M and Komori T. Ine Yaseishu *O. longistaminata* Senshokutai Bubun Donyukeito ni okeru Seiikuouseisei ni kakawaru Genin-idenshi Tanri to Kinoukaiseki (QT2002) 40-43, Kenkyuseika Dai-473 Shu, Genomu Ikushu ni yoru Kouritsuteki Hinshuikusei Gijyutsu no Kaihatsu QTL Idenshikaiseki no Suishin, published Feb. 20, 2009, edited and published by Norinsuisansho (MAFF) Norinsuisan Gijyutsu Kaigi Jimukyoku
Non-Patent Document 4: Matsushika A., Makino S., Kojima M. and Mizuno T. (2000) Circadian Waves of Expression of the APRR1/TOC1 Family of Pseudo-Response Regulators in *Arabidopsis thaliana*: Insight into the Plant Circadian Clock Plant Cell Physiol. 41: 1002-1012
Non-Patent Document 5: Murakami M., Ashikari M., Miura K., Yamashino T. and Mizuno T. (2003) The Evolutionarily Conserved OsPRR Quintet: Rice Pseudo-Response Regulators Implicated in Circadian Rhythm Plant Cell Physiol. 44: 1229-1236
Non-Patent Document 6: MURAKAMI, M., Y. TAGO, et al. (2007). "Characterization of the Rice Circadian Clock-Associated Pseudo-Response Regulators in *Arabidopsis thaliana*. Bioscience, Biotechnology, and Biochemistry 71(4): 1107-1110.
Non-Patent Document 7: Murakami M., Matsushika A., Ashikari M., Yamashino T. and Mizuno T. (2005) Circadian-associated rice pseudo-response regulators (OsPRRs): Insight into the control of flowering time Biosci. Biotechnol. Biochem. 69:410-414
Non-Patent Document 8: Harushima, Y., Yano, M., Shomura, A., Sato, M., Shimano, T., Kuboki, Y., Yamamoto, T., Lin, S. Y., Antonio, B. A., Parco, A., Kajiya, H., Huang, N., Yamamoto, K., Nagamura, Y., Kurata, N., Khush, G. S., and Sasaki, T. (1998) A high-density rice genetic linkage map with 2275 markers using a single $F_2$ population. Genetics, 148, 479-494.
Non-Patent Document 9: Hiei et al. (1994) Efficient transformation of rice (*Oryza Sativa* L.) mediated by *Agrobacterium* and sequence analysis of boundaries of the T-DNA Plant J. 6:271-282.
Non-Patent Document 10: Komari et al. (1996) Vectors carrying two separate T-DNAs for co-transformation of higher plants mediated by *Agrobacterium tumefaciens* and segregation of transformants free from selection markers. Plant J. 10, 165-174.
Non-Patent Document 11: Ditta et al. (1980) Broad host range DNA cloning system for gram-negative bacteria: construction of a gene bank of *Rhizobium meliloti*. Proceedings of the National Academy of Sciences of the United States of America 77:7347-7351.
Non-Patent Document 12: Ishida et al. (2007) *Agrobacterium*-mediated transformation of maize. Nature Protocols 2:1614-1621.
Non-Patent Document 13: Ogiso et al. (2010) The role of casein kinase II in flowering time regulation has diversified during evolution. Plant Physiology. 152:808-820

SUMMARY OF INVENTION

Technical Problem

As described above, there exists a need to develop means for increasing quantitative traits of plants. It is therefore an object of the present invention to provide nucleic acids capable of imparting high-yielding ability to plants. A further object of the present invention is to use such nucleic acids to produce transgenic plants with increased yield, as well as to provide methods for increasing the yield of plants.

Solution to Problem

As a result of the investigation through map-based cloning of the increased growth imparting region residing in the farthest end portion of *O. longistaminata* chromosome 7, the present inventors had already narrowed down the region to within approximately 180 kb in the farthest end portion of chromosome 7. The inventors subsequently determined the nucleotide sequence of 82 kb of that region and found the presence of a larger-than-1 kbp deletion at five locations as well as an insertion of approximately 3 kbp at a terminal end. Thus, although the region of interest was narrowed down to within approximately 180 kbp, the above-mentioned differences made further narrowing down difficult to achieve.

Based on this 82 kb region and also considering the position of full-length cDNA of Nipponbare, the present inventors designed, created and investigated seven constructs. As a result, the inventors revealed that a PRR7 gene homolog residing in the ca. 82 kb region is a responsible gene for imparting high-yielding ability. Even more surprising was the finding that the high-yielding ability of *O. longistaminata* is not imparted by the coding region of the gene alone but that a promoter region of *O. longistaminata* also makes great contribution.

Based on these findings, the present invention provides a nucleic acid comprising the nucleotide sequence of a promoter of a pseudo-response regulator gene in *O. longistaminata*, as well as a nucleic acid in which the promoter and a structural gene of the pseudo-response regulator are operably linked. These nucleic acids are capable of imparting high-yielding ability to plants.

The present invention is preferably implemented as described in the following embodiments, to which the present invention is by no means limited.

Embodiment 1

A nucleic acid comprising
(1) a nucleotide sequence represented by 34845-35044 of SEQ ID NO: 1 or
(2) a nucleotide sequence that has at least 90% identity to the nucleotide sequence represented by 34845-35044 of SEQ ID NO: 1 and which shows an activity for promoting the transcription of a plant gene.

Embodiment 2

(1) a nucleotide sequence represented by 33045-35044 of SEQ ID NO: 1 or
(2) a nucleotide sequence that has at least 90% identity to the nucleotide sequence represented by 33045-35044 of SEQ ID NO: 1 and which shows an activity for promoting the transcription of a plant gene.

Embodiment 3

(1) a nucleotide sequence represented by 26779-35044 of SEQ ID NO: 1 or
(2) a nucleotide sequence that has at least 80% identity to the nucleotide sequence represented by 26779-35044 of SEQ ID NO: 1 and which shows an activity for promoting the transcription of a plant gene.

Embodiment 4

A nucleic acid comprising a nucleotide sequence which is derived from O. longistaminata and represented by at least 34845-35044 of SEQ ID NO: 1, said nucleic acid showing an activity for promoting the transcription of a plant gene.

Embodiment 5

The nucleic acid as recited in embodiment 4 which comprises a fragment of a nucleic acid consisting of a nucleotide sequence represented by 33045-35044 of SEQ ID NO: 1.

Embodiment 6

The nucleic acid as recited in embodiment 4 or 5 which comprises a fragment of a nucleic acid consisting of a nucleotide sequence represented by 26779-35044 of SEQ ID NO: 1.

Embodiment 7

A nucleic acid in which
(1) the nucleic acid as defined in any one of embodiments 1 to 6 and
(2) a nucleic acid encoding a protein characterized by the following (a) to (c):
  (a) having an amino acid sequence having at least 80% identity to an amino acid sequence represented by SEQ ID NO: 3 or an amino acid sequence represented by SEQ ID NO: 5;
  (b) comprising an amino acid sequence of a pseudo-receiver domain in a pseudo-response regulator protein of a plant or an amino acid sequence having at least 90% identity to said amino acid sequence, and an amino acid sequence of a CCT motif in a pseudo-response regulator protein of a plant or an amino acid sequence having at least 90% identity to said amino acid sequence; and
  (c) having an activity for suppressing the transcription of a LHY (Late Elongated Hypocotyl) gene and a CCA1 (Circadian Clock-Associated 1) gene are operably linked.

Embodiment 8

The nucleic acid as recited in embodiment 7 which enables an increase in plant yield.

Embodiment 9

A vector comprising the nucleic acid as recited in any one of embodiments 1 to 8.

Embodiment 10

A transgenic plant comprising the nucleic acid as recited in embodiment 7 or 8.

Embodiment 11

The transgenic plant as recited in embodiment 10 wherein the plant is a monocotyledon.

Embodiment 12

The transgenic plant as recited in embodiment 11 wherein the plant is rice or corn.

Embodiment 13

A method for producing a transgenic plant with increased yield which comprises the step of introducing into a plant the nucleic acid as recited in embodiment 7 or 8 or the vector of embodiment 9.

Embodiment 14

The method as recited in embodiment 13 wherein the plant is a monocotyledon.

Embodiment 15

The method as recited in embodiment 14 wherein the plant is rice or corn.

Embodiment 16

A method for increasing plant yield characterized by introducing the nucleic acid as recited in embodiment 7 or 8 into a plant.

Embodiment 17

A DNA marker for selecting a plant with increased yield which comprises 15 to 2000 nucleotides in a nucleotide sequence represented by 26779-35044 of SEQ ID NO: 1 and/or a nucleotide sequence represented by 35825-46721 of SEQ ID NO: 1.

Embodiment 18

A method for determining high-yielding ability of a plant which comprises detection of the DNA marker recited in embodiment 17 in a plant and concluding that the plant has high-yielding ability if the DNA marker is detected.

Embodiment 19

A method for promoting the transcriptional activity of a plant gene by using a nucleic acid comprising a nucleotide sequence represented by 34845-35044 of SEQ ID NO: 1 or a nucleotide sequence having at least 90% identity to the nucleotide sequence represented by 34845-35044 of SEQ ID NO: 1.

Embodiment 20

A method for promoting the transcriptional activity of a plant gene by using a nucleic acid comprising a nucleotide sequence represented by 33045-35044 of SEQ ID NO: 1 or a nucleotide sequence having at least 90% identity to the nucleotide sequence represented by 33045-35044 of SEQ ID NO: 1.

Embodiment 21

A method for increasing plant yield characterized in that the nucleic acids recited below in (1) and (2) which are operably linked and introduced into a plant:
(1) a nucleic acid comprising a nucleotide sequence characterized by the following (a) or (b):
(a) a nucleotide sequence represented by 26779-35044 of SEQ ID NO: 1 or a fragment that comprises part of this nucleotide sequence and which shows an activity for promoting the transcription of a plant gene or
(b) a nucleotide sequence that has at least 90% identity to the nucleotide sequence represented by (a) above and which shows an activity for promoting the transcription of a plant gene;
(2) a nucleic acid encoding a protein characterized by the following (c) to (e):
(c) having an amino acid sequence having at least 80% identity to an amino acid sequence represented by SEQ ID NO: 3 or an amino acid sequence represented by SEQ ID NO: 5;
(d) comprising an amino acid sequence of a pseudo-receiver domain in a pseudo-response regulator protein of a plant or an amino acid sequence having at least 90% identity to said amino acid sequence, and an amino acid sequence of a CCT motif in a pseudo-response regulator protein of a plant or an amino acid sequence having at least 90% identity to said amino acid sequence; and
(e) having an activity for suppressing the transcription of a LHY (Late Elongated Hypocotyl) gene and a CCA1 (Circadian Clock-Associated 1) gene.

Embodiment 22

A nucleic acid encoding a protein having an amino acid sequence represented by SEQ ID NO: 3.

Embodiment 23

A protein having an amino acid sequence represented by SEQ ID NO: 3.

Embodiment 24

A nucleic acid in which the nucleic acids recited below in (1) and (2) are operably linked:
(1) a nucleic acid comprising a nucleotide sequence defined by the following (a) or (b):
(a) a nucleotide sequence represented by SEQ ID NO: 19 or
(b) a nucleotide sequence that has at least 80% identity to the nucleotide sequence represented by SEQ ID NO: 19 and which shows an activity for promoting the transcription of a plant gene;

(2) a nucleic acid encoding a protein defined by the following (c) to (e):
(c) having an amino acid sequence represented by SEQ ID NO: 17, or an amino acid sequence having at least 80% identity to an amino acid sequence represented by SEQ ID NO: Y SEQ ID NO: 17
(d) comprising an amino acid sequence of a pseudo-receiver domain in a pseudo-response regulator protein of a plant or an amino acid sequence having at least 90% identity to said amino acid sequence, and an amino acid sequence of a CCT motif in a pseudo-response regulator protein of a plant or an amino acid sequence having at least 90% identity to said amino acid sequence; and
(e) having an activity for suppressing the transcription of a LHY (Late Elongated Hypocotyl) gene and a CCA1 (Circadian Clock-Associated 1) gene.

Advantageous Effects of Invention

By introducing into a plant the construct, in which the promoter of the present invention and the structural gene PRR7 are operably linked, the plant can be imparted high-yielding ability.

BRIEF DESCRIPTION OF DRAWINGS

The patent or application file contains at least one color drawing. Copies of this patent or patent application publication with color drawing will be provided by the USPTO upon request and payment of the necessary fee.

FIG. 7 is a diagram showing the percent identity and similarity for amino acid sequences encoded by the translated regions of isolated PRR7 gene derived from Nipponbare, *O. longistaminata, Sorghum*, and *Arabidopsis*; percent identity and similarity were determined with the gene analysis software Genetyx (registered trademark) network version (ver. 11.0.4) (product of GENETYX CORPORATION) by executing Protein vs Protein Global Homology by default (with "Unit size to compare" set to 2).

DESCRIPTION OF EMBODIMENTS

Figure 1:
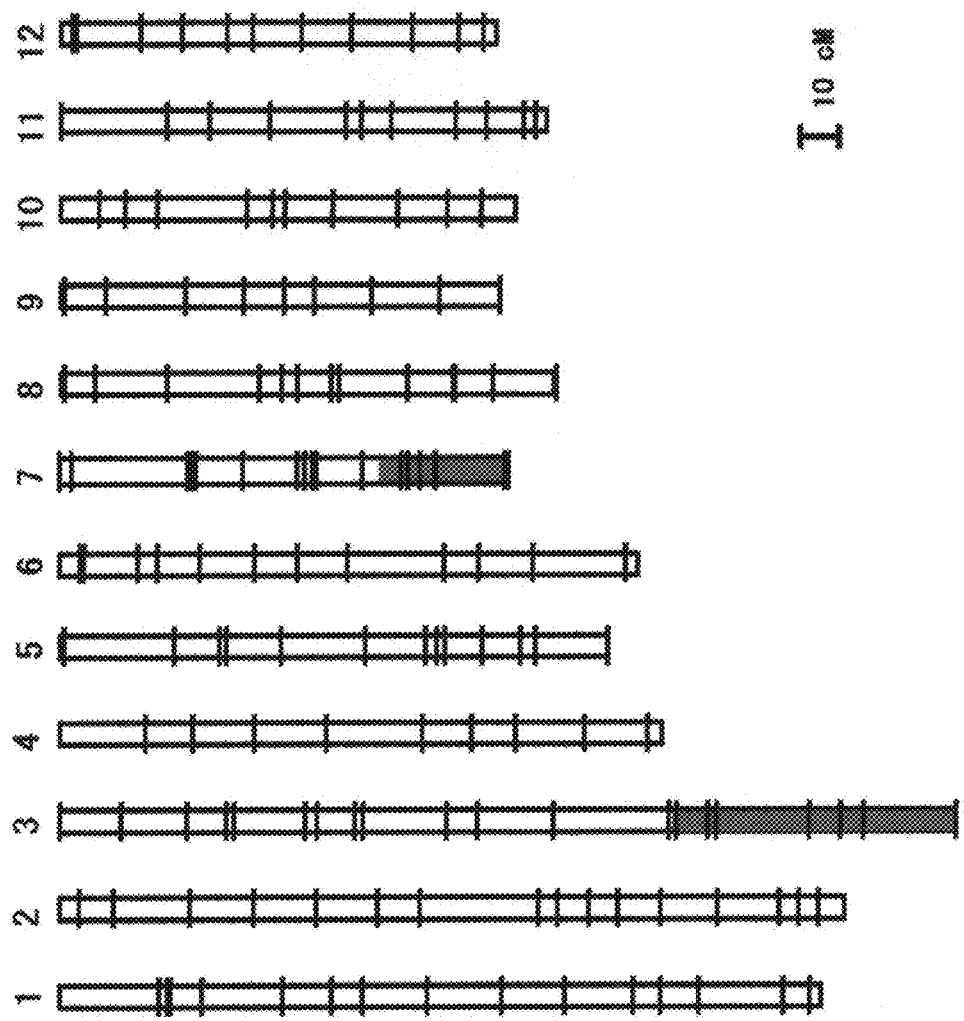
FIG. 1 is a diagram showing genotypes of line No. 645, which carries a chromosomal segment derived from the wild rice species *O. longistaminata*; the dark regions are the chromosomal segment derived from *O. longistaminata*.

The constitution of the present invention is described below more specifically.

(1) Promoter of PRR7 Gene Derived from *O. longistaminata*

As described in Examples given later in this specification, the present inventors searched through fosmid libraries of *O. longistaminata* to select four fosmid clones (Fos1, Fos2, Fos10, and Fos12) located in the terminal portion of chromosome 7 (of *O. longistaminata*) involved in high-yielding ability and decoded the nucleotide sequence of that contig. The identified nucleotide sequence is depicted in SEQ ID NO: 1.

Using those four fosmid clones, the present inventors prepared seven constructs for use in a complementation test; the largest fragment obtained by treating Fos10 with SmaI and PstI was linked to the fourth largest fragment obtained by treating Fos1 with PstI and SacI to create fragment (Fr) 4. Fr4 is a genomic fragment involved in high-yielding ability and comprises the $26779^{th}$ to $49155^{th}$ nucleotides in SEQ ID NO: 1.

The promoter of PRR7 gene derived from the wild rice species *O. longistaminata* (hereinafter referred to as "the promoter of the present invention") is a nucleic acid comprising a nucleotide sequence represented by 34845-35044 of SEQ ID NO: 1, preferably a nucleic acid comprising a nucleotide sequence represented by 33045-35044 of SEQ ID NO: 1, and more preferably a nucleic acid comprising a nucleotide sequence represented by 26779-35044 of SEQ ID NO: 1.

The term "promoter" as used herein means a nucleic acid which is capable of activating the transcription of any plant's structural gene that is present immediately downstream thereof. The "promoter" as used herein should be interpreted in the broad sense of the term and is by no means limited to have a narrow sense such as a core promoter region to which a transcription factor binds to induce the correct initiation of transcription. The promoter of the present invention has an action for promoting the transcriptional activity of not only the coding region of PRR gene but also any structural gene in various plants. In other words, the present invention embraces nucleic acids in which the promoter of the present invention is operably linked to any plant's structural gene. Preferably, such nucleic acids are not naturally occurring genomic fragments.

The term "the action for promoting the transcriptional activity of a structural gene" as used herein encompasses a mode in which a stimulus such as light induces the promotion of the transcriptional activity of a structural gene to thereby modulate or control said activity. Here the induced promotion of the transcriptional activity of a structural gene upon photo-stimulation of the promoter means that in a light period where light is present, the promoter promotes the transcriptional activity of a structural gene but in other periods, the promoter does not promote the transcriptional activity of the structural gene.

The promoter of the present invention is a nucleic acid comprising a nucleotide sequence represented by 34845-35044 of SEQ ID NO: 1, preferably a nucleic acid comprising a nucleotide sequence represented by 33045-35044 of SEQ ID NO: 1, and more preferably a nucleic acid comprising a nucleotide sequence represented by 26779-35044 of SEQ ID NO: 1. It should be noted that the promoter of the present invention is by no means limited to these nucleic acids and encompasses nucleic acids having at least a certain level of sequence identity to those nucleic acids, as well as fragments of such nucleic acids; for details, see below.

High-yielding ability can be imparted to a plant by introducing the above-described promoter operably linked to PRR7 gene into a plant. To be more specific, the promoter of the present invention can increase plant yield when it is operably linked to a nucleic acid encoding a protein having an amino acid sequence represented by SEQ ID NO: 3.

The definition of the PRR7 protein as used herein is given below under (2) "Nucleic acids in which the promoter of the present invention is operably linked to PRR structural gene."

As used herein, the term "high-yielding ability" refers to an increase in one or more traits of a plant including its total weight, aboveground weight, yield, stem diameter, the number of stems, culm length, leaf area, the number of leaves, the number of panicles or heads, the number of grains per panicle or head, panicle length, total panicle weight, and seed yield. The term preferably refers to an increased total panicle weight and/or seed yield, more preferably refers to an increase in the yield of filled seeds. In cereal plants such as rice and corn, the yield of filled seeds is an extremely important trait. A measure for evaluating the increase may be by comparison with a control plant (e.g. parent plant or non-transgenic plant). As used hereinafter, the terms "high-yielding ability" and "increased growth" mean the same.

In SEQ ID NO: 1, the sequence spanning 26779-35044 is the promoter region of the PRR7 gene of *O. longistaminata*, the sequence spanning 35825-46721 is the coding region of the PRR7 gene of *O. longistaminata*, and the sequence spanning 46722-49157 is the terminator region of the PRR7 gene of *O. longistaminata*. In the above-mentioned promoter region, the nucleotide sequence represented by 34845-35044 of SEQ ID NO: 1 corresponds to 200 nucleotides in a region upstream of the transcription initiation point and the nucleotide sequence represented by 33045-35044 of SEQ ID NO: 1 corresponds to 2000 nucleotides in a region upstream of the transcription initiation point.

The nucleotide sequence of the promoter of the present invention is not limited to the one represented by 34845-35044 of SEQ ID NO: 1, or the one represented by 33045-35044 of SEQ ID NO: 1, or the one represented by 26779-35044 of SEQ ID NO: 1, and it also contains nucleic acids that comprise nucleotide sequences that have at least 80%, 85%, 90%, 95%, 97%, 99% or 99.5% identity to the above-identified nucleotide sequences and which show an activity for promoting the transcription of plant's coding regions.

In another aspect of the present invention, the promoter of interest is a nucleic acid that comprises a nucleotide sequence derived from *O. longistaminata* and represented by at least 34845-35044 of SEQ ID NO: 1 and which shows an activity for promoting the transcription of a plant gene. This nucleic acid preferably comprises a fragment of a nucleic acid that consists of a nucleotide sequence represented by 33045-35044 of SEQ ID NO: 1, more preferably comprises a fragment of a nucleic acid that consists of a nucleotide sequence represented by 26779-35044 of SEQ ID NO: 1. Here the term "a fragment of a nucleic acid" means a nucleic acid as a portion of a nucleotide sequence whose range is defined by any one of the nucleotide numbers set forth above with reference to SEQ ID NO: 1. Specific, but by no means limiting, examples include shorter sequences as obtained from 26779-35044 of SEQ ID NO: 1, namely, a sequence corresponding to 6000 nucleotides, a sequence corresponding to 5000 nucleotides, a sequence corresponding to 4000 nucleotides, a sequence corresponding to 3000 nucleotides, a sequence corresponding to 2000 nucleotides, and a sequence corresponding to 1000 nucleotides, all being in a region upstream of the transcription initiation point.

The percent identity between two nucleic acid sequences can be determined by visual inspection and mathematical calculations, or more preferably, the comparison is done by comparing sequence information using a computer program. A representative, preferred computer program is the Genetics Computer Program (GCG; Madison, Wis.) Wisconsin Package Version 10.0 Program, GAP (Devereux et al., 1984, Nucl. Acids Res., 12:387). Use of this GAP program enables not only comparison between two nucleic acid sequences but also comparison between two amino acid sequences as well as comparison between a nucleic acid sequence and an amino acid sequence. Here preferred default parameters for the GAP program include: (1) the GCG implementation of a unary comparison matrix (including a value of 1 for identities and a value of 0 for non-identities) for nucleotides and the weighted amino acid comparison matrix of Gribskov and Burgess, Nucl. Acids Res., 14: 6745, 1986 as described in Schwartz and Dayhoff eds., "Atlas of Polypeptide Sequence and Structure," National Biomedical Research Foundation, pp. 353-358, 1979, or other comparable comparison matrices; (2) a penalty of 30 for each gap and an additional penalty of 1 for each symbol in each gap for amino acid sequences, or a penalty of 50 for each gap and an additional penalty of 3 for each symbol in each gap for nucleotide sequences; (3) no penalty for end gaps; and (4) no maximum penalty for long gaps. Other programs that can be used by those skilled in the art for sequence comparison include, for example, the BLASTN Program Version 2.2.7 accessible to use from the U.S. National Library of Medicine website http://www.ncbi.nlm.nih.gov/blast/bl2seq/bls.html, or the UW-BLAST 2.0 algorithm. Standard default parameter settings for UW-BLAST 2.0 are described at the following internet site: http://blast.wustl.edu. In addition, the BLAST algorithm uses the BLOSUM62 amino acid scoring matrix and optional parameters that can be used are as follows: (A) inclusion of a filter to mask segments of the query sequence that have low compositional complexity [as determined by the SEG program of Wootton and Federhen (Computers and Chemistry, 1993); also see Wootton and Federhen, 1996, "Analysis of compositionally biased regions in sequence databases," Methods Enzymol., 266: 544-71] or segments consisting of short-periodicity internal repeats [as determined by the XNU program of Clayerie and States (Computers and Chemistry, 1993)], and (B) a statistical significance threshold for reporting matches against database sequences, or E-score (the expected probability of matches that are found merely by chance according to the stochastic model of Karlin and Altschul, 1990; if the statistical significance ascribed to a match is greater than this E-score threshold, the match will not be reported); a preferred E-score threshold value is 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

A variant of the promoter of the present invention may be a nucleic acid that comprises a nucleotide sequence hybridizing under stringent conditions with the complementary strand of the nucleotide sequence represented by 34845-35044 of SEQ ID NO: 1, preferably the nucleotide sequence represented by 33045-35044 of SEQ ID NO: 1, and more preferably the nucleotide sequence represented by 26779-35044 of SEQ ID NO: 1, and which has promoter activity.

The term "under stringent conditions" as used herein means that two sequences hybridize under moderately or highly stringent conditions. To be more specific, moderately stringent conditions can be readily determined by those having ordinary skill in the art based on the length of DNA, for example. The basic conditions are set forth in Sambrook et al., Molecular Cloning: A Laboratory Manual, $3^{rd}$ ed., Chapter 6, Cold Spring Harbor Laboratory Press, 2001 and include the use of a prewashing solution comprising 5×SSC, 0.5% SDS, and 1.0 mM EDTA (pH 8.0), hybridization conditions consisting of ca. 50% formamide, 2× to 6×SSC, preferably 5× to 6×SSC, and 0.5% SDS at ca. 42° C. (or other similar hybridization solutions, such as Stark's solution in ca. 50% formamide at ca. 42° C.), and washing conditions as consisting of 0.1× to 6×SSC and 0.1% SDS at ca. 50-68° C. The moderately stringent conditions preferably include hybridization conditions (and washing conditions) consisting of 6×SSC and 0.5% SDS at ca. 50° C.

Highly stringent conditions can also be readily determined by those skilled in the art based on the length of DNA, for example. Generally, these conditions include hybridization at higher temperatures and/or lower salt conditions than under moderately stringent conditions (for example, hybridization in the presence of ca. 0.5% SDS using 6×SSC to 0.2×SSC, preferably 6×SSC, more preferably 2×SSC, and even more preferably 0.2×SSC, or 0.1×SSC) and/or washing; highly stringent conditions may, for example, be defined as ones that involve the above-described hybridization conditions and washing in 0.2× to 0.1×SSC and 0.1% SDS at ca. 65-68° C. In the hybridization and washing buffers, SSPE (1×SSPE consists of 0.15 M NaCl, 10 mM NaH$_2$PO$_4$, and 1.25 mM EDTA at pH 7.4) may be substituted for SSC (1×SSC consists of 0.15 M NaCl and 15 mM sodium citrate) and washing is performed for about 15 minutes to an hour after completion of the hybridization.

If desired, a commercial hybridization kit can be used that does not use any radioactive substance as a probe. A specific example is hybridization using an ECL direct labeling & detection system (Amersham). Exemplary stringent conditions for hybridization are such that it is performed at 42° C. for 4 hours with 5% (w/v) blocking reagent and 0.5 M NaCl added to the hybridization buffer in the kit whereas washing is done twice in 0.4% SDS and 0.5×SSC at 55° C. for 20 minutes and once in 2×SSC at room temperature for 5 minutes.

(2) Nucleic Acid in which the Promoter of the Present Invention and PRR7 Structural Gene are Operably Linked The construct to be used in the present invention is a nucleic acid in which the promoter of the present invention and a nucleic acid comprising a nucleotide sequence encoding the PRR7 protein of a plant (i.e., the PRR7 structural gene) are operably linked. The promoter of the present invention as referred to hereinabove is as described above in (1) Promoter of PRR7 gene derived from *O. longistaminata*. By introducing such nucleic acid (in which the promoter of the present invention and the PRR7 structural gene are operably linked) into a plant, high-yielding ability can be imparted to the plant. It is actually shown in Examples to be described later that when a nucleic acid, in which the promoter of the present invention comprising a nucleotide sequence represented by 26779-35044 of SEQ ID NO: 1 and the PRR7 structural gene are operably linked, was introduced into a plant, the plant acquired high-yielding ability. Shorter sequences as obtained from 26779-35044 of SEQ ID NO: 1, namely, a sequence corresponding to 6000 nucleotides, a sequence corresponding to 5000 nucleotides, a sequence corresponding to 4000 nucleotides, a sequence corresponding to 3000 nucleotides, a sequence corresponding to 2000 nucleotides, and a sequence corresponding to 1000 nucleotides, all being in a region upstream of the transcription initiation point, may be selected appropriately as the promoter and used to impart high-yielding ability to plants; this is a matter that skilled artisans can readily perform in view of the findings disclosed herein. To be more specific, a skilled artisan, based on the disclosure of the subject specification, can easily select a suitable promoter by a method in which any one of the shorter sequences mentioned above and a nucleic acid encoding a protein having an amino acid sequence represented by SEQ ID NO: 3 are operably linked, thus the prepared construct is introduced into a plant, and the yield of the transgenic plant is checked. The nucleic acid having such ability to impart high-yielding to plants is preferably one in which the promoter of the present invention having an activity to modulate or control a structural gene through induction of transcriptional activity of such a gene in response to a stimulus such as light is linked to the PRR7 structural gene.

The term "operably linked" as used herein means that the nucleic acid of the promoter of the present invention and the nucleic acid of the PRR7 structural gene are joined in such a manner that the function of promoter activity, i.e., the promoter promotes the transcriptional activity of a structural gene, can be materialized.

The term "PRR7 protein" as used herein means proteins that satisfy the conditions set forth below.

(a) The protein should have an amino acid sequence represented by SEQ ID NO: 3 or an amino acid sequence represented by SEQ ID NO: 5.

The PRR7 protein as referred to herein is a protein having an amino acid sequence represented by SEQ ID NO: 3 or an amino acid sequence represented by SEQ ID NO: 5. The PRR7 protein derived from *O. longistaminata* consists of the 740 amino acids represented by SEQ ID NO: 3 and is encoded by a nucleic acid comprising a nucleotide sequence represented by SEQ ID NO: 2. The PRR7 protein derived from Nipponbare consists of the 742 amino acids represented by SEQ ID NO: 5 in the Sequence Listing and is encoded by a nucleic acid comprising a nucleotide sequence represented by SEQ ID NO: 4.

The PRR7 protein as referred to herein is by no means limited to one comprising the amino acid sequence represented by SEQ ID NO: 3 or SEQ ID NO: 5 and may comprise proteins having amino acid sequences with at least 65%, 70%, 75%, 80%, 85%, 90%, 95%, 97% or 99% identity to the amino acid sequence represented by SEQ ID NO: 3 or SEQ ID NO: 5.

In addition, the PRR7 protein as referred to herein may comprise proteins having amino acid sequences with at least 90%, 95%, 97% or 99% similarity to the amino acid sequence represented by SEQ ID NO: 3 or SEQ ID NO: 5.

The percent similarity of amino acid sequences as referred to herein means the degree of similarity between proteins that takes difference levels of amino acids into account. In short, when amino acids undergo conservative substitution or the like as will be described later herein, the resulting amino acids may be regarded as similar amino acids and accordingly percent similarity is calculated.

(b) the Protein should Comprise a PR Domain and a CCT Motif.

The PRR7 protein as referred to herein is one that comprises a PR domain and a CCT motif. It is known that PRR proteins are associated with the circadian clock of plants and ubiquitous in plants. PRR proteins comprise highly conserved pseudo-receiver (PR) domains and CCT motifs. The PR domain is known to be a common motif of PRR proteins that has the ability to provide interaction between proteins. Being rich in basicity, CCT motifs are considered to be involved in forming bonds between proteins. The PRR7 protein is a member of PRR proteins and comprises the PR domain and the CCT motif.

The PR domain corresponds to amino acid numbers 62 to 176 in the amino acid sequence of SEQ ID NO: 3 and corresponds to amino acid numbers 62 to 176 in the amino acid sequence of SEQ ID NO: 5. As for the CCT motif, it corresponds to amino acid numbers 676 to 722 in the amino acid sequence of SEQ ID NO: 3 and corresponds to amino acid numbers 678 to 724 in the amino acid sequence of SEQ ID NO: 5. Hence, the PR domain as referred to herein means an amino acid sequence corresponding to amino acid numbers 62 to 176 in the amino acid sequence of SEQ ID NO: 3. In contrast, the CCT motif as referred to herein means an amino acid sequence corresponding to amino acid numbers 676 to 722 in the amino acid sequence of SEQ ID NO: 3. However, the amino acid sequences of the PR domain and CCT motif in the PRR7 protein as referred to herein are in no way limited to those mentioned above and may contain ones having at least 80%, 85%, 90%, 95%, 97% or 99% identity to those amino acid sequences.

In the amino acid sequence of the PR domain, the following amino acid residues are preferably not substituted but conserved: valine (Val) with amino acid number 64 in SEQ ID NO: 3; leucine (Leu), 66 (in the following list, all amino acid numbers are those in SEQ ID NO: 3); valine (Val), 67; aspartic acid (Asp), 70; aspartic acid (Asp), 71; threonine (Thr), 73; arginine (Arg), 74; valine (Val), 77; alanine (Ala), 79; leucine (Leu), 80; leucine (Leu), 81; arginine (Arg), 82; cysteine (Cys), 84; tyrosine (Tyr), 86; glutamic acid (Glu), 87; valine (Val), 88; alanine (Ala), 91; asparagine (Asn), 93; glycine (Gly), 94; alanine (Ala), 97; tryptophan (Trp), 98; leucine (Leu), 101; glutamic acid (Glu), 102; aspartic acid (Asp), 103; asparagine (Asn), 106; isoleucine (Ile), 108; aspartic acid (Asp), 109; valine (Val), 111; leucine (Leu), 112; threonine (Thr), 113; glutamic acid (Glu), 114; valine (Val), 115; methionine (Met), 117; proline (Pro), 118; serine (Ser), 121; glycine (Gly), 122; isoleucine (Ile), 123; leucine (Leu), 125; leucine (Leu), 126; isoleucine (Ile), 129; histidine (His), 132; isoleucine (Ile), 138; proline (Pro), 139; valine (Val), 140; isoleucine (Ile), 141; methionine (Met), 142; methionine (Met), 143; serine (Ser), 144; serine (Ser), 145; aspartic acid (Asp), 147; methionine (Met), 149; valine (Val), 152; phenylalanine (Phe), 153; lysine (Lys), 154; cysteine (Cys), 155; leucine (Leu), 156; serine (Ser), 157; lysine (Lys), 158; glycine (Gly), 159; alanine (Ala), 160; valine (Val), 161; aspartic acid (Asp), 162; phenylalanine (Phe), 163; leucine (Leu), 164; valine (Val), 165; lysine (Lys), 166; proline (Pro), 167; arginine (Arg), 169; lysine (Lys), 170; asparagine (Asn), 171; glutamic acid (Glu), 172; leucine (Leu), 173; lysine (Lys), 174; and leucine (Leu), 176. In the subject specification, these amino acid residues are designated "pseudo-receiver (PR) domain conserved amino acids".

Further preferably, in addition to the above-mentioned pseudo-receiver (PR) domain conserved amino acids, the following amino acid residues are not substituted but conserved in the amino acid sequence of the PR domain: glutamic acid (Glu) with amino acid number 68 in SEQ ID NO: 3; serine (Ser), 72 (in the following list, all amino acid numbers are those in SEQ ID NO: 3); glutamine (Gln), 75; valine (Val), 76; serine (Ser), 78; isoleucine (Ile), 89; proline (Pro), 90; glutamic acid (Glu), 92; tyrosine (Tyr), 100; glutamine (Gln), 105; leucine (Leu), 110; serine (Ser), 127; isoleucine (Ile), 134; cysteine (Cys), 135; lysine (Lys), 136; asparagine (Asn), 146; and asparagine (Asn), 175. It should be noted that glutamic acid (Glu) with amino acid number 68 may be replaced by aspartic acid (Asp) with amino acid number 68 in SEQ ID NO: 5. Even more preferably, in addition to the above-mentioned pseudo-receiver (PR) domain conserved amino acids, the following amino acid residues may also be conserved unsubstituted in the amino acid sequence of the PR domain: isoleucine (Ile) with amino acid number 62 in SEQ ID NO: 3; leucine (Leu), 65 (in the following list, all amino acid numbers are those in SEQ ID NO: 3); glutamine (Gln), 96; asparagine (Asn), 131; asparagine (Asn), 137; glycine (Gly), 150, and isoleucine (Ile), 168.

In the amino acid sequence of the CCT motif, the following amino acid residues are preferably not substituted but conserved: glutamine (Gln) with amino acid number 676 in SEQ ID NO: 3; glutamic acid (Glu), 678 (in the following list, all amino acid numbers are those in SEQ ID NO: 3); alanine (Ala), 682; alanine (Ala), 683; lysine (Lys), 686; phenylalanine (Phe), 687; arginine (Arg), 688; lysine (Lys), 690; arginine (Arg), 691; lysine (Lys), 692; arginine (Arg), 694; phenylalanine (Phe), 696; lysine (Lys), 698; lysine (Lys), 699; valine (Val), 700; arginine (Arg), 701; tyrosine (Tyr), 702; glutamine (Gln), 703; serine (Ser), 704; arginine (Arg), 705; lysine (Lys), 706; leucine (Leu), 708; alanine (Ala), 709; glutamic acid (Glu), 710; glutamine (Gln), 711; arginine (Arg), 712; proline (Pro), 713; arginine (Arg), 714; valine (Val), 715; arginine (Arg), 716; glycine (Gly), 717; glutamine (Gln), 718; phenylalanine (Phe), 719; valine (Val), 720; and arginine (Arg), 721. In the subject specification, these amino acid residues are designated "CCT motif conserved amino acids."

Further preferably, in addition to the above-mentioned CCT motif conserved amino acids, the following amino acid residues are not substituted but conserved in the amino acid sequence of the CCT motif: glutamine (Gln) with amino acid number 677 in SEQ ID NO: 3; asparagine (Asn), 695 (in the following list, all amino acid numbers are those in SEQ ID NO: 3); glycine (Gly), 697; arginine (Arg), 707; and glutamine (Gln), 722. It should be noted that glutamine (Gln) with amino acid number 677 may be replaced by arginine (Arg) with amino acid number 679 in SEQ ID NO: 5. Even more preferably, in addition to the above-mentioned CCT motif conserved amino acids, the following amino acid residues may also be conserved unsubstituted in the amino acid sequence of the CCT motif: glutamine (Gln) with amino acid number 689 in SEQ ID NO: 3 and glutamic acid (Glu) with amino acid number 693 in SEQ ID NO: 3.

Amino acid sequences having identity to the PR domain as referred to herein maintain the PR domain conserved amino acids and the amino acid sequence of the PR domain may be modified with respect to amino acids other than the PR domain conserved amino acids.

Amino acid sequences having identity to the CCT motif as referred to herein maintain the CCT motif conserved amino acids and the amino acid sequence of the CCT motif may be modified with respect to amino acids other than the CCT motif conserved amino acids.

These amino acid modifications may be deletion, substitution, insertion and/or addition of amino acids. The substitution of amino acids may be conservative substitution, in which a particular amino acid residue is replaced by a residue having a similar physicochemical feature. Non-limiting examples of conservative substitution include substitution between aliphatic group containing amino acid residues, as exemplified by substitution involving Ile, Val, Leu or Ala, and substitution between polar residues, as exemplified by substitution between Lys and Arg, between Glu and Asp, and between Gln and Asn.

(c) Has activity for suppressing the transcription of LHY (Late Elongated Hypocotyl) gene and CCA1 (Circadian Clock-Associated 1) gene.

The present inventors have found that a PRR gene residing at the terminal of chromosome 7 in *O. longistaminata* and having the nucleotide sequence represented by SEQ ID NO: 2 and a PRR gene (OsPRR37) residing at the terminal of chromosome 7 in Nipponbare and having the nucleotide sequence represented by SEQ ID NO: 4 are genes associated with high-yielding ability. These PRR genes are classified as PRR7 and the PRR7 protein has activity for suppressing the transcription of LHY (Late Elongated Hypocotyl) gene and CCA1 (Circadian Clock-Associated 1) gene. Thus, the PRR7 protein as referred to herein is a protein that has an activity for suppressing the transcription of LHY (Late Elongated Hypocotyl) gene and CCA1 (Circadian Clock-Associated 1) gene.

As will be shown in Examples to given later, when nucleic acids, in which the PRR7 promoter derived from *O. longistaminata* and the PRR7 structural gene derived from Nipponbare had been operably linked, were introduced into plants, the yield of the plants could also be increased, i.e., high-yielding ability could be imparted to the plants. It is therefore presumed that the *O. longistaminata* derived PRR7 promoter of the present invention plays an important role for the present invention to obtain the intended effect.

The present invention further relates to a nucleic acid in which a nucleic acid encoding a protein having at least 65%, 70%, 75%, 80%, 85%, 90%, 95%, 97% or 99% identity to the amino acid sequence represented by SEQ ID NO: 3 or the amino acid sequence represented by SEQ ID NO: 5 and having an activity for increasing plant yield when it is operably linked to the *O. longistaminata* derived PRR7 promoter is operably linked to the *O. longistaminata* derived PRR7 promoter. This nucleic acid can also impart high-yielding ability to plants if introduced therein. In a preferred embodiment of the present invention, this nucleic acid may be one that encodes a protein comprising both the PR domain and the CCT motif and/or may be one that encodes a protein that has an activity for suppressing the transcription of the LHY gene and the CCA1 gene. Note that this nucleic acid can be used as the nucleic acid for implementing the present invention in the embodiments described below in (3) to (6).

(3) Vector comprising the promoter of the present invention or a nucleic acid in which the promoter of the present invention and the PRR7 structural gene are operably linked.

The present invention relates to a vector that comprises the promoter of the present invention on its own or a vector that comprises a nucleic acid in which the promoter of the present invention and a nucleic acid (PRR7 structural gene) comprising a nucleotide sequence coding for the PRR7 protein are operably linked. These vectors are useful in imparting high-yielding ability to plants.

The present invention further relates to using the second type of vector, i.e., a vector that comprises a nucleic acid in which the promoter of the present invention and a nucleic acid (PRR7 structural gene) comprising a nucleotide sequence coding for the PRR7 protein are operably linked, for the purpose of imparting high-yielding ability to plants.

Vectors can conveniently be prepared by linking a desired gene in the usual manner to a recombination vector that is commercially available in the art. When high-yielding ability is to be imparted to plants by using the nucleic acid of the present invention, a vector for plant transformation is especially useful. The vector to be used in the present invention is not particularly limited if it can be used in plant cells in order to achieve the intended effect of the present invention and examples include pBI vectors, pBluescript vectors, and pUC vectors. Exemplary pBI vectors include pBI121, pBI101, pBI101.2, pBI101.3, pBI221, etc. Binary vectors such as pBI vectors are preferred in that a desired DNA can be introduced into plants via *Agrobacterium*. Exemplary pBluescript vectors include pBluescript SK(+), pBluescript SK(−), pBluescript II KS(+), pBluescript II KS(−), pBluescript II SK(+), pBluescript II SK(−), etc. Exemplary pUC vectors include pUC19, pUC119, etc. pBluescript vectors and pUC vectors are preferred in that DNA can be directly introduced into plants. In addition, binary vectors including pGreen series (www.pgreen.ac.uk) and pCAMBIA series (www.cambia.org), as well as super-binary vectors including pSB11 (Komari et al, 1996, Plant J, 10: 165-174) and pSB200 (Komori et al, 2004, Plant J, 37: 315-325) may also be used with preference.

The above-mentioned vectors preferably contain a transcription terminator sequence including a polyadenylation site necessary for stabilizing transcriptional products. Any skilled artisan can select an appropriate transcription terminator sequence.

The transcription terminator sequence is not particularly limited if it has a function as the transcription termination site and known types will do. For example, Nos terminator (the transcription termination region of nopaline synthase gene) and CaMV35S terminator (the transcription termination region of cauliflower mosaic virus 35S) can preferably be used. By providing the transcription terminator sequence at an appropriate position in the above-mentioned recombination/expression vectors, the occurrence of undesirable phenomena such as the synthesis of unduly long transcripts after introducing the vectors into plant cells can be prevented.

The above-mentioned recombination/expression vectors may further contain other DNA segments. Such other DNA segments are not particularly limited, but to mention a few examples, they are a transformant selection marker, an enhancer, and a nucleotide sequence for enhancing translation efficiency. The above-mentioned recombination/expression vectors may further contain a T-DNA region. The T-DNA region has the advantage that it enhances the efficiency of gene transfer, particularly in the case of introducing the above-mentioned recombination/expression vectors into a plant body using *Agrobacterium*.

A drug resistance gene may typically be used as the transformant selection marker. Specific examples of such drug resistance gene may include hygromycin, bleomycin, kanamycin, gentamicin, and chloramphenicol resistance genes (as exemplified by a neomycin phosphotrasnferase gene which expresses resistance to the antibiotic kanamycin or gentamicin, and a hygromycin phosphotransferase gene which expresses resistance to hygromycin). Also applicable is phosphinothricin acetyltransferase gene which expresses resistance to the herbicide phosphinothricin. By using these drug resistance genes to select plant bodies that grow in media containing the above-mentioned antibiotics or herbicide, transgenic plants can be easily sorted out.

An omega sequence derived from tobacco mosaic virus may typically be mentioned as the nucleotide sequence for enhancing translation efficiency. By providing this omega sequence in the untranslated region (5' UTR) of the promoter, the translation efficiency of the above-described fusion gene can be enhanced.

An applicable enhancer is an enhancer region including a sequence upstream in the CaMV35S promoter. In this way, the above-mentioned recombination/expression vectors may contain various DNA segments depending on the specific object of their use.

The method of constructing the recombination/expression vector is not particularly limited, either, and the promoter of the present invention, the PRR7 structural gene, and the terminator sequence, optionally together with the other DNA segments mentioned above, may be transferred into an appropriately selected vector (matrix) in a predetermined order. The PRR7 structural gene may typically be inserted into the vector serving as a matrix in accordance with the usual manner: DNA in a purified gene is cleaved with suitable restriction enzymes and inserted into a suitable vector DNA at the associated restriction enzyme sites or multi-cloning sites (see, for example, Molecular Cloning, 5.61-5.63).

A vector having a desired gene can be prepared as appropriate by skilled artisans using general procedures of genetic engineering technology. The vector of interest can usually be prepared by employing various commercial vectors.

(4) Transgenic Plant into which the Promoter of the Present Invention and the PRR7 Structural Gene have been Introduced.

The present invention further relates to a transgenic plant having introduced therein to a nucleic acid in which the promoter of the present invention and a nucleic acid (PPR7 structural gene) comprising a nucleotide sequence coding for the PRR7 protein are operably linked. The first mentioned nucleic acid is usually inserted into a suitable vector and then introduced into a plant cell which is to be transformed. Thus, the present invention provides a plant cell (transgenic plant) that carries the above-mentioned nucleic acid or recombination/expression vector. This plant cell includes various forms of plant cells, say, cells in suspension culture, protoplasts, and cells in a plant body. The transgenic plant according to the present invention embraces not only plant cells but also any of a whole plant, plant organs (e.g. root, stem, leaf, petal, seed, fruit, fully mature embryo, immature embryo, ovule, ovary, shoot apex, anther, pollen, etc.), plant tissues (e.g. epidermis, phloem, parenchyma, xylem, vascular bundle, etc.), sections thereof, callus, shoot primordium, multiple shoot, hairy root, cultured root, and so on.

An exemplary method for expressing the PRR7 structural gene in a host cell may comprise incorporating the gene into a suitable vector and transferring the vector in vivo by any procedure known to skilled artisans, such as the polyethylene glycol method, the *Agrobacterium* method, the liposome method, the cationic liposome method, calcium phosphate precipitation, electroporation (Current protocols in Molecular Biology edit. Ausubel et al. (1987) Publish. John Wiley & Sons. Section 9.1-9.9), lipofection (GIBCO-BRL), microinjection, and the particle gun method. In the present invention, the *Agrobacterium* method may preferably be used. To introduce the gene of the present invention into a plant body, the gene may be directly introduced into a plant cell by microinjection, electroporation, the polyethylene glycol method, etc.; alternatively, the gene of interest may be incorporated into a gene transfer plasmid and, with this plasmid being used as a vector, indirectly introduced into a plant cell via a virus or bacterium having plant infectivity. Viruses having plant infectivity may typically be exemplified by cauliflower mosaic virus, tobacco mosaic virus, geminivirus, etc., and an exemplary bacterium having plant infectivity is *Agrobacterium*. If gene transfer into plants is to be performed by the *Agrobacterium* method, commercially available plasmids may be used.

The present invention encompasses not only the plant cell into which the above-described nucleic acid or vector has been directly introduced but also a plant body grown from such plant cell, a plant which is progeny, offspring or clone of that plant, as well as reproductive materials (e.g. seed, fruit, cut panicle, tuber, tuberous root, stub, callus, protoplast, etc.). Regeneration of a plant body from the transgenic plant cell can be performed by any methods known to skilled artisans, depending on the type of the plant cell. The above-described technology which has already been established in the art is being widely used in the technical field of the present invention and the above-described method can advantageously be employed in the present invention.

The method of regenerating a plant body through rediffusion of the transformed plant cell varies with the type of the plant cell; if it is rice, the method of Fujimura et al. (Plant Tissue Culture Lett. 2:74 (1995) may be used and if it is corn, the method of Shillito et al. (Bio/Technology 7:581 (1989) and the method of Gorden-Kamm et al. (Plant Cell 2:603(1990) may be used. The presence of an exogenous gene as transferred into the transgenic plant that has been regenerated and cultivated by the above-described procedure can be verified by the known PCR and southern hybridization methods, or by analyzing the nucleotide sequences of the DNAs in the plant body. In the latter case, DNA extraction from the transgenic plant body can be carried out in accordance with the known method of J. Sambrook et al. (Molecular Cloning, $2^{nd}$ ed., Cold Spring Harbor Laboratory Press, 1989).

If the gene of the present invention occurring in the regenerated plant body is to be analyzed by the PCR method, DNA extracted from the regenerated plant as described above is used as a template to perform amplification reaction. Alternatively, synthesized oligonucleotides having nucleotide sequences as appropriately selected in accordance with the nucleotide sequence of the gene of the present invention or a modified gene may be used as primers to perform amplification reaction in a reaction solution containing a mixture of these primers. In the amplification reaction, DNA denaturation, annealing, and extension reactions may be repeated several tens of times to give an amplified product of DNA fragments containing the nucleotide sequence of the gene of the present invention. When the reaction solution containing the amplified product is subjected to agarose electrophoresis, for example, a variety of amplified DNA fragments are fractionated, making it possible to confirm that those DNA fragments correspond to the gene of the present invention.

Once the transgenic plant body which has the gene of the present invention introduced into the genome is available, offspring can be obtained from this plant body by either sexual or asexual reproduction. Alternatively, a reproductive material may be obtained from the plant body per se or from its offspring or clone and used as a starter for large-scale production of the plant body. The present invention encompasses a plant cell into which the gene or recombination/expression vector of the present invention has been introduced, a plant body containing the cell, offspring and clone of the plant body, as well as reproductive materials derived from the plant body, its offspring, or clone. In other words, the present invention encompasses T0 generation which is the plant redifferentiated through transformation, a progeny plant such as T1 generation which is a self-fertilizing seed of the T0 generation plant, as well as a hybrid plant produced by crossing with the T0 or T1 generation plant used as a parent, and progeny plants of such hybrid plant.

The transgenic plant thus created is expected to have the advantageous feature of high-yielding ability as compared with ordinary plants. The plant to be transformed in the present invention is not particularly limited and various transgenic plants having high-yielding ability can be created by the method of the present invention.

The plant to be transformed in a preferred embodiment of the present invention is an angiosperm, preferably a monocotyledon, more preferably rice, corn, and *Sorghum*, and most preferably rice and corn. The plant to be transformed in another preferred embodiment is a short-day plant.

Examples to be described later demonstrate the creation of a transgenic corn into which the promoter of the present invention and the PRR7 structural gene derived from *O. longistaminata* were introduced.

(5) A Method for Producing a Transgenic Plant with Increased Yield by Using the Promoter of the Present Invention and the PRR7 Structural Gene.

The present invention further relates to a method for producing a transgenic plant with increased yield which comprises the step of introducing into a plant a nucleic acid in which the promoter of the present invention and a nucleic acid (PRR7 structural gene) comprising a nucleotide sequence coding for the PRR7 protein are operably linked. More specifically, a nucleic acid is created in which the promoter of the present invention and a PRR7 protein coding for nucleic acid (PRR7 structural gene) are operably linked; the nucleic acid is then transferred into a plant cell; and a plant body is regenerated from the thus transfected plant cell, whereby a transgenic plant with increased yield can be created. Plant materials into which the nucleic acid is to be introduced include, for example, plant tissues such as root, stem, leaf, seed, fully mature embryo, immature embryo, ovule, ovary, shoot apex, anther, and pollen, sections of such plant tissues, their cells, callus, as well as plant cells like protoplasts that are obtained by removing cell walls through enzymatic treatment; a fully mature embryo or immature embryo may preferably be used. The method for producing a transgenic plant of the present invention is not particularly limited and various methods of plant transformation commonly employed in the technical field of interest may be adopted. For example, the method of transformation descried above in (4) can be applied as appropriate.

The plant to be transformed in a preferred embodiment of the present invention is an angiosperm, preferably a monocotyledon, more preferably rice, corn, and *Sorghum*, and most preferably rice and corn. The plant to be transformed in another preferred embodiment is a short-day plant. Examples to be described later demonstrate that by introducing the promoter of the present invention and the *O. longistaminata* derived PRR7 structural gene into corn, high-yielding ability could be imparted to the latter.

(6) Method for Increasing Plant Yield.

The present invention further relates to a method for increasing plant yield which is characterized by introducing into a plant a nucleic acid in which the promoter of the present invention and a nucleic acid (PRR7 structural gene) comprising a nucleotide sequence coding for the PRR7 protein are operably linked. By introducing the nucleic acid (described above in (2)) into a plant, its yield can be increased. The PRR7 protein to be used in this method satisfies the definition of the PRR7 protein set forth above in (2). Specifically, it is a protein that has an amino acid sequence having at least 65%, 70%, 75%, 80%, 85%, 90%, 95%, 97% or 99% identity to an amino acid sequence represented by SEQ ID NO: 3 or an amino acid sequence represented by SEQ ID NO: 5, which comprises a PR domain and a CCT motif, and which has an activity for suppressing the transcription of a LHY gene and a CCA1 gene. Amino acid sequences having identity to the PR domain maintain the PR domain conserved amino acids and the amino acid sequence of the PR domain may be modified with respect to amino acids other than the PR domain conserved amino acids. Amino acid sequences having identity to the CCT motif maintain the CCT motif conserved amino acids and the amino acid sequence of the CCT motif may be modified with respect to amino acids other than the CCT motif conserved amino acids.

The promoter to be operably linked to the PRR7 protein encoding nucleotide sequence is preferably a nucleic acid comprising a nucleotide sequence represented by 34845-35044 of SEQ ID NO: 1, a nucleic acid comprising a nucleotide sequence represented by 33045-35044 of SEQ ID NO: 1, or a nucleic acid comprising a nucleotide sequence represented by 26779-35044 of SEQ ID NO: 1. The promoter to be used in the method of the present invention is by no means limited to these nucleic acids and encompasses nucleic acids comprising nucleotide sequences which are fragments as a portion of the nucleotide sequence represented by 34845-35044 of SEQ ID NO: 1, a portion of the nucleotide sequence represented by 33045-35044 of SEQ ID NO: 1, or a portion of the nucleotide sequence represented by 26779-35044 of SEQ ID NO: 1 and which show an activity for promoting the transcription of a plant gene. The promoter to be used in the method of the present invention further contains nucleic acids comprising nucleotide sequences which have at least 80%, 85%, 90%, 95%, 97%, 99%, or 99.5% identity to the nucleotide sequence represented by 34845-35044 of SEQ ID NO: 1, the nucleotide sequence represented by 33045-35044 of SEQ ID NO: 1, or the nucleotide sequence represented by 26779-35044 of SEQ ID NO: 1 and which show an activity for promoting the transcription of a plant gene. The promoter to be used in the method of the present invention further encompasses nucleic acids that comprise nucleotide sequences derived from *O. longistaminata* and represented by at least 34845-35044 of SEQ ID NO: 1 and which show an activity for promoting the transcription of a plant gene.

(7) Use of the Promoter of the Present Invention and the *O. longistaminata* Derived PRR7 Structural Gene as DNA Markers A whole or partial sequence of the promoter of the present invention and/or the PRR7 structural gene derived from *O. longistaminata* is useful as a DNA marker for the high-yielding ability of plants. If the sequence of the promoter of the present invention or that of the PRR7 structural gene derived from *O. longistaminata* is detected in a plant, the plant is expected to display a trait of high-yielding ability like that of *O. longistaminata*. As such marker, a nucleotide sequence derived from the promoter of the present invention is more preferred.

The DNA marker of the present invention which is used for the above-described purpose preferably comprises 15 to 2000 nucleotides in a nucleotide sequence represented by 26779-35044 of SEQ ID NO: 1 and/or a nucleotide sequence represented by 35825-46721 of SEQ ID NO: 1; more preferably, it comprises 20 to 500 nucleotides in a nucleotide sequence represented by 26779-35044 of SEQ ID NO: 1 and/or a nucleotide sequence represented by 35825-46721 of SEQ ID NO: 1; even more preferably, it comprises 30 to 100 nucleotides in a nucleotide sequence represented by 26779-35044 of SEQ ID NO: 1 and/or a nucleotide sequence represented by 35825-46721 of SEQ ID NO: 1. However, the DNA marker for high-yielding ability of the present invention is by no means limited to these cases.

In an advantageous embodiment, the nucleotide sequence of the promoter of the present invention or that of the *O. longistaminata* PRR7 structural gene may be compared with the nucleotide sequence of the corresponding portion of Nipponbare and a partial sequence of *O. longistaminata* that corresponds to the region that differs between the two nucleotide sequences may be selected as the DNA marker described above.

If, as the result of detection procedure, the DNA marker of the present invention is found to be present in a plant, it can be determined that the plant has high-yielding ability. Consider, for example, a plant created by crossing Nipponbare with *O. longistaminata*. To select a rice variety having high-yielding ability, the above-described partial sequence of *O. longistaminata* which corresponds to the region that differs between *O. longistaminata* and Nipponbare may be used as the DNA marker.

The means for detecting the DNA marker of the present invention is not particularly limited and various methods known in the technical field of interest may be adopted, as exemplified by PCR, RFLP, and nucleotide sequence decoding. It should also be noted that the procedure of detecting the DNA marker of the present invention may be taken at any stage of the growth of plants created by crossing. Detecting the DNA marker at the stage where the hybrid plant is still a seedling is advantageous for the purpose of the present invention since this enables one to know whether the hybrid has high-yielding ability or not before it grows to maturity.

(8) Method for Promoting the Transcriptional Activity of a Plant Gene by Using the Promoter of the Present Invention.

The present invention provides a method for promoting the transcriptional activity of a plant gene by using the promoter of the present invention. Specifically, the present invention relates to a method for promoting the transcriptional activity of a plant gene by using a nucleic acid comprising a nucleotide sequence represented by 34845-35044 of SEQ ID NO: 1 or a nucleotide sequence having at least 90% identity to the nucleotide sequence represented by 34845-35044 of SEQ ID NO: 1. The present invention also relates to a method for promoting the transcriptional activity of a plant gene by using a nucleic acid comprising a nucleotide sequence represented by 33045-35044 of SEQ ID NO: 1 or a nucleotide sequence having at least 90% identity to the nucleotide sequence represented by 33045-35044 of SEQ ID NO: 1. The present invention further relates to a method for promoting the transcriptional activity of a plant gene by using a nucleic acid that comprises a nucleotide sequence derived from *O. longistaminata* and represented by at least 34845-35044 of SEQ ID NO: 1 and which has an activity for promoting the transcriptional activity of a plant gene. Such nucleic acid preferably contains a fragment of a nucleic acid consisting of the nucleotide sequence represented by 33045-35044 of SEQ ID NO: 1 and more preferably contains a fragment of a nucleic acid consisting of the nucleotide sequence represented by 26779-35044 of SEQ ID NO: 1. In Examples to be described later, it was actually confirmed that a nucleic acid comprising nucleotide sequences corresponding to 34845-35044 of SEQ ID NO: 1 or 33045-35044 of SEQ ID NO: 1 had an activity for promoting the transcription of GUS gene.

(9) *O. longistaminata* Derived PRR7 Protein and a Nucleic Acid Encoding the Same The present invention further provides PRR7 protein derived from *O. longistaminata* and a nucleic acid that encodes the same. As already mentioned, the PRR7 protein derived from *O. longistaminata* consists of the amino acids depicted in SEQ ID NO: 3 and is encoded by a nucleic acid having a nucleotide sequence represented by SEQ ID NO: 2. Hence, the present invention relates to a protein having the amino acid sequence represented by SEQ ID NO: 3 and a nucleic acid that encodes this protein. The present invention further relates to a nucleic acid having the nucleotide sequence represented by SEQ ID NO: 2. In Examples that follow, it was shown that transfer of a construct having the *O. longistaminata* derived PRR7 promoter linked to a gene coding for the *O. longistaminata* derived PRR7 protein was more effective in imparting high-yielding ability than transfer of a construct having the same promoter joined to a gene coding for the Nipponbare derived PRR7 protein. In other words, the nucleic acid encoding the *O. longistaminata* derived PRR7 protein has a tendency to impart greater high-yielding ability to plants when it is expressed after being operably linked to the *O. longistaminata* derived PRR7 promoter than when a nucleic acid encoding the PRR7 protein derived from other plants is operably linked to the promoter of PRR7 derived from *O. longistaminata*. Hence, using the nucleic acid encoding the *O. longistaminata* derived PRR7 protein together with the *O. longistaminata* derived PRR7 promoter is advantageous for the purpose of the present invention, i.e., imparting high-yielding ability to plants. In view of this characteristic feature of the nucleic acid encoding the *O. longistaminata* derived PRR7 protein, the present invention further provides use of a nucleic acid encoding a protein having the amino acid sequence represented by SEQ ID NO: 3 in order to impart high-yielding ability to a plant, a method for increasing plant yield characterized by introducing into a plant a nucleic acid encoding a protein having the amino acid sequence represented by SEQ ID NO: 3, and a method for producing a transgenic plant with increased yield characterized by introducing into a plant a nucleic acid encoding a protein having the amino acid sequence represented by SEQ ID NO: 3.

(10) Nucleic Acid in which *Sorghum* Derived PRR7 Promoter and *Sorghum* PRR7 Structural Gene are Operably Linked.

The present invention further relates to a nucleic acid in which *Sorghum* derived PRR7 promoter and *Sorghum* PRR7 structural gene are operably linked. The *Sorghum* derived PRR7 promoter is a nucleic acid comprising a nucleotide sequence consisting of the 9049 nucleotides depicted in SEQ ID NO: 19. The nucleotide sequence of the *Sorghum* derived PRR7 promoter as used herein is not limited to the one represented by SEQ ID NO: 19 and may contain a nucleic acid comprising a nucleotide sequence that has at least 80%, 85%, 90%, 95%, 97%, 99% or 99.5% identity to the one represented by SEQ ID NO: 19 and which shows an activity for promoting the transcription of a plant's coding region.

The *Sorghum* derived PRR7 protein consists of the 765 amino acids depicted in SEQ ID NO: 17 and is encoded by a nucleic acid having a nucleotide sequence represented by SEQ ID NO: 16. The *Sorghum* derived PRR7 protein as used herein is not limited to this particular case and may contain a protein having an amino acid sequence that has at least 50%, 55%, 60%, 65%, 70%, 75%, 80%, 85%, 90%, 95%, 97%, or 99% similarity to the one represented by SEQ ID NO: 17. Further, the *Sorghum* derived PRR7 protein as used herein comprises a PR domain and a CCT motif and has an activity for suppressing the transcription of LHYgene and CCA1 gene, as explained above in (2) in connection with the *O. longistaminata* derived PRR7 protein. The PR domain of the *Sorghum* derived PRR7 protein corresponds to amino acid numbers 80-194 in the amino acid sequence of SEQ ID NO: 17 whereas the CCT motif corresponds to amino acid numbers 709-752 in the same amino acid sequence. It should, however, be noted that the amino acid sequences of the PR domain and CCT motif of the *Sorghum* derived PRR7 protein as referred to herein are by no means limited to the PR domain and CCT motif described above and may include ones that have at least 70%, 75%, 80%, 85%, 90%, 95%, 97%, or 99% identity to the above-identified amino acid sequences.

Plant yield can be increased by using the nucleic acid in which the *Sorghum* derived PRR7 promoter and the *Sorghum* PRR7 structural gene are operably linked. It is shown in the following Examples section that when a construct comprising a nucleic acid of the nucleotide sequence depicted in SEQ ID NO: 19 and a nucleic acid of the nucleotide sequence depicted in SEQ ID NO: 16 was introduced into rice, the yield of the plant could effectively be increased.

EXAMPLES

Example 1: Creation of Cultivated Rice Line Having the High-Yielding Ability of Wild Rice Species O. longistaminata and Identification of High-Yielding Ability Gene Region

*Oryza longistaminata* (*O. longistaminata*), a wild rice species native of Africa, is known to have the same A genome as the cultivated species *Oryza sativa* (*O. sativa* L) but show a larger biomass than the latter. With a view to introducing this superior trait of *O. longistaminata* into a cultivated species, the present inventors continued the cross and selection efforts on the rice cultivar Shiokari and *O. longistaminata* to eventually obtain BC7F6 line No. 645 which showed higher yield than Shiokari; No. 645 surpassed Shiokari in most agricultural traits, among which "increased culm base diameter" was prominent (Table 1). This high-yielding line was investigated for its genotype using 80 DNA markers covering a total of 12 chromosomes and it was found to have only the terminal portions of chromosomes 3 and 7 in *O. longistaminata* (FIG. 1).

Figure 2:
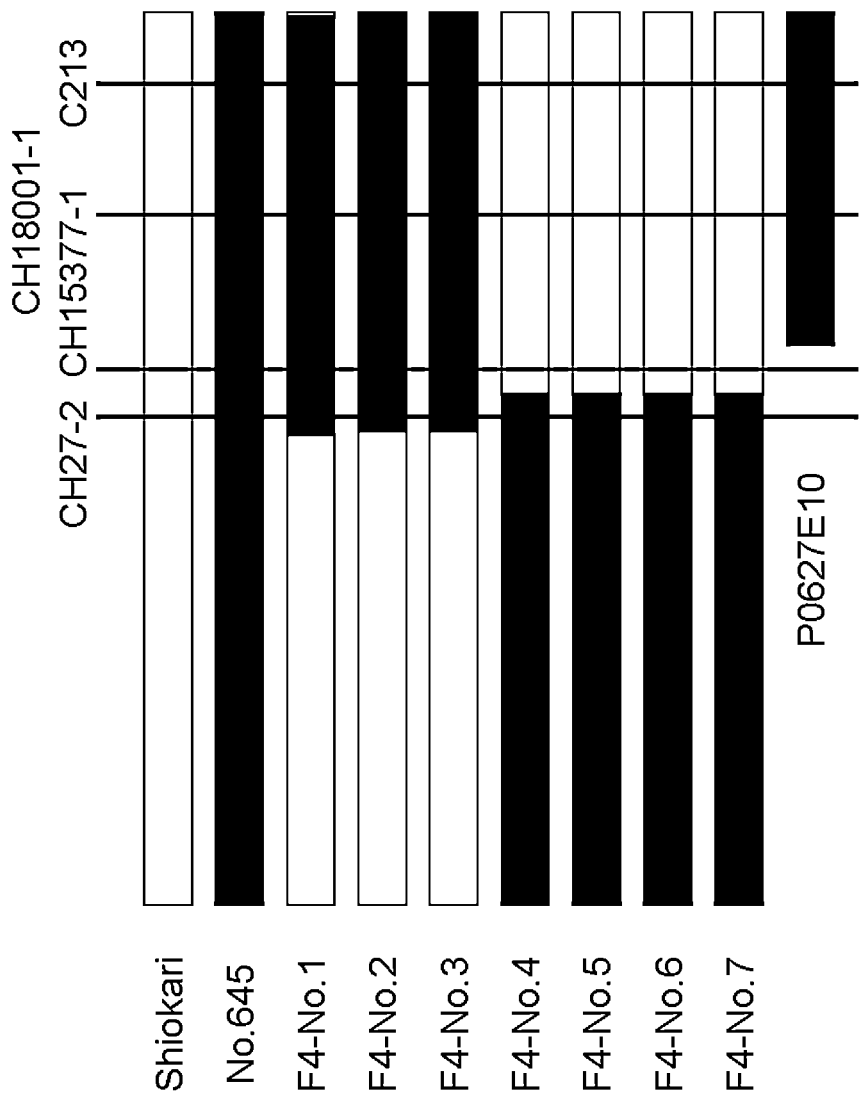
FIG. 2 is a diagram showing the genotypes of seven individuals that experienced recombination in the terminal portion of chromosome 7 so that the farthest end was fixed in No. 645 type or Shiokari type.

Then, in order to identify the gene region involved in the high-yielding ability of No. 645, the present inventors performed QTL analysis on yield-associated traits using 133 individuals of F2, derived from a cross between No. 645 and the recurrent parent Shiokari. As a consequence, QTL concerning days to heading, culm length, panicle length, spikelet number per panicle, and culm base diameter were detected in the terminal portion of chromosome 7 (Table 2). Subsequently, from the individuals of hybrid progeny F3, the inventors selected one group of individuals in which the terminal portion of chromosome 7 was heterozygous and the other region of chromosome 7 was Shiokari homozygous type and another group in which the terminal portion of chromosome 7 was heterozygous but the other region of chromosome 7 was No. 645 homozygous type, and using progeny of each group (4313 individuals of the first group and 4944 of the second group), individuals that experienced recombination in the terminal portion were selected. As a result, three individuals having the farthest end of chromosome 7 fixed as No. 645 type (F4-No. 1, No. 2, and No. 3) and four individuals having the farthest end of chromosome 7 fixed as Shiokari type (F4-No. 4, No. 5, No. 6, and No. 7) could be selected (FIG. 2). The individuals having the farthest end of chromosome 7 fixed as No. 645 type had nearly the same traits as No. 645. Similarly, the individuals having the farthest end of chromosome 7 fixed as Shiokari type had nearly the same traits as Shiokari (Table 3). Since marker CH15377-1 was located ca. 180 kb away from the right end of the PAC clone P0627E10 (see FIG. 2), it was speculated that the high-yielding ability gene region of *O. longistaminata* could be narrowed down to within ca. 180 kb of the terminal portion of chromosome 7.

TABLE 1

Comparison of yield-associated traits between Shiokari and No. 645

| Variety/Line name | Days to heading | Culm length (cm) | Panicle length (cm) | No. of panicles | No. of grains per panicle | Culm base diameter (mm) |
|---|---|---|---|---|---|---|
| No. 645 | 87.1 | 64.4 | 17.6 | 6.8 | 108.9 | 5.37 |
| Shiokari | 78.6 | 47.4 | 14.1 | 9.9 | 52.9 | 3.60 |

TABLE 2

QTL analysis of agricultural traits in F2 population of a cross between Shiokari and No. 645

| Agricultural trait | Chromosome | Marker | LOD value | Additive effect | Dominant effect | Variance |
|---|---|---|---|---|---|---|
| Days to heading | 7 | R2577S | 27.4 | −4.38 | 0.09 | 0.61 |
| Culm length | 7 | S21019S | 13.9 | −5.69 | 1.60 | 0.38 |
| Panicle length | 7 | RM118 | 6.0 | −1.06 | 0.31 | 0.19 |
| Panicle length | 3 | R3385 | 2.8 | −0.64 | 0.43 | 0.09 |
| No. of spikelet per panicle | 7 | R1789 | 6.7 | −12.26 | 0.61 | 0.21 |
| No. of spikelet per panicle | 3 | S151795 | 7.1 | −12.40 | −1.58 | 0.22 |
| No. of panicles | 3 | RM55 | 10.1 | 2.00 | −0.23 | 0.30 |
| Culm base diameter | 7 | S21019S | 11.0 | −0.79 | 0.14 | 0.32 |
| Culm base diameter | 3 | R3386 | 2.9 | −0.39 | 0.11 | 0.10 |

TABLE 3

Growth characteristics of 7 individuals that experienced recombination in the terminal portion of chromosome 7, with the farthest end fixed as No. 645 type or Shiokari type

| Variety/Line name | Days to heading (day) | Culm length (cm) | Panicle length (cm) | No. of grains per panicle | No. of panicles | Culm base diameter (mm) |
|---|---|---|---|---|---|---|
| Shiokari | 78.6 | 47.4 | 14.1 | 52.9 | 9.9 | 3.60 |
| No. 645 | 87.1 | 64.4 | 17.6 | 108.9 | 6.8 | 5.37 |
| F4-No. 1 | 85.8 | 62.3 | 18.1 | 123.7 | 6.3 | 5.76 |
| F4-No. 2 | 87.3 | 64.5 | 17.7 | 115.5 | 5.9 | 5.57 |
| F4-No. 3 | 87.4 | 62.8 | 18.3 | 126.1 | 6.3 | 5.43 |
| F4-No. 4 | 73.8 | 47.9 | 15.0 | 60.8 | 8.4 | 4.12 |
| F4-No. 5 | 74.6 | 49.2 | 14.4 | 59.9 | 7.9 | 4.02 |
| F4-No. 6 | 74.5 | 48.5 | 14.6 | 66.9 | 9.1 | 4.17 |
| F4-No. 7 | 73.8 | 47.8 | 14.1 | 60.8 | 8.8 | 4.04 |

Example 2: Complementation Test (1) by Transformation Test for the Terminal Region of Chromosome 7 in *O. longistaminata*

By the genetic analysis conducted in Example 1, the high-yielding ability gene region of *O. longistaminata* could be narrowed down to within ca. 180 kb of the terminal portion of chromosome 7. Seven constructs were created that covered a ca. 82-kb region of that area and they were each introduced into Shiokari; the resulting transgenic plants were evaluated for their traits.

A genomic library of No. 645 was prepared using the fosmid vector pCC1FOS (EPICENTRE). Since it was shown by genetic analysis in Example 1 that the gene involved in high-yielding ability resided in the terminal portion of the longer arm of chromosome 7, the library was screened using C213 and C728, two DNA markers for that region (Harushima et al, 1998), to select four clones (Fos1, 2, 10, and 12). The terminal nucleotide sequences of each clone were decoded and compared with the genomic sequence of Nipponbare to identify their relative positions. Further, primer walking was performed to decode the nucleotide sequence of that contig. The decoded nucleotide sequence is depicted in SEQ ID NO: 1.

Figure 3:
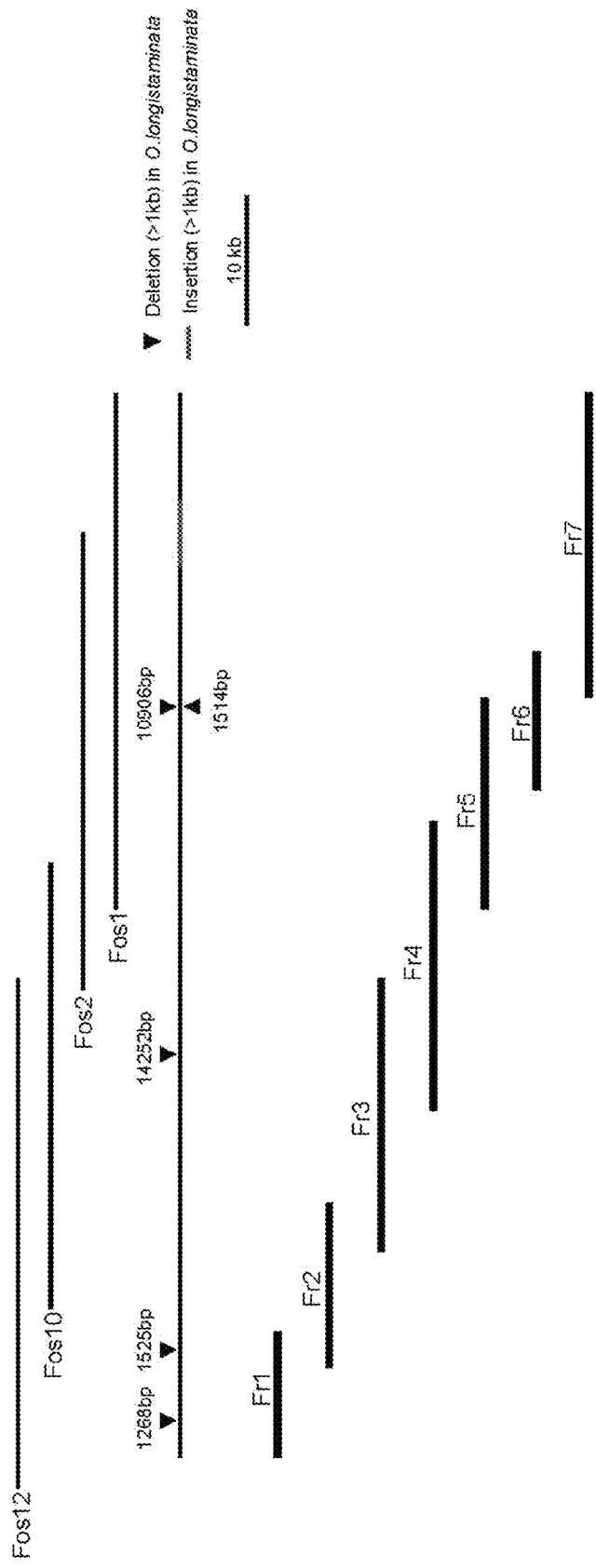
FIG. 3 is a physical map of the area around a gene for increased growth, showing the relation between four fosmid clones and the seven constructs (Fr1 to Fr7) which were prepared in Example 2.

Using the above-mentioned four fosmid clones, seven constructs for use in complementation test were prepared as described below (FIG. 3).

(1) Preparation of Fr3

The largest fragment (including the $15961^{st}$ to $37129^{th}$ nucleotides in SEQ ID NO: 1) that could be obtained by treating Fos 12 with NotI was purified from agarose gel using QIAEXII Gel Extraction Kit (QIAGEN).

Plasmid vector pSB200 (an intermediate vector having a hygromycin resistance gene cassette) was completely digested with NotI and then DNA was recovered by ethanol precipitation. The recovered DNA was dissolved in TE solution and dephosphorylated with CIAP (TAKARA-BIO). The reaction solution was electrophoresed on agarose gel and then a vector fragment was purified from the gel using QIAEXII Gel Extraction Kit.

The thus provided two fragments were used as test samples which were subjected to ligation reaction using DNA Ligation Kit "Mighty Mix" (TAKARA-BIO). After the reaction, DNA was recovered by ethanol precipitation. The recovered DNA was dissolved in pure water (as prepared with an apparatus manufactured by Millipore), mixed with *E. coli* DH5α, and then subjected to electroporation. The solution after electroporation was shake-cultured (37° C.×1 hr) in LB medium, then spread on an LB plate supplemented with spectinomycin (50 μg/ml) and warmed (37° C.×16 hr). Plasmids were isolated from 24 colonies that appeared, and restriction fragment length patterns and boundary sequences of the plasmids were investigated to select the desired *E. coli* clone.

(2) Preparation of Fr1

The second largest fragment (including the $3^{rd}$ to $9746^{th}$ nucleotides in SEQ ID NO: 1) that could be obtained by treating Fos 12 with NotI was purified from agarose gel using QIAEXII Gel Extraction Kit (QIAGEN).

This fragment as well as the NotI-CIAP treated pSB200 fragment used in (1) were used as test samples which were subjected to ligation reaction using DNA Ligation Kit "Mighty Mix". Subsequently, a modification of the procedure described in (1) was employed to select the desired *E. coli*.

(3) Preparation of Fr7

The largest fragment (including the $58805^{th}$ to $82355^{th}$ nucleotides in SEQ ID NO: 1) that could be obtained by treating Fos 1 with NotI was purified from agarose gel using QIAEXII Gel Extraction Kit (QIAGEN).

This fragment as well as the NotI-CIAP treated pSB200 fragment used in (1) were used as test samples which were subjected to ligation reaction using DNA Ligation Kit "Mighty Mix". Subsequently, a modification of the procedure described in (1) was employed to select the desired *E. coli*.

(4) Preparation of Fr5

The second largest fragment (including the $42409^{th}$ to $58808^{th}$ in SEQ ID NO: 1) that could be obtained by treating Fos 1 with NotI was purified from agarose gel using QIAEXII Gel Extraction Kit (QIAGEN).

This fragment as well as the NotI-CIAP treated pSB200 fragment used in (1) were used as test samples which were subjected to ligation reaction using DNA Ligation Kit "Mighty Mix". Subsequently, a modification of the procedure described in (1) was employed to select the desired *E. coli*.

(5) Preparation of Fr2

The second largest fragment (including the $6929^{th}$ to $19723^{rd}$ nucleotides in SEQ ID NO: 1) that could be obtained by treating Fos 12 with PspOMI was purified from agarose gel using QIAEXII Gel Extraction Kit (QIAGEN).

This fragment as well as the NotI-CIAP treated pSB200 fragment used in (1) were used as test samples which were subjected to ligation reaction using DNA Ligation Kit "Mighty Mix". Subsequently, a modification of the procedure described in (1) was employed to select the desired *E. coli*.

(6) Preparation of Fr6

The second largest fragment (including the $51665^{th}$ to $62366^{th}$ nucleotides in SEQ ID NO: 1) that could be obtained by treating Fos 1 with PspOMI was purified from agarose gel using QIAEXII Gel Extraction Kit (QIAGEN).

This fragment as well as the NotI-CIAP treated pSB200 fragment used in (1) were used as test samples which were subjected to ligation reaction using DNA Ligation Kit "Mighty Mix". Subsequently, a modification of the procedure described in (1) was employed to select the desired *E. coli*.

(7) Preparation of Fr4

The largest fragment (including the $26779^{th}$ to $46059^{th}$ nucleotides in SEQ ID NO: 1) that could be obtained by treating Fos 10 with SmaI and PstI was purified from agarose gel using QIAEXII Gel Extraction Kit (QIAGEN).

The fourth largest fragment (including the $46056^{th}$ to $49155^{th}$ nucleotides in SEQ ID NO: 1) that could be obtained by treating Fos 1 with PstI and SacI was purified from agarose gel using QIAEXII Gel Extraction Kit (QIAGEN).

Plasmid vector pSB200 was completely digested with EcoRV and SacI and then DNA was recovered by ethanol precipitation. The recovered DNA was CIAP treated by the method described in (1) and a vector fragment was purified.

The three fragments described above were subjected to ligation reaction using DNA Ligation Kit "Mighty Mix". Subsequently, a modification of the procedure described in (1) was employed to select the desired *E. coli*.

The seven types of E. coli selected in (1) to (7) were used as test samples together with Agrobacterium tumefaciens strain LB4404/pSB1 (Komari et al, 1996) and helper E. coli HB101/pRK2013 (Ditta et al, 1980) and triparental mating was performed in accordance with the method of Ditta et al. (1980). Using Agrobacterium selected on an AB plate loaded with spectinomycin (50 µg/ml), tetracycline (15 µg/ml) and hygromycin (35 µg/ml), Shiokari was transformed by a modified version of the method of Hiei et al. (1994). The transgenic rice plants were first acclimatized and then cultivated in a greenhouse. For each construct, about 20 independent transformants were grown and T1 seeds were produced.

For the T1 generation, two lines per construct were selected as test samples in a total number of 18 individuals (9 per line). Seeding was performed on Jun. 25, 2007; transplanting was conducted in 3.5-L buckets containing paddy field soil with 3 individuals (3 buckets per line to make a total of 9 individuals.) on July 9. In addition to the control Shiokari, line No. 645 having the terminal regions of chromosomes 3 and 7 in O. longistaminata introduced into Shiokari was planted as a reference variety. Cultivation was performed in a greenhouse of closed system for dedicated use in recombination experiment (under long-day condition with a day length of 14 hours and a half) at the Plant Innovation Center of Japan Tobacco Inc. with no fertilizer applied. Harvesting was conducted on September 21. Agronomic traits including days to heading, culm length, the number of panicles, culm base diameter, panicle length, the number of grains per panicle, spikelet fertility, and the weight of fertilized spikelet per panicle (hereinafter referred to as weight per panicle) of maximum panicle were evaluated.

The average values of the agricultural trait data for the two lines of each construct are listed in Table 4. All seven constructs under test were just comparable or inferior to the control Shiokari as regards the number of grains per panicle and the weight per panicle and there was no construct that surpassed Shiokari.

Example 3: Complementation Test (2) by Transformation Test for the Terminal Region of Chromosome 7 in O. longistaminata The seven constructs that did not show increased growth in the 2007 test were tested again, with the number of lines per construct (each line derived from independent T0 individuals) being increased to five (12 individuals per line, different from the lines tested in 2007). Seeding was performed on May 30, 2008; transplanting was conducted in 3.5-L buckets containing paddy field soil with 4 individuals (3 buckets per line to make a total of 12 individuals.) on June 16. Cultivation was performed in the greenhouse of closed system for dedicated use in recombination experiment (under long-day condition with a day length of 14 hours and a half) at the Plant Innovation Center of Japan Tobacco Inc. with no fertilizer applied. Harvesting was conducted on September 8. Agronomic traits including days to heading, culm length, the number of panicles, culm base diameter, panicle length, the number of grains per panicle, spikelet fertility, and the weight of fertilized spikelet per panicle (hereinafter referred to as weight per panicle) of maximum panicle were evaluated. In the 2008 test, in addition to the control Shiokari, line No. 240 having only the terminal region of chromosome 7 in O. longistaminata introduced into Shiokari was planted as a reference variety.

The average values of the agricultural trait data for the five lines of each construct are listed in Table 5. Fr4 construct far excelled Shiokari as regards seven traits, i.e., the days to heading, culm length, panicle length, the number of grains per panicle, spikelet fertility, weight per panicle, and culm base diameter whereas the other six constructs were just comparable or inferior to Shiokari as regards all those traits.

TABLE 4

Trait evaluation test on recombinants

| Construct/ Variety name | Days to heading (day) | Culm length (cm) | No. of panicles | Panicle length (cm) | No. of grains per panicle | Ratio relative to control (No. of grains per panicle) (%) | Spikelet fertility (%) | Weight per panicle (g) | Ratio relative to control (Weight per panicle) (%) | Culm base diameter (cm) |
|---|---|---|---|---|---|---|---|---|---|---|
| Fr1 | 43.0 | 59.3 | 3.7 | 13.9 | 56 | 97 | 86 | 1.28 | 98 | 4.34 |
| Fr2 | 44.5 | 60.5 | 3.5 | 13.8 | 59 | 103 | 84 | 1.21 | 92 | 4.53 |
| Fr3 | 43.9 | 60.2 | 3.6 | 14.3 | 58 | 100 | 72 | 1.05 | 80 | 5.33 |
| Fr4 | 47.3 | 62.8 | 3.3 | 13.9 | 58 | 100 | 80 | 1.22 | 94 | 4.91 |
| Fr5 | 44.0 | 58.7 | 3.5 | 13.7 | 53 | 92 | 84 | 1.15 | 88 | 4.26 |
| Fr6 | 42.6 | 59.9 | 3.7 | 13.8 | 58 | 100 | 88 | 1.26 | 96 | 4.02 |
| Fr7 | 44.1 | 60.3 | 3.7 | 14.3 | 57 | 98 | 87 | 1.21 | 93 | 4.43 |
| Shiokari (control) | 41.3 | 60.6 | 3.1 | 13.4 | 58 | 100 | 88 | 1.31 | 100 | 3.68 |
| No. 645 (reference) | 55.0 | 62.9 | 3.0 | 14.7 | 90 | 156 | 92 | 2.22 | 170 | 7.74 |

TABLE 5

Trait evaluation test on recombinants

| Construct/ Variety name | Days to heading (day) | Culm length (cm) | No. of panicles | Panicle length (cm) | No. of grains per panicle | Ratio relative to control (No. of grains per panicle) (%) | Spikelet fertility (%) | Weight per panicle (g) | Ratio relative to control (Weight per panicle) (%) | Culm base diameter (cm) |
|---|---|---|---|---|---|---|---|---|---|---|
| Fr1 | 51.7 | 59.1 | 2.7 | 12.5 | 51.6 | 91 | 71 | 0.95 | 92 | 3.02 |
| Fr2 | 51.0 | 59.7 | 2.9 | 12.2 | 52.0 | 92 | 63 | 0.81 | 78 | 2.87 |
| Fr3 | 49.2 | 62.7 | 2.8 | 12.4 | 52.7 | 93 | 68 | 0.90 | 86 | 2.93 |
| Fr4 | 53.7 | 65.5 | 2.8 | 13.4 | 62.6 | 111 | 81 | 1.30 | 124 | 3.13 |
| Fr5 | 50.0 | 61.0 | 2.7 | 12.7 | 54.3 | 96 | 67 | 0.93 | 89 | 2.91 |
| Fr6 | 49.9 | 59.0 | 3.1 | 12.3 | 54.0 | 95 | 75 | 0.98 | 94 | 2.74 |
| Fr7 | 47.9 | 59.5 | 2.9 | 12.6 | 51.7 | 91 | 67 | 0.83 | 80 | 2.80 |
| Shiokari (control) | 49.4 | 62.0 | 3.1 | 12.2 | 56.6 | 100 | 75 | 1.04 | 100 | 3.01 |
| No. 240 (reference) | 59.3 | 73.8 | 3.0 | 14.1 | 76.3 | 135 | 94 | 2.02 | 194 | 3.79 |

Figure 4:
FIG. 4 is a photo showing panicles of a transformant (Fr4-4) in which fragment Fr4 was transferred into the rice variety Shiokari; shown on the left is a gene lacking individual having no fragment Fr4 and shown on the right is a gene carrying individual having fragment Fr4.

Since the characteristics of Fr4 line were the most marked in Fr4-4, its individuals were separately subjected to PCR to examine the relationship between the presence/absence of the transferred gene and the magnitude of the measured trait. The results are shown in Table 6 and FIG. 4. Obviously, the gene carrying individuals excelled the lacking individuals as regards the days to heading, culm length, panicle length, the number of grains per panicle, weight per panicle, and culm base diameter under long-day condition (14 hours and a half). It was also revealed that the gene carrying individuals had a higher panicle density (the number of grains per centimeter of panicle) than the lacking individuals.

The above results strongly suggested that the genomic fragment responsible for the high-yielding ability of Shiokari is the Fr4 fragment.

TABLE 6

Relation between the presence/absence of gene in line Fr4-4 and the yield-associated traits

| Presence/ absence of gene | No. of individuals | Days to heading (day) | Culm length (cm) | No. of panicles | Panicle length (cm) | No. of grains per panicle | Panicle density (grains/ cm) | Spikelet fertility (%) | Weight per panicle (g) | Culm base diameter (mm) |
|---|---|---|---|---|---|---|---|---|---|---|
| Present | 8 | 57.9 | 62.9 | 2.9 | 13.5 | 75.8 | 5.60 | 80.5 | 1.53 | 3.47 |
| Absent | 4 | 50.5 | 58.3 | 2.8 | 11.6 | 47.3 | 4.06 | 83.8 | 1.00 | 3.09 |

In 2009, progeny (T2 generation) of the gene carrying or lacking individuals of Fr4-4 were cultivated together with the control Shiokari and No. 240 (12 individuals per line) and their yield-associated traits were evaluated. Seeding was performed on May 1, 2009; transplanting was conducted in 3.5-L buckets containing paddy field soil with 4 individuals on May 11. Cultivation was performed in the greenhouse of closed system for dedicated use in recombination experiment (under long-day condition with a day length of 14 hours and a half) at the Plant Innovation Center of Japan Tobacco Inc. with no fertilizer applied. Harvesting was conducted on August 19. Agronomic traits including days to heading, culm length, the number of panicles, culm base diameter, panicle length, the number of grains per panicle, spikelet fertility, and the weight of fertilized spikelet per panicle (hereinafter referred to as weight per panicle) of maximum panicle were evaluated.

The results are shown in Table 7. Obviously, Fr4-4-1 and Fr4-4-2, progeny of the gene carrying individuals, excelled Fr4-4-3 (progeny of the gene lacking individuals) as regards the days to heading, culm length, panicle length, the number of grains per panicle, weight per panicle, and culm base diameter. It was also revealed that the gene carrying line had higher values of panicle density (number of grains per centimeter of panicle) than the lacking line. On the other hand, all trait measurements for Fr4-4-3 were found to be nearly comparable to those of Shiokari.

Based on these results, the present inventors concluded that the genomic fragment responsible for the high-yielding ability of Shiokari is the Fr4 fragment. According to the annotation information on a Nipponbare sequence (AP005199), the Fr4 fragment included an allele of, a full-length cDNA of Nipponbare AK066112, and thus it was suggested that this allele would impart high-yielding ability. Note that the locus AK066112 is quoted as OsPRR37 in Murakami et al. (2005). It was therefore estimated that the PRR7 gene in *O. longistaminata* is a responsible gene for imparting high-yielding ability to Shiokari. It was also assumed that this Fr4 fragment includes the coding region of the PRR7 gene and all regions required to express this gene.

TABLE 7

Evaluation test on T2 progeny of line Fr4-4

| Construct/ variety name | Presence/ absence of gene | Days to heading (day) | Culm length (cm) | No. of panicles | Panicle length (cm) | No. of grains per panicle | Panicle density (grains/ cm) | Spikelet fertility (%) | Weight per panicle (g) | Ratio relative to control (weight per panicle) (%) | Culm base diameter (cm) |
|---|---|---|---|---|---|---|---|---|---|---|---|
| Fr4-4-1 | Present | 55.4 | 70.0 | 2.92 | 12.8 | 77 | 5.99 | 91 | 1.63 | 139 | 4.92 |
| Fr4-4-2 | Present | 55.6 | 69.9 | 2.92 | 13.1 | 74 | 5.68 | 93 | 1.69 | 144 | 5.00 |
| Fr4-4-3 | Absent | 50.0 | 63.0 | 3.17 | 12.7 | 59 | 4.62 | 88 | 1.22 | 104 | 4.58 |
| Shiokari (control) | Absent | 49.8 | 62.4 | 3.17 | 12.3 | 56 | 4.54 | 87 | 1.17 | 100 | 4.25 |
| No. 240 (reference) | Present | 58.4 | 78.3 | 3.00 | 14.4 | 71 | 4.91 | 98 | 1.82 | 155 | 5.33 |

Example 4: Verification of the Effect of the Coding Region of *O. longistaminata* PRR Gene Based on the results of Example 3, the present inventors assumed that the PRR7 gene in *O. longistaminata* would be a gene responsible for high-yielding ability. To confirm this, the inventors investigated the effect the coding region of the *O. longistaminata* PRR gene might have on the yield-associated traits.

Specifically, a construct having a ubiquitin promoter and the terminator region of *O. longistaminata* PRR7 gene linked to the coding region of that gene was prepared in the following manner. Being a constitutive promoter commonly used in monocotyledons, the ubiquitin promoter was considered to be suitable for examining the effect of the PRR gene. The construct was introduced into the cultivated rice Yukihikari to conduct an evaluation of the yield-associated traits.

A construct for expressing the coding region (SEQ ID NO: 2) of the *O. longistaminata* derived PRR7 gene under control of the ubiquitin promoter was prepared by employing a usual procedure such as overlap extension PCR. Specifically, a region of pSB200 including the ubiquitin promoter and the ubiquitin intron was PCR amplified and immediately downstream of this region were connected a region upstream of the translation initiation codon of *O. longistaminata* (from the $35045^{th}$ to $35824^{th}$ nucleotides of SEQ ID NO: 1), SEQ ID NO: 2, and a region downstream of the translation termination codon of *O. longistaminata* (from the $46722^{nd}$ to $49157^{th}$ nucleotides of SEQ ID NO: 1) to make a chimeric gene, which was a construct inserted into a multiple cloning site of pSB200. A plasmid carrying only a selection marker gene (hygromycin resistance gene) was used as a control.

Figure 5:
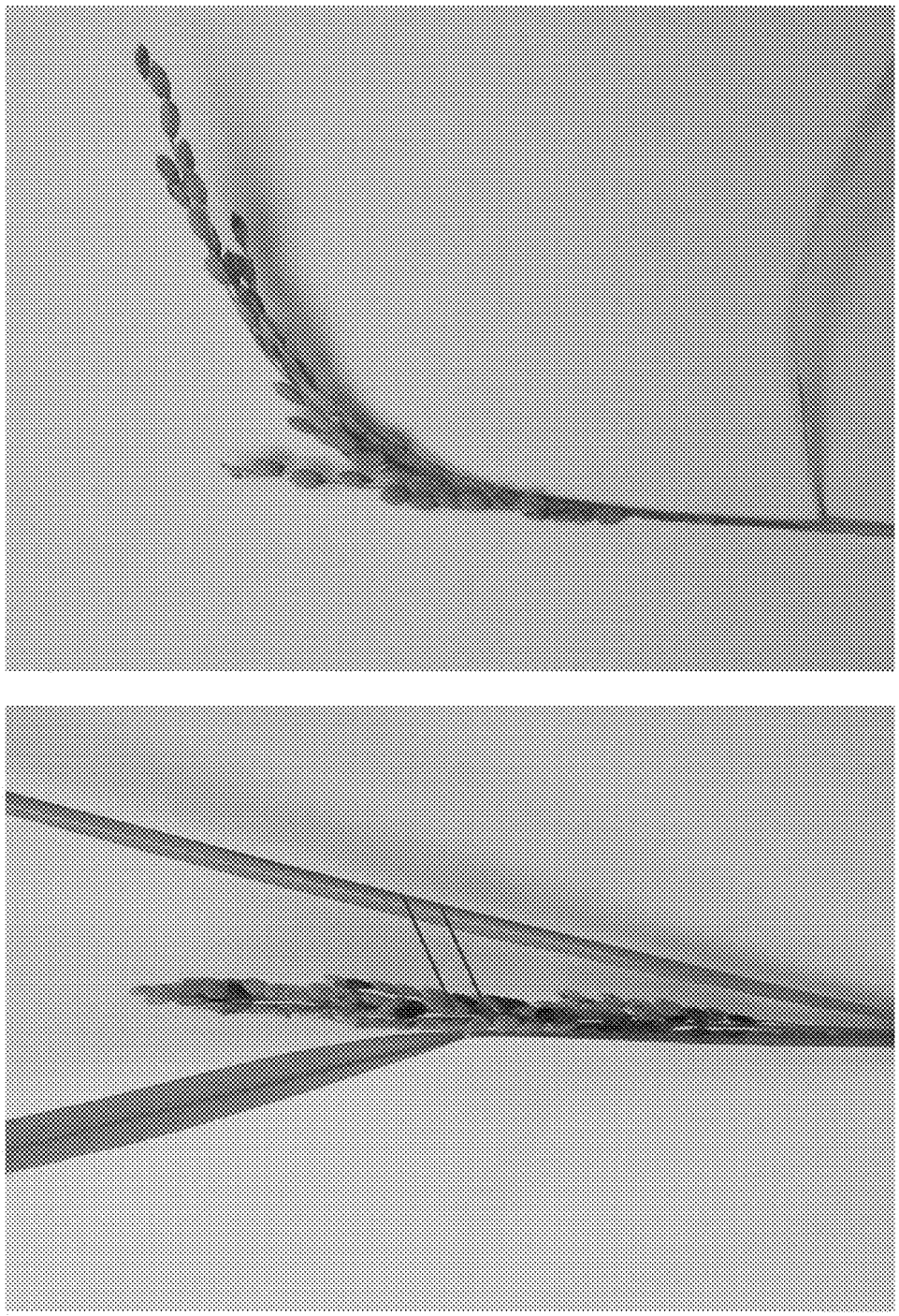
FIG. 5 is a photo showing a panicle of a rice plant transformed with a construct comprising the coding region of a PRR gene derived from *O. longistaminata* under the control of a ubiquitin promoter (left panel) and a panicle of a control rice plant transformed with a construct comprising only a selection marker gene (right panel). The panicle in the left panel is sterile and the unhulled rice remains green whereas the panicle in the right panel is fertile and the unhulled rice has turned yellow; in addition, two glumaceous flowers are seen to remain unclosed in the left panel (indicated by arrows).

Using *E. coli* carrying the two kinds of construct described above, triparental mating and the transformation of the cultivated rice Yukihikari were carried out by the methods described in Example 2. The transgenic rice plants were first acclimatized and then cultivated in a greenhouse of closed system. For the PRR7 gene construct, 60 independent transgenic individuals were grown, and 20 for the control construct. Eighteen out of the 60 individuals under test were observed to display the following characteristics associated with high-yielding ability: (1) higher plant height, (2) thicker culm, and (3) more days to heading. The traits of the panicles of those 18 individuals were observed in the period of their maturation and in all of them, one or more of the following conditions were found: (1) spikelet fertility was low (less than 20%); (2) panicle was not adequately emerged from the flag leaf; or (3) spikelets did not close after flowering. In addition, the final seed yield dropped considerably as compared with the control (FIG. 5). In contrast, the remaining 42 individuals displayed nearly the same characteristics as the control 20 individuals and the above-mentioned deteriorated traits were hardly observable.

It was therefore impossible to confirm from the above results that the coding region of the PRR7 gene in *O. longistaminata* is a gene responsible for high-yielding ability.

Example 5: Effects of Constructs Having the *O. longistaminata* Derived Promoter Linked to Coding Regions of Various Kinds of PRR Gene It was impossible to conclude from the results of Example 4 that the coding region of the PRR7 gene in *O. longistaminata* is a gene responsible for high-yielding ability. As a result of ensuing intensive studies, the present inventors came to wonder if the promoter region of *O. longistaminata* PRR7 gene might be necessary for the expression of *O. longistaminata* PRR7 gene; they then prepared a construct in which the promoter region of *O. longistaminata* PRR7 gene and the terminator region of *O. longistaminata* PRR7 gene were linked to the coding region of *O. longistaminata* PRR7 gene and introduced the construct into cultivated rice to evaluate the yield-associated traits. A construct was also prepared in which the coding region of the PRR7 gene of the conventional cultivated rice Nipponbare was linked to the above-described promoter and terminator and this construct was also used as a control for evaluating the effect of *O. longistaminata* PRR7 gene.

Isolation of *O. longistaminata* PRR7 Gene and the PRR7 Gene of Cultivated Rice Nipponbare Total RNA was extracted from seedlings of line No. 645 (into which a chromosomal fragment of *O. longistaminata* had been introduced) and Nipponbare using RNeasy Plant Mini Kit (QIAGEN). The operation was in accordance with the manual for the kit, except that instead of mercaptoethanol, DTT was added to the RLT buffer to give a final concentration of 40 mM. After eluting total RNA with the attachment RNase free water (40-50 µl), DNase treatment (TURBO DNA-free Kit, Ambion) was performed. The thus treated RNA solution was electrophoresed on agarose gel to check for the concentration and purity and, thereafter, cDNA synthesis was performed with QuantiTect Rev. Transcription kit (QIAGEN). With the resulting cDNA solution being used as a template, RT-PCR was performed to isolate the coding region of PRR gene using the following two kinds of primer: longi-PRR 2F corresponds to the nucleotide sequence represented by 35847-35869 of SEQ ID NO: 1 and longi-PRR 2R corresponds to the nucleotide sequence represented by 46713-46735 of SEQ ID NO: 1.

```
                                        (SEQ ID NO: 6)
  longi-PRR 2F: ACCAAACCGCCGGCTCTGCCCTC (SEQ ID NO: 7)
  longi-PRR 2R: GGTAGGTAGGTAGGTCATCTGTC
```

Using the nucleotide sequence thus obtained, the present inventors determined the nucleotide sequence (SEQ ID NO: 2) of the *O. longistaminata* derived PRR7 structural gene in No. 645. This nucleotide sequence was presumed to encode a protein consisting of 740 amino acid residues (SEQ ID NO: 3). The region corresponding to amino acid numbers 62 to 176 in SEQ ID NO: 3 is the PR domain and the region corresponding to amino acid numbers 676 to 722 is the CCT motif. The same technique was employed to determine the nucleotide sequence of Nipponbare PRR7 structural gene and this sequence (SEQ ID NO: 4) was presumed to encode a protein consisting of 742 amino acid residues (SEQ ID NO: 5). The region corresponding to amino acid numbers 62 to 176 in SEQ ID NO: 5 is the PR domain and the region corresponding to amino acid numbers 678 to 724 is the CCT motif.

Figure 6:
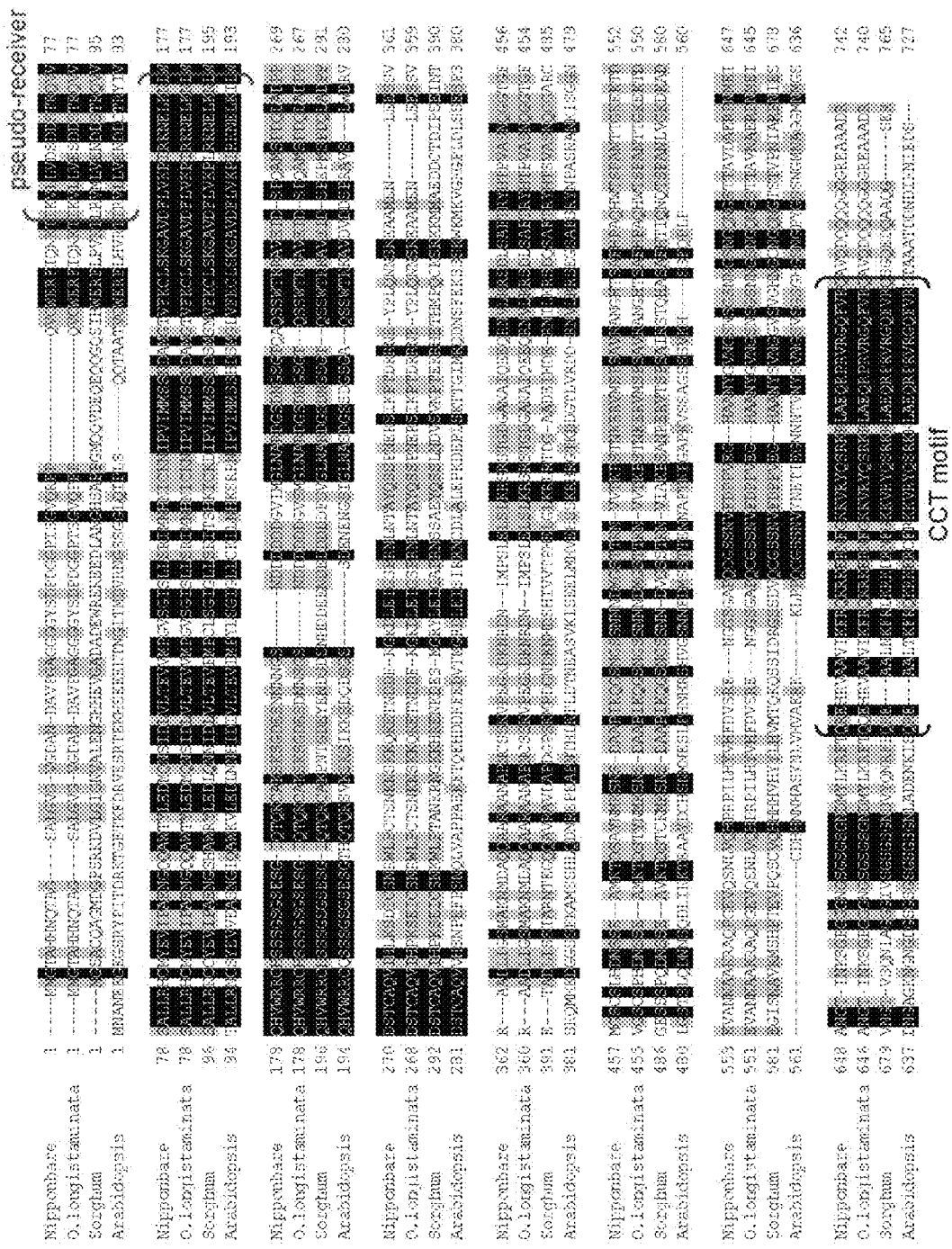
FIG. 6 is a diagram showing the alignment of amino acid sequences encoded by the translated regions of isolated PRR7 gene derived from Nipponbare (SEQ ID NO: 5), *O. longistaminata* (SEQ ID NO: 3), *Sorghum* (SEQ ID NO: 17), and *Arabidopsis* (SEQ ID NO: pseudo-receiver domains (bracketed in red) and CCT motifs (bracketed in blue) were determined by referring to Takata et al., (2010) BMC Evolutionary Biology 10: 126.

The alignment of the amino acid sequences encoded by the translated regions of the isolated PRR7 genes derived from Nipponbare, *O. longistaminata* and *Arabidopsis* is shown in FIG. 6. The values of percent identity and similarity between the amino acid sequences encoded by the translated regions of the isolated PRR7 genes derived from Nipponbare, *O. longistaminata* and *Arabidopsis* are shown in FIG. 7.

Preparation of Constructs Containing Respective PRR Genes

Figure 8:
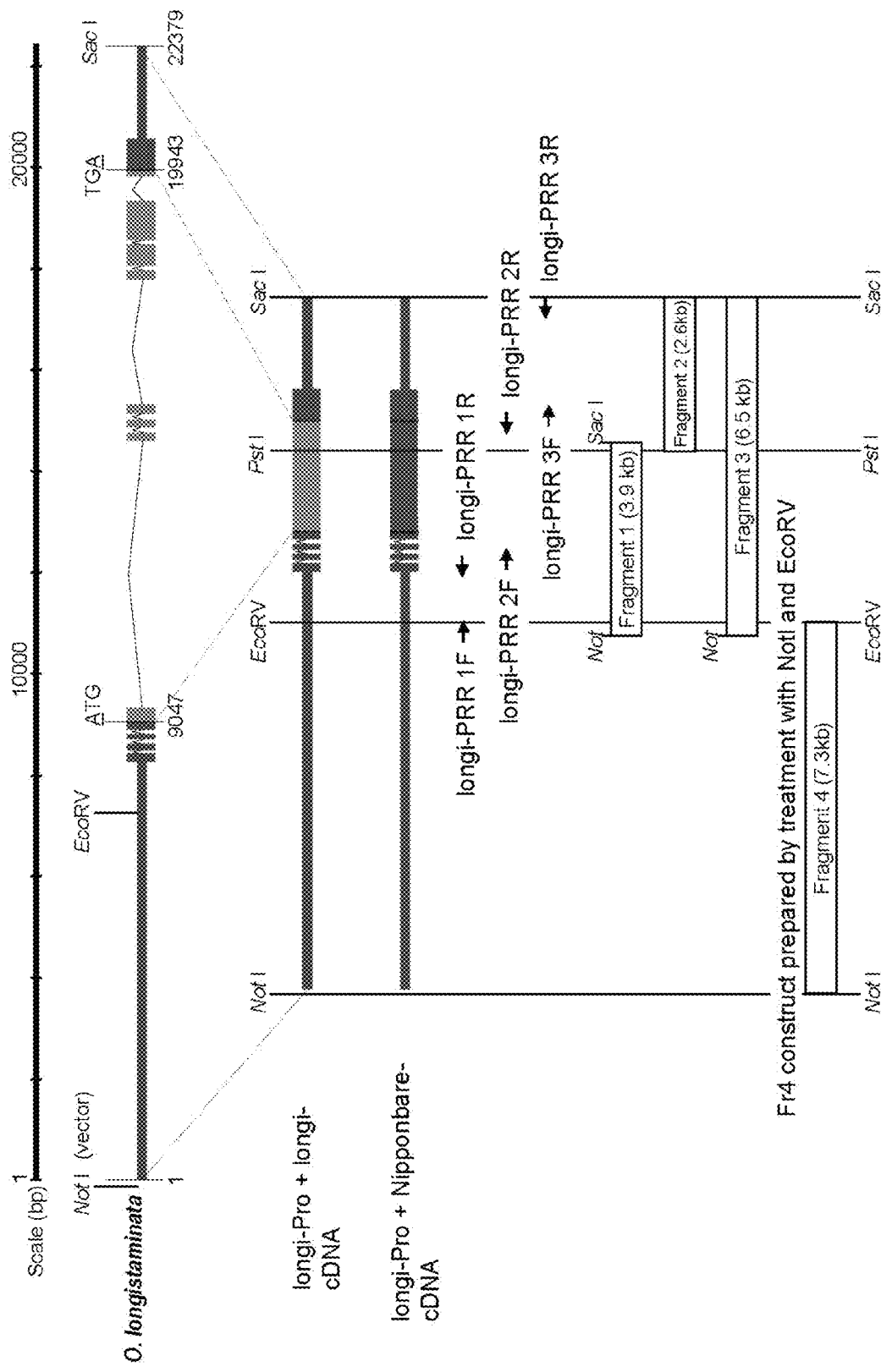
FIG. 8 is a diagram illustrating the strategy for preparing (1) constructs comprising a PRR gene derived from *O. longistaminata* and (2) constructs comprising a PRR gene derived from Nipponbare.

Constructs having the isolated cDNA inserted between the promoter and terminator regions of PRR7 gene derived from *O. longistaminata* were prepared by the following procedure. PrimeSTAR MAX DNA Polymerase (TAKARA-BIO) was used in PCR and DNA Ligation Kit "Mighty Mix" (TAKARA-BIO) was used in ligation. The strategy for preparing the constructs described below is illustrated in FIG. 8.

(1) Construct Including the Coding Region of *O. longistaminata* Derived PRR7 Gene (Hereinafter Referred to as Longi Construct)

With the Fr4 construct plasmid of Example 2 being used as a template, PCR was performed using the following two primers: longi-PRR 1F corresponds to the nucleotide sequence represented by 34019-34044 of SEQ ID NO: 1 and longi-PRR 1R corresponds to 35838-35861 of SEQ ID NO: 1:

```
                                              (SEQ ID NO: 8)
longi-PRR 1F: CGCTTCGAAGATATCATCATCATTCATGTATGAG (SEQ ID NO: 9)
longi-PRR 1R: AGCCGGCGGTTTGGTTGTGATGAG
```

Subsequently, the resulting PCR product and the above-mentioned No. 645-derived RT-PCR product were subjected to overlap extension PCR using longi-PRR 1F and longi-PRR 2R. The resulting PCR product was tagged with A-Tail using Ex-Taq (TAKARA-BIO) and cloned in pCR-XL-TOPO (Invitrogen); thereafter, this clone was digested with EcoRV and self-ligated to eliminate the PstI site originally present in pCR-XL-TOPO multiple cloning site. After the self-ligation, digestion was performed with SacI and PstI and dephosphorylation was also performed with CIAP (TAKARA-BIO). The reaction solution was electrophoresed on agarose gel and a vector fragment (including fragment 1 of FIG. 8) was recovered.

With the Fr4 construct plasmid of Example 2 being used as a template, PCR was performed using the following two primers: longi-PRR 3F corresponds to the nucleotide sequence represented by 46721-46744 of SEQ ID NO: 1 and longi-PRR 3R corresponds to 49137-49157 of SEQ ID NO: 1:

```
                                         (SEQ ID NO: 10)
  longi-PRR 3F: ACCTACCTACCTACCTACGCAATG (SEQ ID NO: 11)
  longi-PRR 3R: GCTAGAATTCGAGCTCTCCAGGGAGCAGGGA
```

The resulting PCR product and the above-mentioned No. 645-derived RT-PCR product were subjected to overlap extension PCR using longi-PRR 2F and longi-PRR 3R. The resulting PCR product was digested with SacI and PstI and thereafter the reaction solution was electrophoresed on agarose gel and a 2.6-kb fragment (fragment 2 of FIG. 8) was recovered for use as an insert. This 2.6-kb fragment corresponds to a nucleotide sequence represented by 46056-49156 of SEQ ID NO: 1 (provided, however, that on account of the intron 46108-46595, splicing occurs to yield a sequence comprising a tandem joint of 46056-46107 and 46596-49156).

Using the above-described two recovered fragments, ligation was performed. The resulting plasmid was digested with SacI and NotI, the reaction solution was electrophoresed on agarose gel, and a 6.5-kb fragment (fragment 3 of FIG. 8) was recovered. The recovered fragment 3 was cloned in pSB200 (that had been digested with SacI and NotI and subsequently CIAP treated). The resulting plasmid was digested with NotI and EcoRV and dephosphorylated with CIAP. The reaction solution was electrophoresed on agarose gel and a vector fragment (including fragment 3) was recovered. In a separate step, a plasmid carrying the Fr4 construct of Example 2 was digested with NotI and EcoRV, the reaction solution was electrophoresed on agarose gel, and a 7.3-kb fragment (fragment 4) was recovered. This 7.3-kb fragment corresponds to a nucleotide sequence represented by 26779-34022 of SEQ ID NO: 1. Using both of the above-described fragments, ligation was performed to yield the desired plasmid.

(2) Construct Including the Coding Region of Nipponbare Derived PRR7 Gene (Hereinafter Referred to as Nipponbare Construct)

With the Fr4 construct plasmid of Example 2 being used as a template, PCR was performed using longi-PRR 1F and longi-PRR 1R. The resulting PCR product and the above-mentioned Nipponbare-derived RT-PCR product were subjected to overlap extension PCR using longi-PRR 1F and longi-PRR 2R. The resulting PCR product was tagged with A-Tail using Ex-Taq and cloned in pCR-XL-TOPO. The resulting plasmid was digested with PstI and NotI, the reaction solution was electrophoresed on agarose gel, and a 3.9-kb fragment (Nipponbare cDNA derived fragment 1 of FIG. 8) was recovered for use as insert 1.

With the Fr4 construct plasmid of Example 2 being used as a template, PCR was performed using longi-PRR 3F and longi-PRR 3R. The resulting PCR product and the above-mentioned Nipponbare-derived RT-PCR product were subjected to overlap extension PCR using longi-PRR 2F and longi-PRR 3R. The resulting PCR product was tagged with A-Tail using Ex-Taq and cloned in pCR-XL-TOPO. The resulting plasmid was digested with SacI and PstI, the reaction solution was electrophoresed on agarose gel, and a 2.6-kb fragment (Nipponbare cDNA derived fragment 2 of FIG. 8) was recovered for use as insert 2. This 2.6-kb fragment corresponds to a nucleotide sequence represented by 46056-49156 of SEQ ID NO: 1 (provided, however, that on account of the intron 46108-46595, splicing occurred to yield a sequence comprising a tandem joint of 46056-46107 and 46596-49156).

The above-described two insert fragments and pSB200 (that had been digested with SacI and NotI and subsequently CIAP treated) were subjected to ligation. The resulting plasmid was digested with NotI and EcoRV and dephosphorylated with CIAP. The reaction solution was electrophoresed on agarose gel, and a vector fragment (including Nipponbare cDNA derived fragment 3 of FIG. 8) was recovered.

In a separate step, a plasmid carrying the Fr4 construct of Example 2 was digested with NotI and EcoRV, the reaction solution was electrophoresed on agarose gel, and a 7.3-kb fragment (fragment 4 of FIG. 8) was recovered. Using the two fragments, ligation was performed to yield the desired plasmid. The 7.3-kb fragment corresponds to a nucleotide sequence represented by 26779-34022 of SEQ ID NO: 1.

Using *E. coli* carrying the plasmid of interest as obtained in (1) and (2), triparental mating and the transformation of Shiokari were carried out by the methods described in Example 2. The transgenic rice plants were first acclimatized and then cultivated in a greenhouse of closed system. For each construct, 60 independent transgenic individuals were grown and T1 seeds were produced. From each construct, 18 individuals were selected in the decreasing order of seed production and subjected to a T1 evaluation test.

For the T1 generation, 18 lines per construct (12 individuals per line) were selected as test samples. Seeding was performed on June 25. Before transplantation, a leaf as cut from each individual was immersed in a hygromycin solution and only the individuals that showed resistance to hygromycin (those individuals presumably carrying the gene) were transplanted. On July 12, transplanting was conducted in polyethylene pots (capacity: 570 ml) containing soil for raising rice seedlings with one individual (12 pots per line for a total of 12 individuals). For fertilizing, N, P and K were applied in respective amounts of 0.21 g, 0.33 g, and 0.05 g per pot. In addition to the control Shiokari, line No. 240 having the terminal region of chromosome 7 in wild rice introduced into Shiokari was planted as a reference variety. Cultivation was performed in the greenhouse of closed system for dedicated use in recombination experiment (under long-day condition with a day length of 14 hours and a half) at the Plant Innovation Center of Japan Tobacco Inc. Agronomic traits including days to heading, culm length, the number of panicles, culm base diameter, panicle length, the number of grains per panicle, spikelet fertility, and the weight of fertilized spikelet per panicle (hereinafter referred to as weight per panicle) of maximum panicle were evaluated.

The results are shown in Table 8. In view of the average values for the total of 18 lines of longi construct and Nipponbare construct, the plants transformed with either of the two construct were obviously superior to the control Shiokari as regards the days to heading, culm length, panicle length, the number of grains per panicle, weight per panicle, and culm base diameter. The plants transformed with either of the two constructs also excelled significantly the control Shiokari as regards the days to heading, culm length, panicle length, the number of grains per panicle, weight per panicle, and culm base diameter in more than one line. In addition, the total of 18 lines of the plants transformed with the longi construct as well as the total of 18 lines of the plants transformed with the Nipponbare construct had mean values of panicle density (the number of grains per centimeter of panicle) at 5.15 grains/cm and 4.80 grains/cm, which were obviously greater than the mean value of panicle density for Shiokari which was 4.40 grains/cm.

From the above, it was verified that the PRR7 gene is responsible for high-yielding ability. In addition, the results of Examples 3 and 4 taken together led to a quite surprising conclusion that the high-yielding ability of *O. longistaminata* would be due more to the promoter region of the PRR7 gene than to its coding region.

In addition, a comparison between the yield of the plant transformed with the longi construct and that of the plant transformed with the Nipponbare construct showed that the former had a more marked effect than the latter. Hence, the structural region of the longi PRR7 was more advantageous than that of the Nipponbare PRR7 gene as a structural gene to be introduced into plants together with the promoter.

TABLE 8

Evaluation of yield-associated traits of cDNA constructs of PRR genes in wild rice *O. longistaminata* and cultivated rice Nipponbare

| Construct/ Variety name | Days to heading (day) | Culm length (cm) | No. of panicles | Panicle length (cm) | No. of grains per panicle | Ratio relative to control (No. of grains per panicle) (%) | Spikelet fertility (%) | Weight per panicle (g) | Ratio relative to control (Weight per panicle) (%) | Culm base diameter (mm) |
|---|---|---|---|---|---|---|---|---|---|---|
| (longi-Pro+ longi-cDNA) | 54.7 | 84.6 | 3.3 | 15.5 | 79.8 | 124 | 77.8 | 1.50 | 121 | 4.15 |
| (longi-Pro+ Nipponbare-cDNA) | 52.8 | 82.0 | 3.6 | 15.2 | 72.9 | 113 | 78.8 | 1.38 | 112 | 3.91 |
| Shiokari (control) | 49.7 | 76.4 | 3.6 | 14.6 | 64.3 | 100 | 79.8 | 1.24 | 100 | 3.55 |
| No. 240 (reference) | 60.3 | 107.5 | 3.5 | 17.6 | 99.4 | 155 | 98.4 | 2.49 | 201 | 5.55 |

Example 6: Analysis of Expression of *O. longistaminata* and Nipponbare PRR Genes It was speculated from the results of Example 5 that the promoter region of PRR7 gene would influence high-yielding ability, so in order to investigate the difference in expression between the PRR7 gene promoter of *O. longistaminata* and that of the cultivated rice Nipponbare, the expression of PRR7 gene was analyzed using F1 of Nipponbare and No. 240 (a chromosomal segment substitution line having the PRR7 gene of *O. longistaminata* introduced into Shiokari by crossing.

Three weeks after sowing, the youngest fully developed leaves were sampled from Nipponbare (2 individuals), No. 240 (2 individuals), and F1 of Nipponbare and No. 240 (4 individuals), and total RNA extraction and cDNA synthesis were carried out by the methods described in Example 3. RNA samples were also prepared without adding a reverse transcriptase and used as a negative control. Part of a nucleic acid solution before DNase treatment as obtained upon RNA extraction was used as a total DNA solution. With the resulting total DNA solution and cDNA solution being used as templates, PCR was performed under the following conditions using two primers, CGAGGTACCATACACCT-GTGGCTT (SEQ ID NO: 12) and GCATCTGAGTTT-GACTTCATGTTG (SEQ ID NO: 13).

|  | Total DNA | cDNA |
|---|---|---|
| Template DNA | 1.0 µl | 1.0 µl |
| 10 × PCR buffer | 2.0 µl | 2.5 µl |
| 2.5 mM dNTP | 1.0 µl | 1.25 µl |
| rTaq | 0.1 µl | 0.125 µl |
| Forward primer (10 µM) | 0.5 µl | 0.5 µl |
| Reverse primer (10 µM) | 0.5 µl | 0.5 µl |
| H$_2$O | 14.9 µl | 19.125 µl |
| Total | 20.0 µl | 25.0 µl |

94° C. 2 min
94° C. 30 sec
60° C. 30 sec
(35 cycles each of 94° C.×30 sec and 60° C.×30 sec)

The PCR product (130 bp) was treated with the restriction enzyme HpyCH4V (New England Biolabs) at 37° C. overnight and subjected to electrophoresis using 3% Metaphor Agarose (TAKARA-BIO).

Figure 9A:
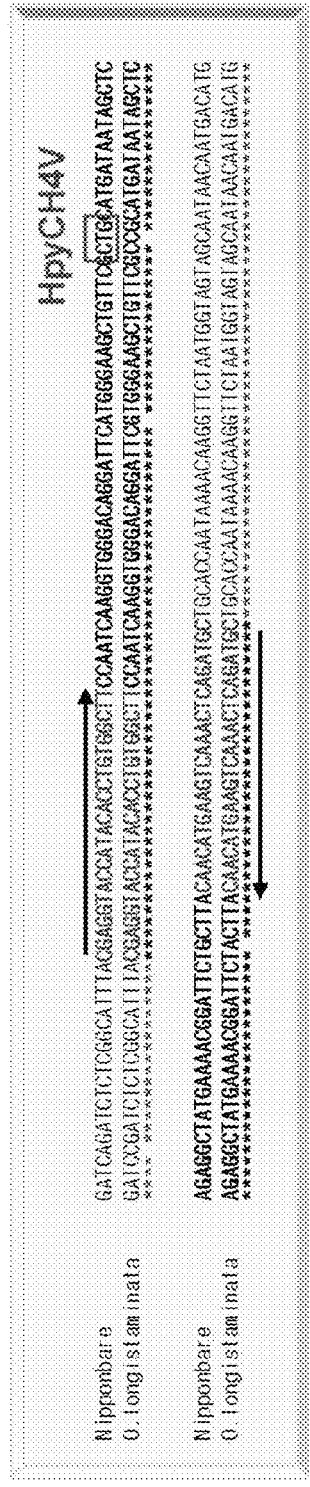
FIG. 9A (SEQ ID NOS: 20 and 21) shows that a PCR product of a PRR gene derived from *O. longistaminata* is cleaved by HpyCH4V.

When the total DNA solution and cDNA solution of Nipponbare were used as templates, the PCR product was cleaved with HpyCH4V whereas when the total DNA solution and cDNA solution of No. 240 were used as templates, the PCR product was not cleaved with HpyCH4V (FIG. 9A). It was accordingly confirmed that by the technique under consideration, the PCR product from the allele of Nipponbare can be distinguished from the PCR product from the allele of *O. longistaminata*.

Figure 9B:
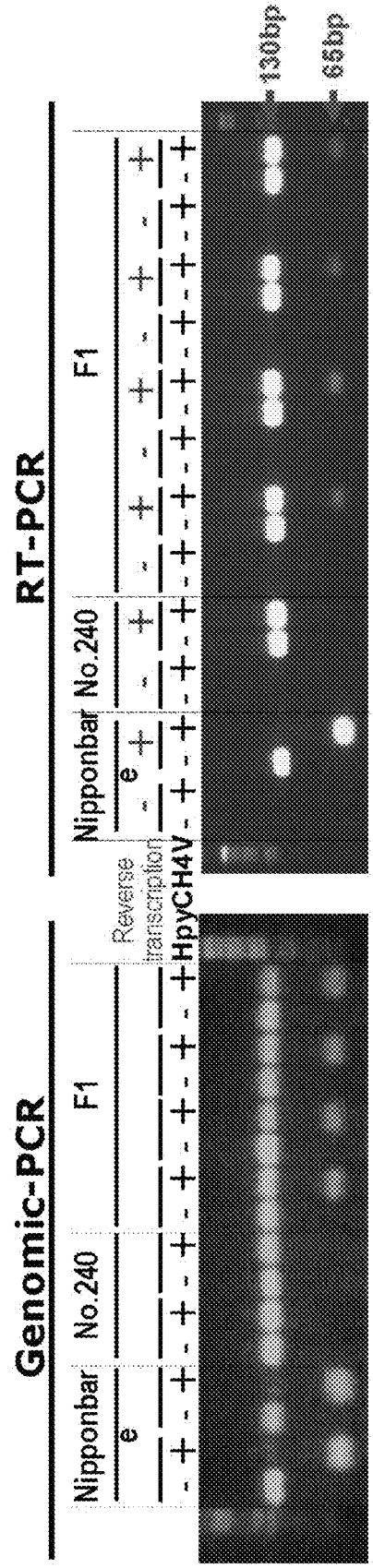
FIG. 9B shows the results of PCR analyses of PRR gene expression using Nipponbare, substituted line No. 240 in which a PRR gene of *O. longistaminata* was transferred into Shiokari by backcrossing, and F1 of Nipponbare and No. 240.

Hence, the band patterns were compared for the F1 samples. As a result, it was indicated that the proportion of the PCR product undigested with HpyCH4V was higher when the cDNA solution was used as a template than when the total DNA solution was used as a template. This result implied that, in F1 of Nipponbare and the substitution line, expression level of the PRR7 allele derived from *O. Longistaminata* was higher than that of the PRR7 allele derived from Nipponbare (FIG. 9B).

Example 7: Effects in Corn of PRR Promoter and PRR Gene of *O. Longistaminata*

The Fr4 fragment prepared in Example 2 (including the PRR7 promoter and PRR7 structural gene of *O. Longistaminata*) was used to transform a corn variety and the T1 generation of the transgenic corn was evaluated for its yield-associated traits.

Immature corn embryos (variety: A188) of about 1.2 mm in size were aseptically taken from the greenhouse-cultivated plants and immersed in a liquid medium for suspension of *Agrobacterium* (LS-inf, Ishida et al. 2007). After heat treatment at 46° C. for 3 minutes, the immature embryos were washed once in the same liquid medium. Subsequently, the embryos were centrifuged at 15,000 rpm and 4° C. for 10 minutes. The immature embryos as centrifuged were immersed in an LS-inf-AS medium (Ishida et al. 2007) having suspended therein about 1×10$^9$ cfu/ml of *Agrobacterium* LBA4404 carrying the Fr4 construct as prepared in Example 2. After 30-sec stirring and 5-min standing at room temperature, the embryos were placed on a co-culture medium (LS-AS, Ishida et al. 2007) and cultured at 25° C. in complete darkness for 7 days.

The co-cultured immature embryos were placed on a hygromycin-loaded selective medium (LSD1.5A and LSD1.5B, Ishida et al. 2007) and cultured at 25° C. in complete darkness. The growing callus was cut in small pieces, placed on a hygromycin-loaded regeneration medium (LSZ, Ishida et al. 2007) and cultured at 25° C. under illumination for 2 weeks. The regenerated plant was placed on a rooting medium (LSF, Ishida et al. 2007) and cultured at 25° C. under illumination for 2 weeks. The rooting plant was transplanted into pots in a greenhouse, where it was cultivated.

The emerged tassel was pulled out for emasculation before flowering. Silk as fully emerged from the ear was crossed with pollen as picked from non-transformed corn (variety: A188). The ears with a withered husk were harvested and after being dried at 30° C. for 2 weeks, seeds were threshed. Seed production was possible from 44 individuals.

Figure 10:
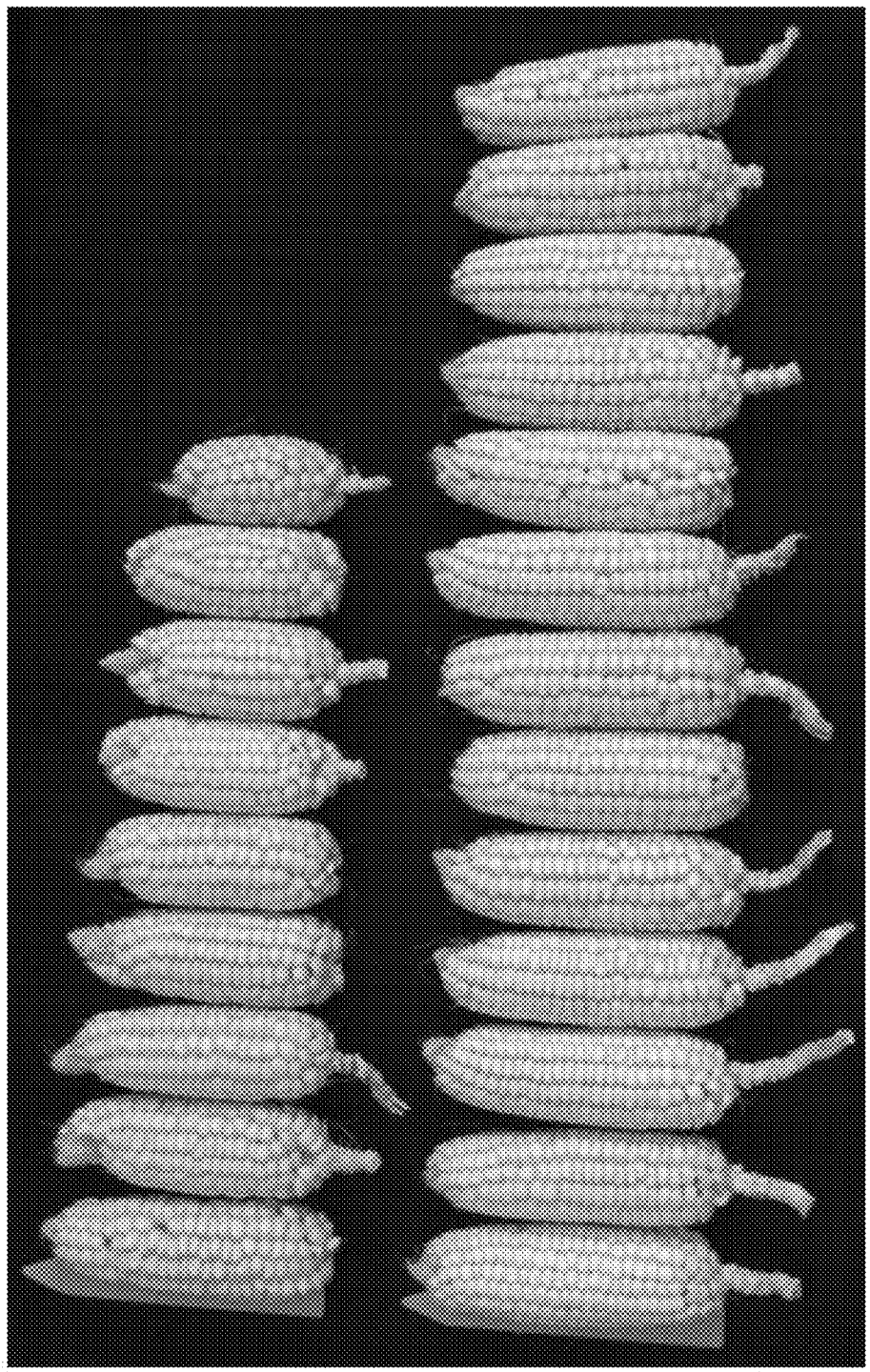
FIG. 10 is a photo showing ears of T1 line No. 4 of transgenic corn into which fragment Fr4 derived from *O. longistaminata* was introduced. The upper row of FIG. 10 shows gene lacking individuals having no fragment Fr4 whereas the lower row shows gene carrying individuals having fragment Fr4.

From among the ears of T0 individuals, 11 were selected in the decreasing order of size and the T1 generation was evaluated for yield-associated traits. Tests were conducted in three separate runs (for a total of 11 lines consisting of 5 lines in the first run, 3 lines in the second run, and 3 lines in the third run). Seeding was done in polyethylene pots (capacity: 360 ml) at a density of one kernel per line (16 kernels in the first test run with a total of 16 pots, and 25 kernels in each of the second and third test runs with a total of 25 pots). About 2 weeks after the seeding, leaves were partially cut off and immersed in a hygromycin solution to examine their resistance or sensitivity to hygromycin. With the number of individuals so adjusted as to ensure that yield-related traits could be evaluated in hygromycin-resistant individuals making a pair with hygromycin-sensitive individuals, they were transplanted in polyethylene pots (capacity: 5100 cc) and cultivated continuously. Fourteen days after the seeding, weekly plant height measurement was begun and continued until 56 days after the seeding. The emerged tassel was pulled out for emasculation before flowering. The day when the silk was emerged from the ear was recorded and silk as fully emerged from the ear was crossed with pollen as picked from non-transformed corn (variety: A188). The ears as harvested were measured for ear length, number of kernels per row, and ear weight. For each line, the hygromycin-resistant individuals (gene carrying individuals) were compared with the hygromycin-sensitive individuals (gene lacking individuals) for yield-associated traits. As a result, among the total of 11 lines, two lines (T1-No. 4 and T1-No. 6) were characterized in that the resistant individuals were greatly different from the sensitive ones in terms of all 3 traits (ear length, number of kernels per row, and ear weight) (Table 9 and FIG. 10). Furthermore, ever since the 35$^{th}$ day after the seeding, the resistant individuals of line T1-No. 4 were consistently higher in plant height than the sensitive ones, suggesting their vigorous growth in the vegetative stage onward.

From the above, it was revealed that the PRR7 gene operably linked to the PRR7 promoter of *O. Longistaminata* increased not only the yield of rice but also the yield of corn. Additionally, it was suggested that this gene enabled vigorous growth in the vegetative stage.

TABLE 9

Data on the yield-associated traits of two lines as verified to be effective

| Name of line | Test run | Hygromycin | Days to silk emergence (day) | Ear length (mm) | No. of kernels per row | Ear weight (g) |
|---|---|---|---|---|---|---|
| T1-No. 4 | 1$^{st}$ run | Resistant | 63.7 | 87.7 | 22.0 | 50.1 |
| T1-No. 4 | 1$^{st}$ run | Sensitive | 63.0 | 73.9 | 17.3 | 40.4 |
| A188 (reference) | 1$^{st}$ run | Sensitive | 60.3 | 73.5 | 18.1 | 39.9 |
| T1-No. 6 | 2$^{nd}$ run | Resistant | 66.8 | 101.8 | 25.5 | 57.8 |
| T1-No. 6 | 2$^{nd}$ run | Sensitive | 64.3 | 86.7 | 21.8 | 49.6 |
| A188 (reference) | 2$^{nd}$ run | Sensitive | 64.0 | 91.5 | 23.1 | 50.8 |

Example 8: Effect in Corn of cDNA Construct of *O. Longistaminata* Derived PRR Gene The cDNA construct of *O. Longistaminata* derived PRR7 gene prepared in Example 5 (the construct is hereinafter referred to as a longi construct) was used to transform a corn variety and the T1 generation of the transgenic corn was evaluated for its yield-associated traits.

A corn variety was transformed with the longi construct in accordance with the method described in Example 7. The obtained transformants were transplanted in pots in a greenhouse, where they were cultivated. The tassel of each T0 plant was pulled out for emasculation before flowering and silk as fully emerged from the ear was dusted with pollen as picked from non-transformed corn (variety: A188). The ears with a withered husk were harvested and after being dried at 30° C. for 2 weeks, seeds were threshed. From among the ears of T0 individuals, 18 were selected as individuals carrying adequate numbers of kernels and the T1 generation was evaluated for yield-associated traits. Tests were conducted in three separate runs (6 lines in each run). Seeding was done in polyethylene pots (capacity: 360 ml) at a density of 25 kernels per line for one pot. Non-transformed corn (variety: A188) was also seeded as a control. About 2 weeks after the seeding, leaves were partially cut off and immersed in a hygromycin solution to examine their resistance or sensitivity to hygromycin. With the number of individuals so adjusted as to ensure that yield-related traits could be evaluated in hygromycin-resistant individuals making a pair with hygromycin-sensitive individuals, they were transplanted in polyethylene pots (capacity: 5100 cc) and cultivated continuously. Fourteen days after the seeding, weekly plant height measurement was begun and continued until 56 days after the seeding. The emerged tassel was pulled out for emasculation before flowering. The day when the silk was emerged from the ear was recorded and silk as fully extracted from the ear was crossed with pollen as picked from non-transformed corn (variety: A188). After drying the ear as harvested, the ear length, the number of kernels per row, and the ear weight were measured. For each line, the hygromycin-resistant individuals (gene carrying individuals) were compared with the hygromycin-sensitive individuals (gene lacking individuals) for yield-associated traits. For the lines experiencing no segregation of hygromycin-sensitive individuals (gene lacking individuals), comparison was made with non-transformed A188.

Figure 11:
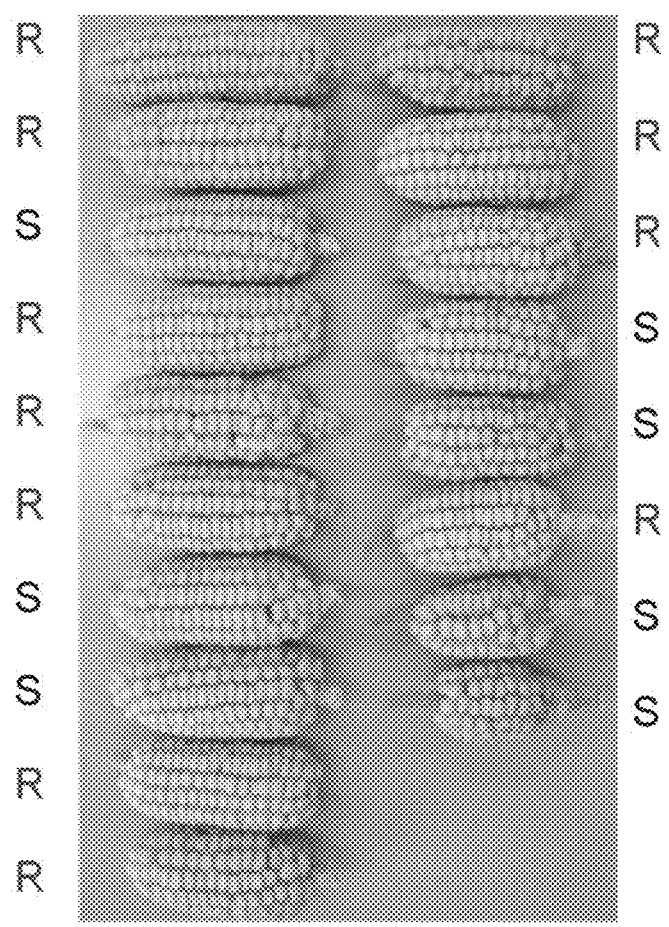
FIG. 11 is a photo showing ears of T1 line No. 11 of transgenic corn into which constructs comprising a PRR promoter of *O. longistaminata* and a PRR gene of *O. longistaminata* were introduced. Symbol R in FIG. 11 refers to hygromycin-resistant individuals (gene carrying individuals) whereas S refers to hygromycin-sensitive individuals (gene lacking individuals).

As a result, among the total of 18 lines, two lines (T1-cDNA No. 11 and T1-cDNA No. 13) were shown to be such that the resistant individuals were greatly different from the sensitive individuals or non-transformed A188 in terms of all 3 traits ('ear length, number of kernels per row, and ear weight) (Table 10 and FIG. 11). In FIG. 11, R refers to a hygromycin-resistant individual (gene carrying individual) and S refers to a hygromycin-sensitive individual (gene lacking individual).

From the above, it was revealed that the transgenic gene having the PRR7 promoter of *O. Longistaminata* PRR7 gene operably linked to the cDNA of the same gene increased the yield of corn. Thus, it was verified that the effect of the present invention was obtained by transferring an intron-free cDNA in the *O. Longistaminata* PRR7 gene.

TABLE 10

Data on the yield-associated traits of two lines of transgenic corn as verified to be effective

| Name of line | Test run | Hygromycin | Days to silk emergence (day) | Ear length (mm) | No. of kernels per row | Ear weight (g) |
|---|---|---|---|---|---|---|
| T1-cDNA No. 11 | 2$^{nd}$ run | Resistant | 66.9 | 82.2 | 20.3 | 51.8 |
| T1-cDNA No. 11 | 2$^{nd}$ run | Sensitive | 68.1 | 71.6 | 15.7 | 44.9 |
| A188 (reference) | 2$^{nd}$ run | Sensitive | 66.5 | 71.5 | 15.3 | 46.1 |
| T1-cDNA No. 13 | 3$^{rd}$ run | Resistant | 63.1 | 110.1 | 24.6 | 63.7 |
| T1-cDNA No. 13 | 3$^{rd}$ run | Sensitive | — | — | — | — |
| A188 (reference) | 3$^{rd}$ run | Sensitive | 61.1 | 99.9 | 23.2 | 59.2 |

Example 9: Effects in Constructs in which the Coding Region of *Arabidopsis* PRR Gene and the Coding Region of *Sorghum* PRR Gene are Respectively Linked to *O. Longistaminata* Derived PRR Promoter From *Arabidopsis* (Columbia), the coding region of PRR7 gene (Accession Number: NM120359) was isolated by RT-PCR, and in accordance with the method described in Example 5, it was substituted for the coding region of *O. Longistaminata* PRR7 gene in the construct of Example 5 to thereby prepare the desired construct. The nucleotide sequence of the isolated *Arabidopsis* PRR gene is depicted in SEQ ID NO: 14 and that of the encoded amino acid sequence is depicted in SEQ ID NO: 15. Subsequently, a construct having the coding region of *Sorghum* PRR gene linked to the *O. Longistaminata* PRR promoter was prepared in substantially the same way: through NCBI blastn search (http://blast.ncbi.nlm.nih.gov/Blast.cgi?PROGRAM= blastn&BLAST_PROGRAMS=megaB1 ast&PAGETYPE= BlastSearch&SHOWDEFAULTS=on&LINKLOC= blast-home), a gene (Accession Number: XM_002465391) having high homology to the coding region of *O. Longistaminata*

PRR7 gene (SEQ ID NO: 4) was isolated as a PRR gene; the sequence of the coding region of this gene was isolated from *Sorghum* (variety: Gold sorgho; KANEKO SEEDS) by RT-PCR and substituted for the coding region of *O. Longistaminata* PRR7 gene in the construct of Example 5 to thereby prepare the desired construct (SEQ ID NO: 18). The isolated coding region of *Sorghum* derived PRR gene was in 100% agreement with the sequence that hit in NCBI blastn search (Accession Number: XM_002465391); it consisted of 2295 nucleotides (SEQ ID NO: 16) encoding 765 amino acid residues (SEQ ID NO: 17). For the homology and identity between the amino acid sequences of the translated regions of these PRR genes, see FIG. 7.

Using these constructs, triparental mating and the transformation of the rice variety Yukihikari were carried out by the methods described in Example 5. The transgenic rice plants were first acclimatized and then cultivated in a greenhouse. For each construct, 60 independent transgenic individuals were grown and T1 seeds were produced. From each construct, 18 individuals were selected in the decreasing order of seed production and subjected to a T1 evaluation test.

For the T1 generation, 18 lines per construct (12 individuals per line) were selected as test samples. Seeding was performed on September 14. Before transplantation, a leaf as cut from each individual was immersed in a hygromycin solution and only the individuals that showed resistance to hygromycin (gene carrying individuals) were transplanted. On September 28, transplanting was conducted in polyethylene pots (capacity: 570 ml) containing soil for raising rice seedlings with one individual (12 pots per line for a total of 12 individuals). For fertilizing, N, P and K were applied in respective amounts of 0.21 g, 0.33 g, and 0.05 g per pot. Yukihikari was planted as a control. Cultivation was performed in the greenhouse of closed system for dedicated use in recombination experiment (under long-day condition with a day length of 14 hours and a half) at the Plant Innovation Center of Japan Tobacco Inc. Agronomic traits including days to heading, culm length, the number of panicles, culm base diameter, panicle length, the number of grains per panicle, spikelet fertility, and the weight of fertilized spikelet per panicle (hereinafter referred to as weight per panicle) of maximum panicle were evaluated.

The results are shown in Table 11. In view of the average values for the total of 18 lines of *Arabidopsis* construct, the plants transformed with this construct were inferior to the control Yukihikari in terms of culm length, the number of grains per panicle, the weight per panicle and culm base diameter, suggesting the absence of any yield increasing effect. The plants transformed with the *Sorghum* construct were almost comparable to the control Yukihikari as regards culm length, panicle length and the number of grains per panicle but inferior in terms of the weight per panicle and culm base diameter; thus, there was no apparent yield increasing effect.

TABLE 11

Evaluation of yield-associated traits of cDNA constructs having *O. longistaminata* PRR promoter joined in it

| Event/ Variety name | Days to heading (day) | Culm length (cm) | No. of panicles | Panicle length (cm) | No. of grains per panicle | Ratio relative to control (No. of grains per panicle) (%) | Spikelet fertility (%) | Weight per panicle (g) | Ratio relative to control (Weight per panicle) (%) | Culm base diameter (mm) |
|---|---|---|---|---|---|---|---|---|---|---|
| (longi-Pro+ *Arabidopsis* cDNA) | 60.0 | 74.1 | 3.5 | 19.3 | 105.3 | 90 | 89.0 | 2.47 | 84 | 4.09 |
| (longi-Pro+ *Sorghum* cDNA) | 61.4 | 80.1 | 3.7 | 19.4 | 118.9 | 102 | 86.9 | 2.73 | 92 | 4.28 |
| Yukihikari (control) | 59.0 | 81.2 | 3.5 | 19.5 | 116.6 | 100 | 96.0 | 2.96 | 100 | 4.38 |

Figure 12:
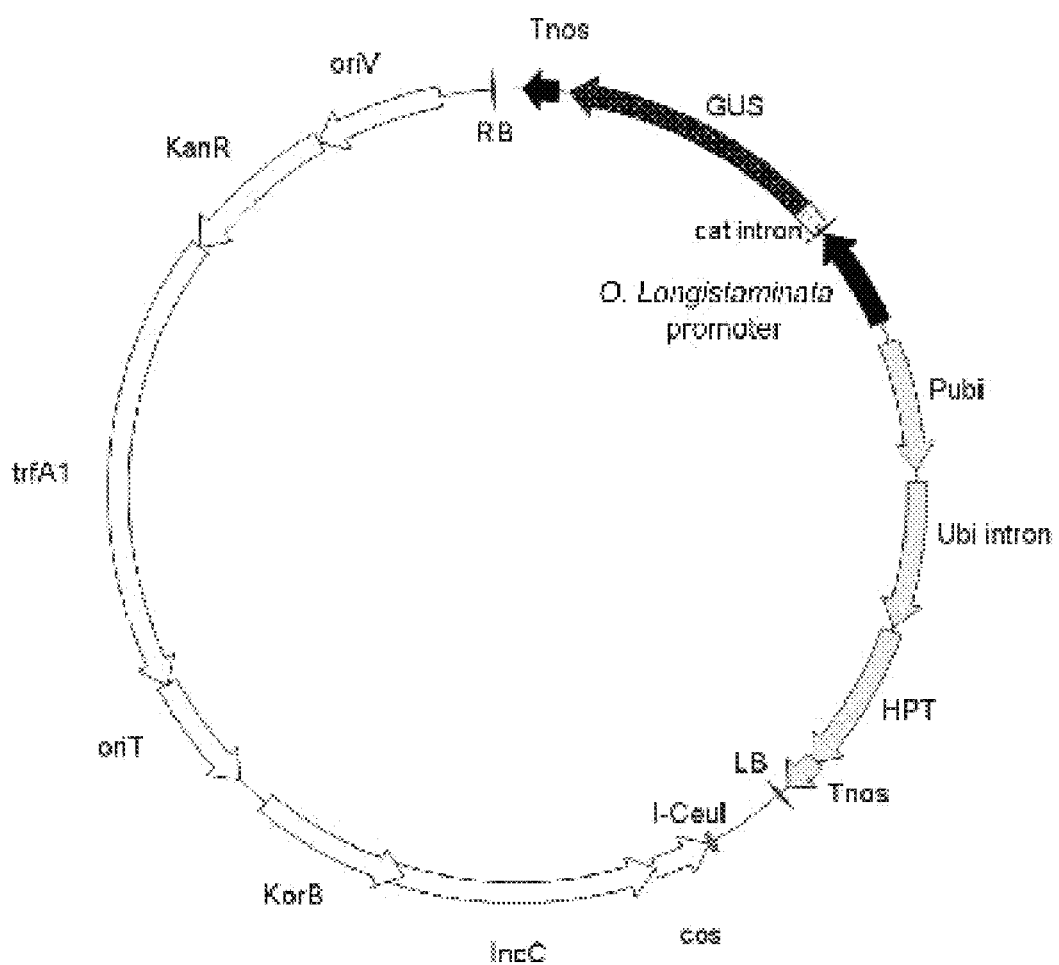
FIG. 12 is a diagram showing the structure of a GUS gene expressing vector that was used in an experiment for evaluating the effect which a PRR promoter of *O. longistaminata* would have on the transcriptional activity of GUS gene.

Example 10: Constructs Having *O. Longistaminata* Derived PRR Promoters Linked to GUS Gene Chimeric constructs of promoter regions of *O. longistaminata* derived PRR7 gene and a GUS gene were prepared and investigated for the presence or absence of transcription. As shown in FIG. 12, the constructs had the coding region of GUS gene linked immediately downstream of promoter regions of the *O. longistaminata* PRR7 gene. Specifically, the promoter regions of the *O. longistaminata* PRR7 gene were one that consisted of 200 nucleotides in a region upstream of the transcription initiation point (34845-35044 nucleotides in SEQ ID NO: 1) and another that consisted of 2000 nucleotides in the same region (33045-35044 nucleotides in SEQ ID NO: 1) and by respectively linking these promoter regions to the GUS gene, constructs P200 and P2000 were prepared. Construct P0 having no promoter regions of PRR7 gene was also prepared as a control.

Figure 13:
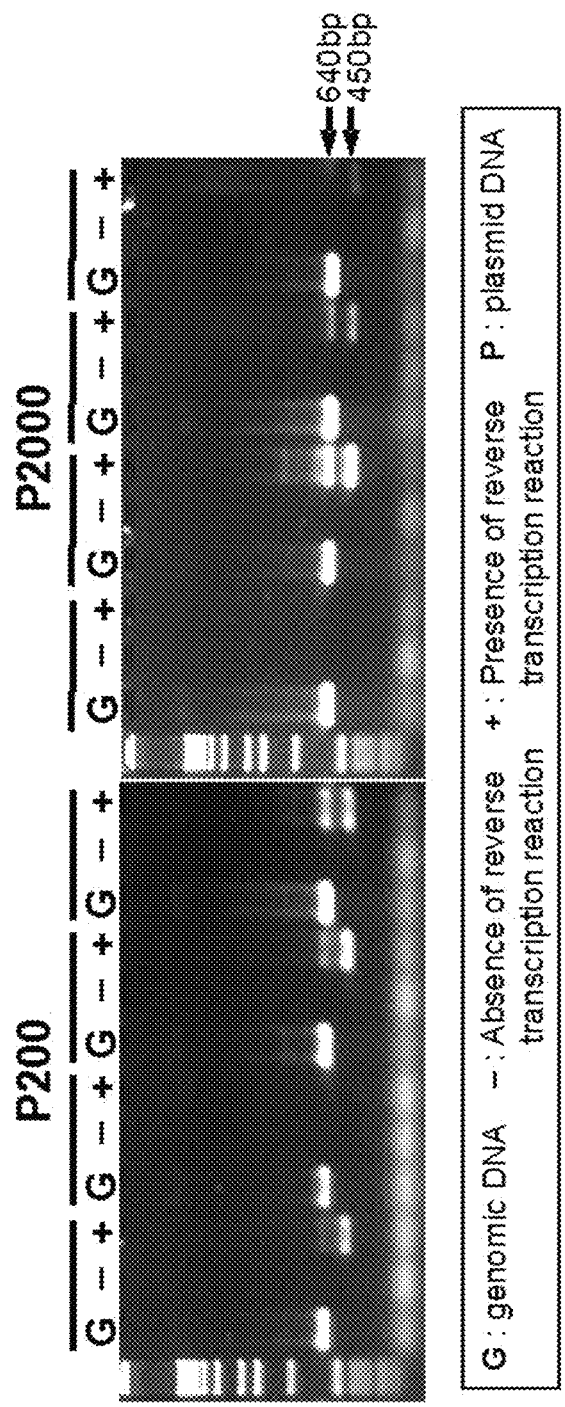
FIG. 13 is a photo of RT-PCR analysis for evaluating promoted transcriptional activity of GUS gene in rice transformed with a construct in which a nucleic acid consisting of 200 nucleotides (P200) or 2000 nucleotides (P2000) in the PRR promoter region of *O. longistaminata* was linked to the coding region of GUS gene; G refers to genomic DNA, the minus sign refers to the absence of reverse transcription reaction, the plus sign refers to the presence of reverse transcription reaction, and P refers to plasmid DNA.

The thus prepared constructs were used to transform the cultivated rice Yukihikari. From seedlings of the transgenic rice that had grown to a height of about 10 cm, four individuals were pulled out by the root for each construct and sampling was done individually. Total RNA extraction and cDNA synthesis were performed by the methods described in Example 5. With the resulting cDNA solution used as a template, PCR based investigation was made to see if the GUS gene had been transcribed. Two primers in pair were designed to flank on opposite sides of an intron sequence (190 nucleotides) incorporated into the coding region of the GUS gene. Thus, any mature mRNA that has been transcribed and subjected to the action of the splicing mechanism would be detected as a PCR amplified product of 450 nucleotides in length. As it turned out, the transformants P200 and P2000 were verified to have transcriptional activity (FIG. 13). On the other hand, no PCR amplified product derived from mature mRNA could be verified in the control P0. Thus it was shown that both P200 and P2000 have the promoter activity in plants.

Example 11: Expression Analysis of *O. longistaminata* PRR Gene

Figure 14:
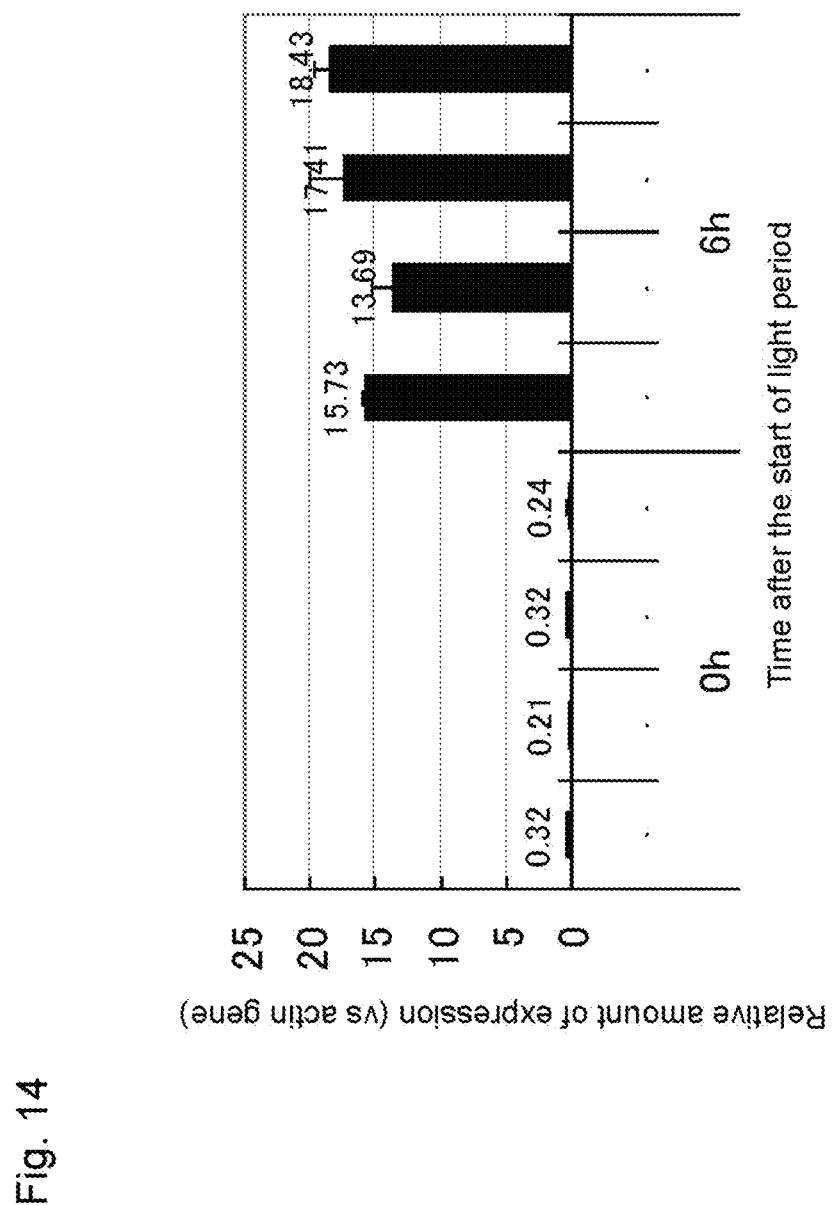
FIG. 14 is a diagram showing the amount of relative expression of *O. longistaminata* PRR gene as measured at 0 and 6 hours after the start of a light period.

Line No. 240 having only the terminal region of chromosome 7 in *O. longistaminata* introduced into Shiokari was cultivated in a phytotron for 4 weeks under long-day conditions with a light period of 14 hours and a half (26° C.) and a dark period of 9 hours and a half (20° C.). A fully foliated leaf was sampled from 4 individuals at zero hour (0 h) and six hours (6 h) after the start of the light period. Total RNA extraction and cDNA synthesis were performed by the methods described in Example 5. With the resulting cDNA solution used as a template, real-time PCR was carried out by the method described in Non-Patent Document 13 (Ogiso et al.). The amount of expression of PRR7 gene was calculated by relative values of the amount of actin gene expressed in the same sample. As it turned out, at zero hour (0 h) after the start of the light period, the amount of expression of PRR7 gene was within the range of 0.21-0.32 (average: 0.27) whereas it was 13.69-18.43 (average: 16.31) at six hours (6 h) after the start of the light period (FIG. 14). It was thus demonstrated that the promoter of *O. longistaminata* PRR7 gene was expressed not constitutively but photoinductively.

Example 12: Effect in Construct Having *Sorghum* Derived PRR Promoter Linked to the Coding Region of *Sorghum* PRR Gene A DNA fragment corresponding to the promoter region of the *Sorghum* PRR gene isolated in Example 9 was amplified from *Sorghum* (variety: Gold sorgho; KANEKO SEEDS) by PCR. A sequence of SEQ ID NO: 19 in the obtained DNA fragment was used to substitute for the sequence of 1-9046 in the construct of Example 9 (SEQ ID NO: 18) to thereby prepare the desired construct (hereinafter referred to as a "*Sorghum* construct").

Using the thus prepared *Sorghum* construct, triparental mating and the transformation of the rice variety Yukihikari were carried out by the methods described in Example 5. The transgenic rice plants were first acclimatized and then cultivated in a greenhouse. Sixty independent individuals of the thus obtained transformant (T0) were grown and T1 seeds were produced. Eighteen individuals were selected in the decreasing order of seed production and subjected to a T1 evaluation test.

For the T1 generation, 18 lines (12 individuals per line) were selected as test samples. Seeding was performed on September 14. Before transplantation, a leaf as cut from each individual was immersed in a hygromycin solution and only the individuals that showed resistance to hygromycin (gene carrying individuals) were transplanted. On September 28, transplanting was conducted in polyethylene pots (capacity: 570 ml) containing soil for raising rice seedlings with one individual (12 pots per line for a total of 12 individuals). For fertilizing, N (nitrogen), P (phosphorus) and K (potassium) were applied in respective amounts of 0.21 g, 0.33 g, and 0.05 g per pot. Yukihikari was planted as a control. Cultivation was performed in the greenhouse of closed system for dedicated use in recombination experiment (under long-day condition with a day length of 14 hours and a half) at the Plant Innovation Center of Japan Tobacco Inc. Agronomic traits including days to heading, culm length, the number of panicles, culm base diameter, panicle length, the number of grains per panicle, spikelet fertility, and the weight of fertilized spikelet per panicle (hereinafter referred to as weight per panicle) of maximum panicle were evaluated.

The results are shown in Table 12. Among the total 18 lines of *Sorghum* construct, two lines (No. 8 and No. 10) surpassed the control Yukihikari in culm length, number of grains per panicle, and weight per panicle. The yield-improving effect was also apparent in the *Sorghum* construct.

TABLE 12

Evaluation of yield-associated traits of constructs having *Sorghum* PRR promoter linked to PRR cDNA

| Line/ Variety name | Days to heading (day) | Culm length (cm) | No. of panicles | Panicle length (cm) | No. of grains per panicle | Ratio relative to control (No. of grains per panicle) (%) | Spikelet fertility (%) | Weight per panicle (g) | Ratio relative to control (Weight per panicle) (%) | Culm base diameter (mm) |
|---|---|---|---|---|---|---|---|---|---|---|
| Line No. 8 | 62.2 | 90.8 | 3.5 | 20.8 | 139.5 | 120 | 96.9 | 3.73 | 126 | 4.74 |
| Line No. 10 | 60.6 | 87.1 | 3.7 | 20.3 | 141.4 | 121 | 93.9 | 3.33 | 113 | 4.58 |
| Yukihikari | 59.0 | 81.2 | 3.5 | 19.5 | 116.6 | 100 | 96.0 | 2.96 | 100 | 4.38 |

The invention claimed is:

1. A method for promoting the transcriptional activity of a plant gene, comprising the step of introducing a nucleic acid molecule of (i) or (ii):
   (i) a nucleic acid comprising (1) nucleotide sequence set forth in nucleotide numbers 34845-35044 of SEQ ID NO: 1 or (2) a nucleotide sequence that has at least 97% identity to the nucleotide sequence set forth in nucleotide numbers 34845-35044 of SEQ ID NO: 1 and which shows an activity for promoting the transcription of a plant gene;
   (ii) a nucleic acid comprising a nucleotide sequence which is derived from *O. longistaminata* and at least comprising the nucleotide sequence set forth in nucleotide numbers 34845-35044 of SEQ ID NO: 1, said nucleic acid showing an activity for promoting the transcription of a plant gene;
   into a plant, wherein the nucleic acid molecule selected from the group consisting of (i) and (ii) is introduced into a region upstream of the plant gene.

2. A transgenic plant with increased yield comprising the nucleic acid construct in which (A) and (B) are operably linked:
   (A) the nucleic acid molecule selected from a group consisting of (i) and (ii):
      (i) a nucleic acid molecule comprising (1) nucleotide sequence set forth in nucleotide numbers 34845-35044 of SEQ ID NO: 1 or (2) a nucleotide sequence that has at least 97% identity to the nucleotide sequence set forth in nucleotide numbers 34845-35044 of SEQ ID NO: 1 and which shows an activity for promoting the transcription of a plant gene;
      (ii) a nucleic acid molecule comprising a nucleotide sequence which is derived from *O. longistaminata* and that at least comprises the nucleotide sequence set forth in nucleotide numbers 34845-35044 of SEQ ID NO: 1, said nucleic acid molecule showing an activity for promoting the transcription of a plant gene; and
   (B) a nucleic acid molecule encoding a protein comprising an amino acid sequence having at least 97% identity to the amino acid sequence set forth in SEQ ID NO: 3.

3. A method for promoting the transcriptional activity of a plant gene, comprising the steps of:
   (1) preparing a nucleic acid construct which comprises a nucleic acid molecule of (i) or (ii):
      (i) a nucleic acid molecule comprising (1) nucleotide sequence set forth in nucleotide numbers 34845-35044 of SEQ ID NO: 1 or (2) a nucleotide sequence that has at least 97% identity to the nucleotide sequence set forth in nucleotide numbers 34845-35044 of SEQ ID NO: 1 and which shows an activity for promoting the transcription of a plant gene;
      (ii) a nucleic acid molecule comprising a nucleotide sequence which is derived from *O. longistaminata* and at least comprises the nucleotide sequence set forth in nucleotide numbers 34845-35044 of SEQ ID NO: 1, said nucleic acid showing an activity for promoting the transcription of a plant gene; and wherein the nucleic acid molecule and a gene are operably linked; and
   (2) introducing the nucleic acid construct into a plant.

* * * * *